United States Patent
Goh et al.

(10) Patent No.: US 9,517,252 B2
(45) Date of Patent: Dec. 13, 2016

(54) P53 ACTIVATING PEPTIDES

(75) Inventors: Walter Goh, Singapore (SG); Farid John Ghadessy, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 39 days.

(21) Appl. No.: 14/350,390

(22) PCT Filed: Sep. 10, 2012

(86) PCT No.: PCT/SG2012/000329
§ 371 (c)(1),
(2), (4) Date: May 30, 2014

(87) PCT Pub. No.: WO2013/036208
PCT Pub. Date: Mar. 14, 2013

(65) Prior Publication Data
US 2015/0359843 A1 Dec. 17, 2015

(30) Foreign Application Priority Data
Sep. 9, 2011 (SG) .................................. 201106590

(51) Int. Cl.
| | | |
|---|---|---|
| *A61K 38/16* | (2006.01) | |
| *C07K 5/083* | (2006.01) | |
| *C07K 7/06* | (2006.01) | |
| *C07K 7/08* | (2006.01) | |
| *C07K 14/00* | (2006.01) | |
| *A61K 38/08* | (2006.01) | |
| *A61K 38/10* | (2006.01) | |
| *A61K 45/06* | (2006.01) | |
| *C12N 15/10* | (2006.01) | |
| *A61K 38/00* | (2006.01) | |

(52) U.S. Cl.
CPC ............... *A61K 38/16* (2013.01); *A61K 38/08* (2013.01); *A61K 38/10* (2013.01); *A61K 45/06* (2013.01); *C07K 5/081* (2013.01); *C07K 7/06* (2013.01); *C07K 7/08* (2013.01); *C07K 14/00* (2013.01); *C07K 14/001* (2013.01); *C12N 15/1058* (2013.01); *A61K 38/00* (2013.01); *C07K 2319/00* (2013.01)

(58) Field of Classification Search
CPC ..................................................... A61K 38/16
See application file for complete search history.

(56) References Cited

U.S. PATENT DOCUMENTS

| | | |
|---|---|---|
| 2006/0236419 A1 | 10/2006 | La Rosa et al. |
| 2009/0087878 A9 | 4/2009 | La Rosa et al. |
| 2011/0214205 A1 | 9/2011 | Dietrich et al. |

FOREIGN PATENT DOCUMENTS

| | | |
|---|---|---|
| EP | 0989136 A1 | 3/2000 |
| NO | WO-2009/039854 A2 | 4/2009 |
| WO | WO-99/45954 A1 | 9/1999 |
| WO | WO-01/75067 A2 | 10/2001 |
| WO | WO-01/92523 A2 | 12/2001 |
| WO | WO-2013/036208 | 3/2013 |

OTHER PUBLICATIONS

"EMBL Accession No. CP002394: Bacillus cellulosilutocis DSM 2522, complete genome", [online]. [retrieved on Apr. 16, 2014]. Retrieved from the Internet: <URL: http://www.ebi.ac.uk/ena/data/view/CP002394>, (Dec. 29, 2010), 5 pgs.

"EMBL Accession No. YP_004094247—Hypothetical protein Bcell_1252 [Bacillus callulosilyticus DSM 2522]", [online]. [retrieved on Apr. 16, 2014]. Retrieved from the Internet: <URL: http://www.ncbi.nlm.nih.gov/protein/YP_004094247.1>, (Jul. 6, 2013), 1 pg.

"GenBank Accession No. ZP_06539153—Hybrid sensory kinase in two-component regulatory system with RcsB and YojN [*Salmonella enerica* subsp. *enterica serovar Typhi* sir. AG3]", [online]. [retrieved on Apr. 16, 2014], Retrieved from the Internet: <URL: http://www.ncbi.nlm.nih.gov/protein/ZP_06539153.1?report.genpeptide . . . >, (Dec. 9, 2010), 1 pg.

"GenBank Accession No. ZP_08746233—Hypothetical protein VIS19158_09447 [Vibrio scophthalmi LMG 19158]", [online]. [retrieved on Apr. 16, 2014]. Retrieved from the Internet: <URL: http://www.ncbi.nlm.nih.gov/protein/ZP_08746233.1?report.genpeptide . . . >, (Aug. 18, 2011), 1 pg.

Brown, C. J., et al., "Reactivation of p53: from peptides to small molecules", *Trends in Pharmacological Sciences*, 32(1), (2011), 53-62.

Issaeva, N., et al., "Rescue of mutants of the tumor suppressor p53 in cancer cells by a designated peptide", *Proc. Natl. Acad. Sci. USA*, 100(23), (2003), 13303-13307.

Yonezawa, M., et al., "DNA Display for in vitro selection of diverse peptide libraries", *Nucleic Acid Research*, 31(19), e118, (2003), 5 pgs.

"International Application No. PCT/SG2012/000329, International Preliminary Report on Patentability mailed Mar. 20, 2014", (Mar. 20, 2014), 11 pgs.

"International Application No. PCT/SG2012/000329, International Search Report and Written Opinion mailed Dec. 3, 2012", (Dec. 3, 2012), 45 pgs.

*Primary Examiner* — Amber D Steele
(74) *Attorney, Agent, or Firm* — Schwegman Lundberg & Woessner, P.A.

(57) ABSTRACT

The present invention is directed to p53 activating peptides. The present further describes methods for generating these peptides and the use of these peptides.

20 Claims, 82 Drawing Sheets

| Clone | G245S | R248Q | R273H |
|---|---|---|---|
| 1 | SPNTNH | ILNVLPLLASRKP | RLQQV |
| 2 | MPHLMAC | VSWSACVLLELCNYFPENPIEEEDWACLG | ARHQHVGATILGWK |
| 3 | SPTTNH | VSWSACVLLELCNYFPENPIEEEDWACLG | VRHQHVGATILGWK |
| 4 | SPTTNH | ILNVLPLLASRKP | TALIDIWEHSVLGKGYPRMS |
| 5 | DELVAIPVRLTYYRGPNIAI | ILNVLPLLASRKP | LM |
| 6 | SPTTNH | VSWSACVLLELCNYFPENPIEEEDWACLG | TALIDIWEHSVLGKGYPRMS |
| 7 | MPHLMAC | ILNVLPLLASRKP | RLQQV |
| 8 | SPTTNH | VSWSACVLLELCNYFPENPIEEEDWACLG | VRHQHVGATILGWK |
| 9 | MPHLMAC | ILNVLPLLASRKP | RLQQV |
| 10 | ERRFPIMGVNSPEGKMWPLI | VSWSACVLLELCNYFPENPIEEEDWACLG | TALIDIWEHSVLGKGYPRMS |
| 11 | SPTTNH | VSWSACVLLELCNYFPENPIEEEDWACLG | TALIDIWEHSVLGKGYPRMS |
| 12 | DELVAIPVRLTYYRGPNIAI | ILNVLPLLASRKP | VRHQHVGATILGWK |
| 13 | ERRFPIMGVNSPEGKMWPLI | ILNVLPLLASRKP | RLQQV |
| 14 | SPTTNH | ILNVLPLLASRKP | VRHQHVGATILGWK |
| 15 | MPHLMAC | ILNVLPLLASRKP | TALIDIWEHSVLGKGYPRMS |
| 16 | MPHLMAC | ILNVLPLLASRKP | VRHQHVGATILGWK |

| No. | Peptide Reference | Amino Acid Sequence | p53 mutant |
|---|---|---|---|
| 1 | Pap-SPT | S P T T N H | G245S |
| 2 | Pap-MPH | M P H L M A C | G245S |
| 3 | Pap-TAL | T A L I D I W E H S V L G K G Y P R M S | R273H/G245S |
| 4 | Pap-ILN | I L N V L P L L A S R K P | R248Q |
| 5 | Pap-VSW | V S W S A C V L L E L C N Y F P E N P I E E E D W A C L G | R248Q |
| 6 | Pap-RLQ | R L Q Q V | R273H |
| 7 | Pap-VRH | V R H Q H V G A T I L G W K | R273H |

Fig. 7
A
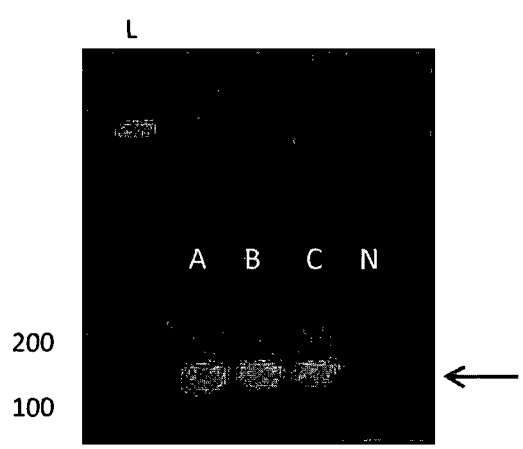
B
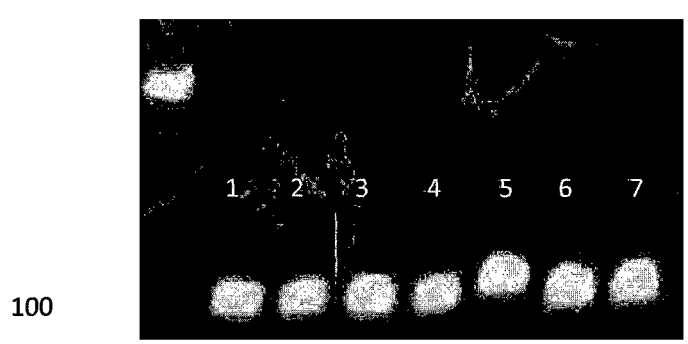

Fig. 9 (continued)
D
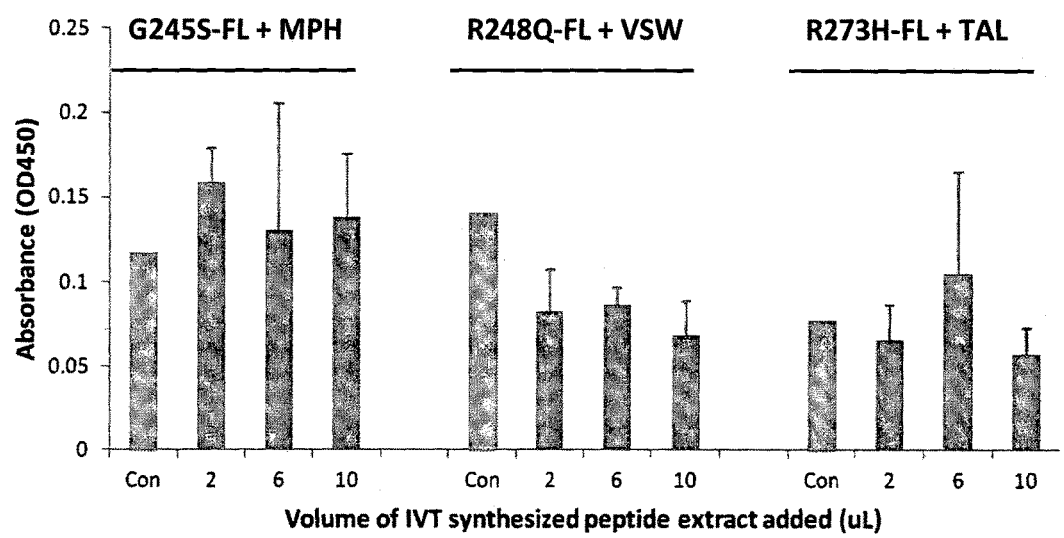
E
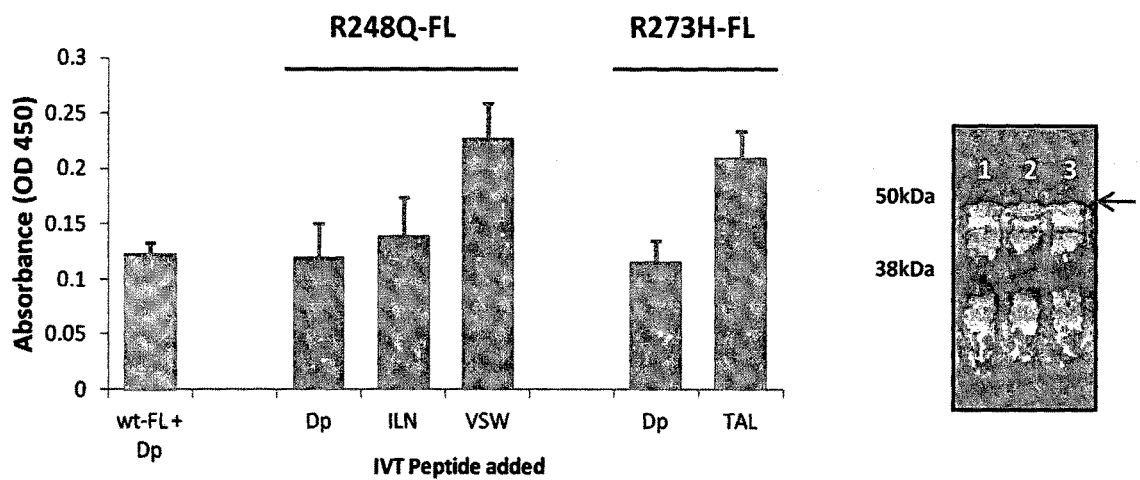

C

Pap-VSW    VSWSACVLLELCNYFPENPIEEEDWACLG

Pap-VSW    11 - LCNYFPENPIEEED - 24
PARP4 protein    118 - LC - - - PDNATEEED - 128
           * *       * # * †   * * * *

Pap-VSW    13 - YFPENPIEE - 22
PARP4 protein    214 - YY - ENYIEE - 221
           * #   * *    * * *

Pap-VSW    20 - IEEEDWAC - 27
Peptide CDB3    REDEDEIEW

D

Pap-TAL    TALIDIWEHSVLGKGYPRMS

Human Lymphoid Tyrosine Phosphatase Catalyic Domain
1 - TALID - - - - IWEHSVL - 12
104 - GPLSTTLLDFWRMIWEYSVLI - 124
      * #.* # *      * * * # * * *

Fig. 14
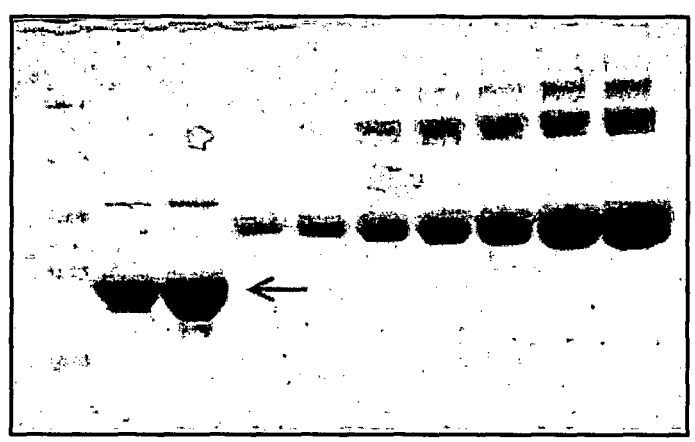
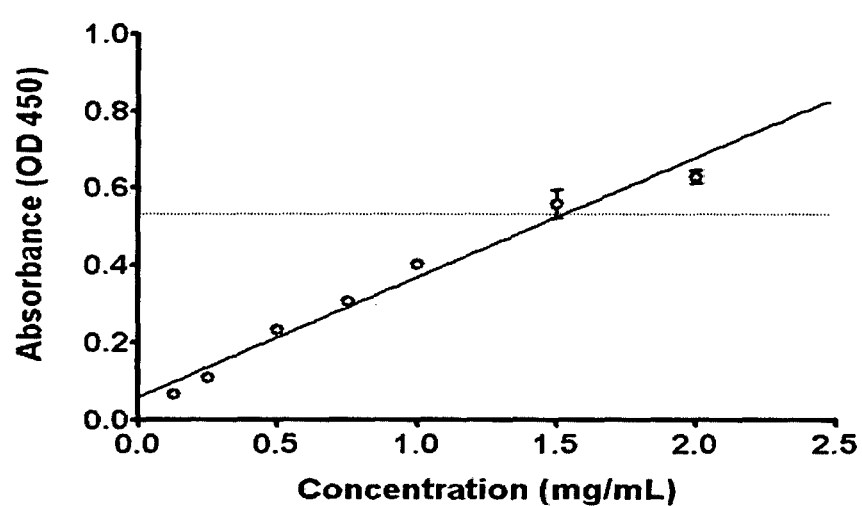

Fig. 14 (continued)
C 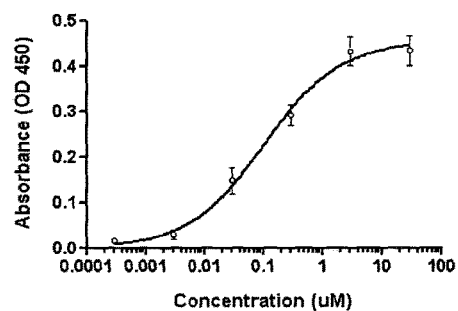 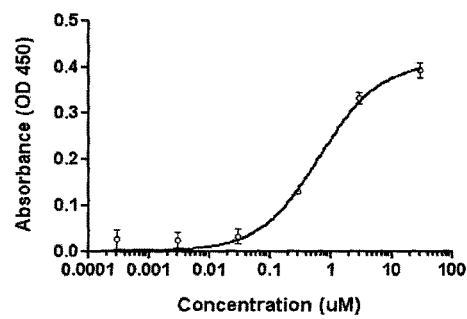
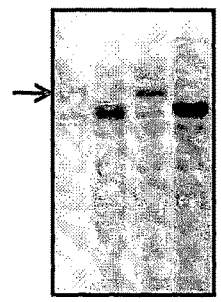
| p53 Sample | DO-1 (uM) | Bp53 10.1 (uM) | Lane | Est. Conc. (nM) |
|---|---|---|---|---|
| wt-FL | 0.086±0.008 | 0.072±0.018 | 1 | 65-80 |
| wt-Δ22 | 0.177±0.029 | 0.130 | 2 | 200-300 |
| wt-FL (5% DMSO) | 0.310±0.05 | 0.273±0.084 | 3 | 200-250 |
| wt-Δ22 (5% DMSO) | 0.760±0.325 | 0.295 | 4 | 700-800 |

Fig. 15
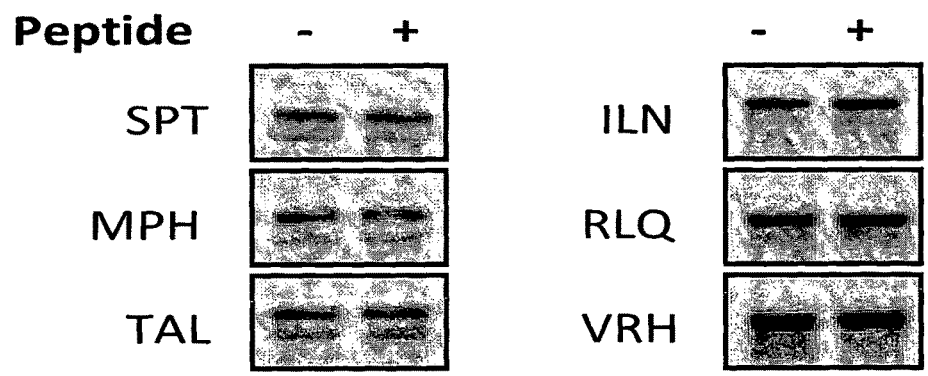
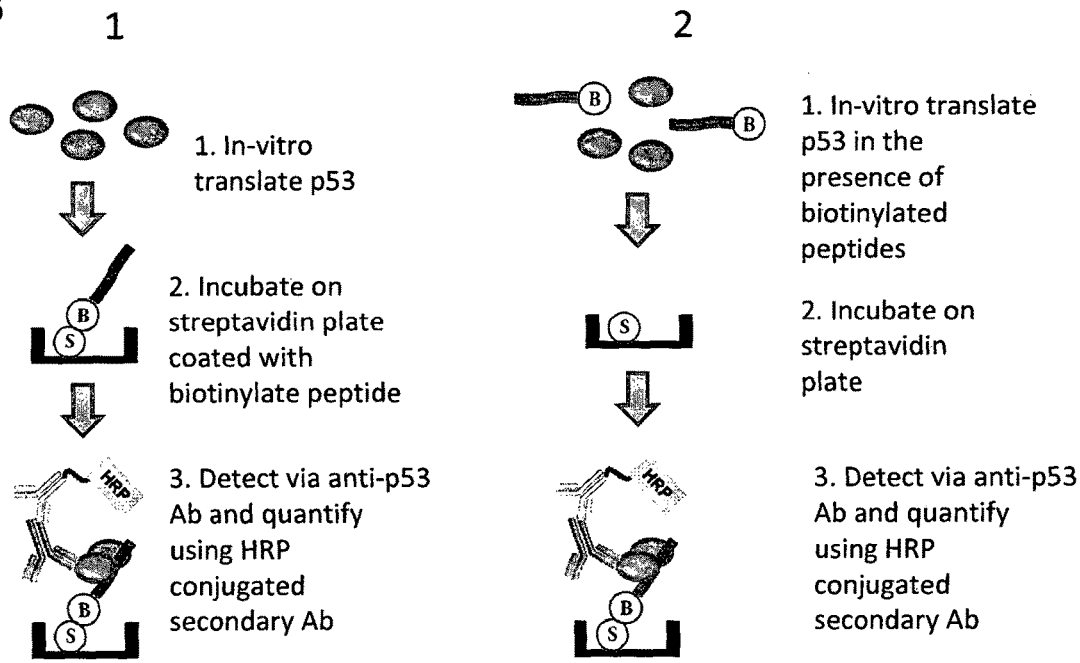

A

Fig. 18 (continued)
B
wt-Δ22
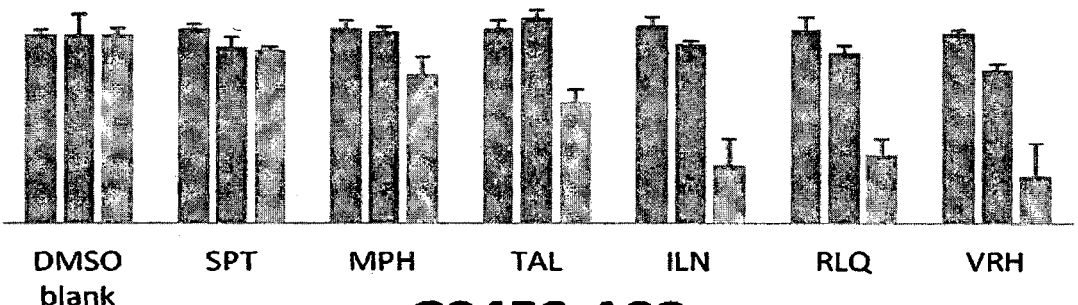
G245S-Δ22
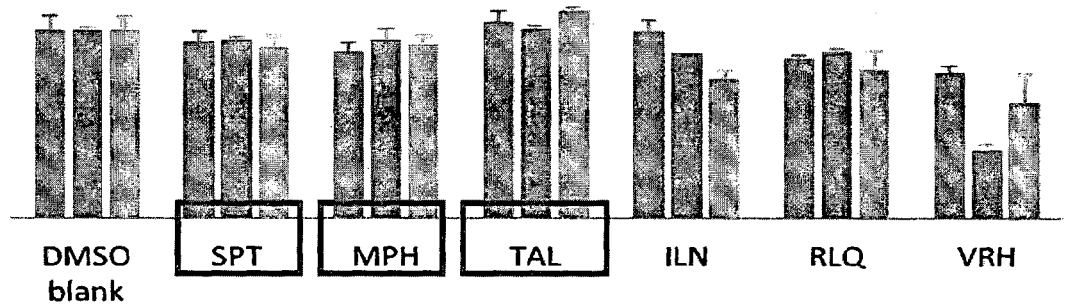

Fig. 19
A
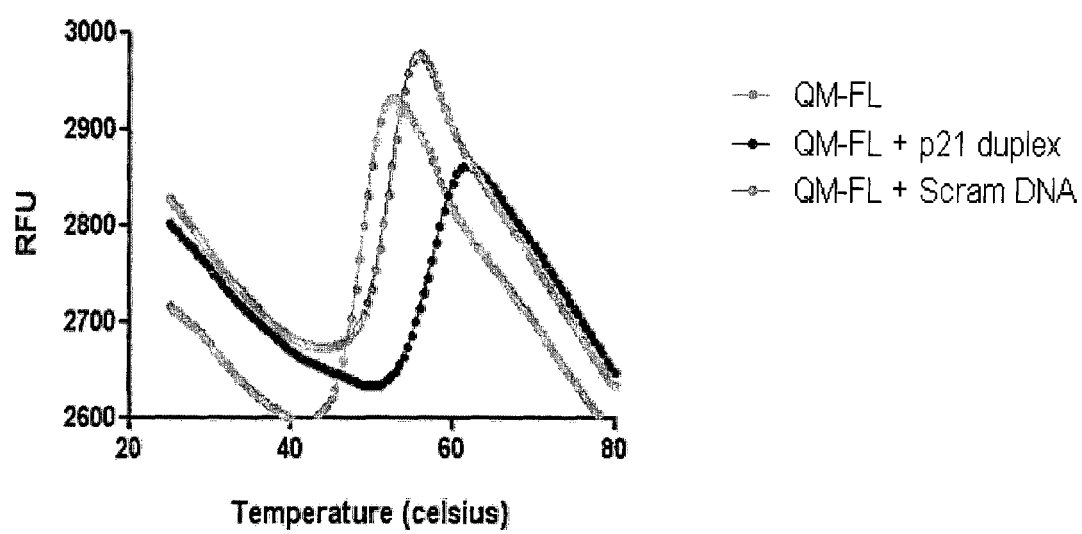
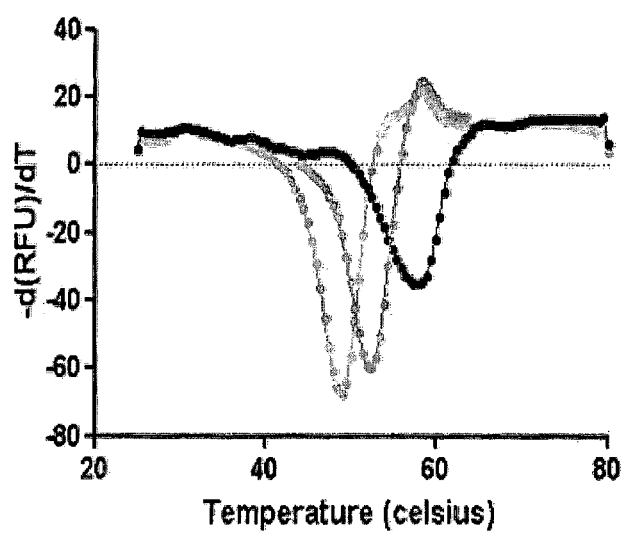
| Sample | $T_m$ (°C) |
|---|---|
| QM-FL | 52.90 ± 0.5 |
| QM-FL (p21) | 62.95 ± 0.7 |
| QM-FL (Scram) | 55.68 ± 0.3 |

Fig. 19 (continued)
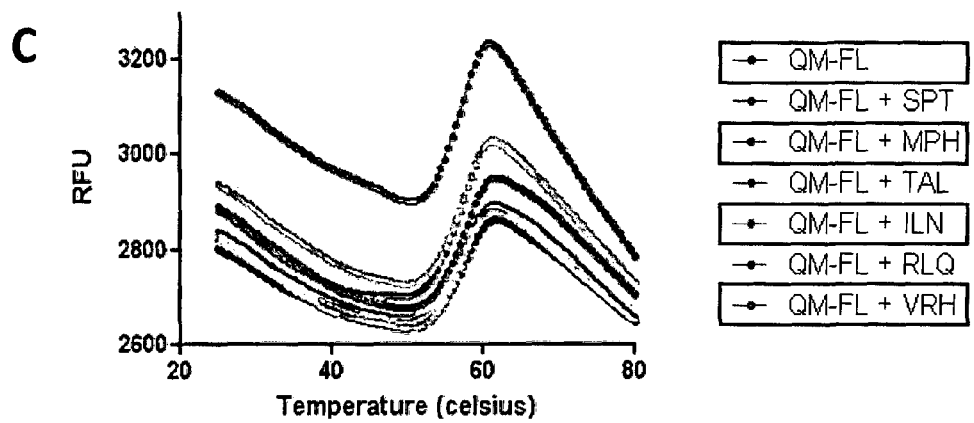
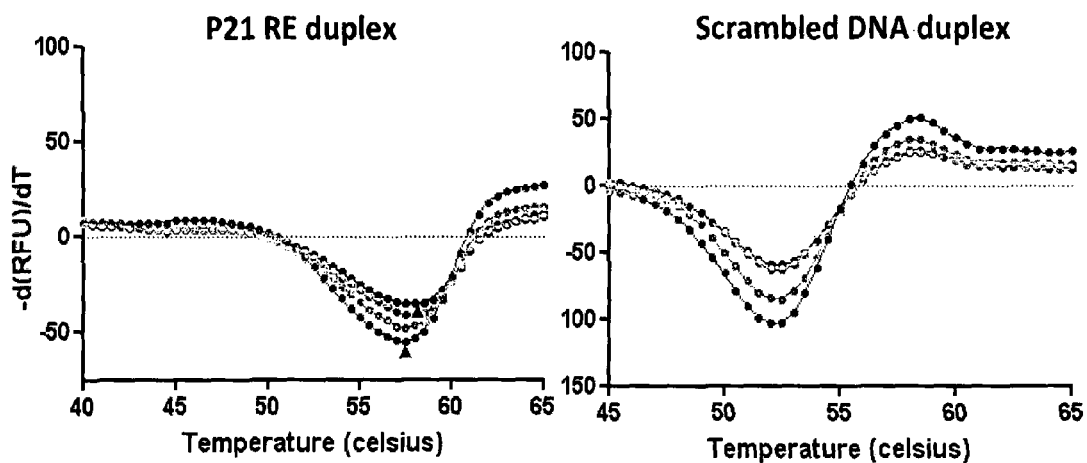
| Sample | P21-RE $T_m$ (°C) | Scram $T_m$ (°C) |
|---|---|---|
| QM-FL +DMSO | 62.95 ± 0.5 | 55.90 ± 0.3 |
| QM-FL +MPH | 63.16 ± 0.9 | 56.06 ± 0.5 |
| QM-FL +ILN | 62.10 ± 0.6 | 55.98 ± 0.3 |
| QM-FL +VRH | 61.56 ± 0.4 | 55.73 ± 0.4 |

Fig. 21 (continued)
B
NTC
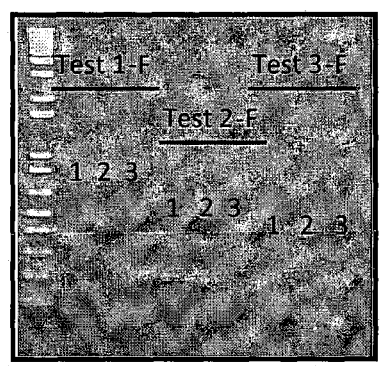
PET22b template
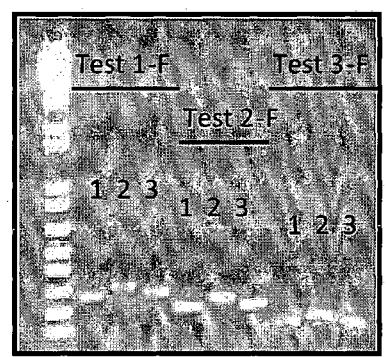
1 – Wpet-R1
2 – Wpet-R2
3 – Wpet-R3
C
1 – control
2 – p21
3 – PUMA-BS2
4 – P2XM
58 °C
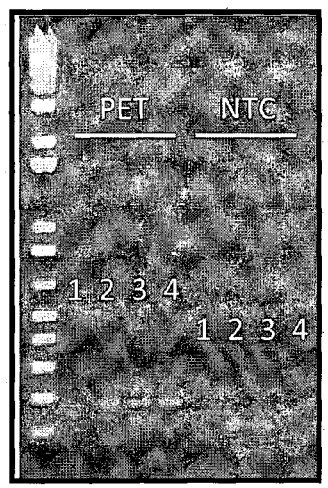
60 °C
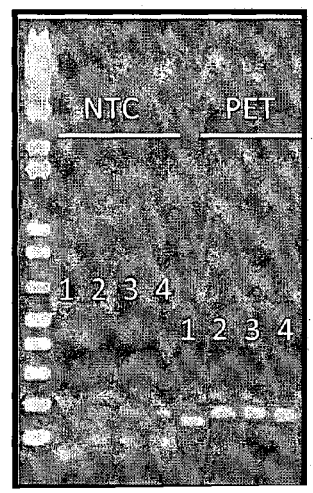

D

1 – control
2 – RGC
3 – p21
4 – PUMA-BS2
5 – P2XM

Fig. 22
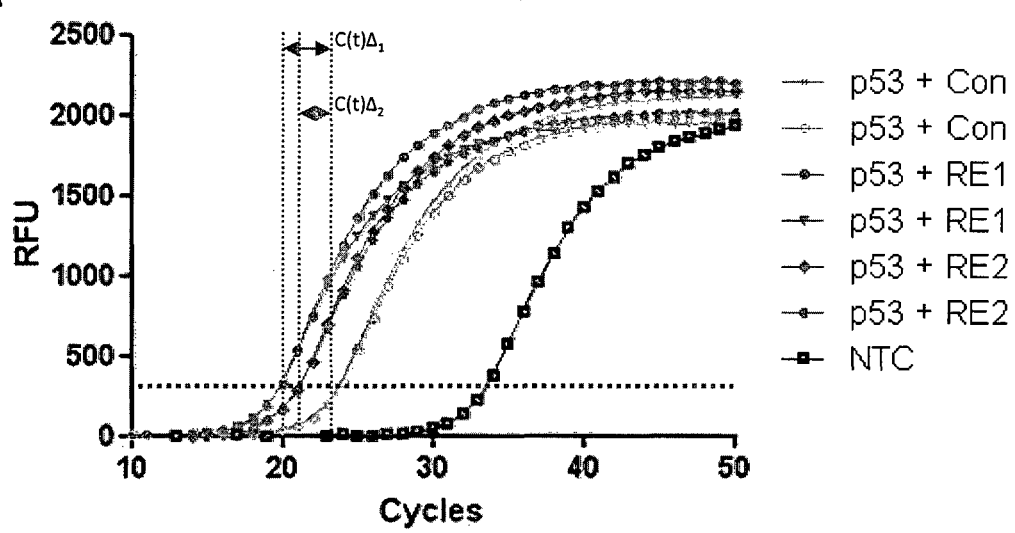
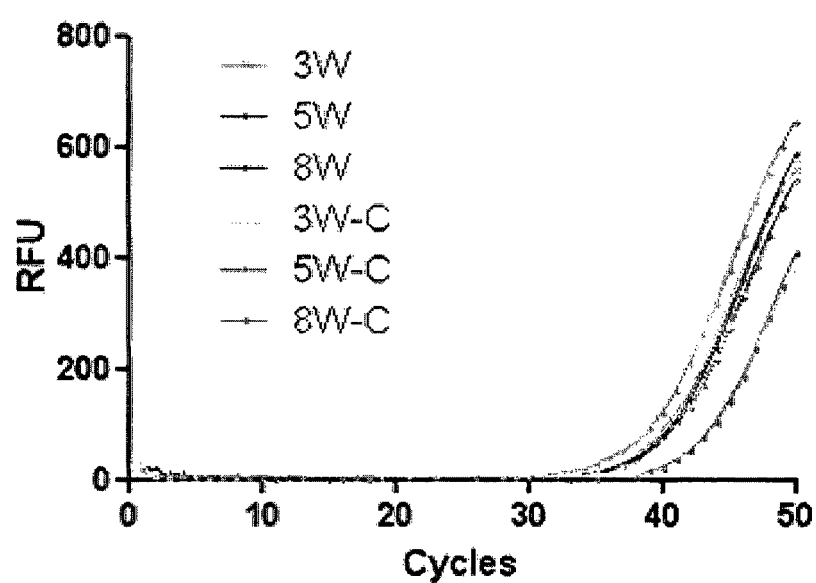

Fig. 22 (continued)
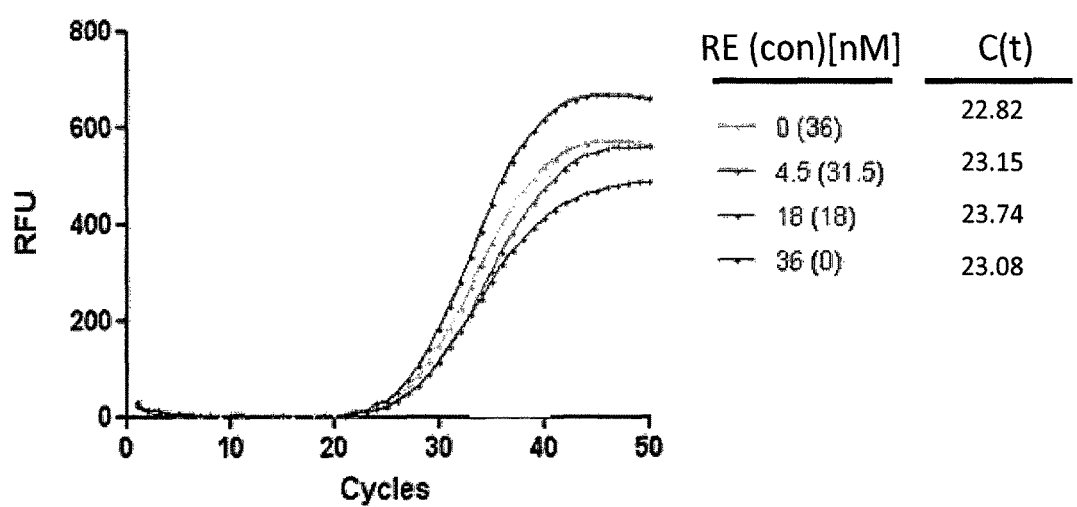
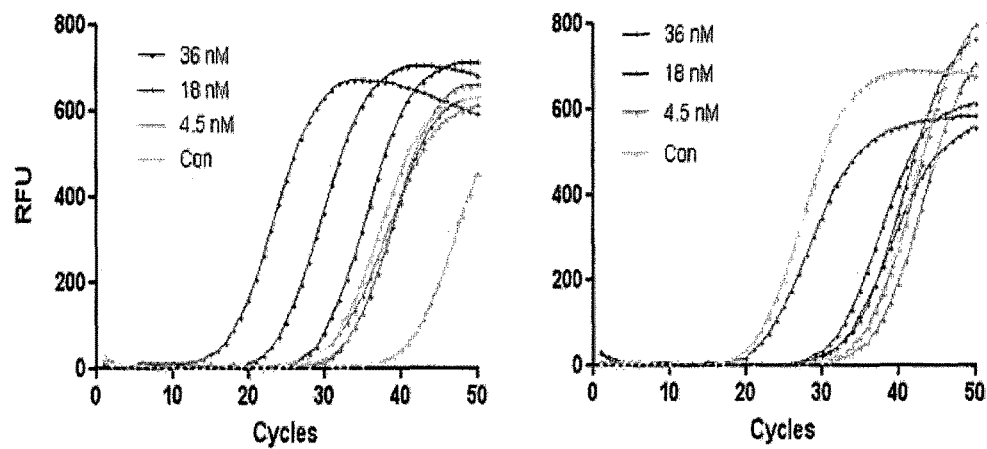

Fig. 22 (continued)
E
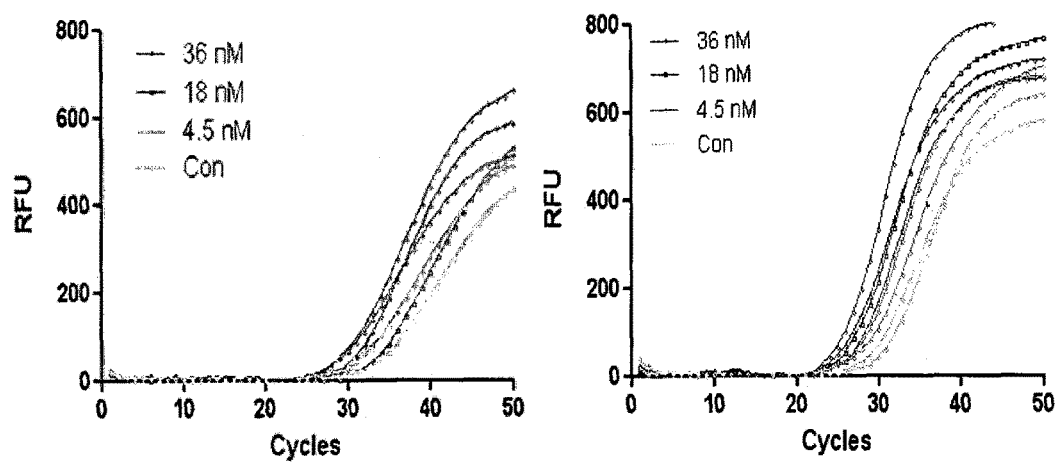
F
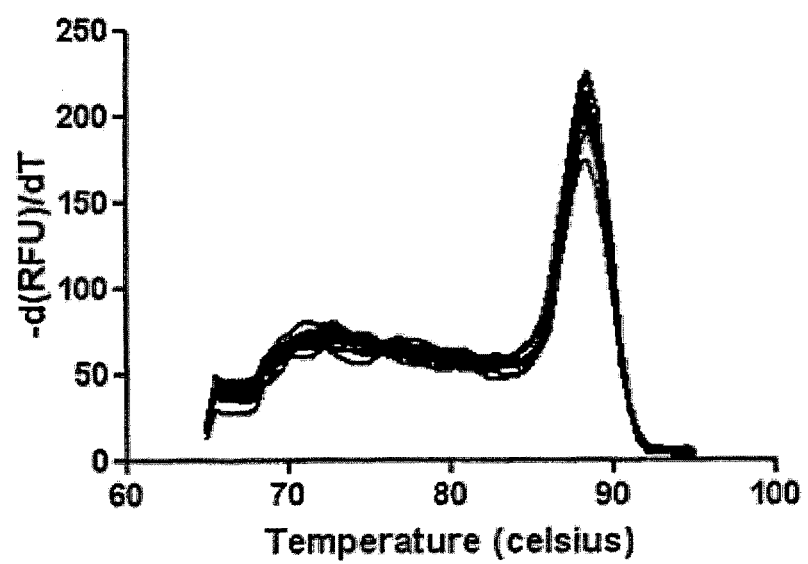

Fig. 24
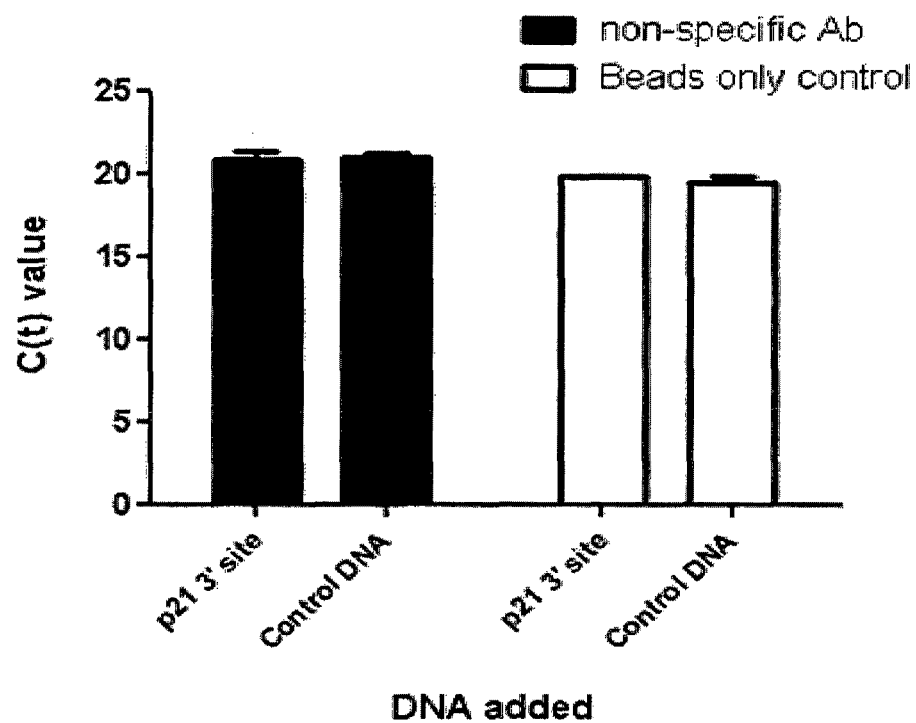
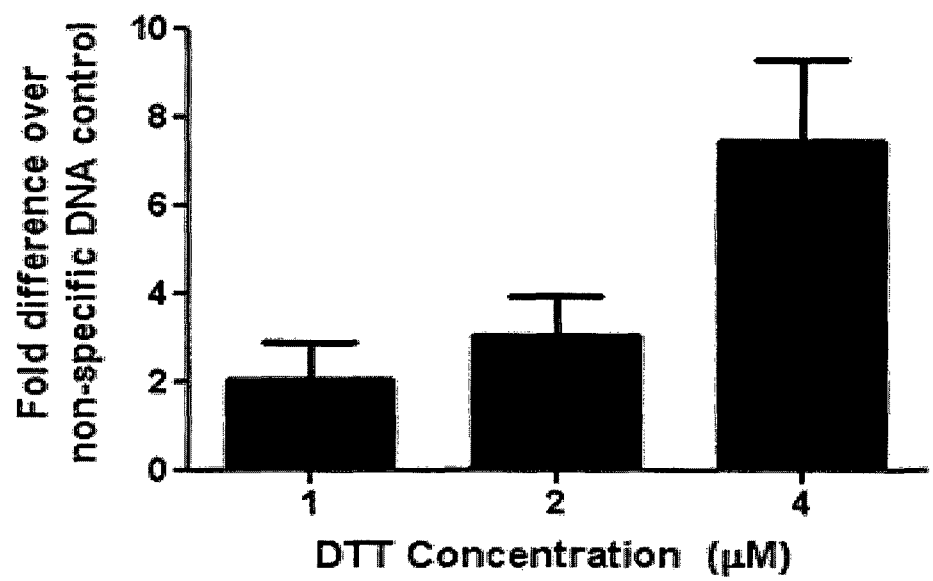

Fig. 25
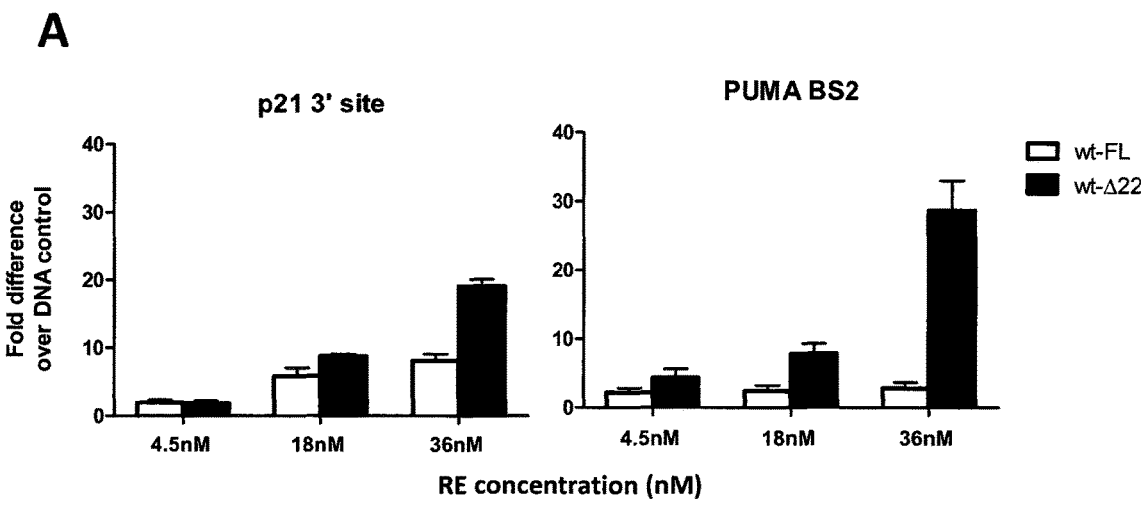
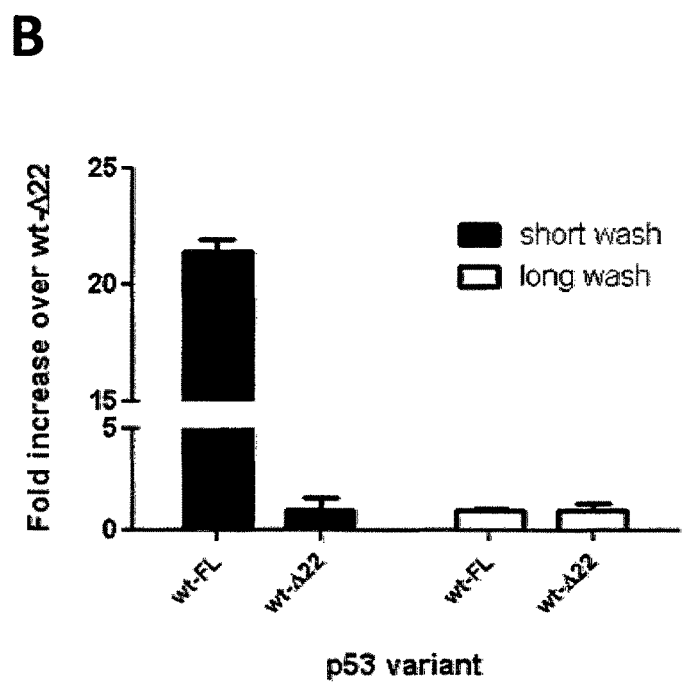

Fig. 28
A
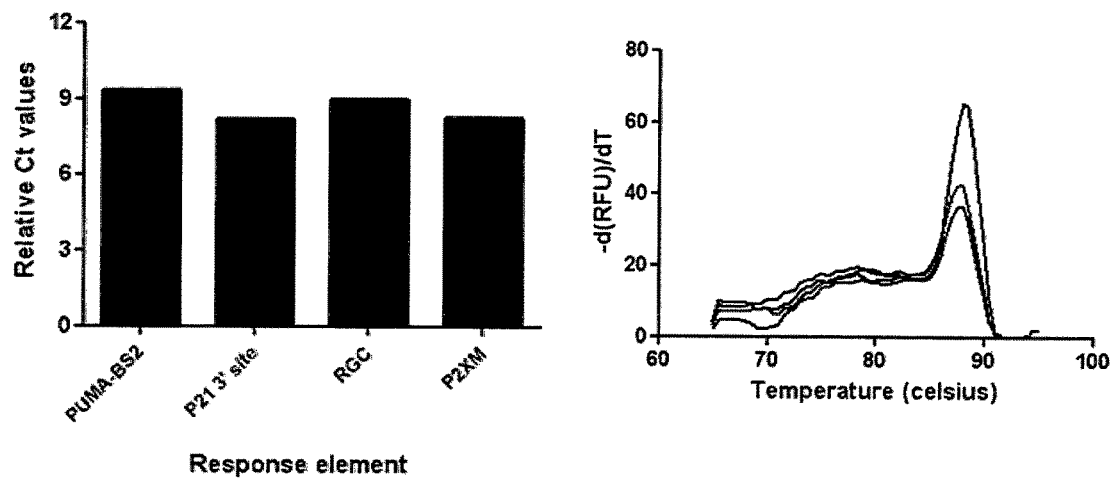
B
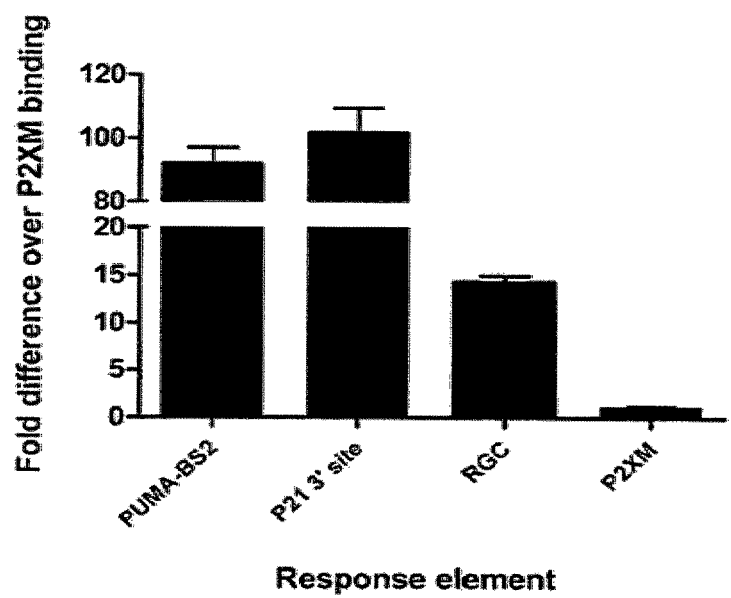

Fig. 30
A
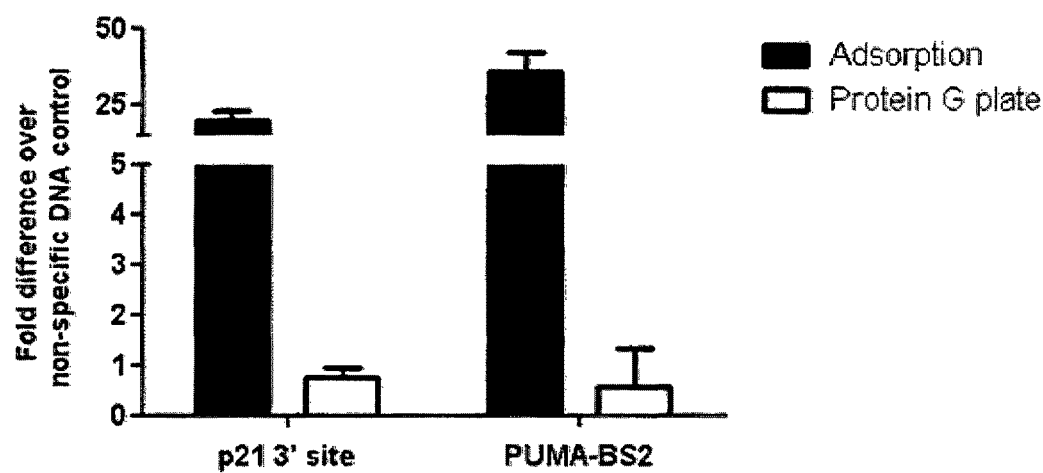
B
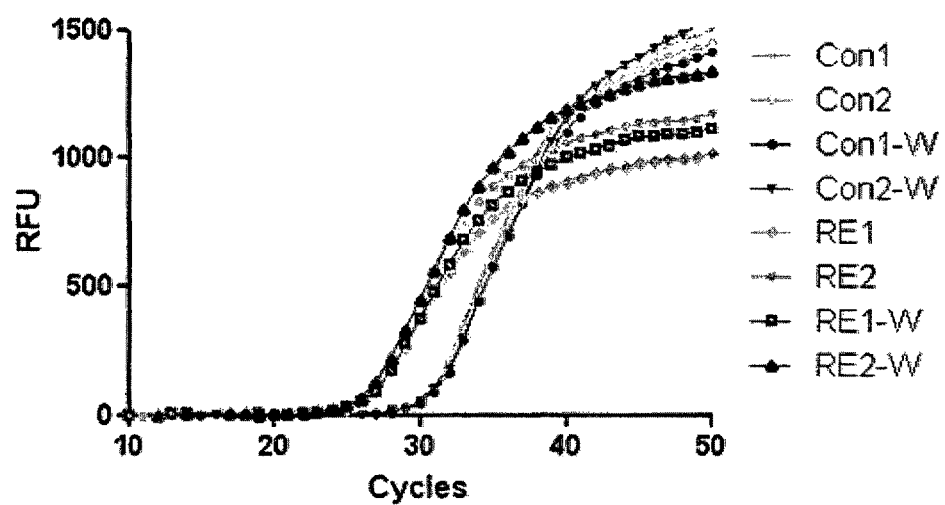

Fig. 32
A
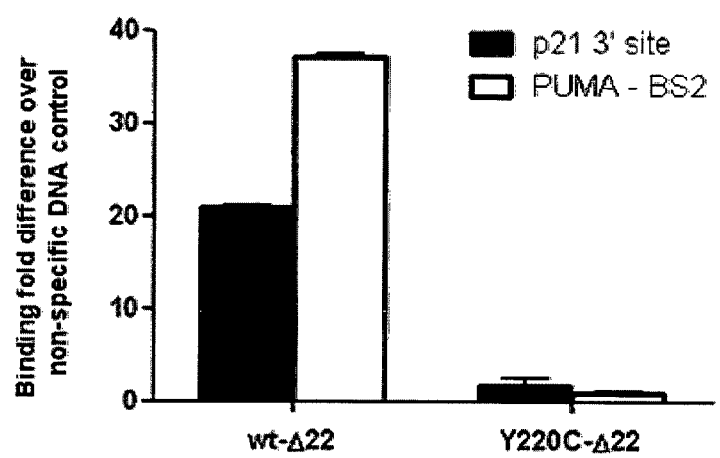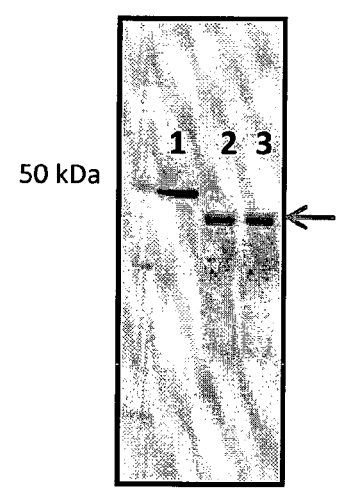
1 – pur.p53QM-FL
2 – IVT-p53wt-Δ22
3 – IVT-p53Y220C-Δ22

Fig. 34
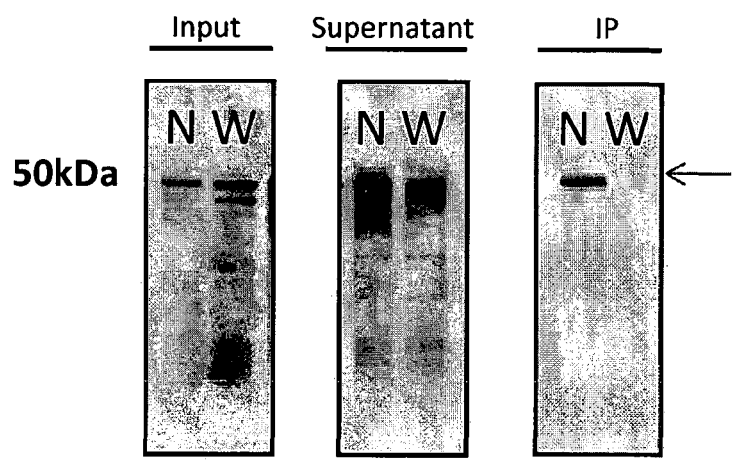
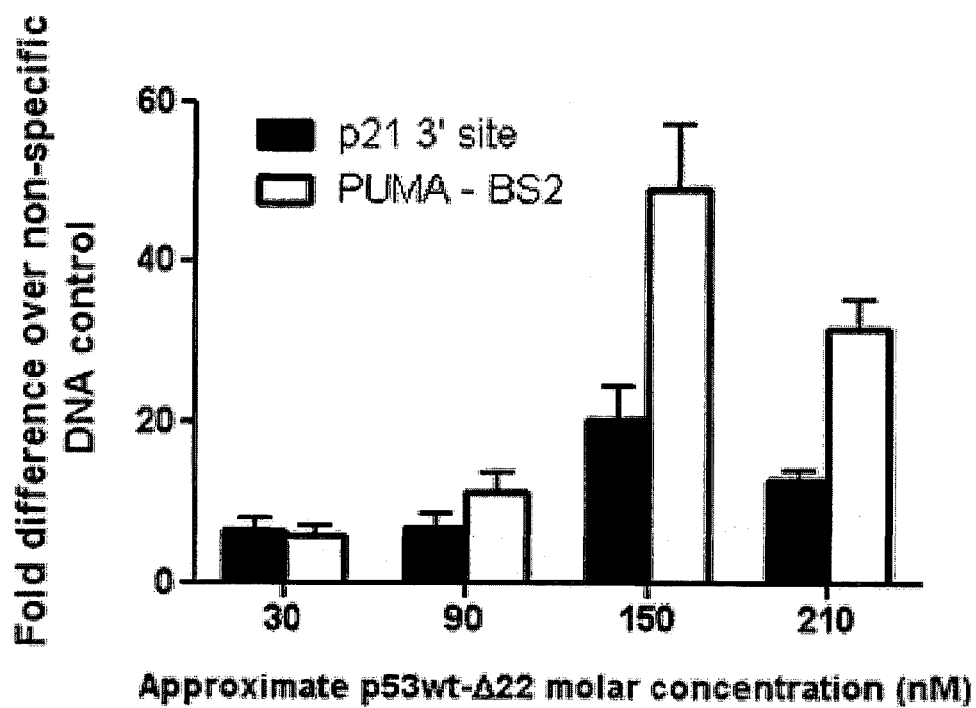

Fig. 35
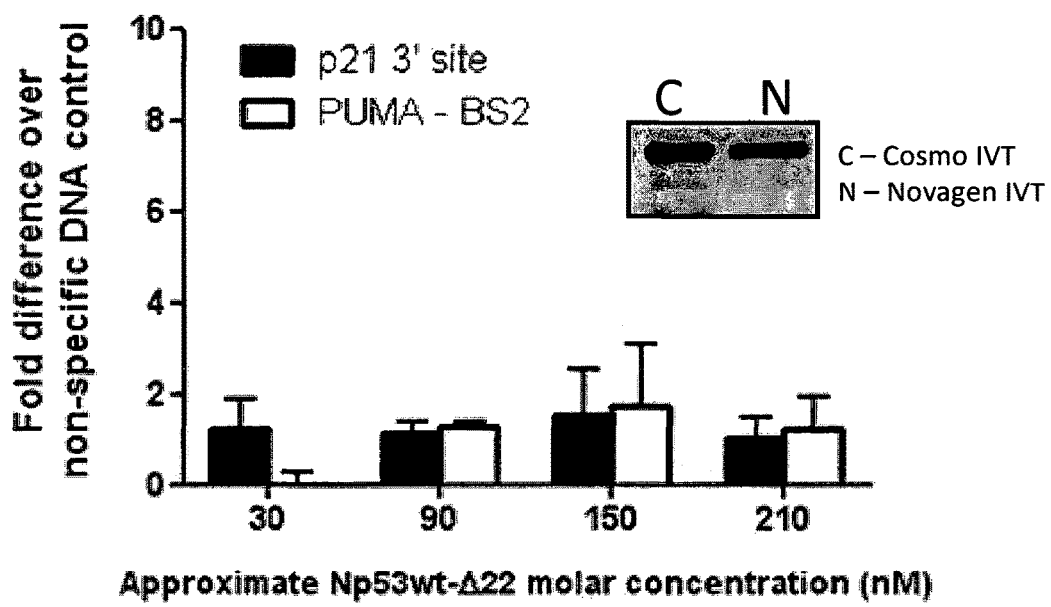
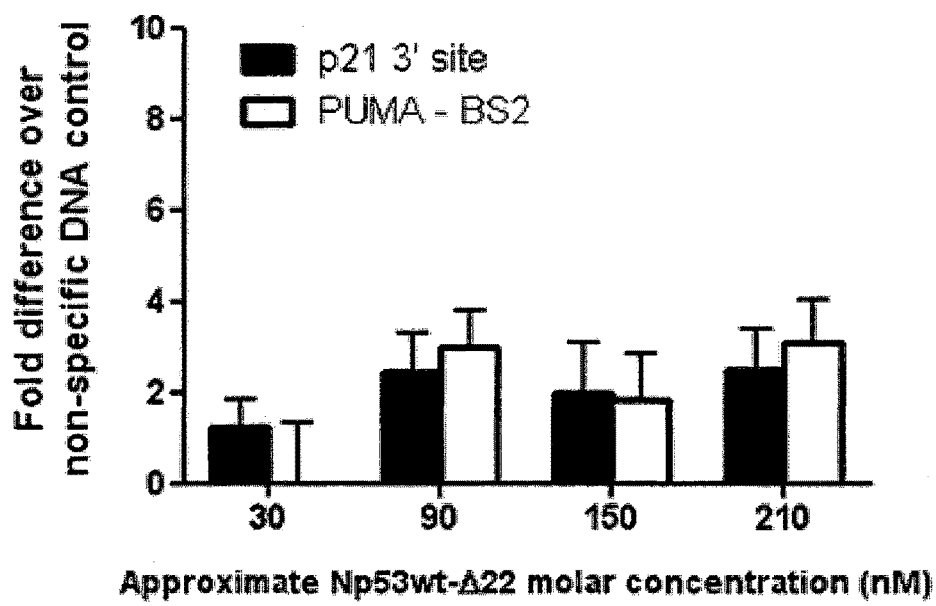

Fig. 36
A
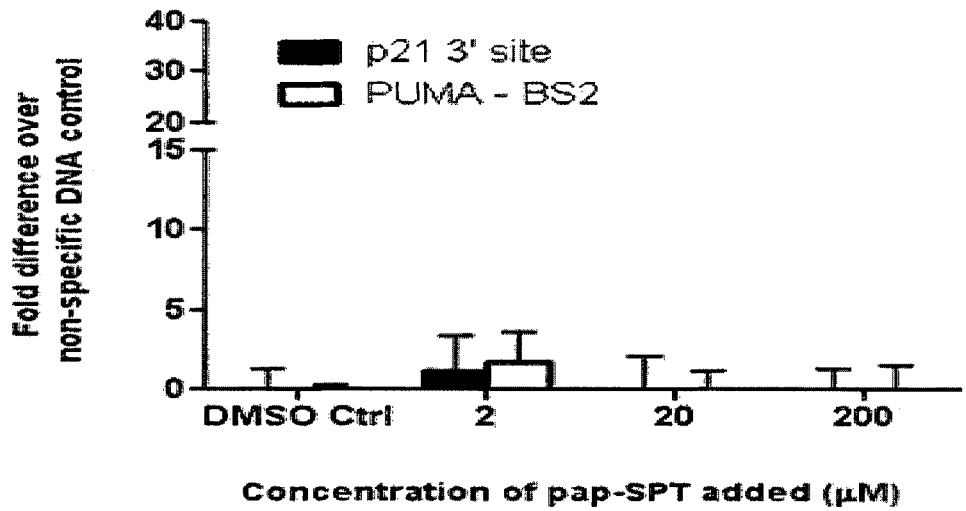
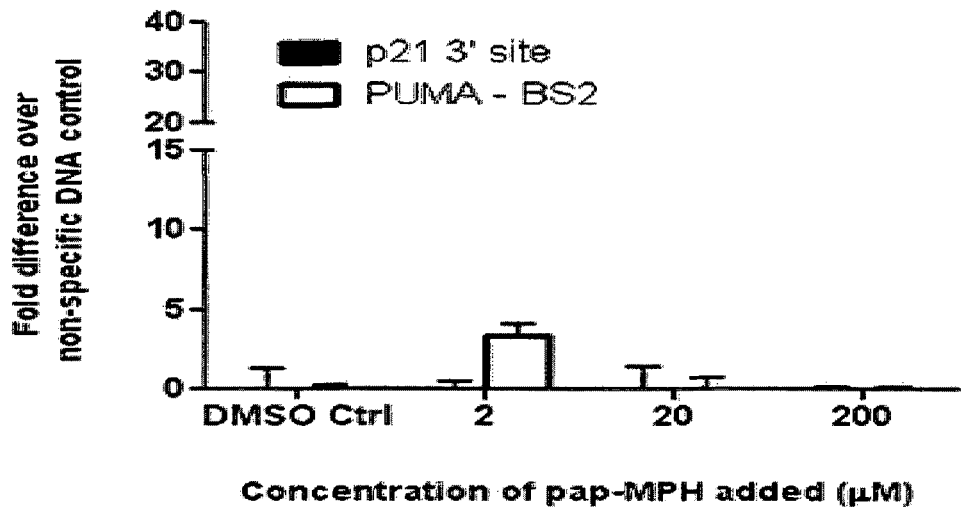
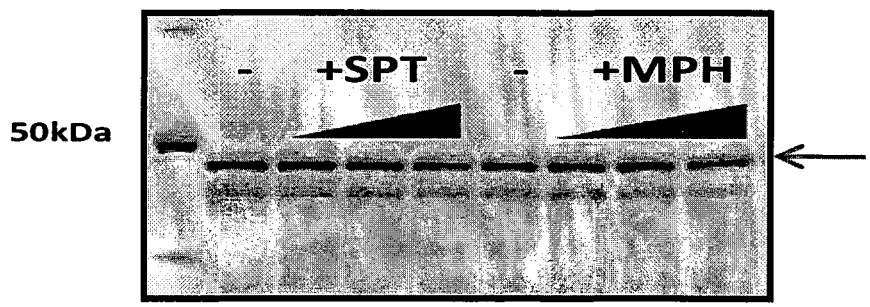

Fig. 36 (continued)
B
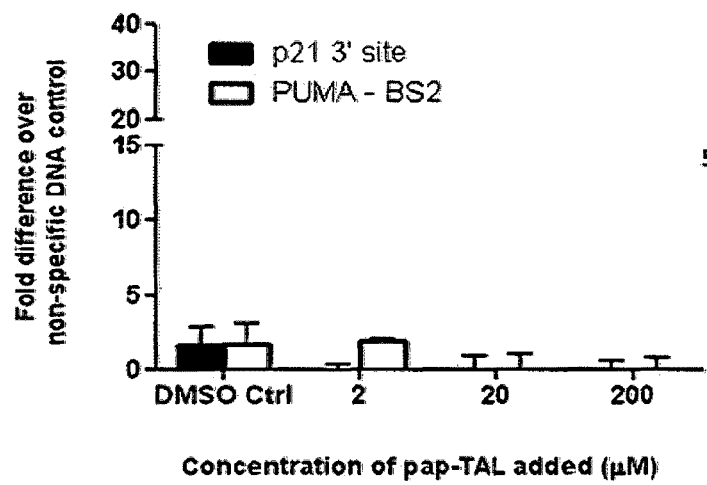 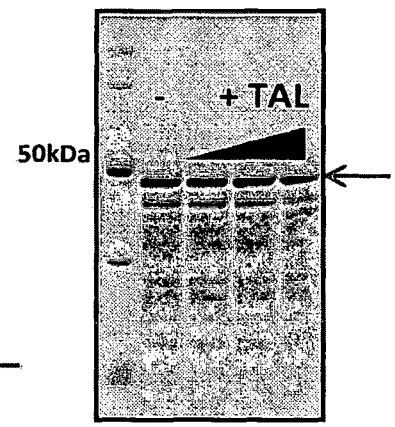
C
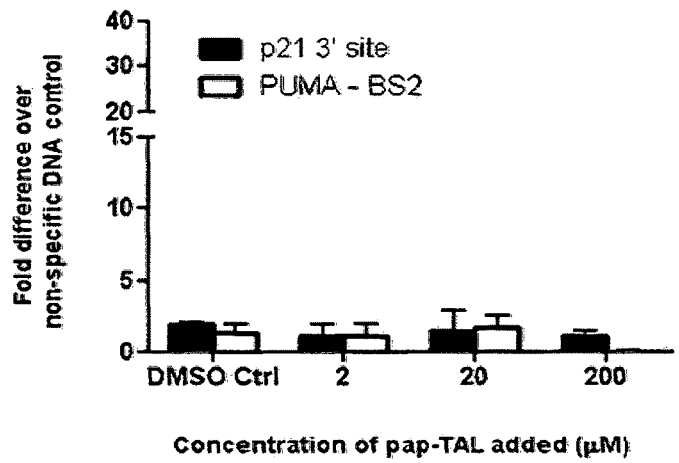 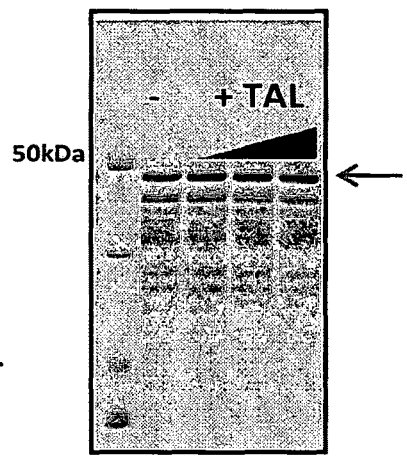

Fig. 36 (continued)
D
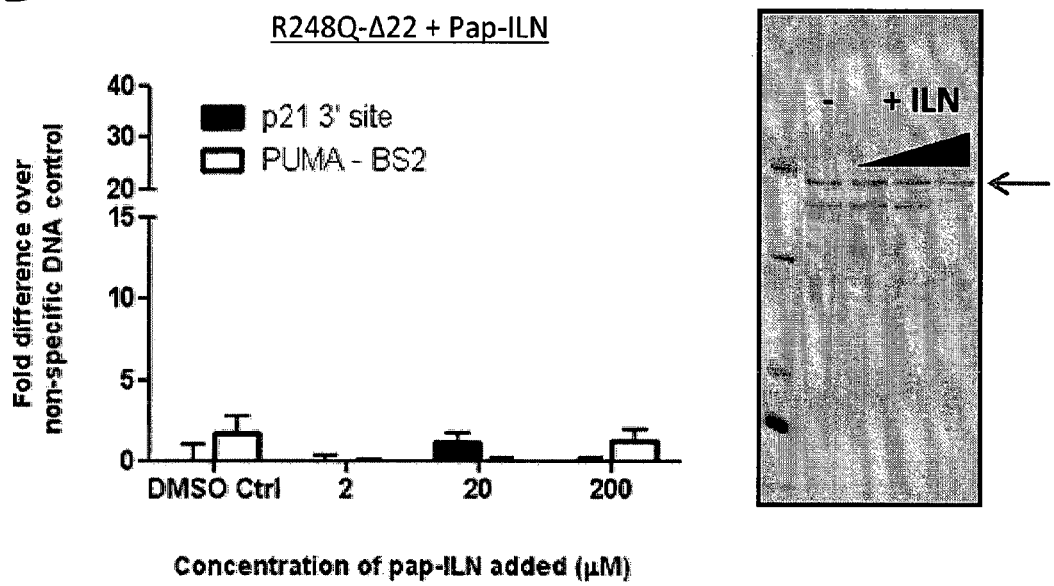
E
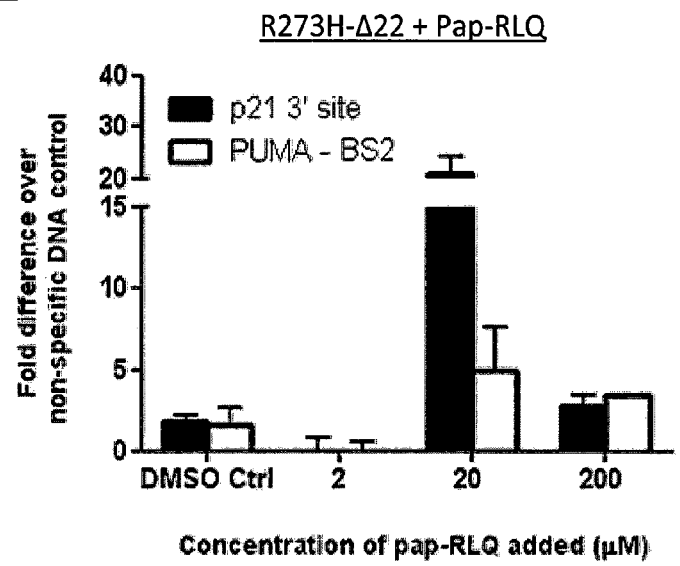

Fig. 36 (continue
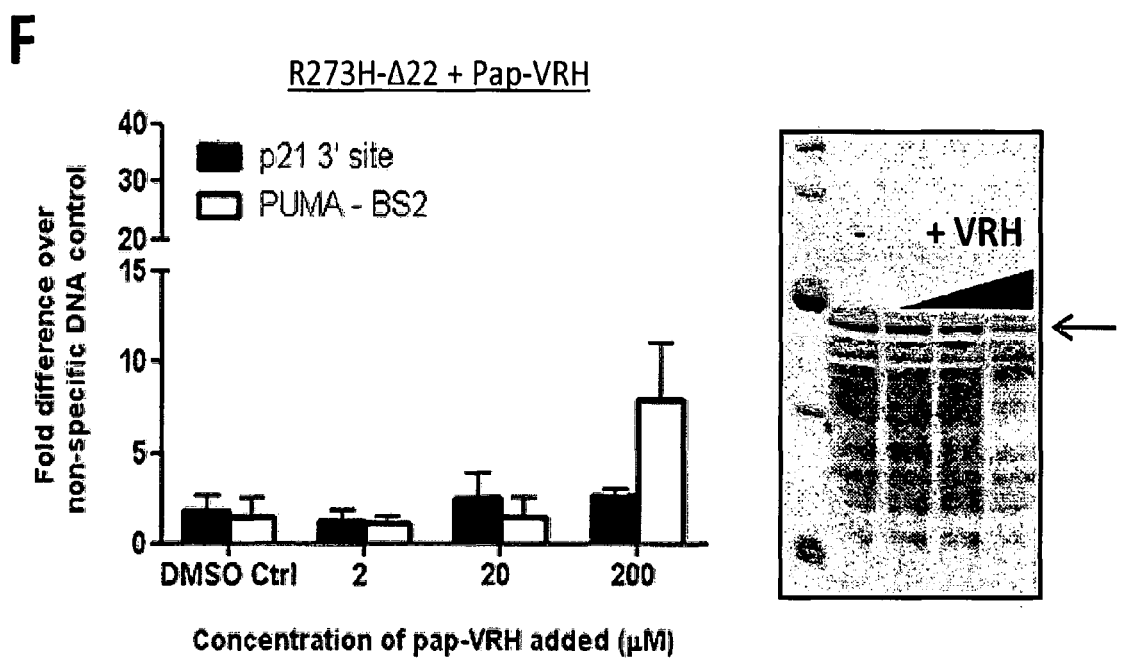

Fig. 37 (continued)
B
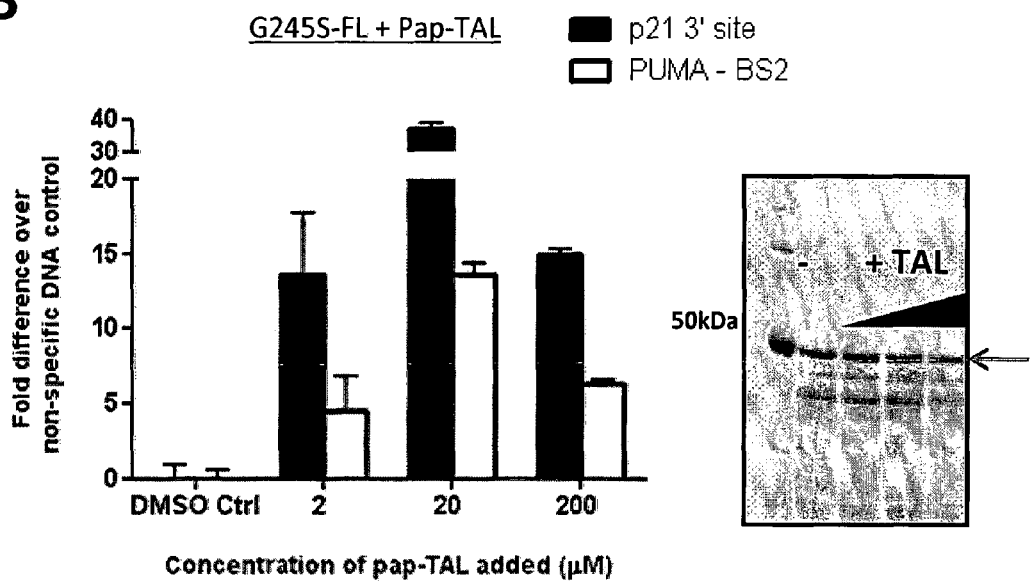
C
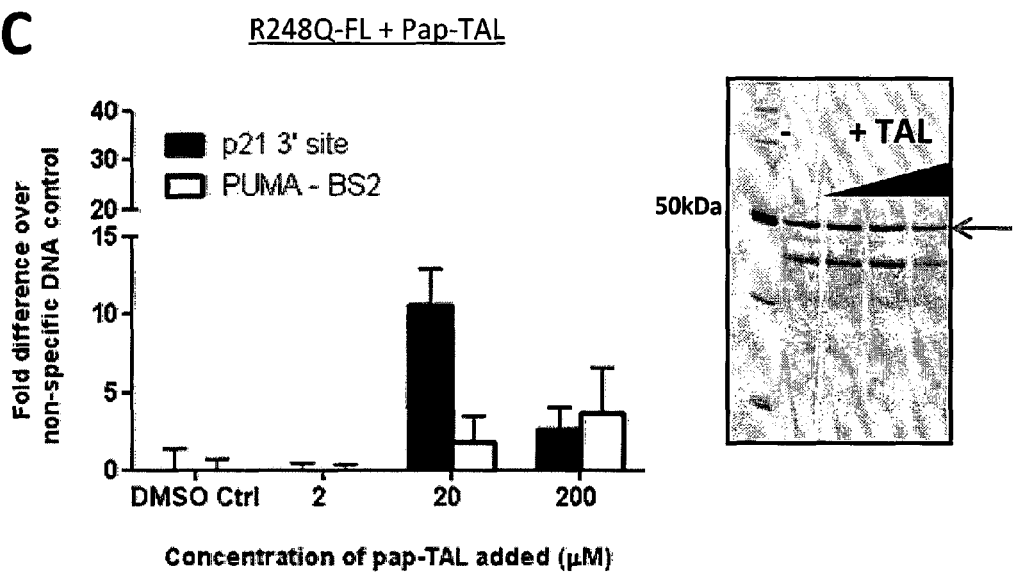

Fig. 39
A
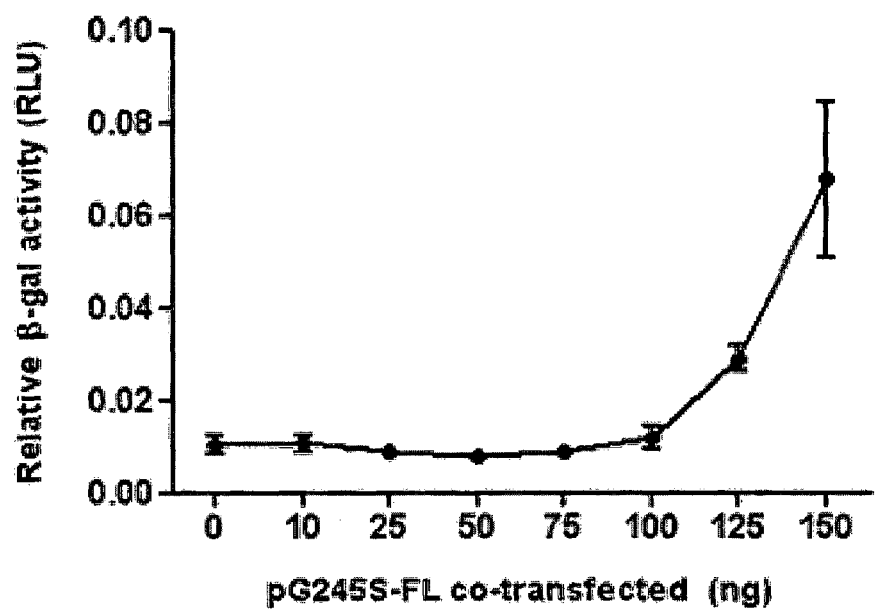
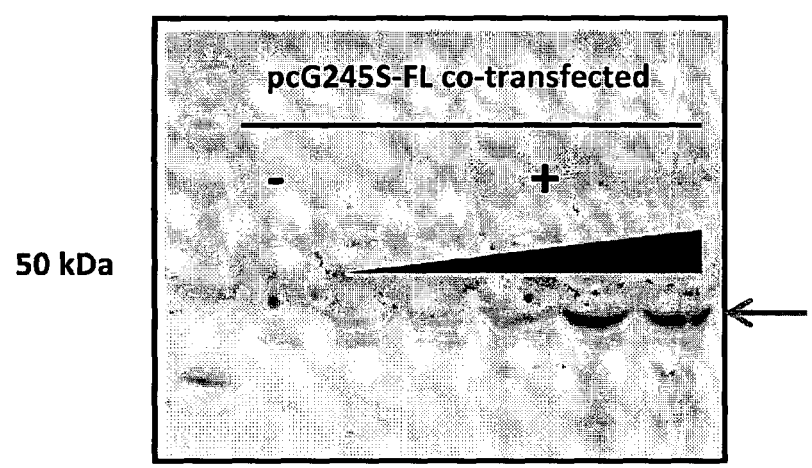

Fig. 40
A
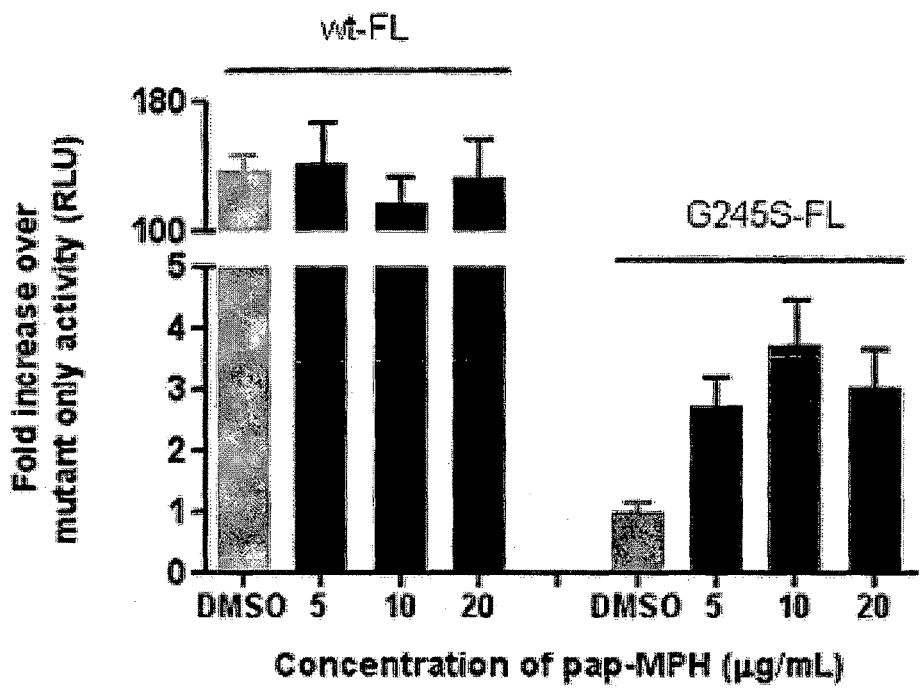
B
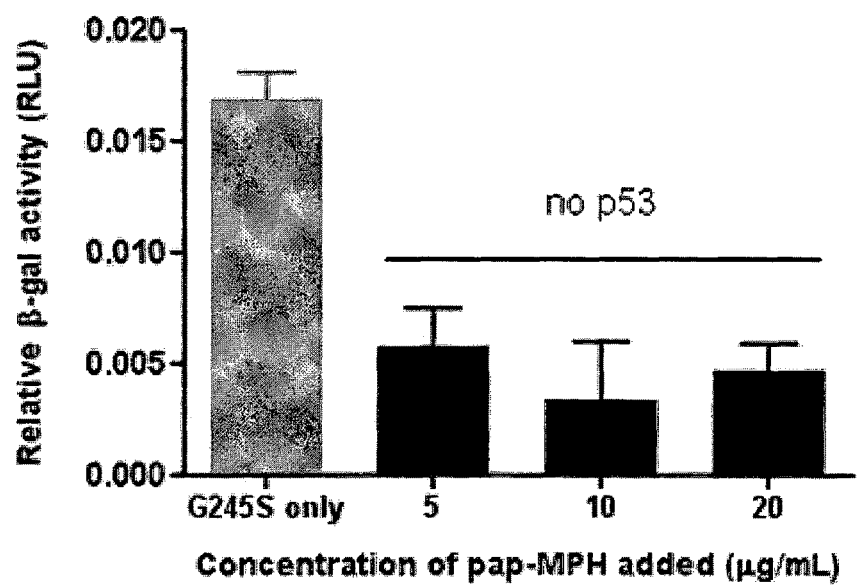

Fig. 41
A
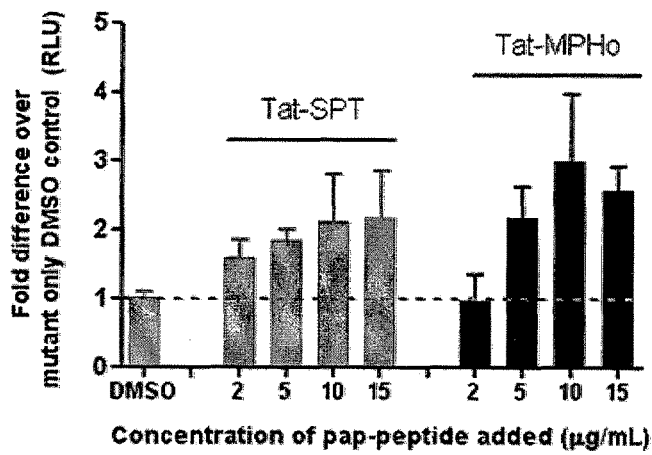
| Peptide reference | Tat tag | p53 activating peptide sequence |
|---|---|---|
| Tat-SPT | GRKKRRQRRR | MSPNTNH |
| Tat-MPHo | GRKKRRQRRR | MMPHLMAC |
| Tat-MPHs | GRKKRRQRRR | MPHLMAC |
| Tat-Scram | GRKKRRQRRR | CMAPMLHM |
B
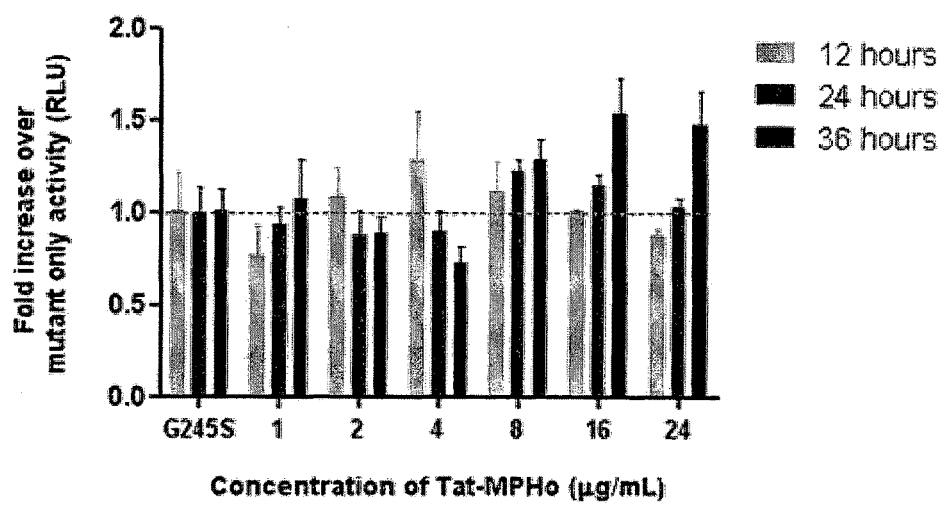

Fig. 41 (continued)
E
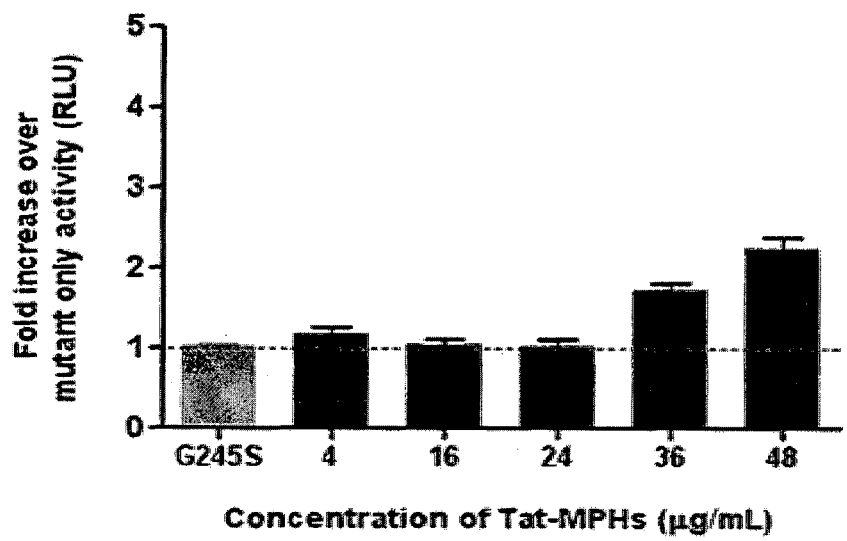
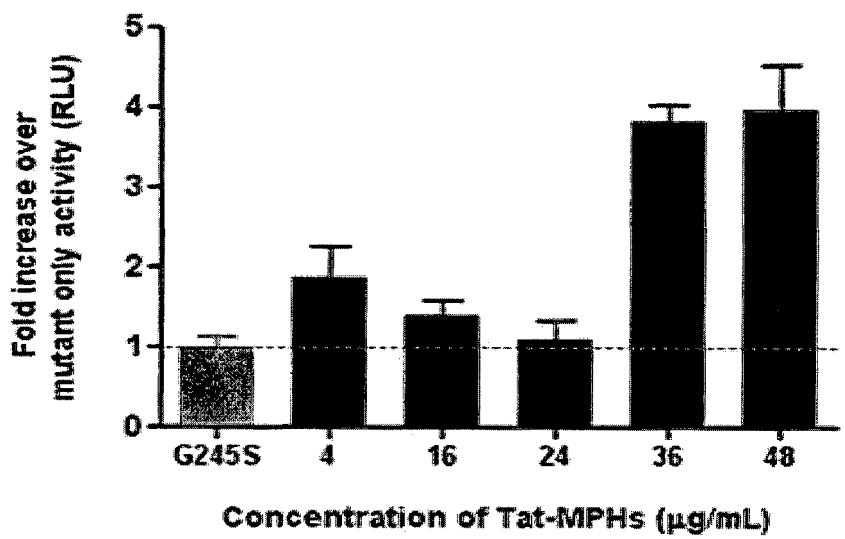

Fig. 41 (continued)
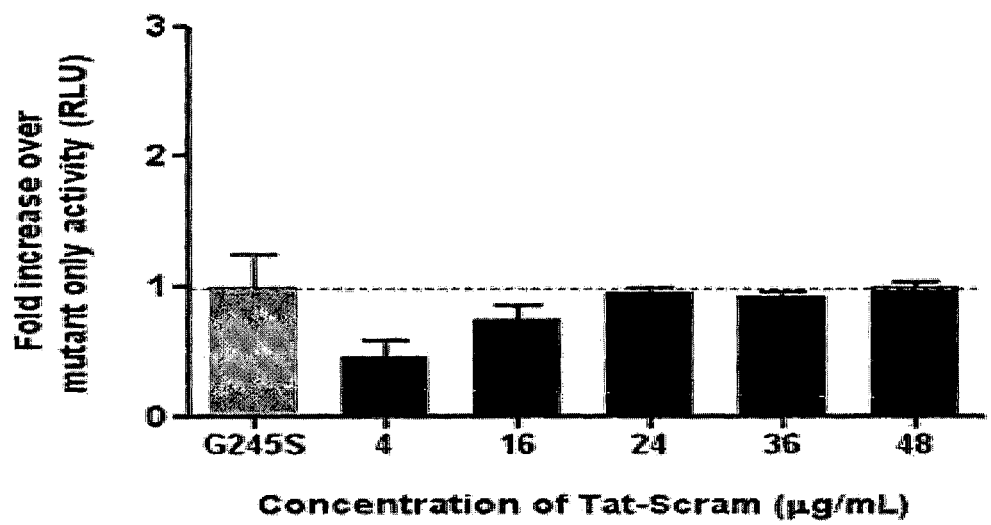
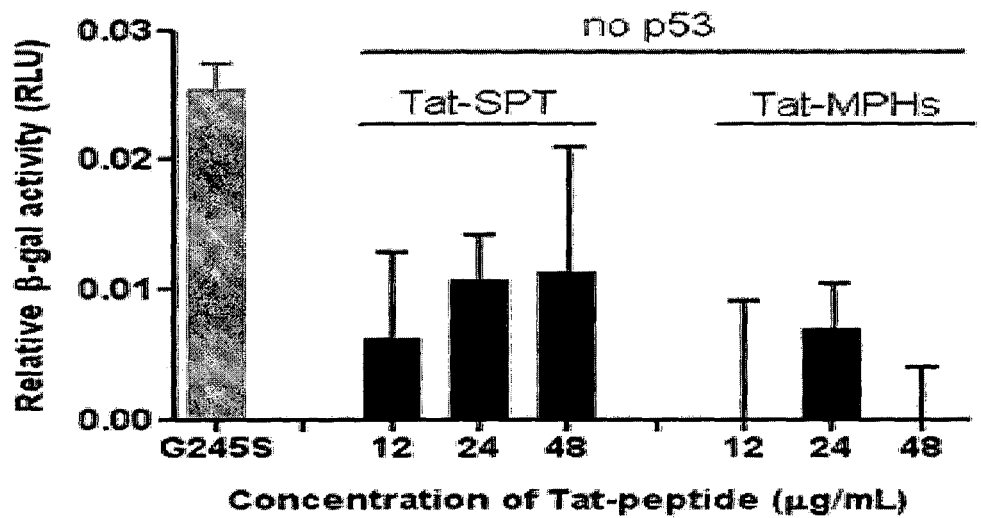

PCR

Trx-MPHS ▓▓▓▓▓ FWAEWCG MPHLMAC PCKMIA ▓▓▓▓▓

Trx-MPHo ▓▓▓▓▓ FWAEWCG MMPHLMACPCKMIA ▓▓▓▓▓

Trx-MPHScram ▓▓▓▓▓ FWAEWCG CMAPMLHM PCKMIA ▓▓▓▓▓

Fig. 42 (continued)
C
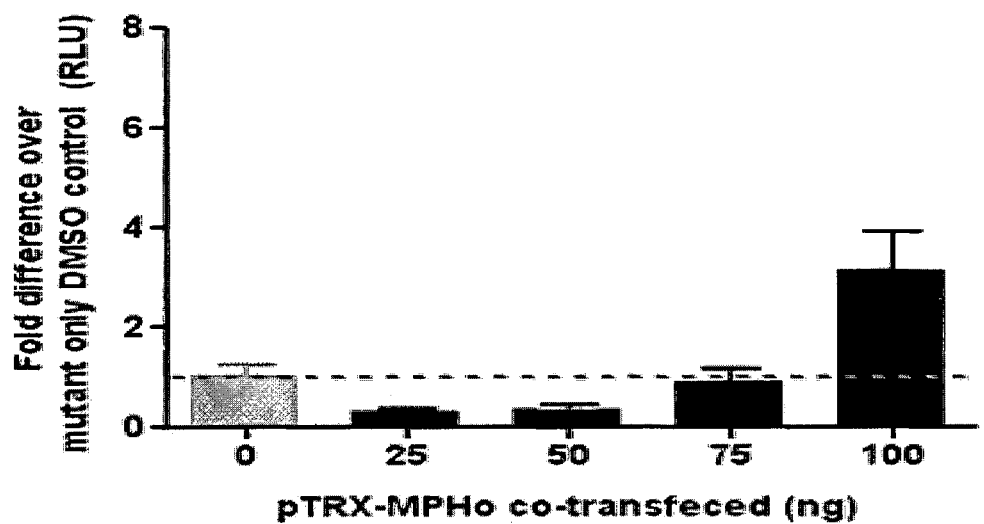
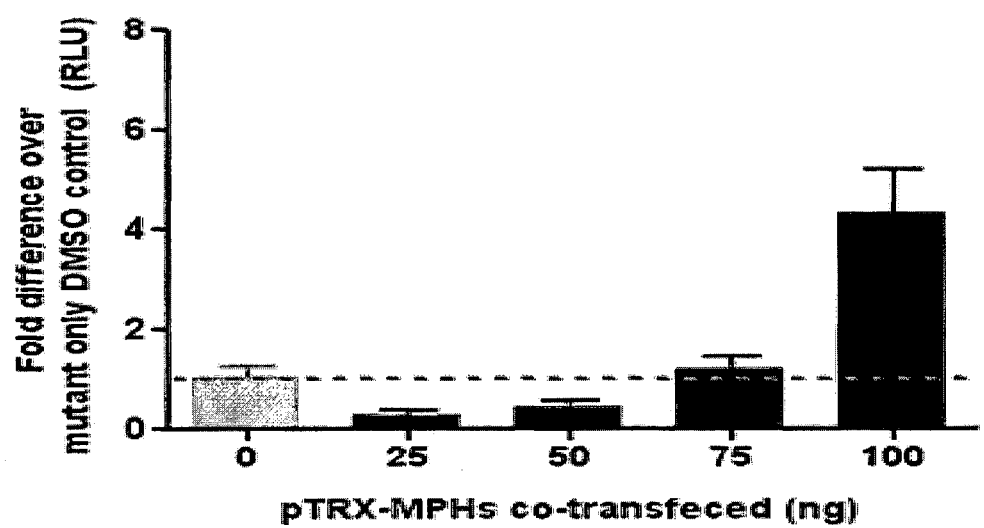

A

Fig. 43 (continued)
B
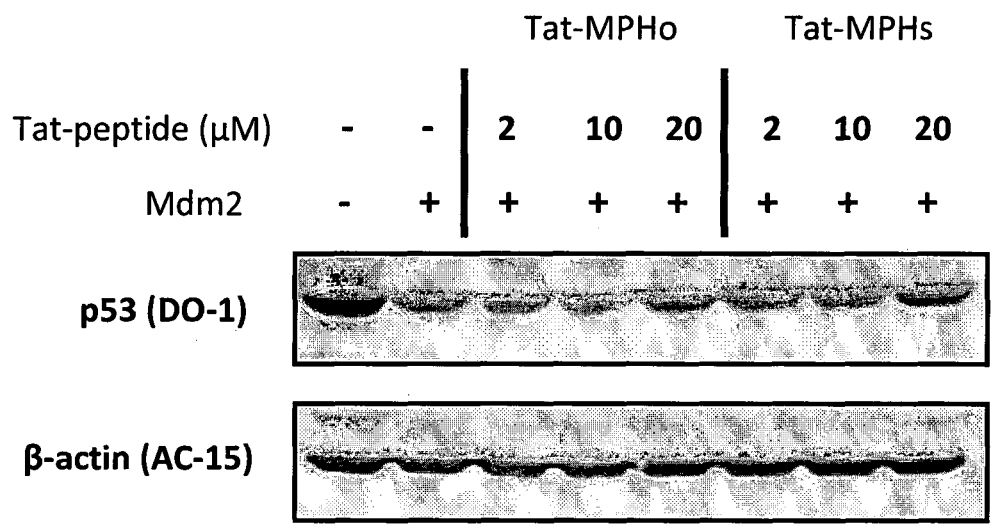
C
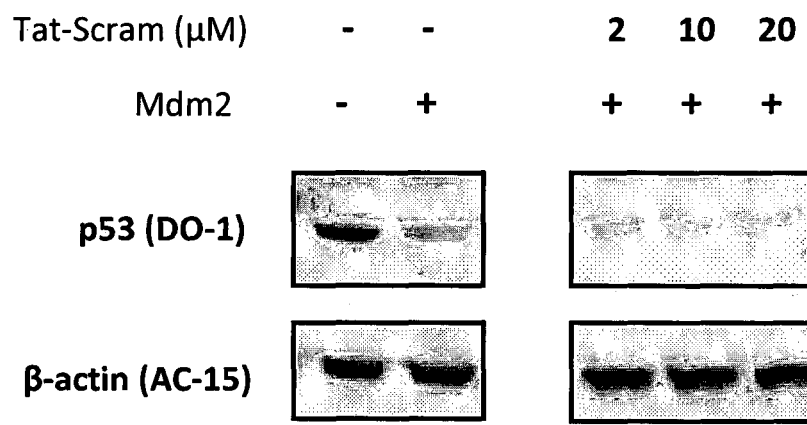

A

Tat-conjugated peptide activity on over-expressed mp53 in H1299 cells

B

Tat-conjugated peptide activity in H1299 ecdysone inducible system

P53 ACTIVATING PEPTIDES

This application is a U.S. national stage application filed under 35 U.S.C. §371 from International Application Serial No. PCT/SG2012/000329, which was filed Sep. 10, 2012, and published as WO 2013/036208 on Mar. 14, 2013, and which claims the benefit of priority of Singapore application no. 201106590-1, filed Sep. 9, 2011, which applications and publication are incorporated by reference as if reproduced herein and made a part hereof in their entirety, and the benefit of priority of each of which is claimed herein.

FIELD OF THE INVENTION

The present invention relates to peptides that bind to and reactivate p53 mutants as well as the use of these peptides. Methods for obtaining such peptides are also provided.

BACKGROUND OF THE INVENTION

The p53 gene controls cell fate and is mutated in at least 50% of all human cancers. The mutations commonly abolish the ability of p53 to bind to DNA as a transcription factor and regulate genes controlling the cell cycle. The loss of p53 function most frequently occurs through random somatic mutations in the TP53 gene, resulting in more than 50% of all human tumors harboring inactivating mutations.

Unlike other tumor suppressor genes which generally undergo deletion mutation during carcinogenesis, approximately 75% of inactivating mutations in TP53 occur due to single base pair missense substitutions, resulting in the synthesis of a stable full-length mutant protein with defective wild-type gene transactivation functions. Other genetic alterations which occur at much lower frequencies include frameshift insertions and deletions, nonsense mutations and silent mutations. Critical amino acid mutations arising from nucleotide substitutions at highly mutable CpG dinucleotides account for 30% of all missense mutations. Missense mutations of the TP53 gene has been detected anywhere within the coding region but tend to cluster within the DNA binding core domain of the protein (>95%), with 6 specific residues being identified as mutational hotspots' in human cancer (R175, G245, R248, G249, R273 and R282). Given that more than 50% of all human tumors harbor inactivating mutations in the TP53 gene, there has been interest in reactivating mutant p53.

Several peptides and compounds have been described which can interact with certain p53 mutants to restore some essential transactivation. However, the efficacy of these tends to be suboptimal and/or they are toxic to cells.

There is therefore a need to provide an alternative peptide capable of reactivating mutant p53 that overcomes or at least ameliorates one or more of the disadvantages above.

SUMMARY OF THE INVENTION

In a first aspect, there is provided a peptide capable of restoring the sequence-specific DNA binding or transactivation function of a mutant p53. The peptide can include, but is not limited to any one of:

(a)

SPTTNH (SEQ ID NO: 55)

MPHLMAC (SEQ ID NO: 56)

TALIDIWEHSVLGKGYPRMS (SEQ ID NO: 57)

ILNVLPLLASRKP (SEQ ID NO: 58)

VSWSACVLLELCNYFPENPIEEEDWACLG (SEQ ID NO: 59)

RLQQV (SEQ ID NO: 60)

VRHQHVGATILGWK (SEQ ID NO: 61)

VRHQHVGATILGW KMGWTDH (SEQ ID NO: 62)

MS PTTNH (SEQ ID NO: 63)

MM PHLMAC (SEQ ID NO: 64)

MT ALIDIWEHSVLGKGYPRMS (SEQ ID NO: 65)

MI LNVLPLLASRKP (SEQ ID NO: 66)

MVSWSACVLLELCNYFPENPIEEEDWACLG (SEQ ID NO: 67)

MR LQQV (SEQ ID NO: 68)

MV RHQHVGATILGWK (SEQ ID NO: 69)

MV RHQHVGATILGW KMGWTDH MLM (SEQ ID NO: 70)

TTLIDIWEHSVLGKGYPRMS (SEQ ID NO: 71)

M TTLIDIWEHSVLGKGYPRMS (SEQ ID NO: 72)

RAVTDRPVPCPNPRLNLVAN (SEQ ID NO: 73)

M RAVTDRPVPCPNPRLNLVAN; (SEQ ID NO: 74)

or
(b) a variant of a peptide as defined in (a) above; or
(c) a derivative of a peptide as defined in (a) or (b) above.

In a second aspect, there is provided an isolated nucleic acid molecule encoding a peptide of the present invention.

In a third aspect, there is provided a vector comprising an isolated nucleic acid molecule of the present invention.

In a fourth aspect, there is provided a pharmaceutical composition comprising a peptide of the present invention, an isolated nucleic acid molecule of the present invention, or a vector of the present invention, wherein the pharmaceutical composition optionally comprises one or more pharmaceutically acceptable excipients, vehicles or carriers.

In a fifth aspect, there is provided a peptide of the present invention, an isolated nucleic acid molecule of the present invention or a vector of the present invention for use in medicine.

In a sixth aspect, there is provided a peptide as defined above, an isolated nucleic acid molecule of the present invention, a vector of the present invention, or a pharmaceutical composition of the present invention for use in the treatment or prophylaxis of a cancer associated with mutant p53 or in the treatment or prophylaxis of a disorder characterized by an undesirably low level or a low activity of p53.

In a seventh aspect, there is provided a method for the prophylaxis or treatment of a cancer associated with mutant p53 or a disorder characterized by an undesirably low level or a low activity of p53, the method comprising administering a peptide of the present invention, an isolated nucleic acid molecule of the present invention, a vector of the present invention, or a pharmaceutical composition of the present invention to a patient in need thereof.

In an eighth aspect, there is provided a use of a peptide of the present invention, an isolated nucleic acid molecule of the present invention, a vector of the present invention, or a pharmaceutical composition of the present invention, in restoring the sequence-specific DNA binding or transactivation function of a mutant p53.

In a ninth aspect, there is provided a use of a peptide of the present invention, an isolated nucleic acid molecule of the present invention, a vector of the present invention, or a pharmaceutical composition of the present invention, in enhancing the sequence-specific DNA binding or transactivation function of p53.

In a tenth aspect, there is provided a method for obtaining a peptide which restores the sequence-specific DNA binding of a mutant p53 (mp53). The method can comprise:
  a) providing a water-in-oil emulsion comprising a plurality of aqueous microcapsules dispersed in the oil phase, wherein the aqueous phase comprises a library of genes encoding a repertoire of randomized peptides, components necessary to transcribe and translate the peptide genes, and mp53 genes, so that a plurality of aqueous microcapsules each comprise a peptide gene, components necessary to transcribe and translate the gene and a mp53 gene;
  b) expressing the peptide genes and mp53 genes to produce their respective gene products within the microcapsules, wherein if the peptide gene encodes a peptide which restores the sequence-specific DNA binding of the mp53 then a mp53/peptide/peptide gene complex forms;
  c) breaking the emulsion; and
  d) enriching for any p53/peptide/peptide gene complexes.

In an eleventh aspect, there is provided a method for obtaining a peptide which increases the sequence-specific DNA binding of a wild-type p53 (p53wt). The method can comprise:
  a) providing a water-in-oil emulsion comprising a plurality of aqueous microcapsules dispersed in the oil phase, wherein the aqueous phase comprises a library of genes encoding a repertoire of randomized peptides, components necessary to transcribe and translate the peptide genes, and p53wt genes, so that a plurality of aqueous microcapsules each comprise a peptide gene, components necessary to transcribe and translate the gene and a p53wt gene;
  b) expressing the peptide genes and p53wt genes to produce their respective gene products within the microcapsules, wherein if the peptide gene encodes a peptide which restores the sequence-specific DNA binding of the p53wt then a p53wt/peptide/peptide gene complex forms;
  c) breaking the emulsion; and
  d) enriching for any p53/peptide/peptide gene complexes.

In a twelfth aspect, there is provided a use of a peptide according to claim to any one of claims 1 to 14, an isolated nucleic acid molecule according to claim 15, a vector according to claim 16, or a pharmaceutical composition according to claim 17 or 18 in the manufacture of a medicament for the prophylaxis or treatment of a cancer associated with mutant p53 or a disorder characterized by an undesirably low level or a low activity of p53.

DEFINITIONS

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The term "transactivation" refers to an increase in gene expression triggered by DNA binding.

The term "conservative substitution" refers to the replacement of an amino acid with another that has similar biochemical properties.

The term "non-conservative substitution" refers to the replacement of an amino acid with another that does not have similar biochemical properties.

The term "heterologous" refers to a peptide that is derived from a different source.

The term "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

The term "excipient" refers to a pharmaceutically acceptable additive, other than the active ingredient, included in a formulation and having different purposes depending, for example, on the nature of the drug, and the mode of administration.

The term "plurality" refers to a number above 1.

The term "NC" refers to in vitro compartmentalization which is an in-vitro, completely cell free, high-throughput selection platform made up of a heterogenous system of two immiscible liquid phases. The system is comprised of numerous water-in-oil emulsified aqueous compartments, typically 1-100 µM in diameter, in which a certain phenotype is selected for. A typical selection scheme is engineered to limit the distribution of the gene library, such that a compartment contains a gene or less on average. A biochemical or enzymatic reaction then occurs within the aqueous phase of each discrete microdroplet such that the critical association (either covalent or non-covalent) of physically linking the genotype with phenotype is established. Once the linkage is created, information pertaining to positive selectants can be retrieved by breaking the emulsion and probing for a property specific to a positive selection event, and later enriched by repeating the selection.

The terms "microdroplet" or "mircrocapsule" refer to a compartment of the IVC system.

The term "sequence identity" refers to the similarity between two nucleic acid or amino acid sequences.

The term "mutant" refers to a gene that has been genetically altered either through single base pair substitutions, insertions, deletions, nonsense mutations and silent mutations.

The term "aptamer" refers to nucleic acids having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule.

The term "post-translational modification" refers to the chemical modification of a protein after translation.

As used herein, the term "amplicon", "amplified product or "amplification product" refers to a product of an amplification reaction. An example of an amplicon is a nucleotide sequence produced as a result of PCR, real-time PCR, RT-PCR, competitive RT-PCR, ligase chain reaction (LCR), gap LCR, strand displacement amplification (SDA), nucleic acid sequence based amplification (NASBA), transcription-mediated amplification (TMA), or the like.

The term "expression", as used herein, refers to the process by which information from a gene is used in the synthesis of a functional expression product, for example a peptide. The term "expression host", as used herein, refers to any target cell of a microorganism capable of being transformed with exogenous genetic material and expressing the exogenous genetic material. The exogenous genetic material may for example be an expression vector or plasmid.

The term "expression vector", as used herein, refers to a plasmid that is used to introduce a specific gene into a target cell.

BRIEF DESCRIPTION OF THE DRAWINGS

The invention will be better understood with reference to the detailed description when considered in conjunction with the non-limiting examples and the accompanying drawings, in which:

FIG. 7 shows the synthesis of peptide cDNA for preliminary validation of functionality. (A) PUMA-2F2 and rPETr amplified PCR product using NC round 3 positively selected DNA library. (B) PCR re-amplification of peptide cDNA using RL2-T7-F1 and peptide specific reverse primer using gel purified PCR amplified DNA product from (A). Arrow indicates expected size of 100 bp.

FIG. 14 shows the quantification of IVT-synthesized p53 protein concentration. (A) Coomasie blue stained SDS gel (arrow indicates expected size of p53-FL), showing 2 uL and 4 uL protein load of affinity purified p53QM-FL, and BSA standards loaded at increasing protein concentrations. (B) BSA protein standard curve quantified using Bradford reagent, red dotted line shows measured concentration of p53QM-FL. (C) Plate ELISA to quantify in-vitro synthesized p53 using standard curve from p53QM-FL of known protein concentration. Plates were either coated with DO-1 (left graph), or Bp5310.1 (right graph) antibodies. Bottom inset shows calculated total protein concentrations from ELISA (underlined figures underestimated values due to absence of full Bp53 10.1 epitope). Error bars show S.D. of 2 independent data points. (Right inset) DO-1 western blot showing total p53 protein of wt-FL, wt-Δ22, wt-FL (5% DMSO), and wt-Δ22 (5% DMSO) (lanes 1, 2, 3, 4 respectively). Arrow indicates expected size of full-length protein migration.

FIG. 15 shows a schematic illustration of 3 different conformations of ELISA to investigate peptide-p53 interaction. (A) DO-1 western blot showing in-vitro synthesis of p53wt-FL protein in the presence of each peptide. (B1) IVT made p53 is added into streptavidin coated wells pre-incubated with biotinylated-peptides. Any p53-peptide complexes are detected via a primary anti-p53 Ab and subsequently, a HRP-conjugated secondary antibody. (B2) p53 is in-vitro translated in the presence of biotinylated-peptides and transferred onto a streptavidin plate, the presence of p53 is then detected via an anti-p53 primary antibody followed by a HRP-conjugated secondary antibody.

FIG. 22 shows (A) a schematic of the data analysis of real-time DNA binding assay. (B) Single point measurement of trial DNA binding assay between p53wt-Δ22 and p21 RE, using manual wash. (C) Real-time PCR measurement showing equal inputs of RE and control DNA mixtures. (D) Real-time PCR measurement of p53wt-Δ22 binding to p21 RE using different washing techniques (Left) manual pipetting (right) timed vortexing. Colored lines of identical shade represent replicate data points. (E) Real-time PCR measurement of p53wt-FL binding to p21 RE using different binding buffers (Left) HEPES binding buffer (Right) Phosphate binding buffer. (F) Melt curve analysis of DNA binding assay real time PCR product showing single PCR product with a Tm of 88.50° C.

FIG. 24 shows (A) negative control with similar background binding signal between non-specific antibody (2A9) and beads only control. (B) Effects of binding buffer DTT concentration on p53wt-Δ22 binding to p21 RE.

FIG. 25 shows binding of 'activated' p53 to the p21 3' site and PUMA-BS2 RE. (A) Comparison of binding affinity on p21 3' site (left), or PUMA-BS2 (right) response element using either latent p53 (white bars represent wt-FL) or 'activated' p53 (black bars represent wt-Δ22), across increasing concentrations of RE (4.5 nM, 18 nM, and 36 nM). Data is represented as fold-difference over non-specific DNA binding between the respective p53 variant and equal molar concentrations of no-RE control DNA. (Inset) Western blot of IVT extract depicting equal input amounts of both p53wt-FL and p53wt-Δ22. (B) p53wt-FL or p53wt-Δ22 protein were synthesized via IVT and incubated with 36 nM of control DNA. Each pair of binding reaction were then either washed using the standard protocol (long wash), or at halved washing durations (short wash). Data is represented as fold-increase over non-specific DNA binding by p53wt-Δ22. Error bars represent mean+/−SD of 2 independent binding experiments.

FIG. 28 shows (A) control real time PCR on 4 different sets of primers used for multiplex assay. (Left) Forward primer complementary to each respective RE was curtailed to give similar $T_m$ with each other, and with Wpet-R1. The result indicates relative C(t) values when 100 nM of each forward primer was used, with equi-molar concentration of reverse primer Wpet-R1, in a real-time PCR reaction using 50 pM of the respective RE as template. (Right) Melt curve analysis of real-time PCR products from 4 primer sets. (B) In a scaled-up binding reaction, p53wt-Δ22 variant was subjected to a mixture of 4 different REs (PUMA-BS2, p21 3' site, RGC, and P2XM) at 9 nM each. Data is represented as binding fold-difference over the weakest RE (P2XM), which was assigned an arbitrary value of 1. Error bars represent mean+/−SD of 2 independent binding experiments.

FIG. 30 shows (A) comparison between using antibody adsorption on polystyrene plate and commercial pre-coated protein G plates. (B) Effects of wash conditions (harsher wash represented by darker shades) on p53wt-Δ22 binding to PUMA-BS2 RE (blue and red lines represent binding to RE and control DNA respectively).

FIG. 34 shows (A) DO-1 western blot showing affinity pull-down of nano-tagged p53wt-FL onto streptavidin coated beads. Lanes W and N represent wildtype and nano-tagged p53, respectively. (B) Protein concentration dependent binding between Nano-p53wt-Δ22 (Cosmo synthesized) to DNA RE using nanotag-streptavidin configuration.

FIG. 35 shows (Top) Np53wt-Δ22 concentration dependent binding to p21 and PUMA RE using Novagen IVT extract with 1.5 μM ZnSO4. (Top inset) DO-1 western blot showing relative expression levels of p53wt-FL protein using Cosmo PURE system (lane C) and Novagen EcoPro IVT systems (lane N). (Bottom) Np53wt-Δ22 concentration dependent binding to p21 and PUMA RE using Novagen IVT extract with 500 μM ZnSO4.

FIG. 36 shows the reactivation of "activated" C-terminal truncated p53 mutant using qPCR Nano tagged p53-DNA binding assay. (A) Np53G245S-Δ22+SPT and MPH, (B) Np53G245S-Δ22+TAL, (C) Np53R273H-Δ22+TAL, (D) Np53R248Q-Δ22+ILN, (E) Np53R273H-Δ22+RLQ, (F) Np53R273H-Δ22+VRH

FIG. 39 shows normalized pRGCΔfos-LacZ reporter activity in the presence of increasing pG245S-FL vector co-transfected into H1299 cells. (Inset) DO-1 western blot showing p53G245S-FL protein levels (arrow) in H1299 p53−/− cells when transfected with increasing amounts of pG245S-FL.

FIG. 40 shows the results of the pRGCΔfos-LacZ reporter assay showing β-galactosidase activity (normalized to G245S mutant only control) when H1299 cells are treated with increasing concentration of pap-MPH (Chariot reagent) in the presence of either p53wt-FL (black bars) or p53G245S-FL (blue bars). (B) Comparison of pRGCΔfos-LacZ reporter activity in H1299 cells between p53G245S-FL mutant only (grey) and increasing pap-MPH in the absence of p53 protein (black).

DISCLOSURE OF OPTIONAL EMBODIMENTS

Figure 1:
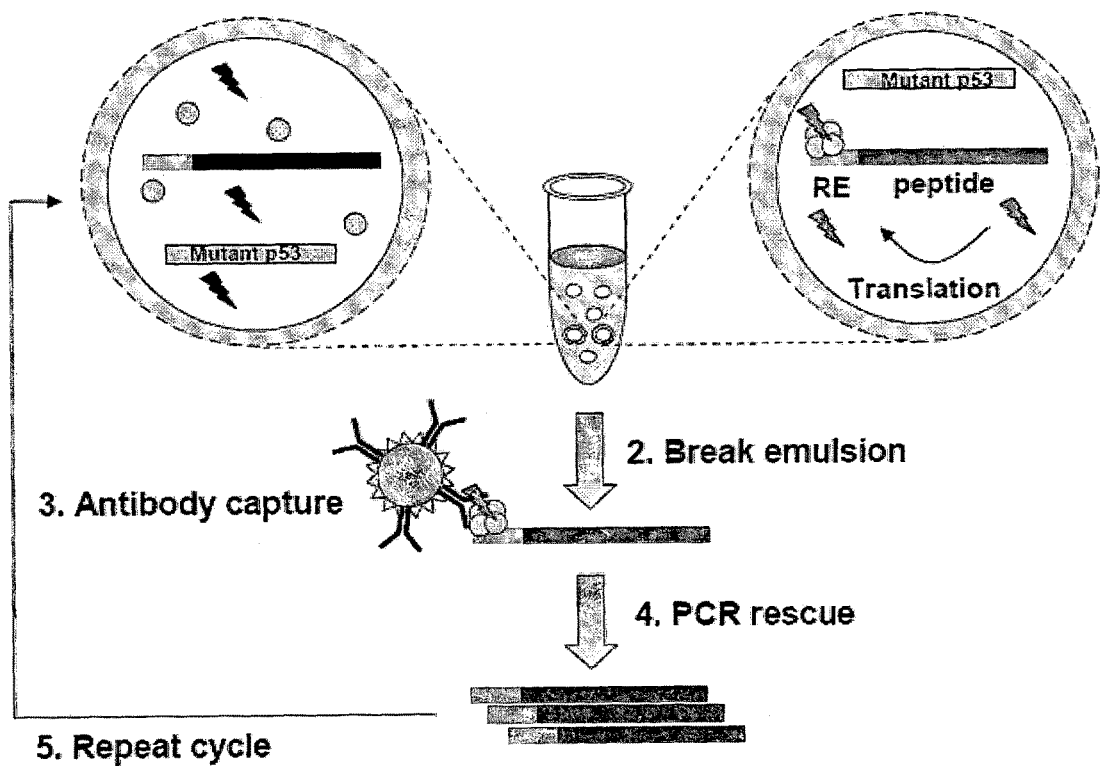
FIG. 1 is a schematic illustration of the IVC system. The steps of compartmentalization, break emulsion, antibody capture and PCT rescue are shown.

Exemplary, non-limiting embodiments of a peptide capable of restoring the sequence-specific DNA binding or transactivation function of a mutant p53 will now be disclosed. The peptide comprises (and optionally consists of) a sequence including, but not limited to:

SPTTNH (SEQ ID NO: 55)

MPHLMAC (SEQ ID NO: 56)

TALIDIWEHSVLGKGYPRMS (SEQ ID NO: 57)

ILNVLPLLASRKP (SEQ ID NO: 58)

VSWSACVLLELCNYFPENPLEEEDWACLG (SEQ ID NO: 59)

RLQQV (SEQ ID NO: 60)

VRHQHVGATILGWK (SEQ ID NO: 61)

VRHQHVGATILGW KMGWTDH (SEQ ID NO: 62)

MS PTTNH (SEQ ID NO: 63)

MM PHLMAC (SEQ ID NO: 64)

MT ALIDIWEHSVLGKGYPRMS (SEQ ID NO: 65)

MI LNVLPLLASRKP (SEQ ID NO: 66)

MVSWSACVLLELCNYFPENPIEEEDWACLG (SEQ ID NO: 67)

MR LQQV (SEQ ID NO: 68)

MV RHQHVGATILGWK (SEQ ID NO: 69)

MV RHQHVGATILGW KMGWTDH MLM (SEQ ID NO: 70)

TTLIDIWEHSVLGKGYPRMS (SEQ ID NO: 71)

M TTLIDIWEHSVLGKGYPRMS (SEQ ID NO: 72)

RAVTDRPVPCPNPRLNLVAN (SEQ ID NO: 73)

M RAVTDRPVPCPNPRLNLVAN; (SEQ ID NO: 74)

or (b) a variant of a peptide as defined in (a) above; or (c) a derivative of a peptide as defined in (a) or (b) above.

In one embodiment the peptide may be 15, 20, 25, 30, 35 or 40 amino acids in length.

In a one embodiment, the peptide is a variant. In one embodiment, the variant may be a fragment of a peptide as defined above wherein said fragment contains single or multiple amino acid deletions. The single or multiple deletions may be from either terminus of the peptide or from internal stretches of the peptide.

In one embodiment, the fragment comprises at least n consecutive amino acids from a sequence as described herein. In one embodiment, n may be 3 or more. In another embodiment, n may be selected from the group consisting of 4 or more, 5 or more, 6 or more, 7 or more, 8 or more, 9 or more, 10 or more, 12 or more, 15 or more, 17 or more, 19 or more, 20 or more, 22 or more, 24 or more, 26 or more, 28 or more or 29 or more consecutive amino acids.

In one embodiment, the variant may have at least 80%, sequence identity with a peptide sequence as defined above. In another embodiment the variant may have a sequence identity selected from the group consisting of at least 82%, 85%, 87%, 90%, 92%, 95%, 97%, 98%, 99% and 99.5% sequence identity.

In a further embodiment, the variant may have at one or more positions an amino acid insertion, deletion, or substitution, either conservative or non-conservative. In a further embodiment each of these types of changes may occur alone, or in combination with one or more of the others, one or more times in a given sequence.

In another embodiment, the peptide may be a derivative as defined above, wherein the derivative has undergone a post-translational modification such as the addition of one or more phosphoryl groups. It will be appreciated that other posttranslational modifications are intended to be encompassed.

In another embodiment, the post-translational modification may comprises the addition of functional groups including, but not limited to, hydrophobic groups, cofactors, acylation, acetylation, malonylation, glycation, biotinylation, the addition of peptide groups including but not limited to sumoylation, ubiquitination. Post-translational modifications may also include changing the chemical nature of amino acids and structural changes such as the formation of disulfide bridges and proteolytic cleavage.

In a one embodiment, the derivative may undergo the addition of one or more ligands, optionally selected from the group consisting of: phosphate, amine, amide, sulphate, sulphide, biotin, a fluorophore, and a chromophore.

In one embodiment, the peptide may be a stably cross-linked peptide (a "stapled" peptide) wherein the cross-linked peptides contain at least two modified amino acids that together form an internal cross-link.

In one embodiment, the mutant p53 may be selected from the group consisting of: p53 G245S mutant, p53 R273H mutant p53 R248Q mutant the p53 R175H mutant.

In yet another embodiment, the peptide as described herein may be used as a lead compound, preferably as a lead compound in the generation of a therapeutic compound.

In a further embodiment, an isolated nucleic acid molecule encoding a peptide as described herein is disclosed.

In still another embodiment, a vector comprising an isolated nucleic acid molecule as described herein is disclosed.

In yet another embodiment, there is disclosed a pharmaceutical composition comprising a peptide as described herein, an isolated nucleic acid molecule as described herein, or a vector as described herein, wherein the pharmaceutical composition optionally comprises one or more pharmaceutically acceptable excipients, vehicles or carriers.

The excipients may comprise carriers, co-solvents, stabilizing agents, solubilizing agents and surfactants, buffers, antioxidants, tonicity agents, bulking agents, lubricating agents, emulsifiers, suspending or viscosity agents, antibacterial agents, chelating agents, preservatives, sweeteners, perfuming agents, flavoring agents, administration aids, and combinations thereof. Some of the excipients or additives may have more than one possible function or use, depending on their properties and the nature of the formulation.

In a one embodiment, the pharmaceutical composition comprises a further therapeutic compound, for example an anti-cancer agent.

In a one embodiment, there is disclosed a peptide as described herein, an isolated nucleic acid molecule as described herein or a vector as described herein for use in medicine.

In another embodiment, there is disclosed a peptide as described herein, an isolated nucleic acid molecule as described herein, a vector as described herein, or a pharmaceutical composition as described herein for use in the treatment or prophylaxis of a cancer associated with mutant p53 or in the treatment or prophylaxis of a disorder characterized by an undesirably low level or a low activity of p53.

In another embodiment, a method for the prophylaxis or treatment of a cancer associated with mutant p53 or a disorder characterized by an undesirably low level or a low activity of p53 is disclosed. The method comprises administering a peptide as described herein, an isolated nucleic acid molecule as described herein, a vector as described herein, or a pharmaceutical composition as described herein to a patient in need thereof.

In a preferred embodiment, the method comprises administering one or more further therapeutic agents (for example an anti-cancer agent) to the patient. In one embodiment, the one or more further therapeutic agents are to be administered simultaneously, sequentially or separately.

In a yet another embodiment, a use of a peptide as described herein, an isolated nucleic acid molecule as described herein, a vector as described herein, or a pharmaceutical composition as described herein, in restoring the sequence-specific DNA binding or transactivation function of a mutant p53 is disclosed.

In a further embodiment, a use of a peptide as described herein, an isolated nucleic acid molecule as described herein, a vector as described herein, or a pharmaceutical composition as described herein, in enhancing the sequence-specific DNA binding or transactivation function of p53.

In still another embodiment, a method for obtaining a peptide which restores the sequence-specific DNA binding of a mutant p53 (mp53) is disclosed. The method comprises the steps of:
  a) providing a water-in-oil emulsion comprising a plurality of aqueous microcapsules dispersed in the oil phase, wherein the aqueous phase comprises a library of genes encoding a repertoire of randomized peptides, components necessary to transcribe and translate the peptide genes, and mp53 genes, so that a plurality of aqueous microcapsules each comprise a peptide gene, components necessary to transcribe and translate the gene and a mp53 gene;
  b) expressing the peptide genes and mp53 genes to produce their respective gene products within the microcapsules, wherein if the peptide gene encodes a peptide which restores the sequence-specific DNA binding of the mp53 then a mp53/peptide/peptide gene complex forms;
  c) breaking the emulsion; and
  d) enriching for any p53/peptide/peptide gene complexes.

In a one embodiment, the mp53 genes may be full-length mutant genes.

In another embodiment, the mutant p53 may be R175H, R273H, G245S, and/or R248Q.

In one embodiment, the library may encode peptides selected from the group consisting of from 1 to 40 amino acid residues, 1 to 35 amino acid residues, 1 to 30 amino acid residues, 1 to 25 amino acid residues and 1 to 20 amino acid residues in length. In one embodiment the peptides optionally vary in length.

In a preferred embodiment, on average there may be a single peptide gene, or less, per microcapsule.

In a further embodiment, the peptide genes may comprise at least one response element (RE) to which mp53 having restored sequence-specific DNA binding can bind to.

In a further embodiment, the peptide genes may comprise a 5' RE and a 3'RE to which mp53 having restored sequence-specific DNA binding can bind to.

In a preferred embodiment, the peptide genes may comprise at least one (and preferably two) response element (RE) to which mp53 having restored sequence-specific DNA binding can bind to, a randomized reading frame (preferably between 40 and 80 base pairs, more preferably between 50 and 70 base pairs, yet more preferably between 55 and 65 base pairs, and still more preferably 60 base pairs), and regulatory elements which are operably linked to the reading frame to thereby enable its expression.

In one embodiment the peptide genes may comprise in the 5' to 3' direction: a RE (e.g. pUMA-BS2 RE), a promoter (e.g. a T7 promoter), a ribosome binding site, an ATG start site, a randomized DNA reading frame, a TAG stop codon downstream, and a RE (e.g. a p21 3' site RE).

In some embodiments, response elements may include but are not limited to p21 5' site, Cyclin G, 14-3-3σ site 1, 14-3-3σ site 2, p21 3' site, MDM2, p53R2, PCNA, GADD45, Maspin, KAI 1, PUMA BS2, Noxa, p53AIP1, PIDD, BAX, IGF-BP3 Box A, p53DINP1, P2XM, PUMA BS1.

In one embodiment, RE may refer to p53-responsive DNA RE or p21-responsive DNA RE.

In a one embodiment of the method as described herein, step d) further comprises isolating the p53/peptide/peptide gene complexes by anti-p53 antibody-coated beads. In one embodiment magnetic or polystyrene beads are used.

In a preferred embodiment, the peptide genes from the p53/peptide/peptide gene complexes may be amplified prior to undergoing one or more further rounds (optionally 2 or 3 further rounds) of renewed encapsulation in aqueous microcapsules of a water-in-emulsion, expression of the peptide genes within the aqueous microcapsules and the formation of mp53/peptide/peptide gene complexes, breaking of the emulsion and enrichment for any p53/peptide/peptide gene complexes or amplification.

In a further embodiment, the method further comprises sequencing at least one peptide encoding sequence from a p53/peptide/peptide gene complex. In another embodiment the peptide encoding sequence is optionally amplified (e.g. by one or more rounds of PCR) prior to sequencing.

In yet another embodiment, a method for obtaining a peptide which increases the sequence-specific DNA binding of a wild-type p53 (p53wt) is disclosed. The method may comprise the steps of:
  a) providing a water-in-oil emulsion comprising a plurality of aqueous microcapsules dispersed in the oil phase, wherein the aqueous phase comprises a library of genes encoding a repertoire of randomized peptides, components necessary to transcribe and translate the peptide genes, and p53wt genes, so that a plurality of aqueous microcapsules each comprise a peptide gene, components necessary to transcribe and translate the gene and a p53wt gene;
  b) expressing the peptide genes and p53wt genes to produce their respective gene products within the microcapsules, wherein if the peptide gene encodes a peptide which restores the sequence-specific DNA binding of the p53wt then a p53wt/peptide/peptide gene complex forms;

c) breaking the emulsion; and d) enriching for any p53/peptide/peptide gene complexes.

In a preferred embodiment, the library of genes is a randomized peptide cDNA library.

In a preferred embodiment, the p53wt genes are full-length wild type genes.

In yet another embodiment, the library may encode peptides selected from the group consisting of from 1 to 40 amino acid residues, 1 to 35 amino acid residues, 1 to 30 amino acid residues, 1 to 25 amino acid residues and 1 to 20 amino acid residues in length. In one embodiment the peptides optionally vary in length.

In a further embodiment, on average there is a single peptide gene, or less, per microcapsule.

In one embodiment, the peptide genes may comprise at least one response element (RE) to which p53wt having increased sequence-specific DNA binding can bind to.

In another embodiment, the peptide genes may comprise a 5' RE and a 3'RE to which p53wt having increased sequence-specific DNA binding can bind to.

In a preferred embodiment, the peptide genes may comprise a 5' RE and a 3'RE to which p53wt having increased sequence-specific DNA binding can bind to.

In a preferred embodiment, the peptide genes may comprise at least one (and preferably two) response element (RE) to which p53wt having increased sequence-specific DNA binding can bind to, a randomized reading frame (preferably between 40 and 80 base pairs, more preferably between 50 and 70 base pairs, yet more preferably between 55 and 65 base pairs, and still more preferably 60 base pairs), and regulatory elements which are operably linked to the reading frame to thereby enable its expression.

In one embodiment, the peptide genes comprise in the 5' to 3' direction: a RE (e.g. pUMA-BS2 RE), a promoter (e.g. a T7 promoter), a ribosome binding site, an ATG start site, a randomized DNA reading frame, a TAG stop codon downstream, and a RE (e.g. a p21 3' site RE).

In one embodiment of the method described herein, step d) further comprises isolating the p53/peptide/peptide gene complexes by anti-p53 antibody-coated beads. In one embodiment the beads may be magnetic or polystyrene beads.

In a preferred embodiment, the peptide genes from the p53/peptide/peptide gene complexes may be amplified prior to undergoing one or more further rounds (optionally 2 or 3 further rounds) of renewed encapsulation in aqueous microcapsules of a water-in-emulsion, expression of the peptide genes within the aqueous microcapsules and the formation of p53wt/peptide/peptide gene complexes, breaking of the emulsion and enrichment for any p53/peptide/peptide gene complexes or amplification.

In a further embodiment, the method further comprises sequencing at least one peptide encoding sequence from a p53/peptide/peptide gene complex. In another embodiment the peptide encoding sequence is optionally amplified (e.g. by one or more rounds of PCR) prior to sequencing.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention, including the best mode, and a comparative example will be further described in greater detail by reference to specific Examples, which should not be construed as in any way limiting the scope of the invention.

Tables 1 to 7 show the sequences of oligonucleotides used in this disclosure.

TABLE 1

The sequences of the oligonucleotides used for the construction of the random peptide DNA library (Ranlib).

| Oligo reference | DNA sequence (5'→3') |
|---|---|
| RANLIB2 | AAT ACG ACT CAC TAT AGG GAG AGG AGG TAT ATA CAT G (60 Ns) TAG AGG AAG AAG ACT GGG CAT GTC TGG GCA (SEQ ID NO: 1) |
| RL2- | CGC GCC TGC AAG TCC TGA CTT GTC CGC GGT AAT ACG ACT CAC (SEQ ID NO: 75) |
| pUMA2-F2 | TAT AGG GAG AGG AGG TAT ATA CAT G (SEQ ID NO: 76) |
| RL2-p21-2R | TGC CCA GAC ATG CCC AGT CTT CTT CCT CTA (SEQ ID NO: 3) |
| PET-F2 | CAT CGG TGA TGT CGG CGA T (SEQ ID NO: 4) |
| PET-RC | CGG ATA TAG TTC CTC CTT TCA GCA (SEQ ID NO: 5) |
| RF2 | GAC TCA CTA TAG GGA GAG GAG GTA TAT ACA TG (SEQ ID NO: 6) |
| rPETr | GCG TCC CAT TCG CCA ATC CG TGC CCA GAC ATG CCC AGT CTT CTT CCT CTA (SEQ ID NO: 7) |
| PetRevWalt | GCG TCC CAT TCG CCA ATC CG (SEQ ID NO: 8) |

TABLE 2

The sequences of the oligonucleotides used for amplifying peptide cDNA.

| Oligo reference | DNA sequence (5'→3') |
| --- | --- |
| RL2-T7-F1 | GCG GTA AAC GAC TCA CTA TAG (SEQ ID NO: 9) |
| SPN-R1 | CTC TAC TAT AAA TGT TGC TAA ACT G (SEQ ID NO: 10) |
| MPH-R1 | CCT CTA AAC TAT GCG TTT GTA AC (SEQ ID NO: 11) |
| VRH-R1 | TCT AAT GGT CGG TCC AAC CC (SEQ ID NO: 12) |
| RLQ-R1 | CTA CGG GCA GTG ACC GAT A (SEQ ID NO: 13) |
| ILN-R1 | CCT CTA CCT AGT GAA GAA AGT G (SEQ ID NO: 14) |
| TALID-R1 | CTC TAT GAC ATT CGA GGA TAA CC (SEQ ID NO: 15) |

TABLE 3

The sequences of oligonucleotides for generating DNA response elements.

| Oligo reference | DNA sequence (5'→3') |
| --- | --- |
| p21-TOP | TAG AGG AAG AAG ACT GGG CAT GTC TGG GCA (SEQ ID NO: 16) |
| p21-BOT | TGC CCA GAC ATG CCC AGT CTT CTT CCT CTA (SEQ ID NO: 17) |
| PUMA-TOP | CGC GCC TGC AAG TCC TGA DT GTC CGC GGC (SEQ ID NO: 18) |
| PUMA-BOT | GCC GCG GAC AAG TCA GGA DT GCA GGC GCG (SEQ ID NO: 19) |
| Scram-TOP | GTC GTT CTG ATC CAG GTG ATG TAG TCG ACG (SEQ ID NO: 20) |
| Scram-BOT | CGT CGA CTA CAT CAC CTG GAT CAG AAC GAC (SEQ ID NO: 21) |
| PUMA2- | CGC GCC TGC AAG TCC TGA CTT GTC CGC GGC CAT CGG TGA TGT (SEQ ID NO: 22) |
| PET-F2 | CGG CGA T |
| RGC-PET-F2 | CAC ATG CCT TGC CTG GAC TTG CCT CAT CGG TGA TGT CGG CGA T (SEQ ID NO: 23) |
| P21-PET-F2 | TAG AGG AAG AAG ACT GGG CAT GTC TGG GCA CAT CGG TGA TGT CGG CGA T (SEQ ID NO: 24) |
| P2XM-PET-F2 | CTT GGG AAC AAG GGC ATG AGC TTG TCT GGG CTC ATC GGT GAT GTC GGC GAT (SEQ ID NO: 25) |
| WPET-R1 | TAA TTT CGC GGG ATC GAG ATC T (SEQ ID NO: 26) |

TABLE 4

The sequences of oligonucleotides used for site-directed mutagenesis

| Oligo reference | DNA sequence (5'→3') |
| --- | --- |
| QC-Y220C-Top | CAT AGT GTG GTG GTG CCC TGT GAG CCG CCT GAG TTG GC (SEQ ID NO: 27) |
| QC-Y220C-Bot | GCC AAC TCA GGC GGC TCA CAG GGC ACC ACC ACT ATG (SEQ ID NO: 28) |
| QC-R175H-Top | CAC ATG ACG GAG GTT GTG AGG CAC TGC CCC ACC ATG AGC GCT GC (SEQ ID NO: 29) |
| QC-R175H-Bot | GCA GCG CTC ATG GTG GGG CAG TGC CTC ACA ACC TCC GTC ATG TG (SEQ ID NO: 30) |
| QC-R273H-Top | ACG GAA CAG CTT TGA GGT GCA TGT TTG TGC CTG TCC TGG GA (SEQ ID NO: 31) |
| QC-R273H-Bot | TCC CAG GAC AGG CAC AAA CAT GCA CCT CAA AGC TGT TCC GT (SEQ ID NO: 32) |
| QC-G245S-Top | GTA ACA GTT CCT GCA TGG GCA GCA TGA ACC GGA GGC CCA TC (SEQ ID NO: 33) |
| QC-G245S-Bot | GAT GGG CCT CCG GTT CAT GCT GCC CAT GCA GGA ACT GTT AC (SEQ ID NO: 34) |
| QC-R248Q-Top | CTG CAT GGG CGG CAT GAA CCA GAG GCC CAT CCT CAC CAT CA (SEQ ID NO: 35) |
| QC-R248Q-Bot | TGA TGG TGA GGA TGG GCC TCT GGT TCA TGC CGC CCA TGC AG (SEQ ID NO: 36) |

TABLE 5

The sequences of oligonucleotide primers for real time PCR

| Oligo reference | DNA sequence (5'→3') |
| --- | --- |
| Pet-F3 (Test_1F) | ATA GGC GCC AGC AAC CGC ACC TG (SEQ ID NO: 37) |
| Test_2F | CTT CCA CTT TTT CCC GCG TTT TC (SEQ ID NO: 38) |
| Test_3F | CTC CTT TCG CTT TCT TCC CTT CCT T (SEQ ID NO: 39) |
| WPET-R1 | TAA TTT CGC GGG ATC GAG ATC T (SEQ ID NO: 26) |
| WPET-R2 | CTC GAT CCC GCG AAA TTA ATA CGA C (SEQ ID NO: 40) |
| WPET-R3 | CCG AAT TAA TTC GAT CCA TGG (SEQ ID NO: 41) |
| Walt_Pet_R2_correct | GTC GTA TTA ATT CGC GGA TCG AG (SEQ ID NO: 42) |
| PumaBS2_short_F | CGC GCC TGC AAG TCC TGA CTT G (SEQ ID NO: 43) |
| P21_short_F | TAG AGG AAG AAG ACT GGG CAT GTC TG (SEQ ID NO: 44) |
| RGC_short_F | CAC ATG CCT TGC CTG GAC TTG CC (SEQ ID NO: 45) |

TABLE 5-continued

The sequences of oligonucleotide primers for real time PCR

| Oligo reference | DNA sequence (5'→3') |
| --- | --- |
| P2XM_short_F | CTT GGG AAC AAG GGC ATG AGC TTG T (SEQ ID NO: 46) |

TABLE 6

The sequences of oligonucleotides for generating expression constructs

| Oligo reference | DNA sequence (5'→3') |
| --- | --- |
| P2inTRX-F | ATG ATG CCA CAC TTA ATG GCA TGT CCG TGC AAA ATG ATC GCC CCG (SEQ ID NO: 47) |
| P2inTRX-R | ACA TGC CAT TAA GTG TGG CAT CAT ACC GCA CCA CTC TGC CCA GAA (SEQ ID NO: 48) |
| T7-F | GAA ATA ATA CGA CTC ACT ATA GG (SEQ ID NO: 49) |
| PeIB-R | CTA GGC CAT CGC CGG CT (SEQ ID NO: 50) |

TABLE 7

The sequences of other oligonucleotides used in this disclosure

| Oligo reference | DNA sequence (5'→3') |
| --- | --- |
| M13-F | GTA AAA CGA CGG CCA GT (SEQ ID NO: 51) |
| M13-R | CAG GAA ACA GCT ATG AC (SEQ ID NO: 52) |
| Δ22-F | TGA GGA TCC GAA TTC GAG CTC (SEQ ID NO: 53) |
| Δ22-R | GGA CTT CAG GTG GCT GGA GT (SEQ ID NO: 54) |

Example 1

IVC Selection

Materials and Methods

An IVC approach has been adopted to select functional peptides that can selectively restore sequence-specific DNA binding to several p53 'hotspot' mutants. The aqueous phase of this selection comprised of a mixture of (i) an in-vitro bacterial WT cocktail containing the necessary ingredients to transcribe and translate polypeptides, (ii) a randomized peptide cDNA library and (iii) p53 genes carrying a specific mutation, and is re-constituted in mineral oil such that each compartment contains less than 1 peptide encoding gene on average. The peptide cDNA library was engineered to carry DNA elements (T7 promoter, ribosome binding site) required for transcription initiation under a prokaryotic system upstream of a 60 base pair randomized reading frame, and is additionally flanked by a PUMA-BS2 RE on the 5' end, and a p21 3' site RE on the 3' end (FIG. 2B). The selection scheme functioned such that only peptide genes belonging to a positive event will be isolated and subsequently enriched in further rounds of selection. In a positive selection event (FIG. 1 right bubble), a peptide gene enclosed in a specific droplet codes for a functional peptide that binds to, and causes the mp53 to bind to either RE adjacent to the peptide gene; the resultant p53/peptide/peptide gene complex is captured on anti-p53 antibody coated beads, preserving the genotype-phenotype linkage. Conversely, in the event of a negative selection (FIG. 1 left bubble), translated peptides do not reinstate DNA binding to the mutant, resulting in the lack of genotype-phenotype association.

Full-length, instead of core domain mutants were used. Additionally, we also avoided deriving peptides that may only selectively activate core domain proteins, and which may lose its activity in full-length proteins. Secondly, instead of using purified proteins, the use of WT and the concomitant synthesis of peptides and proteins were selected. This gives us an added advantage of selecting peptides that may have re-activating functions on nascent p53 during protein translation. Lastly, the library encodes free peptides that vary in length (1-20 amino acid residues), so as to not place unnecessary limitations on the peptide length or the mode of activity. Four p53 mutants were selected to be tested in the NC selection and did so to adequately represent the different classes of mutation in this study; the 4 mutants are the R175H (globally denatured), R273H (contact mutant), G245S, and R248Q (contact mutants with weak local distortions in structure).

Design and Synthesis of Random Peptide Library

The random peptide library was synthesized via standard polymerase chain reaction (PCR) using three commercially synthesized oligo-nucleotides. In the first round of PCR, the oligo-nucleotide RANLIB2, which contained a 60 basepairs (bps) randomized sequence, was used as the template and amplified using forward primer RL2-pUMA-2F2 and reverse primer RL2-p21-2R. Forward primer RL2-pUMA-2F2 added a PUMA-BS2 RE overhang sequence to give the final library product of approximately 156 bps (FIG. 2A). This final construct consists of a randomized 60-bps DNA sequence with a T7 promoter sequence, RBS and an ATG start site upstream and a TAG stop codon downstream (FIG. 2B). Additionally, it is appended with the pUMA-BS2 RE on the 5' end, and a p21 3' site RE on the 3' end. A subsequent round of PCR, using the same primer pair, was performed to further amplify the library product. To detect the size of the PCR product, we added 6x DNA loading dye, separated the DNA fragments using agarose gel electrophoresis (AGE) on a 1% agarose gel, and visualized it using a fluorescence imager. The resulting image showed a single band migrating at an expected size of ~150-bps (FIG. 2C, lane 2). A positive control of the same PCR reaction with a different enzyme (Acuzyme DNA polymerase) also yielded a product of identical intensity and size (FIG. 2C, lane 3). There were also no non-specific PCR products detected in the negative control reaction, which was conducted in the absence of reverse primer RL2-p21-2R (FIG. 2C, lane 1). To ensure that the library sequences are in-frame and contained all the necessary DNA elements for in-vitro transcription/translation, library fragments were cloned into the 2.1-TOPO vector (TOPO TA cloning kit, Invitrogen) following manufacturer's protocol, transformed the plasmids into E. coli (BL21, DE3) bacteria, plated the transformants onto ampicillin selective LB-agar plates, and performed colony PCR on 20 randomly selected bacterial colonies (using primers RF1 and RL2-p21-2R). The colony PCR product was then sent for sequencing, and the resultant chromatogram was analysed using the Lasergene 8 software (DNASTAR). The DNA sequencing revealed that, apart from the randomized peptide reading frame, all other regions of the DNA library were preserved. DNA alignment of all 20 sequences showed no obvious similarities in the reading frames. Translation of each DNA sequence into its resulting amino acid sequence revealed absolute randomness and sequence diversity, with only 25% encoding a full 20-mer polypeptide (Table 8).

TABLE 8

Translation of random peptide library sequence showing absolute randomness and sequence diversity.

| Clone | DNA sequence | Translated amino acid sequence |
|---|---|---|
| 1 | ACATATTCATCACCGCCCTTTGGGCGAGCAGTCGCCTT TGCATTTAGCTAGAAAGGCGT (SEQ ID NO: 77) | TYSSPPFGRAVAFAF S (SEQ ID NO: 78) |
| 2 | TTTACAGTTTCTGTTATAGCTTCCCCATTTTATAATATT TTCCGCCCTTTTCTCGGCGGA (SEQ ID NO: 79) | FTVSVIASPFYNIFR PFLGG (SEQ ID NO: 80) |
| 3 | GGTGGCTCTCGCTTTATAGCGGCACTTCCGGGAACATC GACGGCTTCTTGGATTAGCTCT (SEQ ID NO: 81) | GGSRFIAALPGTST ASWISS (SEQ ID NO: 82) |
| 4 | ATCGTGTAGATGATTCTCGGATTGTCTCTCCTTGGACG GTAATCTGAGAACCTCTTAGAT (SEQ ID NO: 83) | IV |
| 5 | TAGCCTTAAAAGTATGTGTTGTAGACTGGGCCTAGATC CAAGTTGTTGTGGTGAGATTTT (SEQ ID NO: 84) | - |
| 6 | GGGAGTGCACACGTCGTATGTAAGGGTCCTATTATATC TTTGTAACACTAAGATGCTTCC (SEQ ID NO: 85) | GSAHVVCKGPIISL (SEQ ID NO: 86) |
| 7 | ACGATGTAGGTCGACGGCGGTCCCCTGAATACGGGCCC TGTACCCATTGCTCACAGACTG (SEQ ID NO: 87) | TM |
| 8 | TCTACGAGGGGCAGCCATTGAATTAACGGTTTCAGGAA GTTCTAGTGATATTGGAGTGCG (SEQ ID NO: 88) | STRGSH (SEQ ID NO: 89) |
| 9 | AGTAGGCCTATCACATAGAGTACTGTTTAGGTACCACG GGTTCATGGTTGTACCTCACGG (SEQ ID NO: 90) | SRPIT (SEQ ID NO: 91) |
| 10 | GAAACTATAGGCATCCATCTATCCCGTCTGCCTCAGCA ACGTAGTATCATGTGGCGGGGT (SEQ ID NO: 92) | ETIGIHLSRLPQQR SIMWRG (SEQ ID NO: 93) |
| 11 | CCCACATGTTGCCTAGGTACACCCATTATGCCGCCTTG AGAGTAGCTTTTCTGTGTGATT (SEQ ID NO: 94) | PTCCLGTPIMPP (SEQ ID NO: 95) |
| 12 | GAGTGAACCTGAGGGCTCTTAACATGGGAGTATCCCA ATGTGATCGATGGTATCAGCCC (SEQ ID NO: 96) | E |
| 13 | GAACGACGCATCCTTATTTAGCCTTTCTTTGGTGAGAG AACGCCGGGAGGCCAACTCGAA (SEQ ID NO: 97) | ERRILI (SEQ ID NO: 98) |
| 14 | ACTTTATCGTACTACATAATTTGAATACTCCTGATACT ACAGTAAGGCCACGAAAAGATA (SEQ ID NO: 99) | TLSYYII (SEQ ID NO: 100) |
| 15 | ATGATTTTTTCAGTGACGATTGGGCGGAGCCGCAGCAT ACAAAAAGAATGCAATTTTAAA (SEQ ID NO: 101) | MIFSVTIGRSRSIQK ECNFK (SEQ ID NO: 102) |
| 16 | TGGCTCAAGCACTCTTGAAGCGTACCACACACTGTAAG AAGCGATGGCGCTTTAAAGGTC (SEQ ID NO: 103) | WLKHS (SEQ ID NO: 104) |
| 17 | GGTCCATATTTGCGGTGTAGGCTCATGCCAGCTGGTGT TAGGCCTCCGAATGAACTATTT (SEQ ID NO: 105) | GPYLRCRLMPAGV RPPNELF (SEQ ID NO: 106) |
| 18 | GCACTTGGGGTGGAAGCACACAGGGTCGTATCTAATGT GACATATCGTCGTCGCGTGGCG (SEQ ID NO: 107) | ALGVEAHRVVSNV TYRRRVA (SEQ ID NO: 108) |
| 19 | AATAGGACGACGTGAGGACATCCTCGGACTGTCTCGTT GTGTGCCCAGTTCCCGATATAC (SEQ ID NO: 109) | NRTT (SEQ ID NO: 110) |
| 20 | GTCCCTATTGATCATTGAATAGTAGGAATCACCAGCGT TGGACAGAGGTCCCATGTGAGC (SEQ ID NO: 111) | VPIDH (SEQ ID NO: 112) |

These data confirmed our success in synthesizing the peptide library, as well as the sequence diversity it carried.

p53 mutant cDNA fragments for the IVC selection was prepared by first performing site-directed mutagenesis on a PET22b plasmid vector carrying wild-type p53 (cloned between NdeI and NcoI restriction sites within the multiple cloning site, MCS), followed by PCR amplification using primers PET-F2 and PET-RC. DNA was sequenced to ensure that only plasmids carrying the correct mutations were selected. The primer pair PET-F2 and PET-RC amplified a region of the PET22b plasmid which carried the MCS, T7 promoter, RBS, start and stop sites, and hence, the resulting p53 cDNA PCR fragments carried the DNA elements needed for in-vitro transcription and translation. After column purification, the PCR products were separated using AGE and confirmed an expected size of ~1500 bps (FIG. 2D). Next, we checked to see if each of the p53 cDNA fragments can lead to the proper synthesis of full-length p53 by constituting the IVT cocktail (EcoPro™ T7 system, Novagen) with each mutant p53 cDNA (100 ng/10 µL IVT), following manufacturer's protocol. Western blotting on each of the different IVT samples, using DO-1 antibody, confirmed the translation of full-length p53 protein and that the relative protein levels are roughly identical (FIG. 2E).

IVC Selection—Round 1

In the first round of IVC selection, 5 separate selections were performed (p53 mutants R175H, G245S, R248Q, R273H and a negative control selection), each using approximately $5.68 \times 10^9$ molecules of the peptide library, to give <1 library per compartment (~$10^{10}$ aqueous compartments). Peptide library was also diluted in poly-dIdC to decrease non-specific DNA interactions. In the negative control selection, no p53 cDNA was added, and any DNA eluted would be due to non-specific interactions between DNA and beads. In each of the selection reaction, the aqueous phase (which consisted of the IVT mixture, peptide library in poly-dIdC, mutant p53 cDNA, T7 RNA polymerase and $ZnCl_2$) was mixed with pre-chilled oil phase, and stirred for 5 minutes to form the appropriately sized water-in-oil micro-droplets. The IVT emulsion is then incubated at 30° C. for 2-3 hours, after which the emulsion is cracked open, the aqueous phase is extracted and added to magnetic protein-G beads coated with DO-1 antibodies (FIG. 1). This allows any p53/peptide/peptide cDNA complex to be captured on the beads, which are subsequently washed and eluted in nuclease-free water.

The first step to obtaining information from our selection is to enrich the presence of any DNA that may have been eluted. Using 5 µL of the eluate as template, we tried first to amplify any DNA present with the original primers used in synthesizing the library (RL2-pUMA2-F2 and RL2-p21-2R). AGE of the PCR products revealed that a 750 bp product was synthesized for certain samples (control and R175H selection), which was far from the expected size of 150 bp (FIG. 3A). Furthermore, an 850 bp product in the no-template control (NTC) indicated possible mispriming issues. We next repeated the PCR with more DNA template (10 µL eluate) and a different primer pair (RF2—an inward nested forward primer, and rPETr—an outward nested primer that puts on an additional sequence (FIG. 2A). PCR product was then column purified and PCR re-amplified again (using 2 µL of DNA template) using the same primer pair (but at 60° C. annealing to reduce non-specific priming) (FIG. 3B). Sensing how the DNA could be just below the detection threshold, we increased the DNA loaded, switched to ethidium bromide, and could finally visualize PCR products at the expected sizes of ~150 bp (FIG. 3C). This difficulty in recovering positive selectants after the first round of selection is not uncommon due to the diversity of the library and scarcity of positive events. Notably, after 3 rounds of PCR enrichment, we still could not detect any DNA from the eluate of R175H selection (FIG. 3C). In a final attempt to enrich the R175H selectants, PCR re-amplification using RL2-pUMA2-F2 and RL2-p21-2R (using previous PCR product as DNA template) yielded a 100 bp product (FIG. 3D). Because there is only one fragment at a significantly smaller size, we concluded that it was a non-specific PCR product, and that the selection for p53-R175H failed. P53-R175H was therefore removed from subsequent selections.

Figure 3:
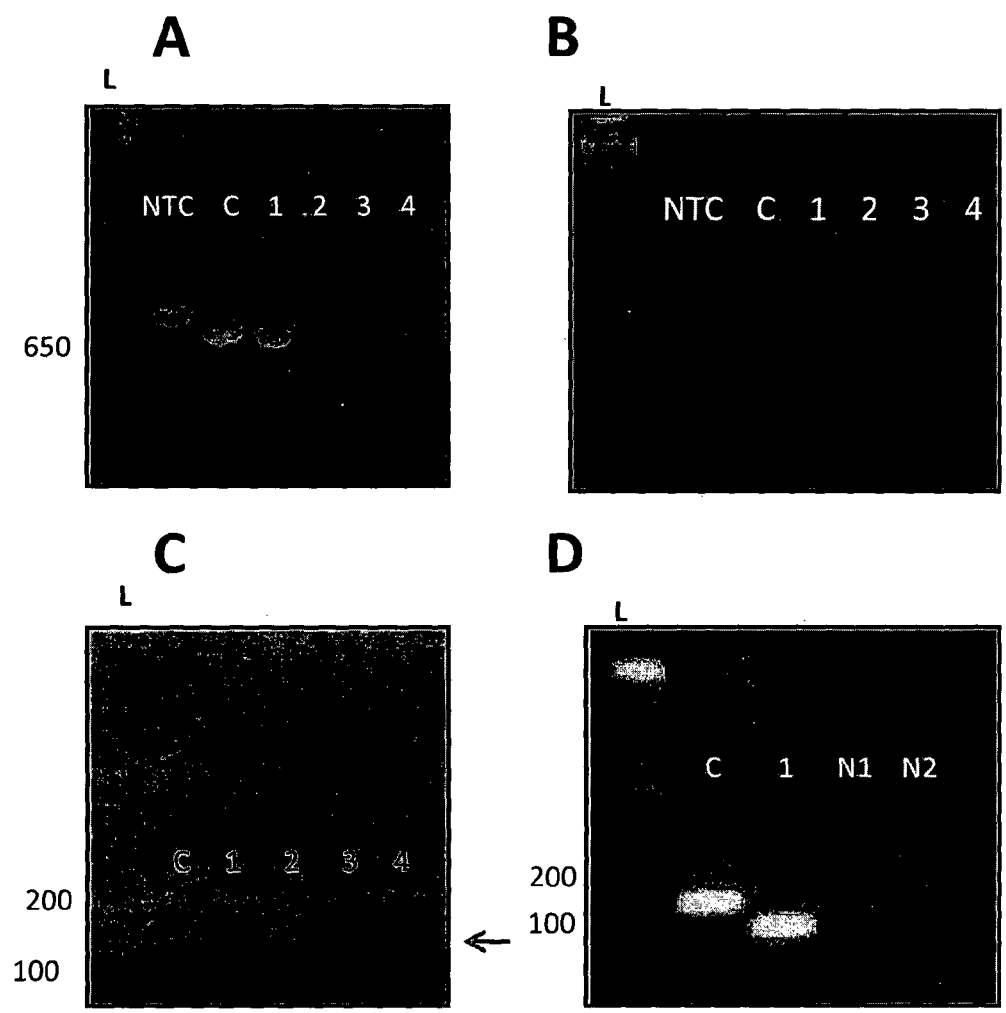
FIG. 3 shows the IVC round 1 selection and PCR rescue of positive hits. (A) First PCR rescue of positively selected DNA library using primers PUMA-2F2 and p21-2R. (B) 2nd PCR rescue using primers inward nested primer RF2 and outward nested primer rPETr. (C) Re-amplification of PCR products from 2nd round rescue attempt using primers RF2 and PETr. (D) Final attempt at PCR recovery of R175H selection product. NTC—no template PCR control, C—control selection.
Figure 4:
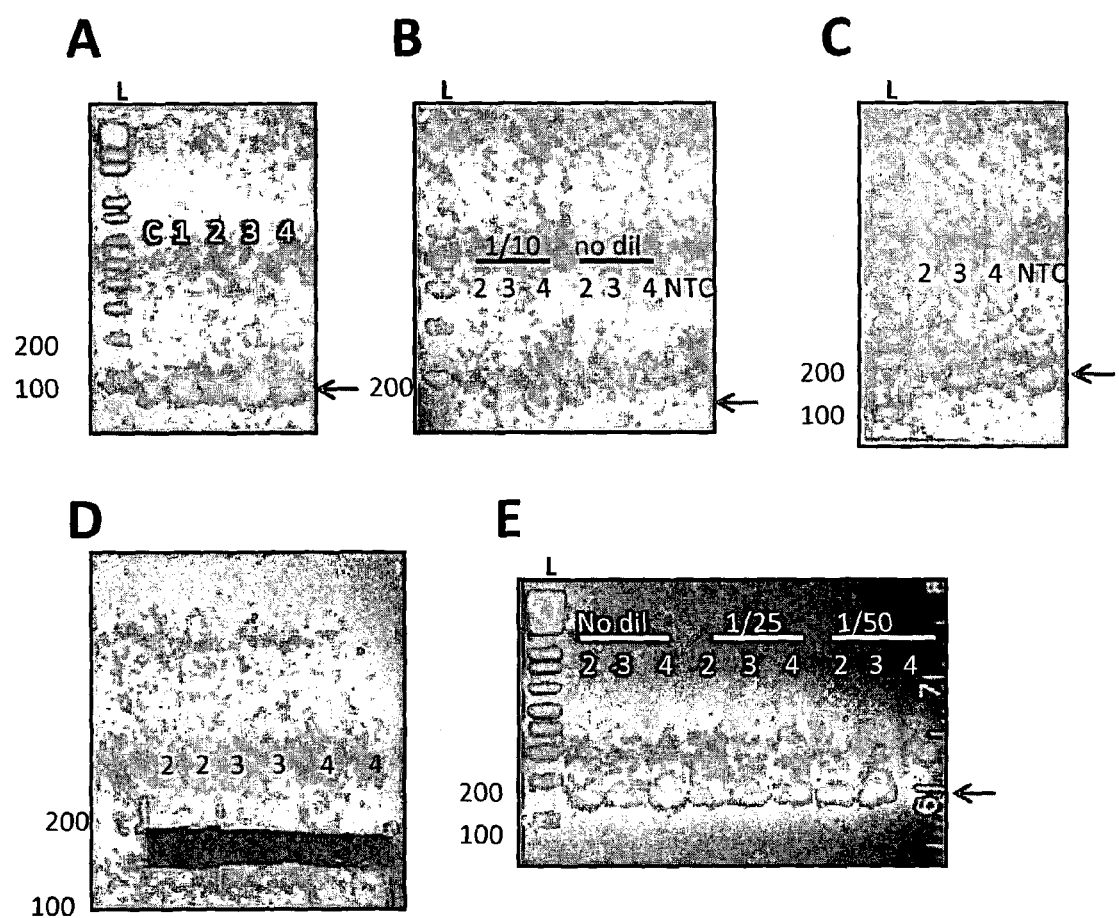
FIG. 4 shows amplification of round 1 post selection random library. (A) PCR product after 2 rounds of re-amplification at 55° C. annealing, using RF2 and PETr, of initial rescued library fragments. (B) Re-attempt at post round-1 library amplification using RF2 and new primer PetRevWalt using different DNA template concentration. (C) Re-amplification of random library using PUMA-2F2 and p21-2R. (D) Pooled PCR products were separated on an agarose gel, excised at ~150 bp, and (E) a PCR with a shortened extension time was used to amplify the final library for round 2 selection of each mutant.

For the remaining mutants, the next time step was to enrich and purify their respective selectants in preparation for the next selection round. However, when we column purified PCR products from before (FIG. 3C, G245S, R248Q and R273H) and re-amplified them using PCR (using RF2 and rPETr, via PCR protocol 4), we obtained a smear of DNA bands, indicative of multiple non-specific products of different sizes (FIG. 4A). It is apparent, from the large amount of unutilized dNTPs observed at the foot of the gel, that the PCR reaction proceeded inefficiently, possibly due to the overwhelming presence of bigger non-specific products. Other reasons for this problem may be due to excessive DNA polymerase, and a long PCR extension time that favored bigger products. Using gel purification, we excised and purified PCR products from the agarose gel at an expected size of ~150 bp and performed PCR amplification with several changes in the protocol. Firstly, we diluted the volume of DNA template by 1/10 (from 2 µL to 0.1 µL), and secondly, halved the PCR extension time to 15 seconds. In addition, we used the primer pair of RF2 and PetRevWalt; the latter oligo-nucleotide primes off a sequence appended by the earlier reverse primer, rPETr (FIG. 2A), and hence, selects for only correctly amplified products. The changes allowed us to positively amplify our product of interest (FIG. 4B), especially in samples that were diluted.

In the attempt to enrich the reading frame of the positively selected peptide cDNAs, we had to utilize priming strategies that altered our library constructs (RF2 removes pUMA-BS2 RE from the 5' end, and rPETr puts on 20 bp on the 3' end). Therefore, we had to rebuild our current library with the necessary DNA elements before the next selection round. We column purified the DNA products from FIG. 4C, before PCR amplifying with the first primers used in the library construction (RL2-pUMA2-F2 and RL2-p21-2R via PCR protocol 4 with a 15s extension time). AGE of the PCR product revealed that the non-specific smear from the previous PCR reaction was equally amplified in this reaction (FIG. 4C). After another round of gel purification by excising DNA bands of the expected size (FIG. 4D), followed by the PCR reaction, we could finally detect our band of interest as the major product (FIG. 4E). We then gel purified this major band again before using it as the random peptide library for our next round of selection.

IVC Selection—Round 2

Figure 5:
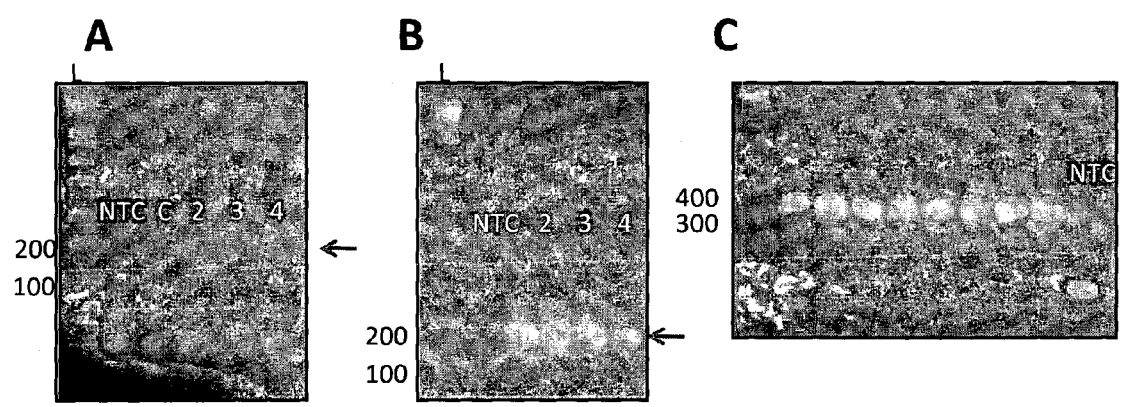
FIG. 5 shows the IVC round 2 selection PCR amplification results and sequencing of positively selected peptide DNA. (A) First attempt at PCR recovery of round 2 post selection DNA library using PUMA-2F2 and rPETr. (B) Re-amplification of initial PCR rescue products using PUMA-2F2 and p21-2R primers. (C) Colony PCR of bacteria clones carrying random library fragment cloned into TA-TOPO vector.

We performed the second round of IVC selection using the same protocol as round one, with the exceptions that (i) p53-R175H selection sample has been omitted, and (ii) peptide library input for the negative selection is now a combination of all inputs (G245S, R248Q and R273H) at equal proportions. Unlike the previous round of selection, we could already visualize DNA products on the agarose gel after one round of PCR enrichment (10 µL of eluate as template, using rPETr and RL2-pUMA2-F2, PCR protocol 4 at 15s extension). There is a clear enrichment of PCR product for all 3 samples at the expected size of ~190 bp (due to the added region by reverse primer rPETr), and additionally, lack of PCR products in both the NTC and control selection sample (FIG. 5A). This was extremely encouraging and is indicative of a true enrichment of positive selectants. We then repeated the PCR reaction, using 0.8 µL of the PCR product as DNA template (reduced template), with a different primer set (RL2-pUMA2-F2 and RL2-p21-2R), and further reduced the extension time to 10 seconds. The result was a relatively specific amplification of the desired product (FIG. 5B).

We next decided to sequence some of the selectants just to check the sequence integrity of the library constructs, as well as some of the sequences that were selected. The enriched PCR products were then cloned into the TOPO vector, transformed into BL21 cells, and grown on selective ampicillin plates before being amplified using colony PCR to check for inserts (using TOPO vector specific M13 forward and reverse primers). Colonies that were positive for vector inserts (~350 bp PCR fragment, FIG. 5C) were sent for sequencing. A total of 8 clones for each mutant were sent for sequencing, the resulting chromatograms were analysed using EditSeq, translated to amino acid sequences and tabulated (Table 9). The fact that all sequences came back with the correct insert displaying in-frame peptide genes was very encouraging, and indicative that molecular methods used did not adversely affect the DNA and that the correct peptide library DNA fragments were used in both selection rounds. Furthermore, we see distinct patterns of peptide sequences from each of the mutants. Peptide selected for G245S are still evolving (several sequences), whereas sequences of R248Q seemed to be almost entirely enriched for a single peptide (ILNVLPLLASRKP (SEQ ID NO:58), Table 9).

TABLE 9

Translation of 8 clones for each mutant showing peptides selected for G245S are still evolving whereas R248Q are almost entirely enriched for a single peptide

| Clone | G245S | R248Q | R273H |
| --- | --- | --- | --- |
| 1 | LM | ILNVLPLLASRKP (SEQ ID NO: 58) | RLQQV (SEQ ID NO: 60) |

TABLE 9-continued

Translation of 8 clones for each mutant showing peptides selected for G245S are still evolving whereas R248Q are almost entirely enriched for a single peptide

| Clone | G245S | R248Q | R273H |
| --- | --- | --- | --- |
| 2 | TALIDIWEHS VLGKGYPRMS (SEQ ID NO: 57) | ILNVLPLLASRKP (SEQ ID NO: 58) | TALIDIWEH SVLGKGYPR MS (SEQ ID NO: 57) |
| 3 | TALIDIWEHS VLGKGYPR Met S (SEQ ID NO: 57) | VSWSACVLLELCNYF PENPIEEEDWACLG (SEQ ID NO: 59) | TALIDIWEH SVLGKGYPR MS (SEQ ID NO: 57) |
| 4 | LM | ILNVLPLLASRKP (SEQ ID NO: 58) | RAVTDRPVP CPNPRLNLV AN (SEQ ID NO: 73) |
| 5 | TALIDIWEHS VLGKGYPRMS (SEQ ID NO: 57) | ILNVLPLLASRKP (SEQ ID NO: 58) | TTLIDIWEH SVLGKGYPR MS (SEQ ID NO: 71) |
| 6 | VRHQHVGAT ILGWKMGW TDH (SEQ ID NO: 62) | ILNVLPLLASRKP (SEQ ID NO: 58) | RLQQV (SEQ ID NO: 60) |
| 7 | TALIDIWEHS VLGKGYPRMS (SEQ ID NO: 57) | ILNVLPLLASRKP (SEQ ID NO: 58) | RLQQV (SEQ ID NO: 60) |
| 8 | — | ILNVLPLLASRKP (SEQ ID NO: 58) | RLQQV (SEQ ID NO: 60) |

Because the final post-selection PCR amplification was done using primers RL2-pUMA2-F2 and RL2-p21-2R, we proceeded directly to gel-purify PCR products from FIG. 5B before commencing on the next round of selection.

IVC Selection—Round 3

Figure 6:
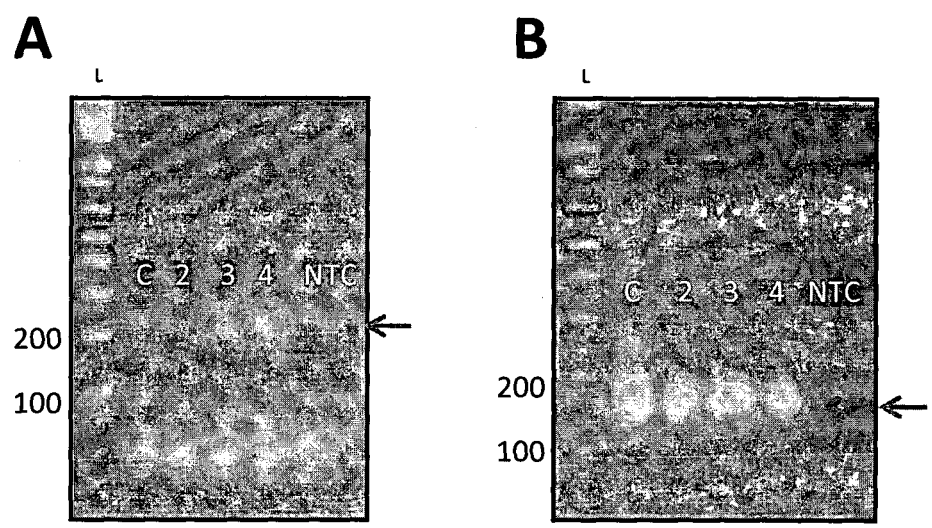
FIG. 6 shows the IVC round 3 selection results. (A) Initial PCR rescue of positively selected random library DNA fragments using PUMA-2F2 and rPETr. (B) Re-amplication of round 3 post selection PCR rescue products using primers PUMA-2F2 and p21-2R. (C) Peptide sequences of round 3 positive selectants (SEQ ID Nos:55-61 and 113-115). (D) Peptide selected for further studies (SEQ ID Nos:55-61).

In the third round of NC selection, we repeated the selection as per previous round, with the exception of halving the mass of input library DNA (from 500 pg to 250 pg) for each sample, so as to increase the selection stringency. Once the selection was complete, we used 10 µL of the eluate in a PCR to enrich for the positive selectants (same protocol as in round 2). The resultant products were easily detectable after separation using AGE, showing further library enrichment from the third round of selection (FIG. 6A). However, unlike in round 2, a PCR product was observable for the control selection sample (FIG. 6A). Without purification, we PCR re-amplified the DNA products using primers RL2-pUMA2-F2 and RL2-p21-2R (FIG. 6B). We then TOPO cloned the PCR products like before into bacterial cells, checked for inserts using colony PCR, before sending positively inserted fragments for sequencing. For each group of selectants, we sequenced up to 16 clones and analyzed the coded peptide sequence using EditSeq (Table 10).

TABLE 10

Translation of positive selectants showing

| Clone | G245S | R248Q | R273H |
|---|---|---|---|
| 1 | S P N T N H (SEQ ID NO: 55) | I L N V L P L L A S R K P (SEQ ID NO: 58) | R L Q Q V (SEQ ID NO: 60) |
| 2 | M P H L M A C (SEQ ID NO: 56) | VSWSACVLLELCNYFPENPIEEEDWACLG (SEQ ID NO: 59) | A R H Q H V G A T I L G W K (SEQ ID NO: 115) |
| 3 | S P T T N H (SEQ ID NO: 55) | VSWSACVLLELCNYFPENPIEEEDWACLG (SEQ ID NO: 59) | V R H Q H V G A T I L G W K (SEQ ID NO: 61) |
| 4 | S P T T N H (SEQ ID NO: 55) | I L N V L P L L A S R K P (SEQ ID NO: 58) | T A L I D I W E H S V L G K G Y P R M S (SEQ ID NO: 57) |
| 5 | D E L V A I P V R L T Y Y R G P N I A I (SEQ ID NO: 113) | I L N V L P L L A S R K P (SEQ ID NO: 58) | L M |
| 6 | S P T T N H (SEQ ID NO: 55) | VSWSACVLLELCNYFPENPIEEEDWACLG (SEQ ID NO: 59) | T A L I D I W E H S V L G K G Y P R M S (SEQ ID NO: 57) |
| 7 | M P H L M A C (SEQ ID NO: 56) | I L N V L P L L A S R K P (SEQ ID NO: 58) | R L Q Q V (SEQ ID NO: 60) |
| 8 | S P T T N H (SEQ ID NO: 55) | VSWSACVLLELCNYFPENPIEEEDWACLG (SEQ ID NO: 59) | V R H Q H V G A T I L G W K (SEQ ID NO: 61) |
| 9 | M P H L M A C (SEQ ID NO: 56) | I L N V L P L L A S R K P (SEQ ID NO: 58) | R L Q Q V (SEQ ID NO: 60) |
| 10 | E R R F P I M G V N S P E G K M W P L I (SEQ ID NO: 114) | VSWSACVLLELCNYFPENPIEEEDWACLG (SEQ ID NO: 59) | T A L I D I W E H S V L G K G Y P R M S (SEQ ID NO: 57) |
| 11 | S P T T N H (SEQ ID NO: 55) | VSWSACVLLELCNYFPENPIEEEDWACLG (SEQ ID NO: 59) | T A L I D I W E H S V L G K G Y P R M S (SEQ ID NO: 57) |
| 12 | D E L V A I P V R L T Y Y R G P N I A I (SEQ ID NO: 113) | I L N V L P L L A S R K P (SEQ ID NO: 58) | V R H Q H V G A T I L G W K (SEQ ID NO: 61) |
| 13 | E R R F P I M G V N S P E G K M W P L I (SEQ ID NO: 114) | I L N V L P L L A S R K P (SEQ ID NO: 58) | R L Q Q V (SEQ ID NO: 60) |
| 14 | S P T T N H (SEQ ID NO: 55) | I L N V L P L L A S R K P (SEQ ID NO: 58) | V R H Q H V G A T I L G W K (SEQ ID NO: 61) |
| 15 | M P H L M A C (SEQ ID NO: 56) | I L N V L P L L A S R K P (SEQ ID NO: 58) | T A L I D I W E H S V L G K G Y P R M S (SEQ ID NO: 57) |
| 16 | M P H L M A C (SEQ ID NO: 56) | I L N V L P L L A S R K P (SEQ ID NO: 58) | V R H Q H V G A T I L G W K (SEQ ID NO: 61) |

Comparing the peptide sequences selected for each mutant, and across selection rounds, several striking observation emerged. The mutants can be grouped into two categories based on the pattern of sequences. Peptides that were selected for R248Q mutant seem to work specifically on itself, and has strongly outcompeted other possible reactivators. Contrastingly, selectants of R273H and G245S mutants consists of a few primary sequences interspersed with several sporadic ones. The latter two mutants also shared a few peptide sequences like TALIDIWEHSVLGK-GYPRMS (SEQ ID NO:57) and VRHQHVGATILGWK (SEQ ID NO:61). Notably, these shared sequences were lost from the G245S selectants in round 3 of the selection. Furthermore, none of the peptide sequences carried regions of positively charged residues, which has been described to confer a false positive sequence-specific DNA binding phenotype to transcription factors through the electrostatic interaction and aggregation of DNA.

Another interesting result is the elongated sequence selected for R248Q which exceeded the original library design encoding 20-mer peptides (VSWSACVLLELCNY-FPENPIEEEDWACLG ((SEQ D NO:59), Table 10) by 10 amino acids.

This was due to a mutation in the stop codon (possibly due to DNA polymerase base pair mismatching) causing the inclusive translation of the sequence from the p21 response element (FIG. 2B). For this sequence to be enriched through 3 rounds of selection, either the preceding sequence is such a strong activator of the mutant p53 it can withstand the addition of an innocuous or even detrimental peptide sequence, or the serendipitous addition of the 'p21' polypeptide has somehow enhanced the activity of the existing sequence.

We next consolidated and selected 7 peptide sequences that will be used for subsequent secondary assays. We decided to name the peptides using the acronym Pap (P53 activating peptide), followed by a peptide reference tag corresponding to the first 3 amino acids of the randomized sequence (Table 11).

cDNA of Pap-VSW was amplified using RL2-T7-F1 and RL2-p21-2R. We amplified the pooled positive selectants from round 3 of the selection using RL2-pUMA2-F2 and rPETr primers (FIG. 7A), followed by PCR amplification using peptide specific primer pairs. The resulting PCR products were then gel purified and individual fragments were checked before further experiments (AGE, FIG. 7B and sequencing).

Preliminary Validation of Peptides Using ELISA-Based DNA Binding Assay

Figure 8:
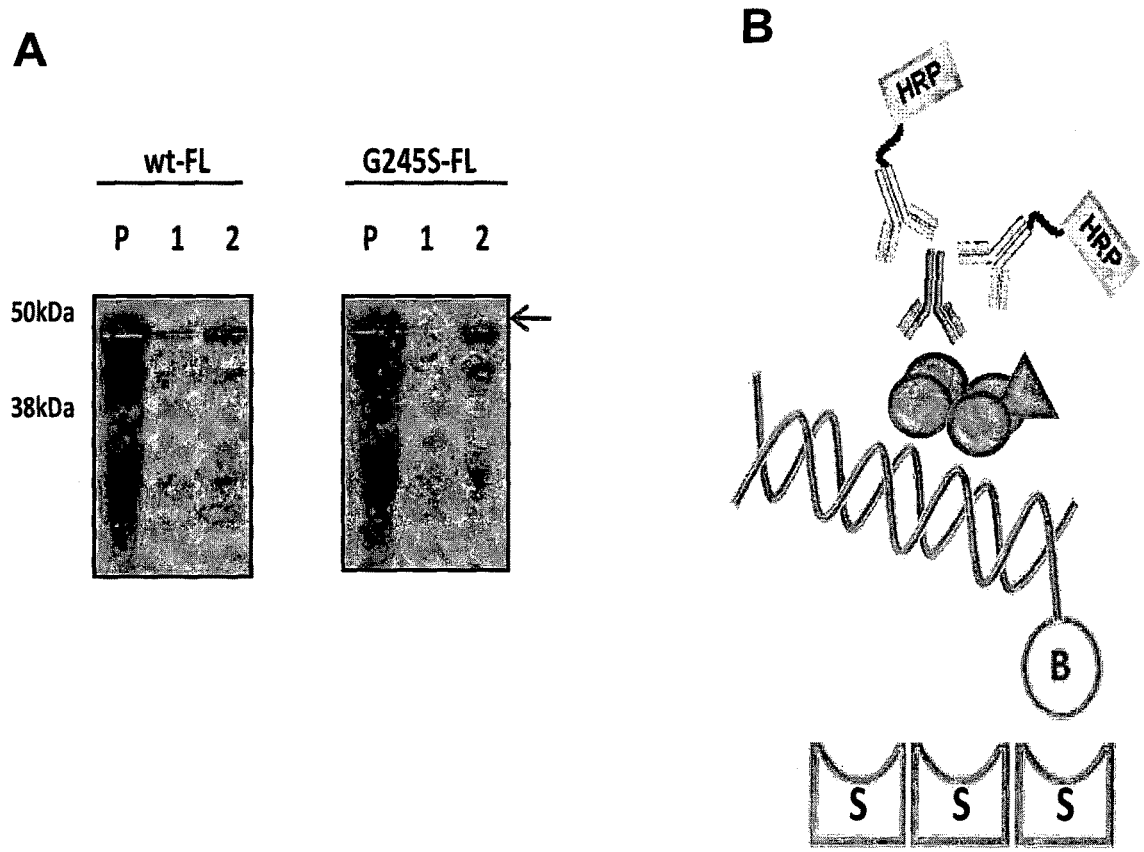
FIG. 8 shows the optimization of experimental conditions for ELISA DNA binding assay. (A) Western blot showing increased protein synthesis using PCR product as IVT template. P, 1 and 2 are PCR template, 1600 ng and 400 ng of plasmid DNA respectively. (B) Schematic representation of ELISA DNA binding assay.

We decided to use an ELISA-based DNA binding assay, previously described for purified p53(21), to validate the functionality of the selected peptides. Briefly, biotin-conjugated RE oligo-nucleotides are incubated with p53-synthesized IVT mixture on a 96-well plate coated with streptavidin. P53-RE complexes formed are then captured on the plate (via biotin-streptavidin interaction) and detected using anti-p53 antibody and a horseradish peroxidase (HRP) conjugated secondary antibody (FIG. 8B).

We next investigated the effects of using plasmid DNA and PCR fragments as p53 coding templates. Although PCR fragments were used as p53 cDNA template in the NC selection, protocol for the Novagen IVT system recommended plasmid DNA (in the range of 500 ng per 50 µL IVT reaction) as they were more stable in the bacterial extract. We compared the amounts of full-length p53 translated using different amounts of plasmid DNA (400 ng, 800 ng and 1200 ng) and discovered that protein synthesis was inversely related to the amount of plasmid DNA added in the concentrations tested. We next compared protein synthesis of p53 between PCR fragment and plasmid DNA by using either 400 ng of PCR fragment, 400 ng of plasmid DNA (equi-mass), or 1600 ng of plasmid DNA (equi-molar).

TABLE 11

List of consolidated peptides used for subsequent assays.

| No. | Peptide Reference | Amino Acid Sequence | p53 mutant |
|---|---|---|---|
| 1 | Pap-SPT | S P T N H (SEQ ID NO: 55) | G245S |
| 2 | Pap-MPH | M P H L M A C (SEQ ID NO: 56) | G245S |
| 3 | Pap-TAL | T A L I D I W E H S V L G K G Y P R M S (SEQ ID NO: 57) | R273H/G245S |
| 4 | Pap-ILN | I L N V L P L L A S R K P (SEQ ID NO: 58) | R248Q |
| 5 | Pap-VSW | VSWSACVLLELCNYFPENPIEEEDWACLG (SEQ ID NO: 59) | R248Q |
| 6 | Pap-RLQ | R L Q Q V (SEQ ID NO: 60) | R273H |
| 7 | Pap-VRH | V R H Q H V G A T I L G W K (SEQ ID NO: 61) | R273H |

Preparation of Specific Peptide cDNA for Secondary Assays

After selecting the peptide sequences, we wanted to clone and isolate just the coding sequence (remove flanking RE regions) of each individual peptide sequence for further experiments. For this purpose, a forward primer, that sits on the T7 promoter sequence (RL2-T7-F1), was used together with peptide specific reverse primer and amplified using PCR (using M13 amplified PCR products as template).

Western blot analysis using DO-1 antibody revealed that the use of PCR cDNA templates gave a significantly higher protein yield (FIG. 8A), and was used for subsequent assays.

Because IVT-synthesized p53 is used in our experiments instead of affinity purified p53 (as described previously), we tried to circumvent possible background issues (from the use of bacterial extract IVT) by performing control binding experiments on full-length proteins (wild-type and mutants) using several experimental conditions. P53 proteins (wildtype, G245S, R248Q and R273H full-length) were synthesized by reconstituting the IVT mixture with the desired amount of PCR cDNA templates, followed by incubation at 30° C. for 2 hours. The p53/IVT mix is then incubated on a 96-well plate pre-coated with p53 RE oligo-nucleotides (equal mix of p21 and PUMA REs), at room temperature, for different durations (30, 45 and 75 minutes), before detection and analysis using a luminometer. Within each set of experiment, we also investigated the effects of protein level and different buffers (with or without binding buffer 1) on positive control binding using p53wt-FL. From the results, we noted that the increase in RE incubation time resulted in an increase in background binding of mutant p53, but not sequence specific binding of wild-type p53; possibly due to the instability of mutant p53 at room temperature. Halving the amount of streptavidin used to pre-coat the plate also led to increased mutant binding, possibly due to non-specific hydrophobic interaction with the polystyrene matrix. We concluded from the results that the optimal condition for the plate binding assay was to use 5 µL of IVT protein in binding buffer 1 and a RE incubation time of 30 minutes.

Figure 9:
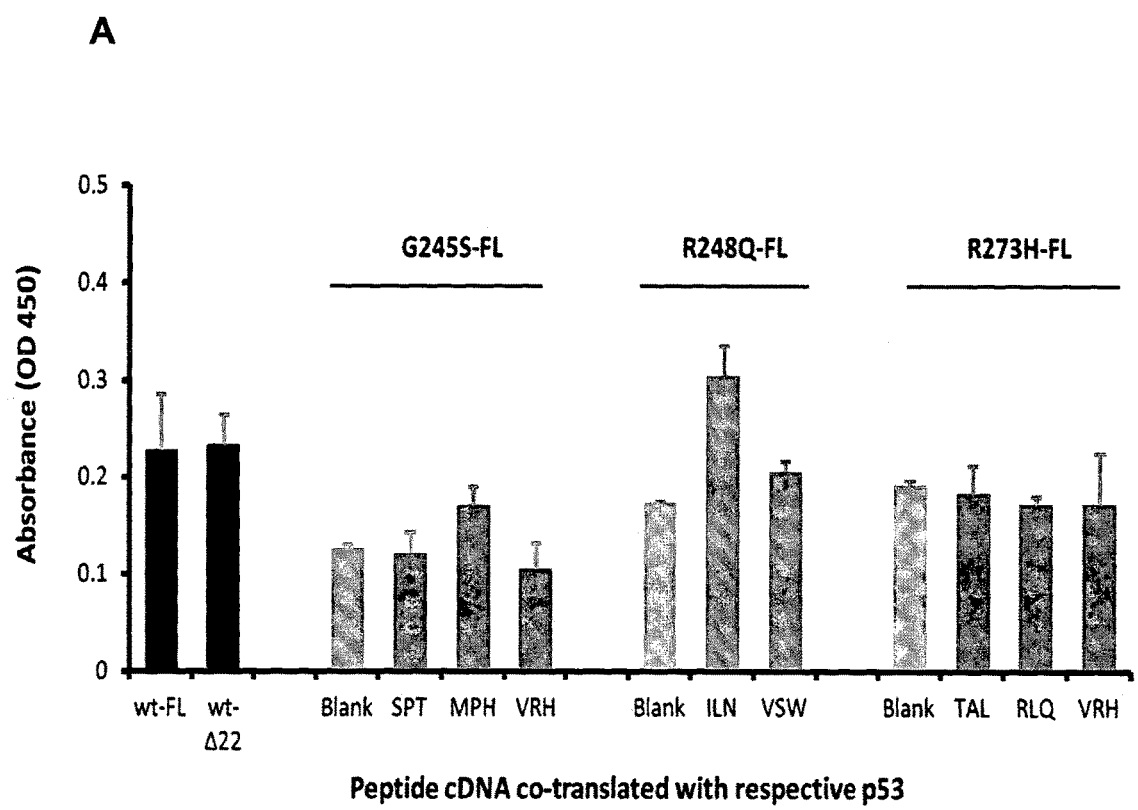
FIG. 9 shows the DNA binding reactivity of mutant p53 when co-translated with cDNA encoding peptide selected for each mutant. Faded bars represent mutant only residual binding (A). (B) Mutant p53 sequence-specific DNA binding reactivation by co-translating peptide using increasing amounts of peptide cDNA. Faded bars represent mutant only residual binding. Error bars represent standard deviation of 2 individual binding experiments. (C) DO-1 Western blot showing NT translated p53 protein levels on the absence/presence (10 or 20 ng) of peptide cDNA. Arrow indicates expected p53 full-length protein of ~49 kDa. (D) Reactivation of mutant p53 when incubated with separately IVT synthesized peptide during DNA binding. (E) Effects of separately IVT synthesized peptides with respective mutant p53 on DNA RE when compared to addition of dummy peptide (Dp). Right inset shows relative protein levels of wt-FL, R248Q-FL, and R273H-FL (1, 2 and 3 respectively).
Figure 9:
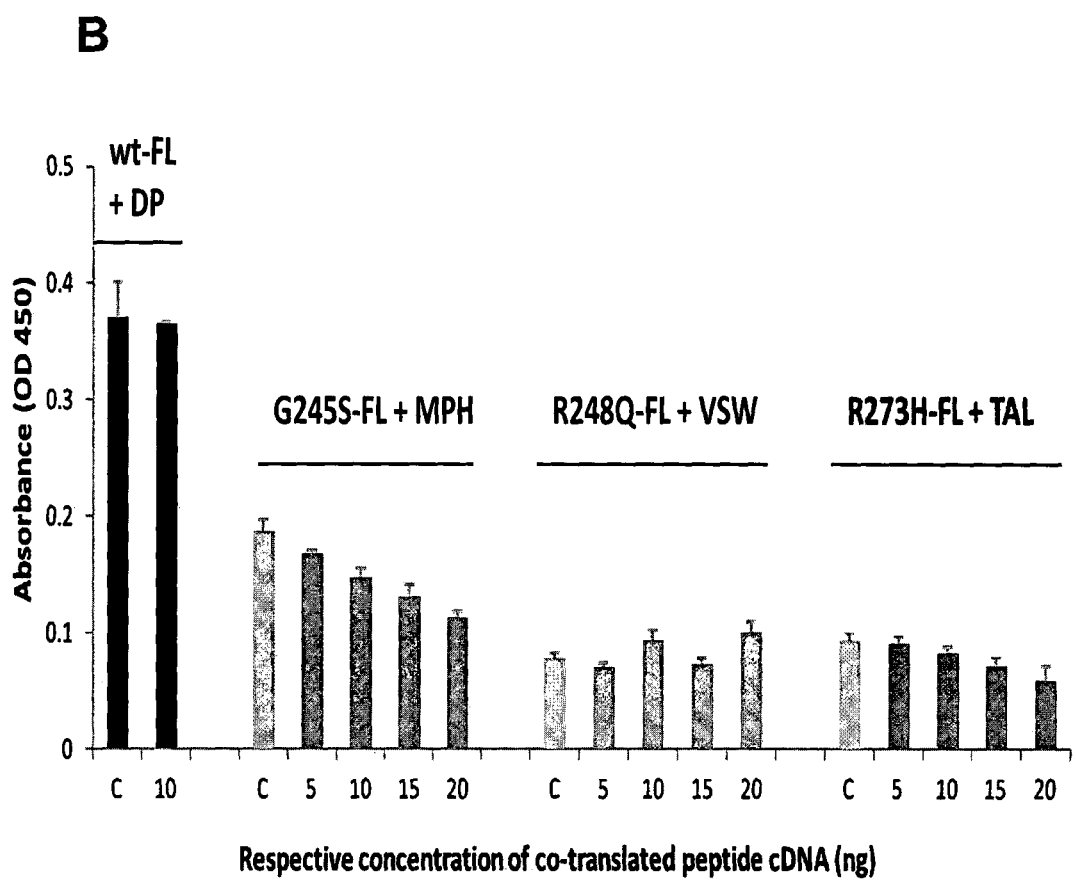
Figure 9:
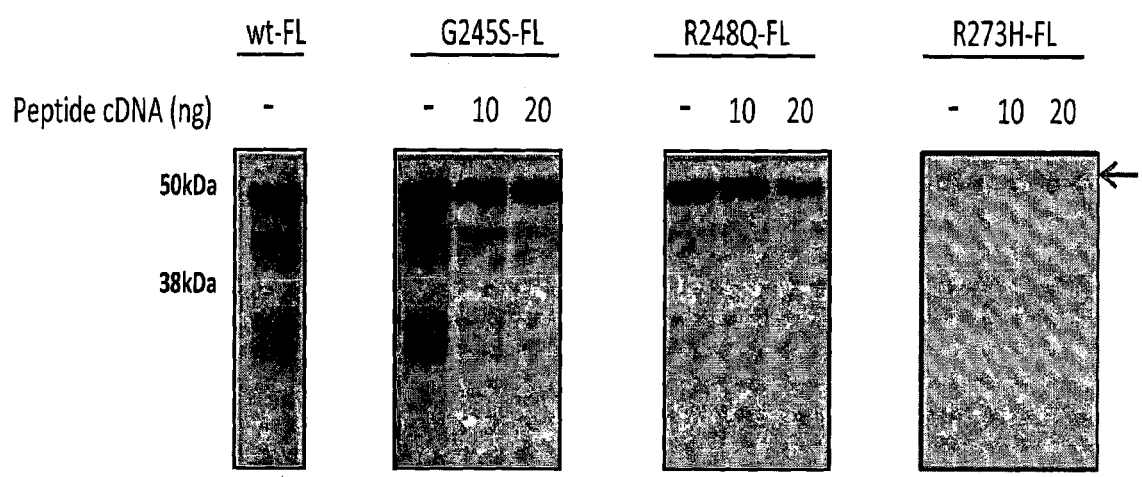

We proceeded to test our peptides by essentially replicating an IVC positive event with or without peptide present; we performed the plate binding assay as above but IVT co-synthesized each mutant p53 protein and their respective peptides by co-incubating the IVT mixture with equal molar amounts of DNA templates (160 ng p53 to 12 ng peptide cDNA). We could detect a slight increase in RE binding for combinations of G245S-FL+Pap-MPH, and R248Q-FL+Pap-VSW (FIG. 9A). Pap-ILN elicited an even bigger binding increase of ~2-fold over mutant only control (FIG. 9A).

We next repeated the assay for selected peptides (one for each mutant), but varied the concentration of peptide cDNA across a range between 5 ng and 20 ng. Additionally as control, we included a cDNA template (10 ng) that encoded a dummy peptide (PelB leader sequence from PET22b vector, ~20 amino acid polypeptide) into the sample for wt-FL. Our results indicated, with the exception of R248Q-FL+Pap-VSW which showed similar binding re-activity as before, a decrease in RE-binding as peptide cDNA increased (FIG. 9B). Western blot analysis of the protein samples used revealed that the relative synthesis of mutant p53 protein was very much affected by the presence of peptide cDNA, causing a significant difference in protein input across samples (FIG. 9C). This phenomenon was, however, not appreciable in wt-FL binding which remained unaffected. To circumvent this problem, we translated proteins and peptides separately before co-incubating (at increasing volumes of IVT-synthesized peptides: 2 µL, 6 µL and 10 µL) them in the presence of RE oligo-nucleotides. We could detect a slight increase in RE-binding only for the G245S-FL mutant in response to Pap-MPH (FIG. 9D), which, however, did not increase with increased amounts of IVT-Pap-MPH added. The observed inactivity from the remaining samples (R248Q-FL+Pap-VSW and R273H-FL Pap-TAL) may be due to an elevated mp53 background binding owing to the absence of a peptide entity. We, therefore, repeated the assay and included an IVT-synthesized dummy peptide in the 'no-peptide' mutant p53 control, and observed p53 activating peptide-dependent increase in RE-binding for R248Q-FL (by Pap-ILN and Pap-VSW) and R273H-FL (by Pap-TAL).

Bioinformatics Analysis and Validation of Peptide Sequences

A simple bioinformatics approach was also taken to validate possible biological relevance to each peptide sequence. Basically, each sequence was (i) compared with previous reports of known p53 interacting peptide sequences, (ii) queried against a non-redundant database of human proteins using the blastp algorithm to identify obvious known or possible interactors of p53 or (iii) queried against non-redundant databases of protein across all taxa to identify protein homology of known structures.

Figure 10:
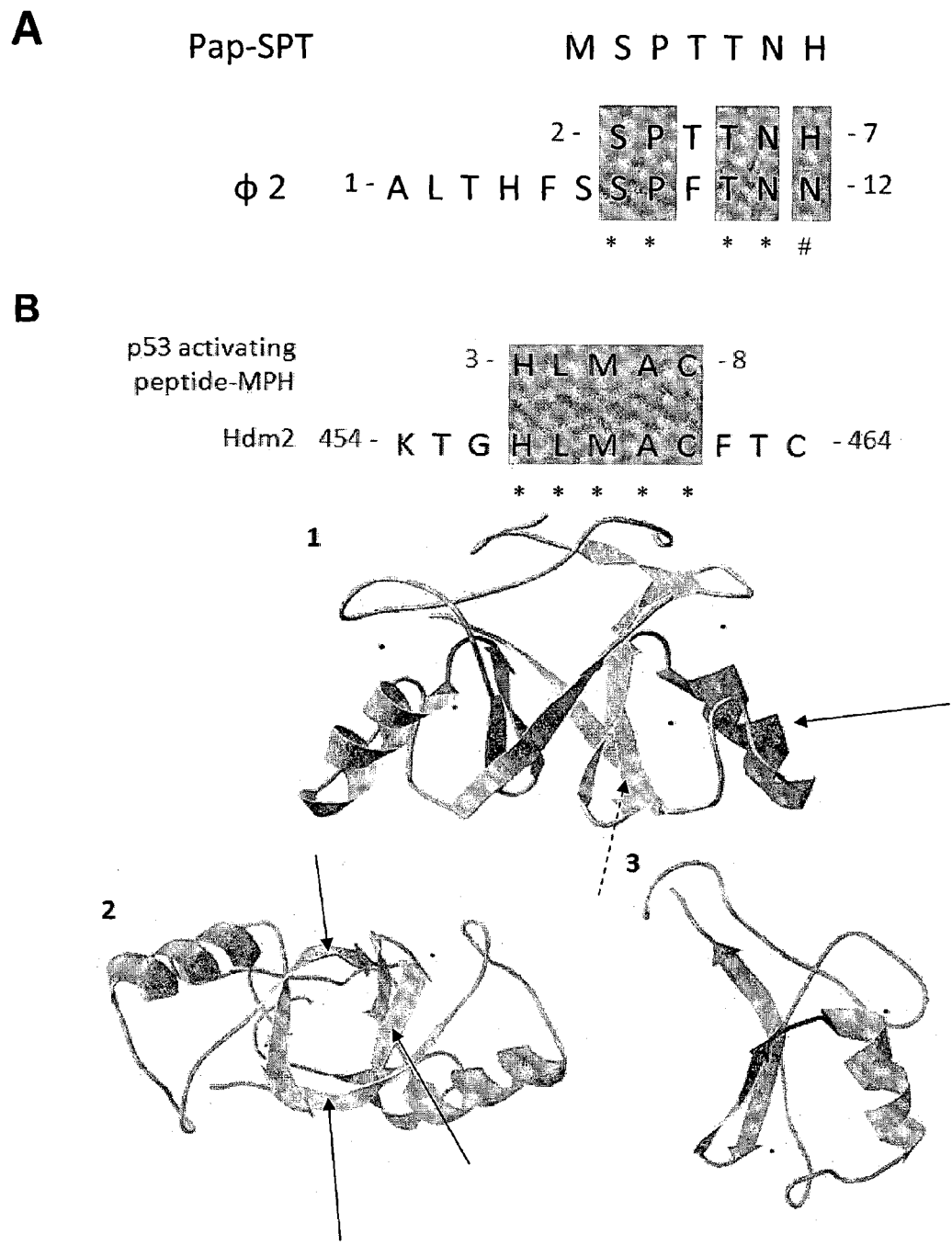
FIG. 10 shows the sequence alignment to known p53 interactors and bioinformatics approach to interactome and structure elucidation. * represents identical residues. # and † indicate conserved and semi-conserved substitutions, respectively. (A) Sequence alignment of peptide SPT with known phage display derived p53 binding peptide φ2 (SEQ ID NOs:55, 63 and 124). (B) Sequence alignment of peptide MPH and RING domain of p53 binding protein Hdm2 (SEQ ID NOs: 125 and 126). (B1) Ribbon representation of Hdm2 homodimer (PDB code 2HDP), showing location of monomer sununit and 4 coordinated zinc atoms (dots). α-helix and β-sheets of monomer subunit are indicated by the solid and dashed arrows respectively. (B2) Top-down view of Hdm2 RING domain homo-dimer showing β-barrel (solid arrows) formed by 3 β-sheets from each monomer. (B3) Hdm2 RING domain showing area of peptide homology. (C) Sequence homology between Pap-VSW and PARP4 protein and between Pap-VSW and Peptide CDB3 (SEQ ID NOs:59 and 127-132). (D1) Ribbon diagram showing a2 helical domain of human lymphoid tyrosine phosphatase catalytic domain (PDB code 3H2X) and regions of peptide TAL homology (SEQ ID NOs:57 and 133-134). Helix indicated by solid arrow represents N-terminal homology (peptide sequence TALID) and helix indicated by dashed arrow show C-terminal homology (peptide sequence IWEHSVL; SEQ ID NO: 141). Ribbon diagrams were generated using Swiss PDBViewer version 4.01.
Figure 10:
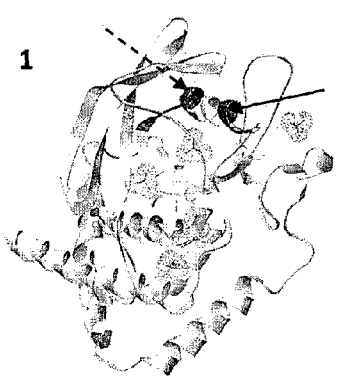

Pap-SPT appeared to have sequence homology to a peptide sequence derived from a p53 binding selection using filamentous phage that displayed a randomized 12-mer peptide library (FIG. 10A). The study also attempted to characterize interaction between p53 and the phage peptide, designated φ2. Accordingly, φ2 seem to have a conformational sensitive binding mechanism and favored interacting with properly folded p53; as demonstrated by an increase binding to wildtype over mutant p53 (R175H and R248Q) and Pab1620 epitope over Pab240 epitope displaying p53. The authors also noted that φ2 bound p53wt-FL and p53wt-Δ30 equally well, and did not bind to any of the 15-mer peptides mapped from the entire linear protein sequence of full-length p53. Another notable observation is the negatively charged patch on Pap-VSW (FIG. 10C), which resembles a similar feature on the previously described re-activating peptide CDB3, possibly indicating the importance or value of an acidic region in re-activating certain mutants.

When we blasted the peptide sequences in search for known p53 interacting proteins, a remarkable hit was the sequence homology between Pap-MPH and p53's cellular antagonist, Mdm2. Interestingly, the region of homology is mapped to the RING domain of Mdm2 (FIG. 10B), far away from the primary region of interaction that lies on the N-terminal end of both proteins. The RING domain of Mdm2 has not been shown to bind p53, but has been described with several associated properties including nucleotide binding, facilitating nuclear export and more importantly, ubiquitin E3-ligase activity. Structural and mutagenesis studies of Mdm2 homo- and hetero-dimers have revealed that dimerization of the RING domain is essential for the stability and E3-ligase activity of Mdm2. Contacts on the flanking residues of the N- and C-terminal of the RING domain brings the monomeric subunits together forming a highly symmetrical structure coordinated by 4 Zinc atoms (two per monomer) (PDB:HDN2) (FIG. 10B1). A compact ββαβ fold present in both Mdm2 subunit comes together and forms a β-barrel made up of 6 β-strands, encasing a mainly hydrophobic core of ~900 Å$^2$(31) (FIG. 10B1, 10B2). Unlike the HECT class of E3-ligases (covalent bound ubiquitin molecule), Mdm2 belongs to the (RING)/U-box and PHD domain family of E3s, and function by bringing ubiquitin-bound E2 enzymes to close proximity with substrate p53 molecules before mediating the attachment of ubiquitin onto target lysine residues, most of which are clustered at the CTD. The solvent accessible α-helix and adjacent loop is projected away from the β-barrel and is the site of recognition and interaction with ubiquitin-bound E2 enzymes. Mutagenesis studies of Mdm2/MdmX heterodimers indicate that each RING domain subunit within the dimeric structure may play distinct roles in conferring E3-ligase activity, where one interacts with E2 enzyme and the other ubiquitinating target substrates. Pap-MPH homology maps structurally to a region of the β2-strand and runs into the first residue of the adjacent α-helix (FIG. 10B3). Incidentally, the first and last residues in this homologous sequence (His and Cys) also act as zinc coordinating ligands in the Mdm2 RING domain. Taken together, this region on Mdm2 may be involved in a process of transient binding, where the β-barrel recognizes and holds the CTD of p53 in place while mediating the transfer of ubiquitin from E2 enzyme onto p53. Pap-MPH may, in this light, be developed to possibly inhibit Mdm2's E3-ligase activity, similar to a previously reported compound.

Pap-TAL was found have a rather significant, extended region of homology to the catalytic domain of human lymphoid tyrosine phosphatase (LYP) (FIG. 10D, PDB: 3H2X). While this protein is not known to interact with p53, the solved crystal structure of LYP indicates that the region of peptide homology lies within second α-helix (FIG. 10D), and suggest a possible structure for a free peptide Pap-TAL.

Lastly, we also found sequence homology between Pap-VSW and poly (ADP-ribose) polymerase 4 (PARP4 or VPARP) (FIG. 10C). PARP proteins are responsible for the detection and repair of single-stranded DNA breaks, and can also mediated apoptosis through the depletion of cellular ATP. Unlike most PARP proteins, PARP4 has a polymerase catalytic domain, but lacks the DNA binding domain. With this in mind, it is conceivable that p53 senses and binds DNA single-stranded breaks, and recruits PARP4 to mediate poly ADP-ribose polymerization. Furthermore, the region of homology lies in the N-terminal region of PARP4; similar to DNA-binding competent PARP proteins, which do so through the N-terminal zinc finger domains. Additionally, PARP1 protein has been reported to interact with p53 and altering its DNA binding properties, establishing a precedence in the biological relationship between the p53 and the PARP family of proteins.

Results

We have designed a novel IVC selection scheme and use it to identify 7 different peptide sequences selected to restore sequence-specific binding to several p53 hotspot mutants. Looking at the selection data and sequencing results, several factors may imply the success of the selection scheme. Initial post-selection PCR enrichment for positive selectants (in selection rounds 2 and 3) showed lower levels of PCR amplification for the negative control selection, indicating that DNA captured during selection was mainly due to the presence of mutant p53. The maintenance and enrichment of certain sequences (eg. Pap-VSW, Pap-TAL), as we progressed through the selection process, indicated a true course of directed evolution. The difficulty in recovering selectants after round 1, followed by the relative ease after rounds 2 and 3 is indicative of a diverse starting library successively enriched for positive selectants. The pattern of sequence emergence could suggest that certain p53 mutants have unifying structures or defects rendering them susceptible to the same peptides (Pap-TAL for G245S and R273H mutants), and other mutants like the R248Q harbor qualities that require distinct re-activating molecules. The selection results for R248Q mutant may also imply that mutant specificity can be achieved in identifying re-activating compounds. Additionally, each peptide may confer RE binding specificity to the p53 mutants, and ideally mediate distinct cellular response; a functionality which has yet been accessed.

Our approach to validating the peptide using the ELISA plate DNA binding assay functioned around recapitulating the events that transpired in an IVC compartment. Although there is evidence of peptide activity from all the peptides in our results, the narrow dynamic range of the assay, and rigidity of experimental conditions meant we had to re-visit this with more appropriate and sensitive ways to measure peptide functionalities.

It was rather remarkable and encouraging to identifying sequence homology to known interacting molecules to p53, especially with a natural binding partner (Pap-MPH and Mdm2). Apart from some sequence validation, it also signifies the applicability of the NC selection schemes and that it can be designed to probe intricate and functional interactions that display techniques cannot. This selection also had the added advantage of identifying novel p53 interacting proteins (PARP4) or revealing previously unknown modes or sites of interactions.

Example 2

Using IVT Systems to Study p53

Materials and Methods

We chose to utilize the IVT system to incorporate a critical element into our selection scheme; to select for peptides that may exert their function during the translation of p53 mutant proteins. In this light, we have decided to continue using IVT systems to investigate the functionalities of our peptides. although the IVT system used here for the selection process, EcoPro T7 system (Novagen), has been previously described in a successful selection involving p53, we decided to switch to a minimal IVT system (CosmoBio PURE system) to minimize unwanted, non-specific background interactions from the proteins in the IVT system.

The CosmoBio PURE system is a minimal IVT system constituted mainly from hexa-histidine affinity purified protein components (32 in total, including aminoacyl-tRNA synthetases, elongation and release factors, polymerases, and ribosomes). Because this system has not been used previously for translating p53, we briefly characterized and evaluated if the system is suitable for synthesizing the p53 protein.

Optimizing p53 synthesis Using CosmoBio PURE System

Figure 11:
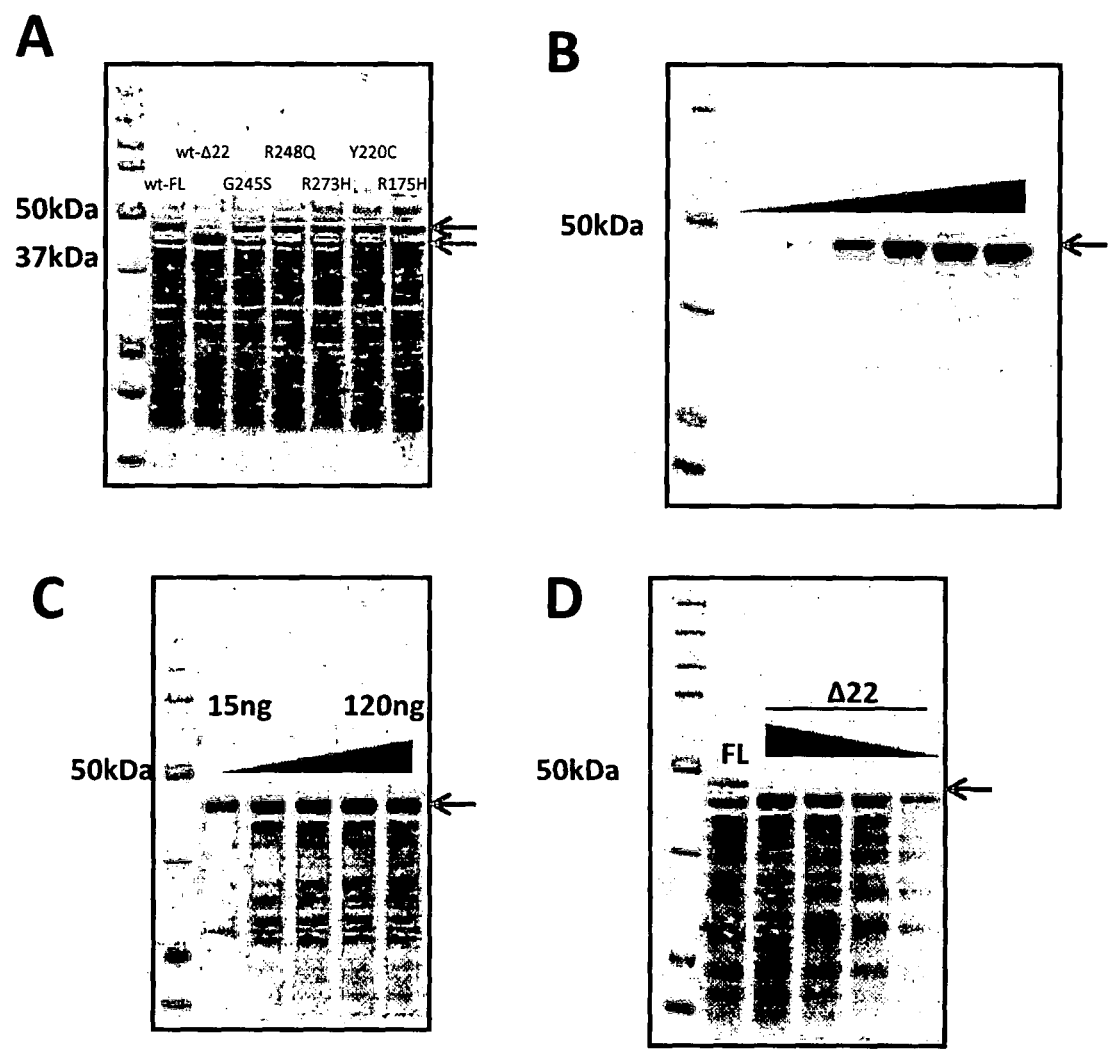
FIG. 11 shows (A) Western blot of various p53 protein levels synthesized via COSMO Bio NT system using DO-1 antibody. Bottom and top arrow indicates expected full-length and unfinished product, respectively. (B) Western blot of p53wt-FL protein with increasing protein load using Bp53-10.1 antibody. (C) Effects of cDNA template concentration on p53wt-Δ22 protein synthesis. (D) Size comparison of unfinished wt full-length product against wt-Δ22 protein. (E) Effects of incubation temperature and duration on in-vitro translation of p53wt-FL protein.
Figure 11:
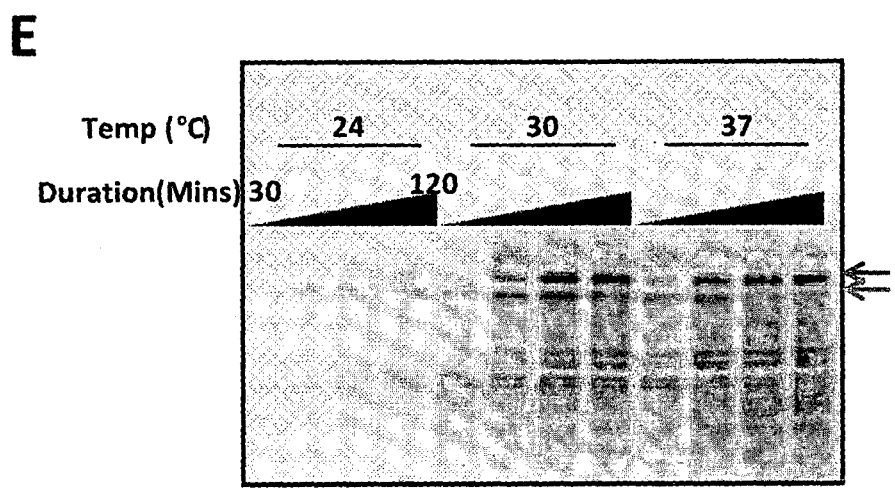
Figure 12:
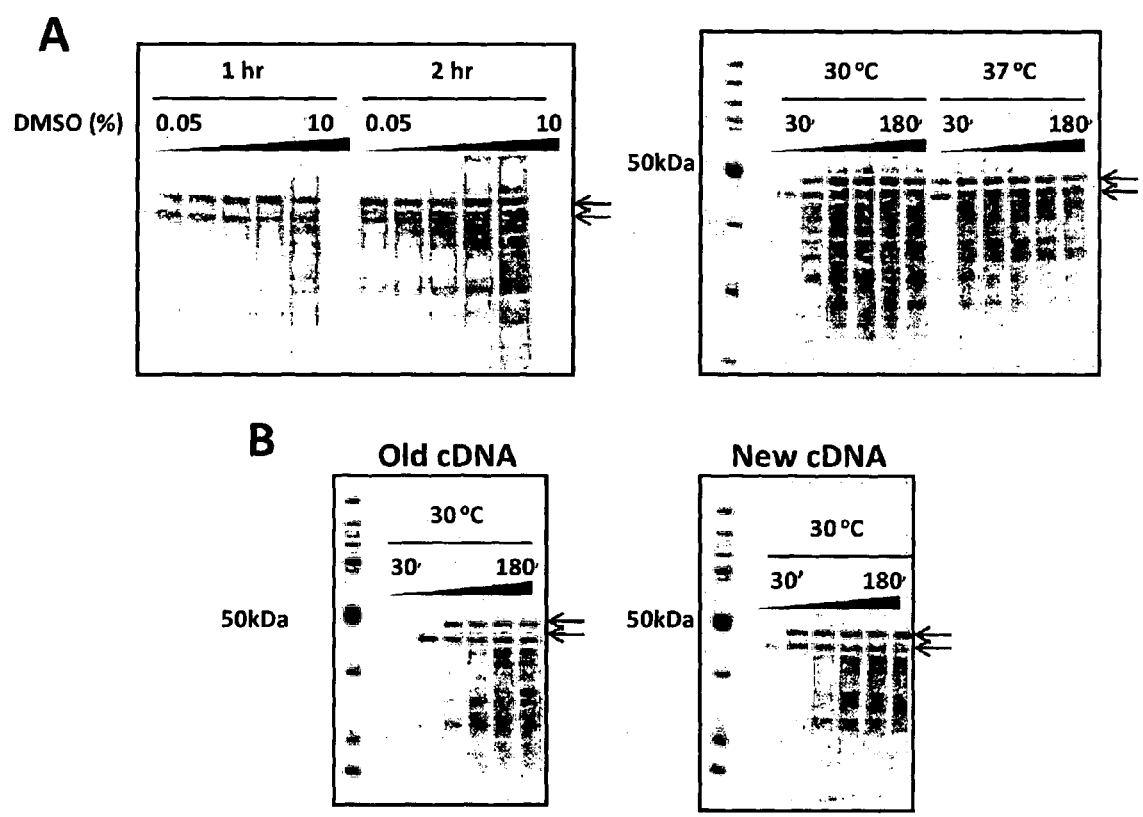
FIG. 12 shows the optimization of p53-FL protein translation using IVT system. (A) Effects of p53wt-FL protein synthesis using 5% DMSO additive under different incubation conditions. (B) Comparison of p53wt-FL protein translation using either old or freshly synthesized PCR cDNA template in IVT system. (C) Effects of varying components A and B (Cosmo Bio Pure System) on in-vitro translated p53. (D) In-vitro translation of Full-length p53 using CosmoBio PURE system at 30° C., with 5% DMSO additive. Top arrows in each figure represent expected full-length p53 protein. Bottom arrows in each figure indicate unfinished p53 product (IVTp53-trunc).
Figure 12:
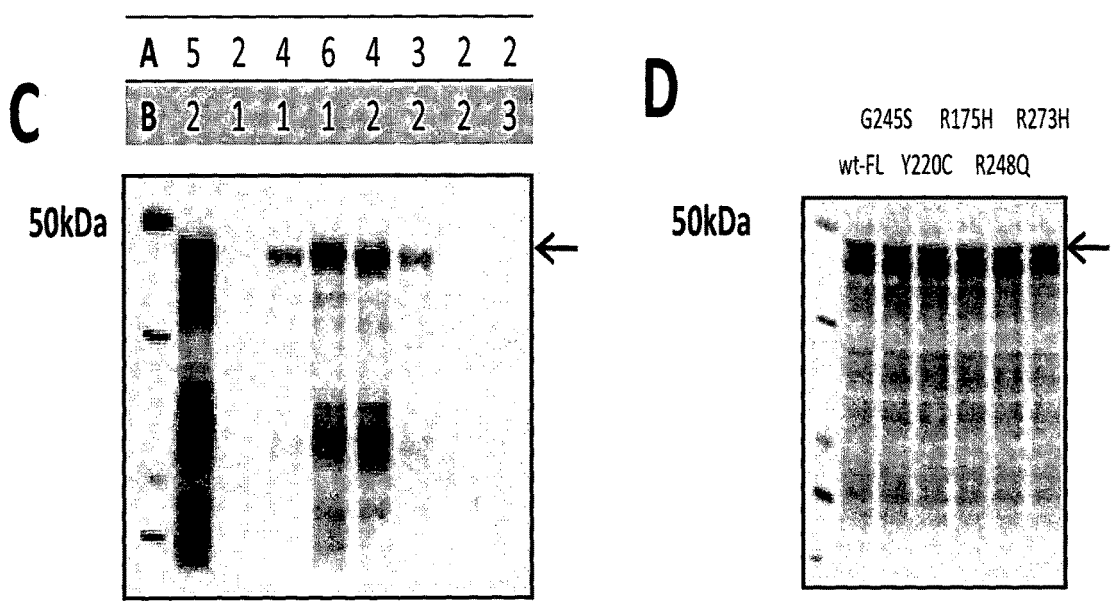

PCR constructs encoding each p53 variant were generated and used for protein synthesis via the PURE system for 2 hours at 30° C., before visualization by western blot. DO-1 western blot of the IVT protein lysates shows p53 protein made at the expected sizes of ~49 kDa for full-length, and ~43 kDa for Δ22 C-terminal truncated constructs (FIG. 11A). While the relative amounts of protein synthesis for the different p53 variants appeared similar, a smaller truncated product of ~42 kDa was observed (migrated at similar size with p53-Δ22 protein). Using an anti-p53 antibody that targets a C-terminal epitope (Bp53-10.1), it was confirmed, using western blot, that the 49 kDa product was indeed a completed p53 product (FIG. 11B). Next, the effects of cDNA template concentration on protein translation were determined by comparing levels of synthesized wt-p53Δ22 over a concentration range of template cDNA (15 ng to 120 ng). Instead of full-length protein, wt-p53Δ22 was selected for this purpose as it gave a single protein product. Western blot analysis using DO-1 showed no significant increase in protein yield when the cDNA template was increased above 30 ng/10 μL IVT (FIG. 11C), prompting the adherence to this template concentration for downstream experiments. Next, we focused on examining the ~42 kDa truncated product (IVTp53-trunc), and investigated if its production can be circumvented. Using western blot, IVT synthesized P53-wtΔ22 was loaded at decreasing concentrations and compared with IVT synthesized p53-wtFL. The result indicated that IVTp53-trunc was slightly smaller than the wt-Δ22 protein (FIG. 11D). This suggested that the IVTp53-trunc product was not due to a premature stop codon, which would otherwise result in a similar truncation in the Δ22 protein lysate. Next, the effects of temperature and IVT incubation duration was examined using a timecourse experiment where the synthesis of p53wt-FL was examined at 30 minutes intervals over 3 different incubation temperatures (24° C., 30° C. and 37° C.). The results showed a transitional appearance of IVTp53-trunc, which accumulated and disappeared with time (after 3 hours) or increased temperature (37° C. IVT) (FIG. 11E). Taken together, the results suggest (possibly due to the lack of certain protein factors in this minimal system) some form of transient and passive translational pausing due to effects pertaining from cDNA or mRNA (possibly due to secondary structures) encoding full-length p53. The effects of DMSO was next tested (conventionally used in PCR reactions to reduce the formation of secondary DNA structures) on IVTp53-trunc by looking at p53wt-FL protein synthesis with increasing amounts of DMSO additive. The results revealed not only an absence of IVTp53-trunc after 2 hours of IVT synthesis (when DMSO used between 0.05%-5%), but a DMSO concentration-dependent increase in protein production (FIG. 12A). The IVT system, however, could not tolerate an addition of 10% DMSO and was completely inactive (FIG. 12A). The observation also supports the hypothesis that the IVTp53-trunc product was due to secondary structures formed by the cDNA or mRNA templates. Comparing the effects of temperature on IVT (FIG. 11E, FIG. 12A right) indicates that translation at 37° C. aided the synthesis of a single full-length p53 product, whereas translation at 30° C. resulted in higher protein yield. The decreased of IVT efficiency at 37° C. was attributed to possible protein aggregation events that retarded the IVT reaction. Because of p53's instability at 37° C. (rate of unfolding in mutant core domains are 40-130 times lesser at 30° C. compared to 37° C.) and the fact that DMSO can partially address the issues with IVTp53-trunc product, we decided to incubated all future IVT reactions at 30° C. in the presence of 5% (v/v) DMSO.

The effects of cDNA template quality on the presence of IVTp53-trunc were also investigated briefly. A comparison between old p53 cDNA (PCR synthesized and left at 4° C. for a week) with freshly PCR amplified p53 cDNA was made by profiling a timecourse (30 minute intervals) of the respective p53-wtFL synthesis at 30° C. The results, analysed via DO-1 western blot, showed an apparent inability, in IVT reactions using 'old' template, for the IVTp53-trunc product to be resolved with time (FIG. 12B left). Protein synthesis in IVT samples using freshly made PCR templates proceeded as expected, with the IVTp53-trunc product almost completely resolved by 3 hours (FIG. 12C right). This further strengthens the notion that the truncated product was due to cDNA secondary structures and demonstrates the sensitivity of DNA template quality when using the CosmoBio PURE system. This has also mandated the appropriate aliquoting and storage of cDNA template constructs for IVT at −20° C.

As the IVT reaction using the CosmoBio PURE system is initiated by reconstituting 2 separate cocktail mixtures (components A and B, in the ratio of 5:2, respectively), protein synthesis and p53-trunc from altering the respective ratios of the cocktail was also examined briefly. Unfortunately, any permutation apart from the manufacturer's prescribed ratio of the 2 components drastically reduced the protein yield (FIG. 12C).

Through the assimilation of the above information, it became possible to translate a relatively clean single full-length protein product for all the p53 variants using the CosmoBio PURE system; a 2 hours incubation at 30° C. using 30 ng of fresh cDNA template with 5% DMSO additive (FIG. 12D).

Assessing the Conformation of IVT-Synthesized p53wt-FL

Figure 13:
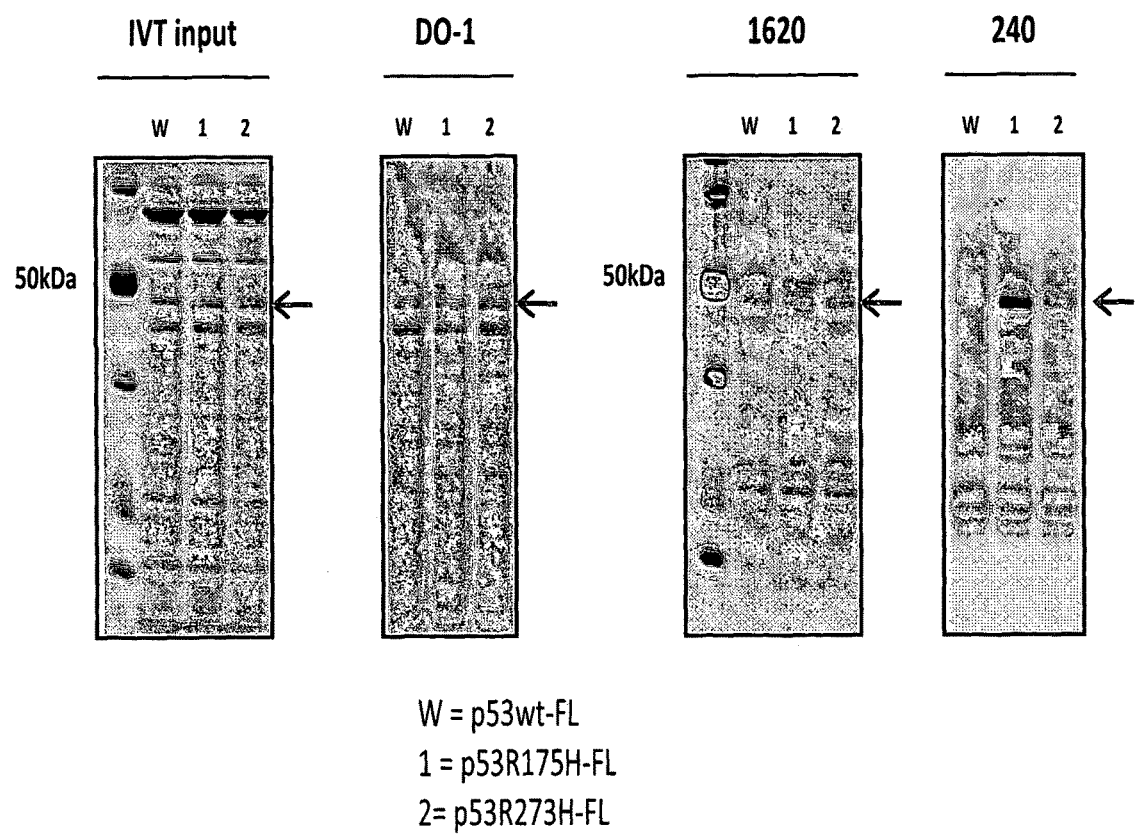
FIG. 13 shows pAb1620/pAb240 immuno-precipitation of IVT synthesized wt-FL, R175H-FL and R273H-FL p53 (W, 1 and 2 respectively).

After synthesizing full-length protein using the current IVT system, we next ascertained if the full-length proteins were in the folded conformation. We performed an immunoprecipitation (IP) using IVT synthesized p53 by immunocapturing p53 protein on magnetic protein-G beads coated with either (1) DO-1 antibody which targets p53 Ntd and is insensitive to protein conformation, (2) Pab240 antibody which detects a buried linear epitope only exposed when the protein core domain is totally unfolded, or (3) Pab1620 antibody targeted at a native epitope present when the core is properly folded. Additionally, we included IVT synthesized R175H-FL (a globally unfolded mutant bearing the Pab240 epitope) and the R273H-FL (a contact mutant with similar conformation as wild-type p53) mutants as additional controls. Proteins eluted off the beads were analysed via western blot using a rabbit polyclonal anti-p53 antibody (CM1). The result showed an expected presence of Pab1620 epitopes in both p53wt-FL and R273H-FL mutant, at similar levels, but not in the R175H-FL IP (FIG. 13). As expected, the level of Pab240 epitope was also high in the IVT-synthesized R175H-FL mutant. Interestingly, IVTp53-trunc product, which was present in this IP experiment (detected in the input and DO-1 blot), was not detected by either conformation sensitive antibodies (FIG. 13). Our results here indicate that the CosmoBio PURE IVT system is capable of synthesizing full-length p53 with expected conformations.

Quantifying IVT-Synthesized p53 Protein Concentration

Because we had to determine the concentration of p53 within a cocktail of IVT proteins, a sandwich ELISA approach was adopted, whereby WT-synthesized p53 is measured against a standard curve using purified p53 of a known concentration. The reference protein used is a purified full-length variant of the p53 wild-type protein which contains 4 stabilizing mutations within the core domain (p53QM-FL), but is otherwise conformationally identical to wild-type p53. We first checked the purity and concentration of the purified p53QM-FL (obtained from a collaborating lab, Alan Fersht, Cambridge), which was determined to be 30 μM in Cambridge. We separated the purified p53QM-FL protein together with titrated BSA standards using polyacrylamide gel-electrophoresis (PAGE) and visualized the protein using Coomasie staining (FIG. 14A). The results displayed a clean product that migrated at the expected size of ~49 kDa with an estimated concentration between 1-1.5 mg/mL (by visual comparison to BSA standards). We then further quantified the purified protein via the Bradford reagent by measuring against a standard concentration curve using BSA standards (FIG. 14B). Using this method, the measured protein concentration was ~1.35 mg/mL which is equivalent to a molar concentration of ~31 μM (p53 $M_w$=43.6 kDa), hence confirming the concentration of 30 μM measured before.

We diluted the purified p53QM-FL protein with equal amounts of the IVT mixture (to account for background non-specific protein-protein binding) to cover a concentration range of 0.3 nM-30 μM and used it to construct 2 standard curves, each by capturing p53 onto plates immobilized with anti-p53 mouse monoclonal antibodies (DO-1 and Bp53-10.1), and detecting with rabbit polyclonal CM-1 anti-p53 antibodies. IVT-synthesized p53 (wild-type FL and Δ22, with or without DMSO) was also concurrently measured using the luminescence plate reader and its concentration determined by extrapolation using the 2 standard curves (FIG. 14B). A western blot (DO-1) of the same IVT-synthesized p53 samples used for ELISA quantification was also used as reference for the concentration estimate (FIG. 14C—right inset). The showed that the concentration estimates for full-length protein (with and without DMSO) was similar using both antibodies (86 nM versus 72 nM, and 310 nM versus 273 nM), confirming the accuracy of the measurement. Additionally, as expected, measurements on the DO-1 plate indicated higher concentrations then on Bp53-10.1 plate, as DO-1 targeted p53 Ntd and hence measured all unfinished protein products. Also consistent with all other results before, DMSO addition causes a significantly higher protein yield and was reflected in the quantification results (FIG. 14C—table).

Finally, an estimated range of the respective concentrations were made based on the plate ELISA measurements (including standard deviation) as well as the western blot, and included in FIG. 14C—table.

Results

We have ascertained that the CosmoBio PURE system is capable of synthesizing full-length p53 proteins that adopt expected conformations based on its coding sequence. However, due to the 'minimalistic' nature of the IVT system in use, several conditions including additives were essential to translating proper p53. In addition, we also managed to determine a relatively accurate estimate of IVT-synthesized p53 concentrations. The presence of a transient IVTp53-trunc protein product (which was only noticeable in a specific window of time) carrying neither the Pab1620 nor the Pab240 epitope was an extremely interesting observation. Its presence suggests that conformational states between folded and unfolded forms of p53 can exist, and may manifest as multiple forms in nature. Furthermore, it also demonstrates how invaluable IVT systems can be to studying certain biochemical occurrences.

Example 3

In Vitro Characterization of p53-Activating Peptides

Materials and Methods

According to the IVC selection scheme, the peptides will need to fulfill two conditions to be considered functionally active; (A) they need to interact physically with the mutant p53 either during or after protein synthesis and (B) somehow instill or restore sequence-specific DNA binding functions to the mutant p53. Accordingly, this example involves determining if the peptides bind to mutant and wild-type p53, and if that binding results in an increase in wild-type conformation.

Using ELISA to Probe for Interaction Between Peptides and p53

As we wanted to translate p53 proteins in the presence of the peptides, we first tested if any of the free peptides might somehow lead to an increase in protein translation and potentially manifest as false positive results. DO-1 western blot of IVT-synthesized wt-FL p53 showed no changes in levels of protein translation when tested with any of the 6 peptides (FIG. 15A), indicating that none of the peptides interacted non-specifically with the IVT components. To ascertain if a physical association exists between peptide and p53, we took an ELISA approach but designed three different experimental conformations to test our hypothesis (FIG. 15B). For this purpose, we synthesized two additional sets of peptides, each with either a biotin molecule attached to the Ntd (designated as biotin-peptide), or the Ctd (designated as peptide-biotin).

Figure 16:
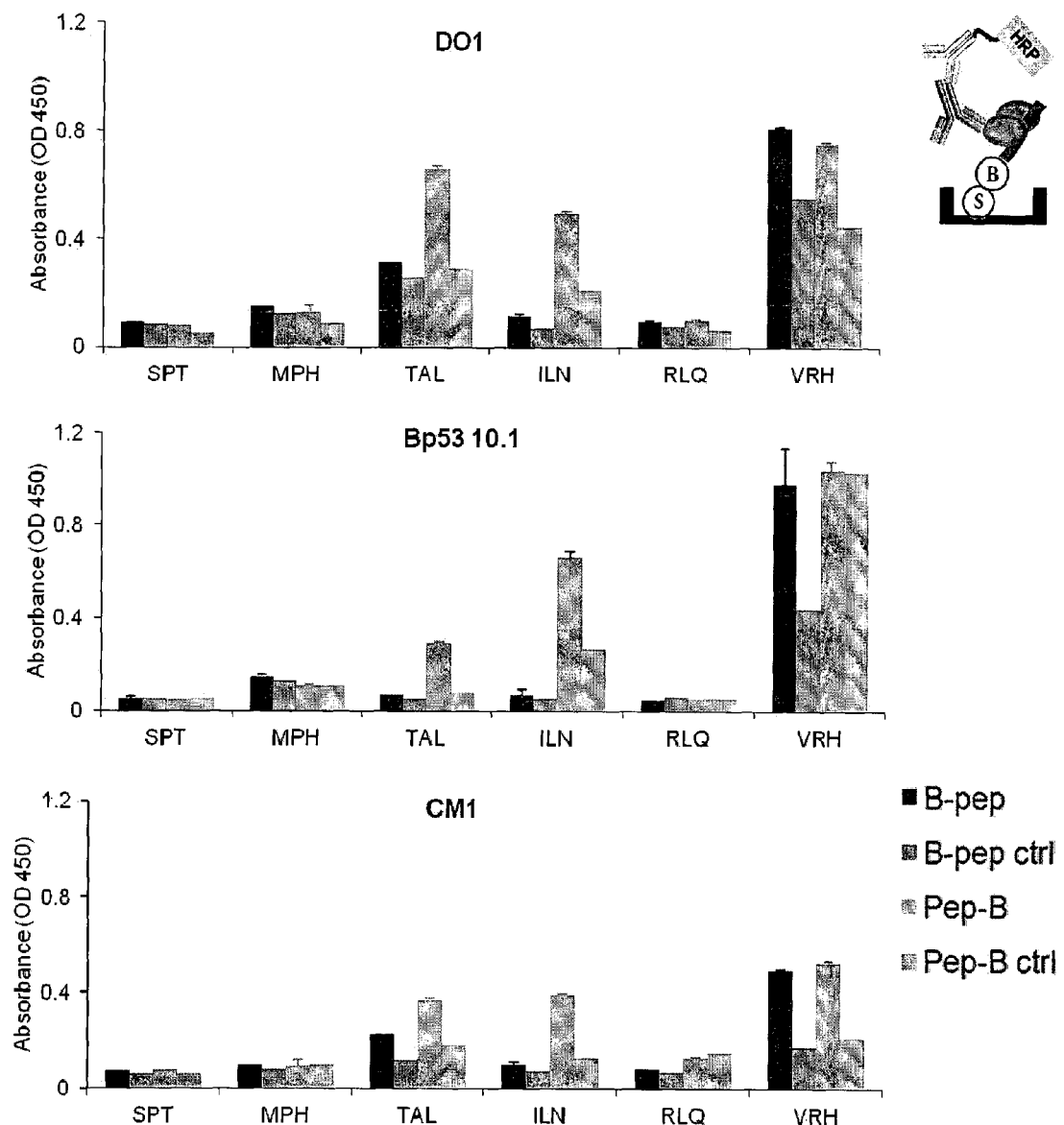
FIG. 16 shows the molecular interaction between biotinylated peptide and IVT synthesized p53wt-FL via ELISA conformation-1 (Top right inset), using 3 different anti-p53 primary antibodies (DO-1, Bp53 10.1 and CM1). Biotin moiety either on Ntd (B-pep) or Ctd (Pep-B), represented by the first and third bars of each group, respectively. Adjacent bars show respective background control binding (no p53 extract). Error bars show S.D. of 2 independent data points.

We first examined if there were any interaction between p53wt-FL protein and any of the 2 sets of biotinylated peptides using ELISA conformation 1 (FIG. 15B1). In this conformation, p53wt-FLprotein was synthesized using IVT in the absence of peptides and incubated on streptavidin coated plates pre-coated with the biotinylated peptides. P53-peptide complexes formed are then detected with anti-p53 antibody, developed and read using a luminescence plate reader. Additionally, three different antibodies (anti-p53 Ntd DO-1, anti-p53 Ctd Bp53-10.1 and anti-p53 polyclonal CM-1) were used to discriminate possible false positive events in which a peptide interacted with a particular antibody. The results showed that wells containing peptides Pap-TAL (maximum of 4-fold increase), Pap-ILN (maximum of 3.5-fold increase), and Pap-VRH (maximum of 2.5-fold increase) (FIG. 16) gave significantly higher when compared to control wells (same setup except incubated with p53 deficient IVT mixture). The three different set-ups each using a different antibody also gave similar trend of results, suggesting a real p53-dependent interaction. Interestingly, the peptides seemed to display different modes of interaction; Pap-ILN and Pap-TAL displayed higher levels of binding with C-terminal biotin modification (peptide-biotin), whereas Pap-VRH showed no preference for either biotin attachments (FIG. 16). The lower signal from N-terminal biotinylated Pap-ILN and Pap-VRH could have resulted from either (i) an interaction between peptide and p53 such that the biotin is inaccessible for binding to streptavidin plate, (ii) the presence of an N-terminal biotin moiety may disrupt binding between peptide and p53, or both. In both cases, the data strongly suggest that p53wt-FL interacts mainly with the N-terminal end of peptides Pap-ILN and Pap-TAL.

Figure 2:
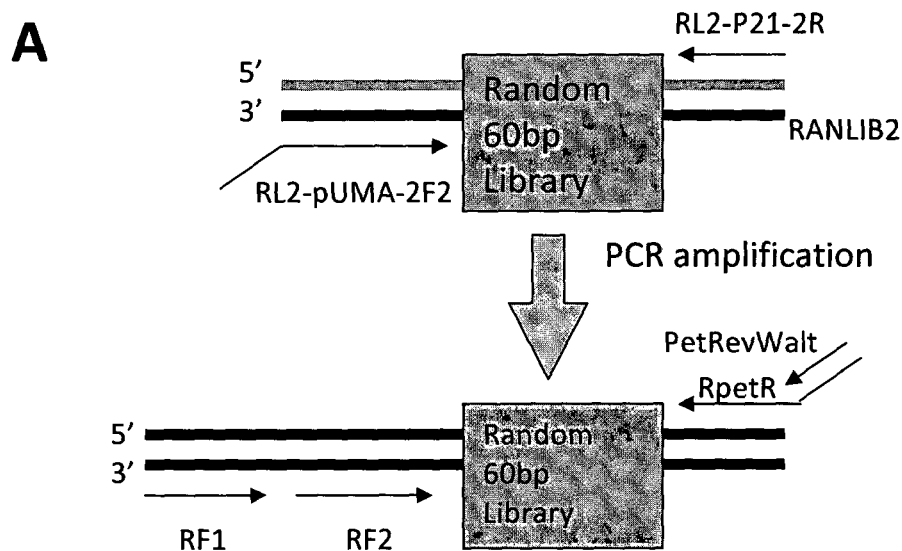
FIG. 2 shows the construction of a random library. (A) Schematic showing library construction using various oligonucleotides. (B) Detailed DNA sequence of random library fragment showing internal transcriptional elements and flanking p53 response elements needed for selection process (SEQ ID Nos:117 and 118). (C) Sybr green stained DNA gel showing migration of random library PCR product at expected size of ~150 bps. (D) Sybr green stained DNA gel of various PCR product carrying mutant p53 gene. (E) Western blot of p53 protein using DO-1 anti-p53 antibody. P53 protein synthesized using Novagen Eco-Pro IVT kit and PCR template (F) Sequence alignment of random library Ranlib2 showing DNA randomization only within peptide reading frame (SEQ ID Nos:119-123).
Figure 2:
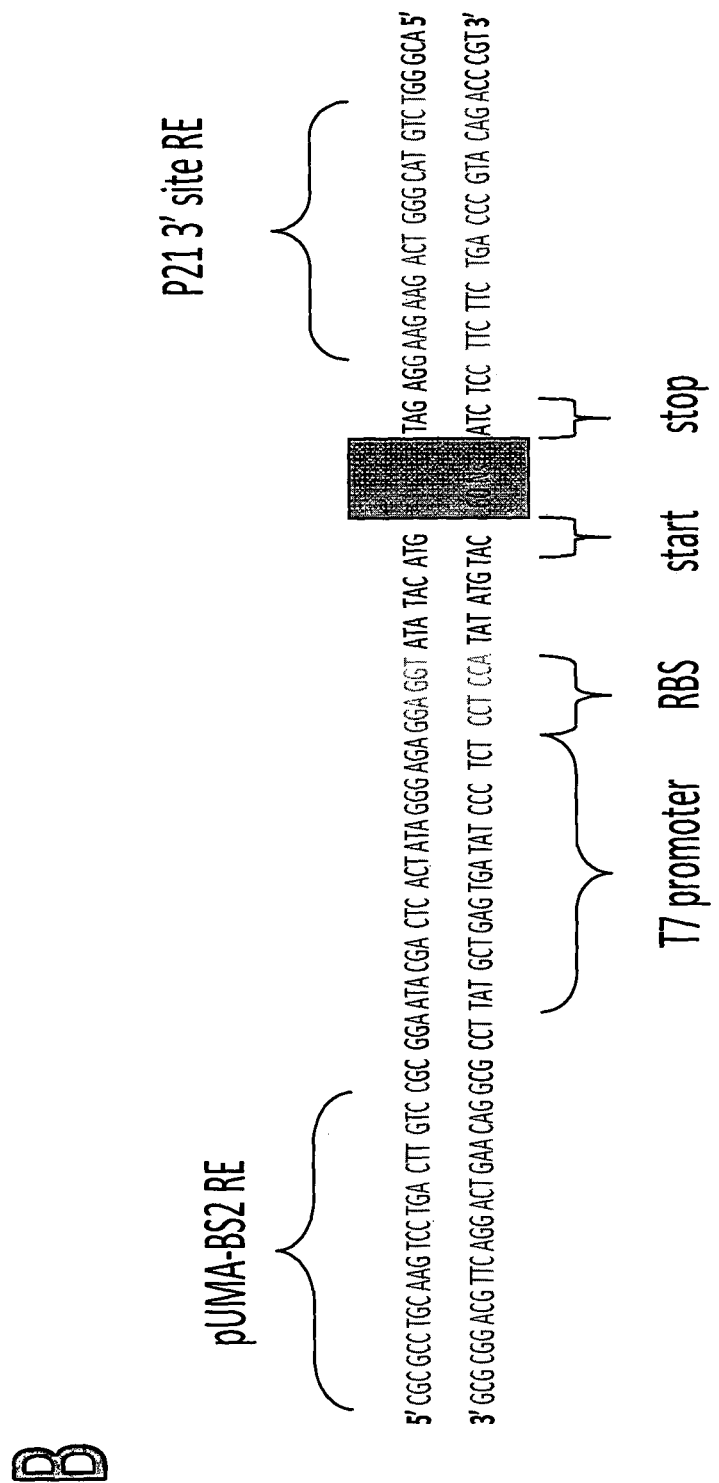
Figure 2:
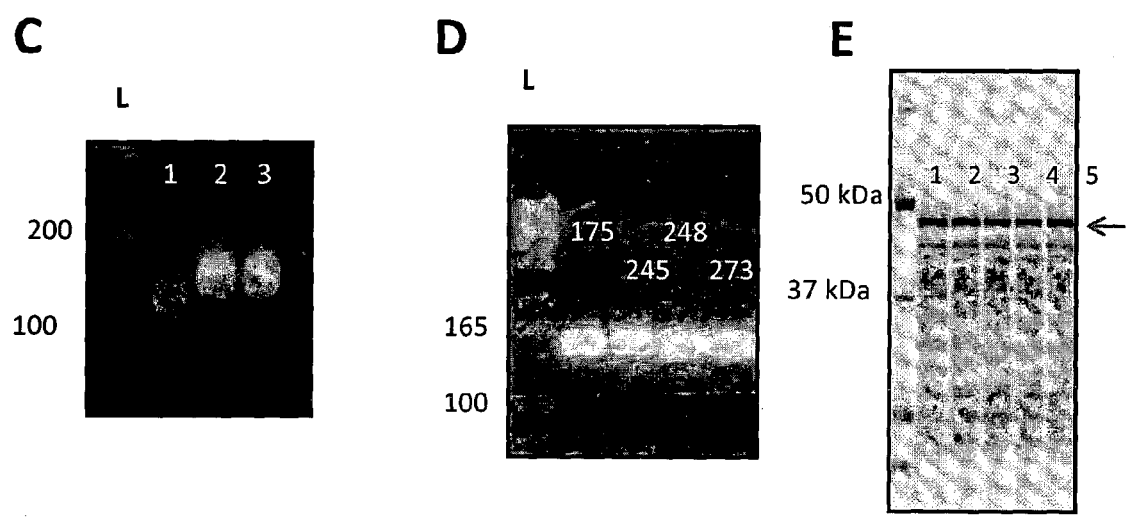
Figure 2:
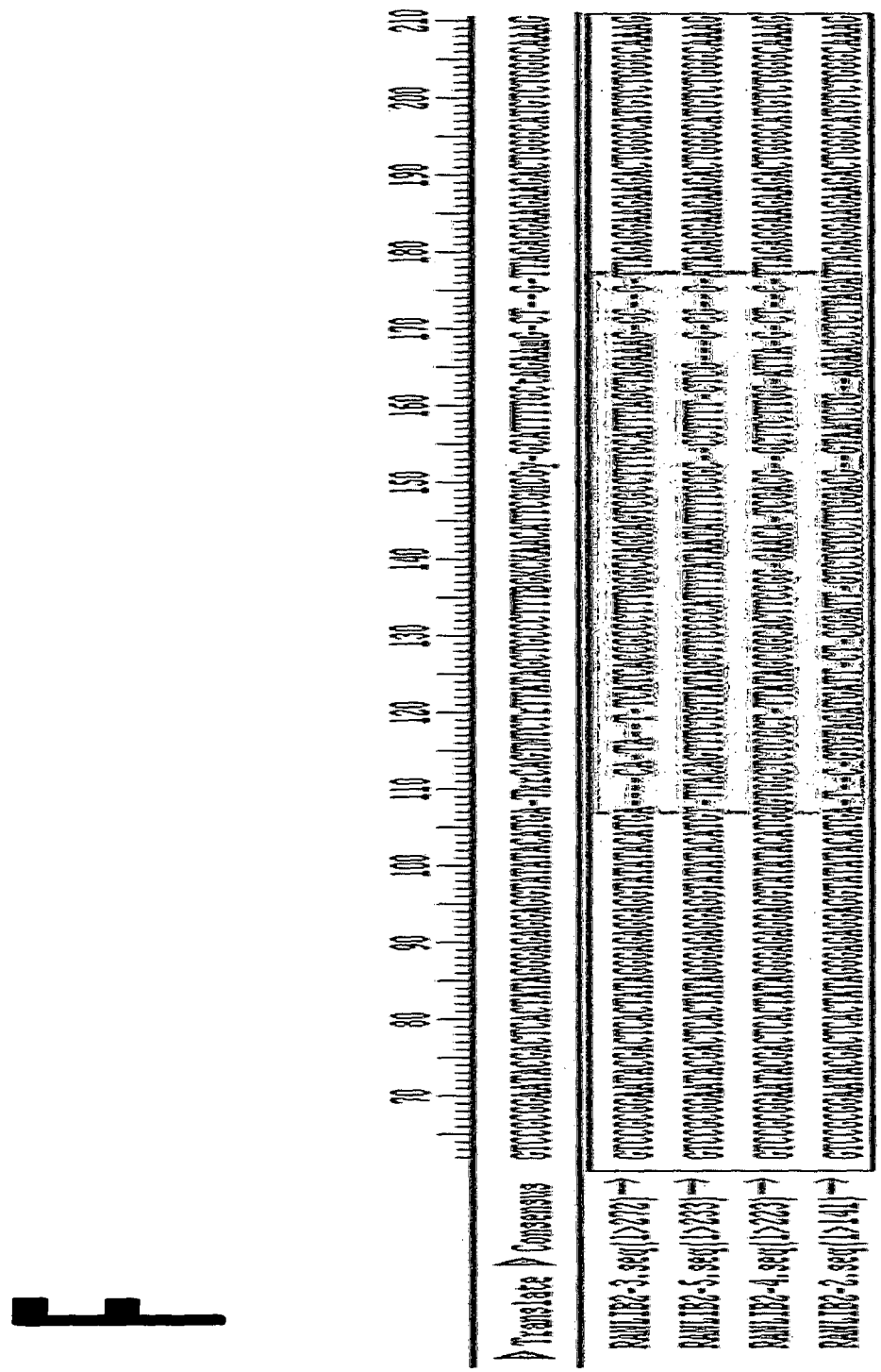

After establishing an interaction between wild-type protein and several peptides, we next focused on detecting this interaction in mutant p53 proteins. p53 mutants are IVT-translated with increasing concentrations of the respective peptide, incubated on the streptavidin plate, and detected using an anti-p53 primary antibody, followed by an HRP-conjugated secondary antibody (FIG. 15B2). Data was interpreted as fold-increase over 'mutant only' negative control (which was assigned a value of 1). Also included was a 'no-p53' control, where background binding was measured using 200 μM of peptide in blank IVT extract. Initial results, using DO-1 primary antibody, p53 mutants are IVT-translated with increasing concentrations of the respective peptide, incubated on the streptavidin plate, and detected using an anti-p53 primary antibody, followed by a HRP-conjugated secondary antibody (FIG. 15B2). Data was interpreted as fold-increase over 'mutant only' negative control (which was assigned a value of 1). Initial results, using DO-1 primary antibody, showed a concentration dependent response in peptide-p53 binding for all the peptides, except Pap-TAL (FIG. 17E—Top) and Pap-VRH (FIG. 17F—Top), which displayed high levels of background peptide binding in the absence of p53 (peptide only control). A true peptide-p53 interaction for these two peptides only became apparent when a different primary detection antibody was used (Bp53-10.1) (FIG. 17E—Bot and FIG. 17F—Bot, respectively), possibly suggesting some degree of DO-1 (or antibody subtype) recognition evolved in these peptides (as DO-1 was used in the selection process). Additionally, IVT-p53 protein were analyzed using western blot (DO-1), and showed comparable levels of p53 when each mutants were IVT-synthesized with either DMSO blank, or 100 μM of the respective biotin-peptides (FIG. 17A-F, inset).

Figure 17:
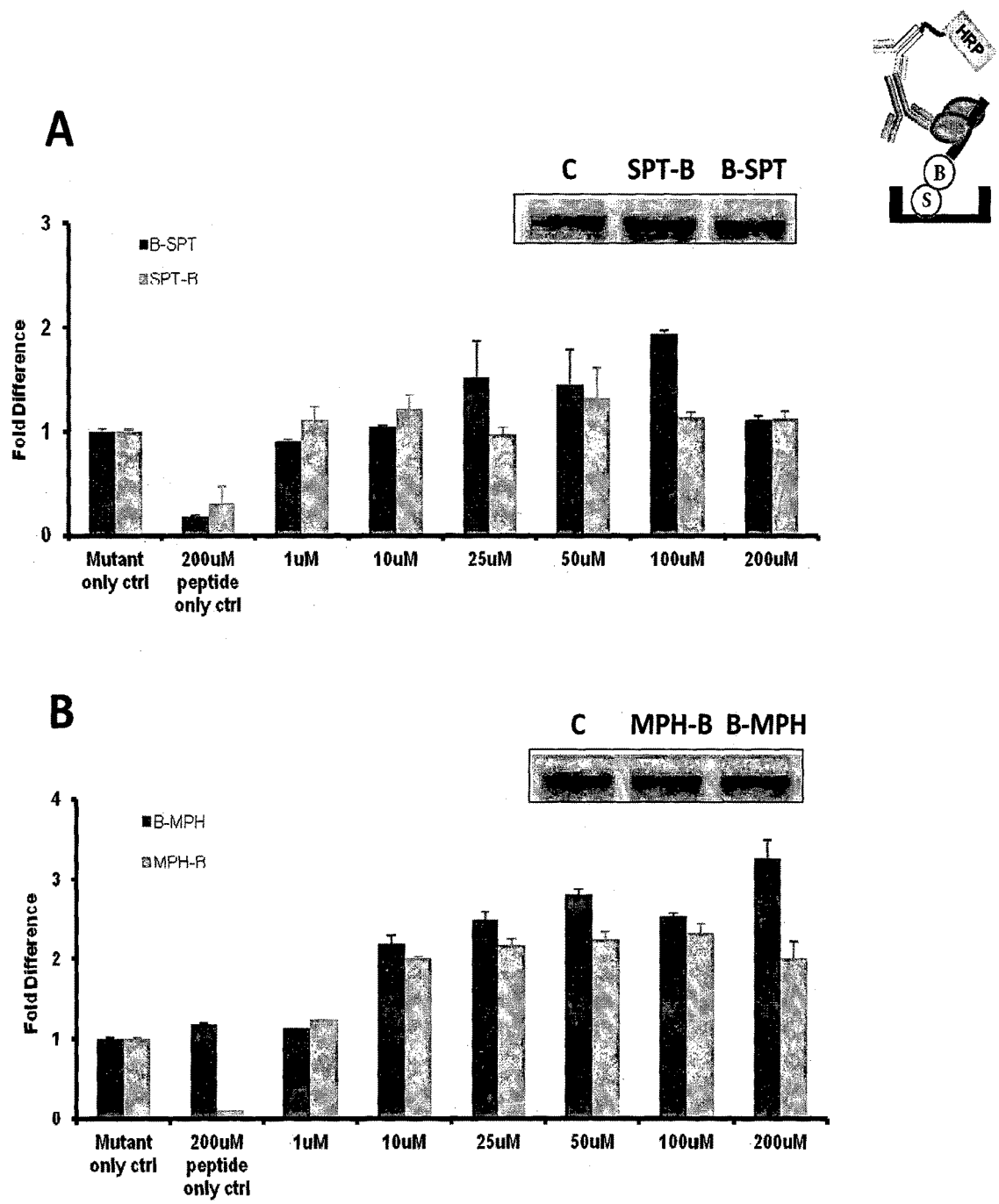
FIG. 17 shows the interrogation of the interaction between biotinylated peptides and IVT synthesized mutant p53 via ELISA conformation-3 (Top right inset), using different anti-p53 detecting antibody. Dark and light shades of bars represent biotin modification on either Ntd or Ctd, respectively. Western blot inset adjacent to graph shows representative effect on p53 translation in the presence of respective peptides. Data is normalized to p53 mutant only control (value of 1). Error bars show S.D. of 2 independent data points. (A) (Top) Interaction between G245S-FL and Pap-SPT, detected via DO-1 antibody. (B) Interaction between G245S-FL and Pap-MPH, detected via DO-1 antibody. (C) Interaction between R248Q-FL and Pap-ILN, detected via DO-1 antibody. (D) Interaction between R273H-FL and Pap-RLQ, detected via DO-1 antibody. (E) (Top) Interaction between R273H-FL and Pap-TAL, detected via DO-1 antibody. (Bot) Interaction between R273H-FL and Pap-TAL, detected via Bp53 10.1 antibody. (F) (Top) Interaction between R273H-FL and Pap-VRH, detected via DO-1 antibody. (Bot) Interaction between R273H-FL and Pap-VRH, detected via Bp53 10.1 antibody.
Figure 17:
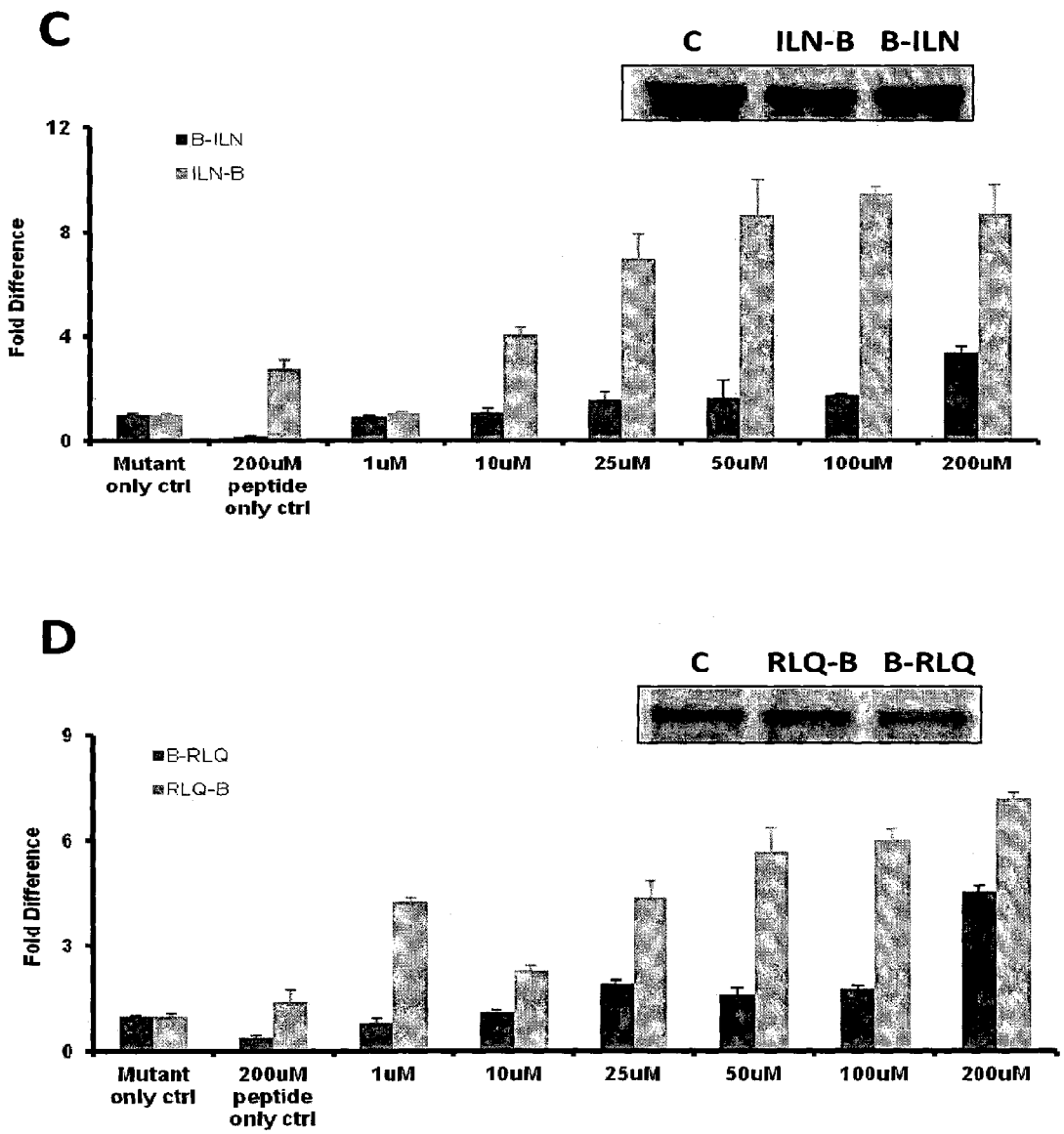
Figure 17:
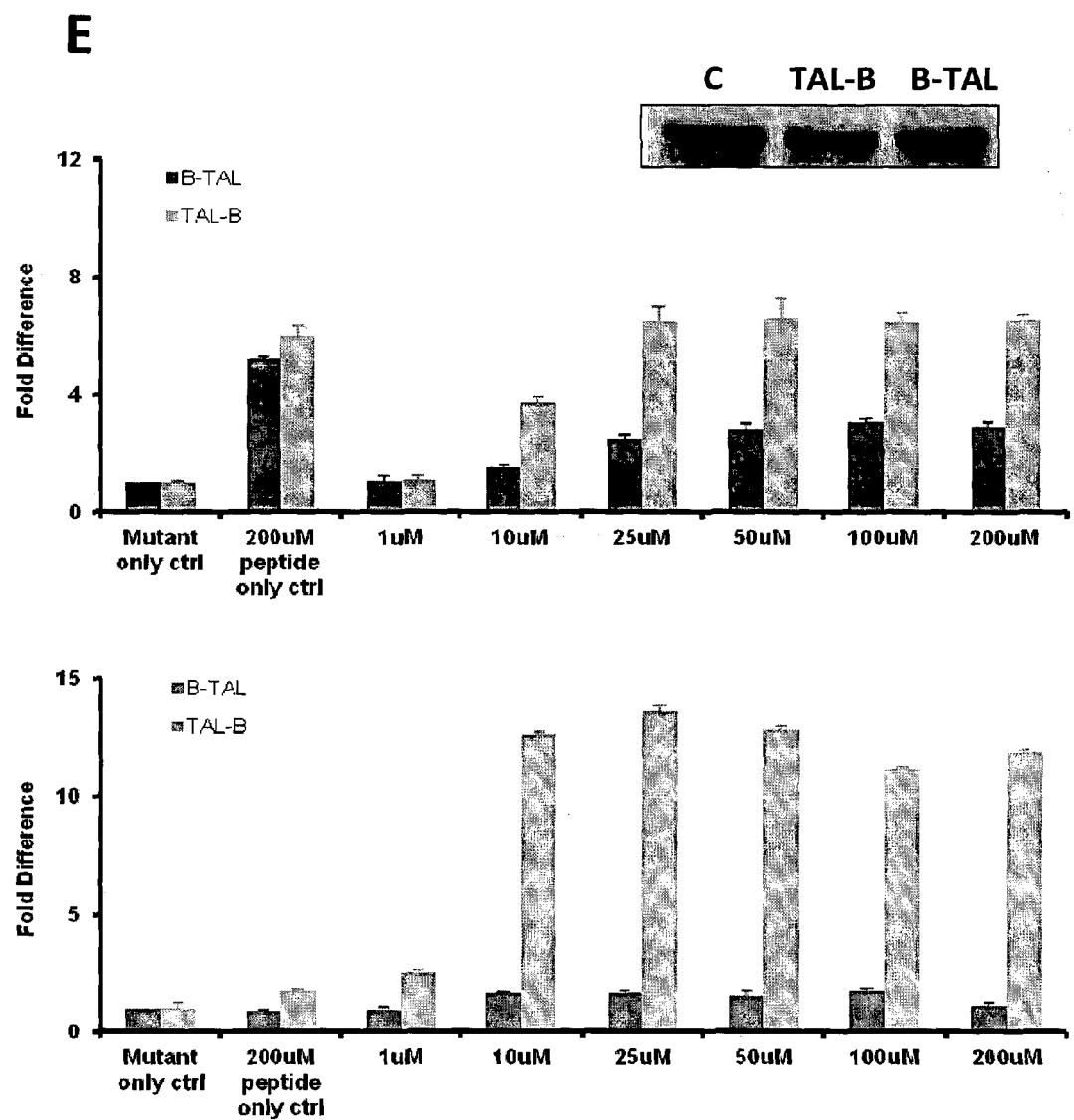
Figure 17:
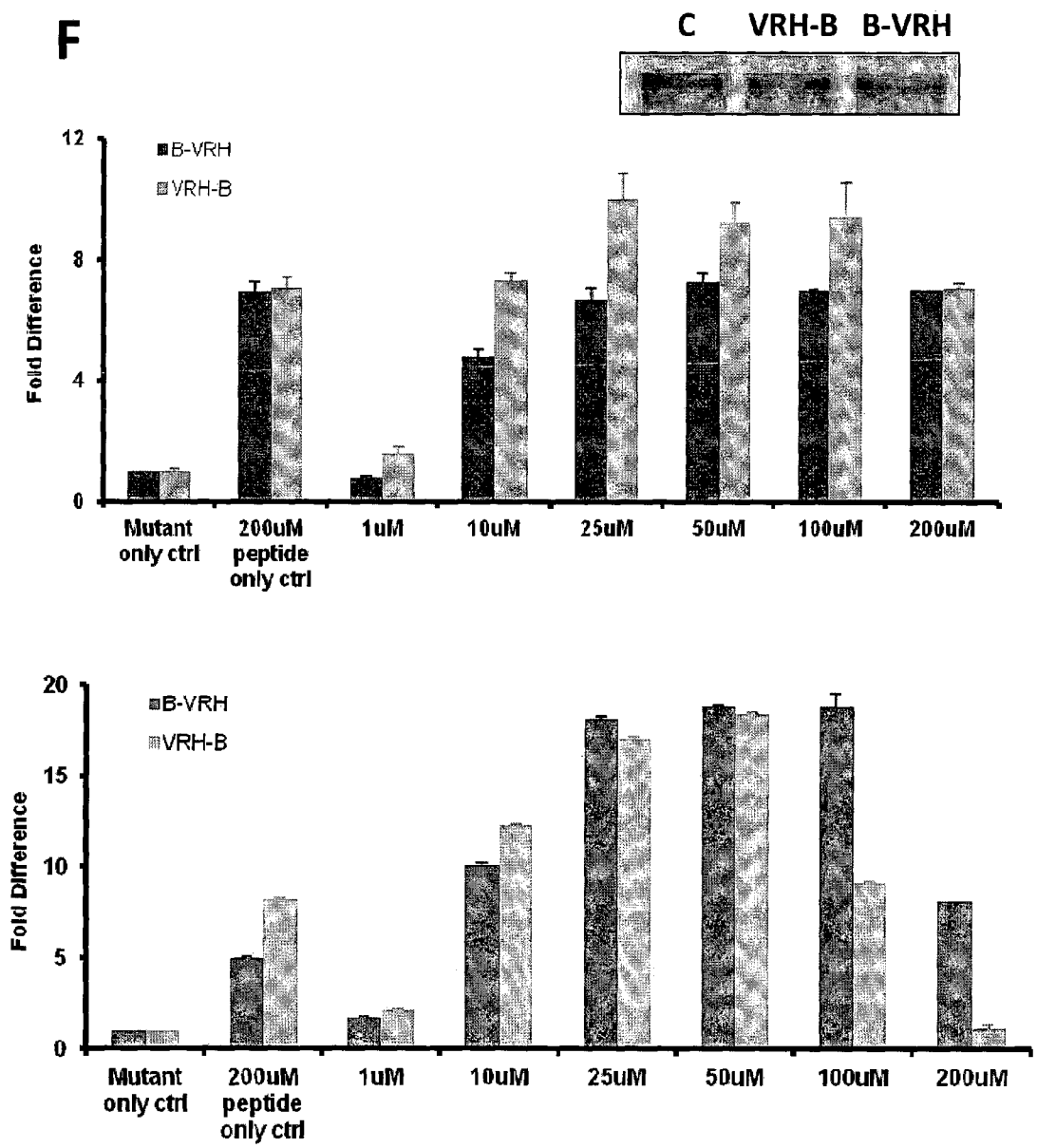

Both peptides selected for p53-G245S-FL mutant interacted comparatively weakly in this assay; Pap-SPT pull-downed a 2-fold increase, and Pap-MPH a 3.5-fold increase of mutant p53 protein (FIG. 17A-B). The interaction between Pap-ILN and R248Q-FL was more appreciable (over 8-fold increase at 50 μM, FIG. 17C), even though some degree of peptide-antibody interaction was detected (~2-fold increase at 200 μM peptide, FIG. 17C). Pap-RLQ also interacted with p53-R273H-FL, displaying a ~4.5-fold increase in binding at 25 μM which increases to ~8-fold at 200 μM (FIG. 17E). As Pap-TAL interacted strongly with the DO-1 antibody and was masking the detection of any real potential interaction (over 5-fold increase at 200 μM, FIG. 17E), the experiment was repeated with Bp53-10.1 antibody (which did not interact with Pap-TAL) and displayed a strong interaction, of ~13-fold increase at 0.10 μM peptide, between Pap-TAL and p53-R273H-FL proteins (FIG. 17E—Bot). Background issues arising from peptide-antibody interaction was also apparent between Pap-VRH and DO-1, and could only be partially eliminated by using. Bp5310.1 (FIG. 17F—Top). The background was however, decreased substantially to discern a decent level of interaction between p53-R273H-FL and Pap-VRH (~18-fold over 'no-p53' control and 10-fold over '200 μM 'peptide-only' control, at 25 μM) (FIG. 17F—Bot). A summary of these results are tabulated in Table 12.

Figure 18:
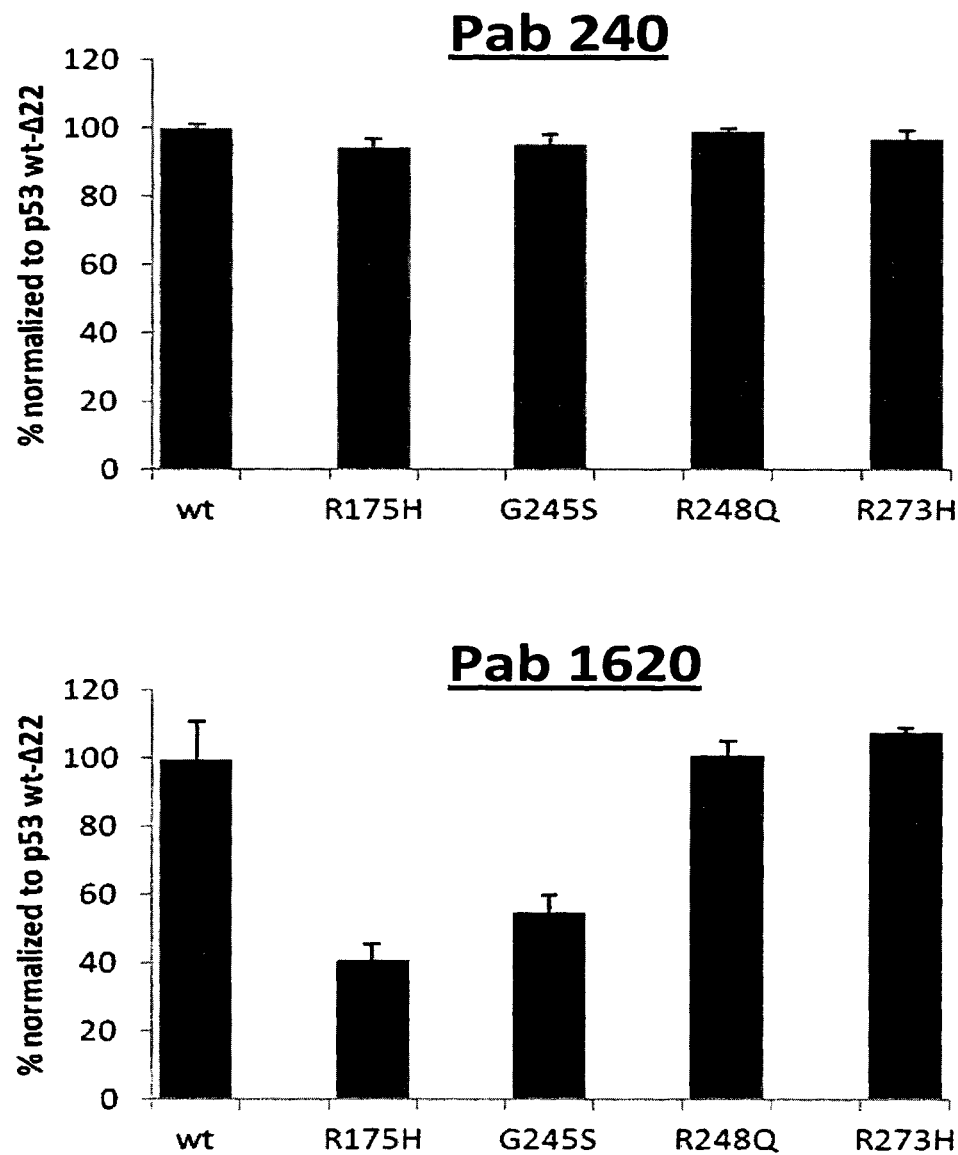
FIG. 18 shows (A) the assessment of p53 conformational stability through detection of conformational sensitive epitopes using capture antibodies Pab 240 (linear epitope indicative of unfolded state), and Pab 1620 (native epitope indicative of folded state) on ELISA. Data was either normalized to, and represented as a percentage of wt-Δ22 (A), or normalized to and represented as percentage of DMSO control in the absence of peptides. Error bars show S.D. of 2 independent data points. (A) Respective baseline levels of detectable 240 (top bars) and 1620 (bottom bars) epitopes on freshly IVT synthesized p53-Δ22 (30° C. for 2 hours). (B and C) Levels of 240 and 1620 epitopes when different p53-Δ22 is IVT synthesized in the presence of 100 µM of each peptide. Amounts of DO-1, Pab 240 and Pab1620 epitopes detected are represented by the left, middle and right bars of each group respectively. DO-1 values were first normalized to DMSO control across each data set before Pab240 and Pab1620 values were further normalized to their respective DO-1 value within peptide-specific data-subsets.
Figure 18:
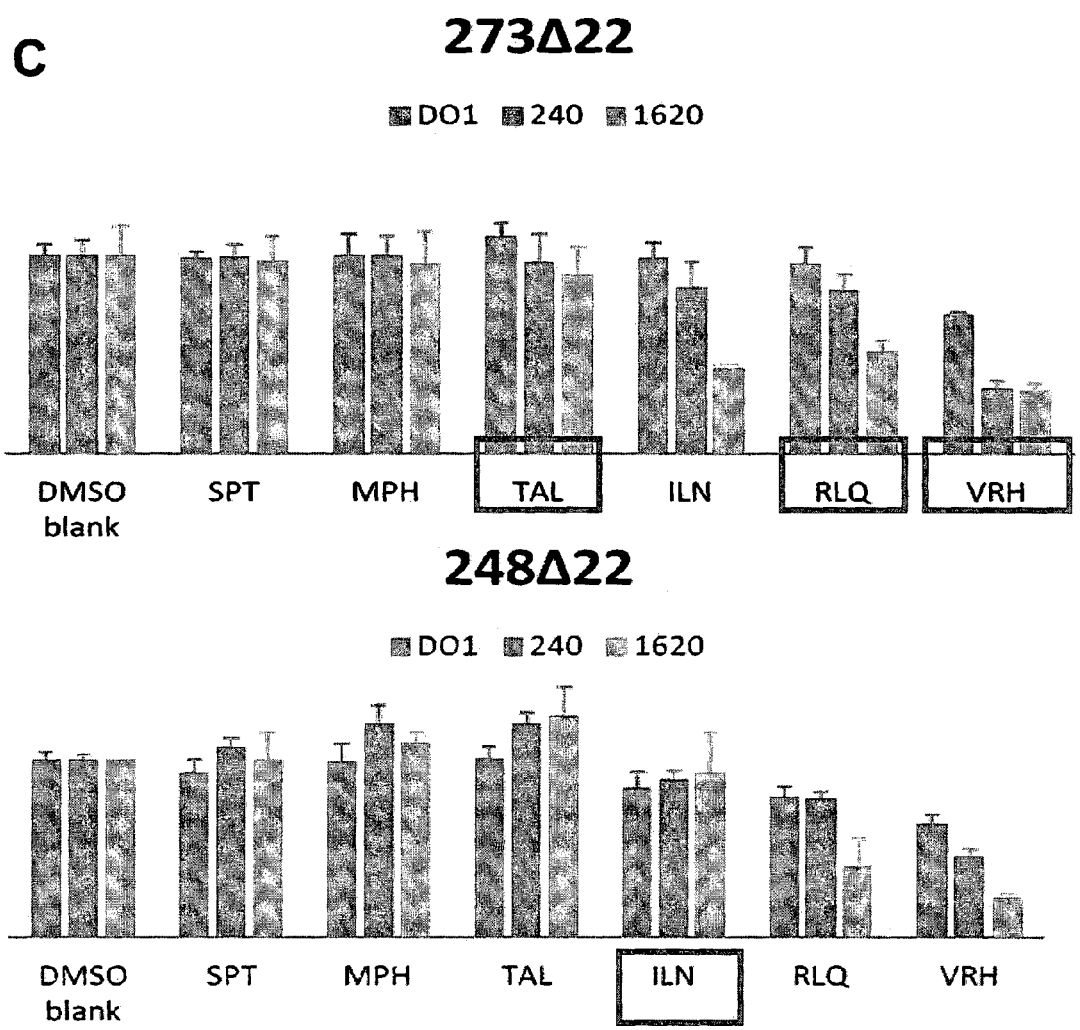

As expected, results from the Pab1620 control experiment placed the R175H and R273H at opposite ends of the spectrum in terms of Pab1620 epitope presence (40% and 100% of wild-type, respectively, FIG. 18A), with the G245S mutant in the middle with 55% compared to wild-type protein. Data from Pab240 pull-down indicated similar levels for all samples (FIG. 18A). This could be due to high levels of Pab240 epitopes in IVT-synthesized p53 (present also in unfinished and nascent protein products), or indicative of higher epitope affinity from the Pab240 antibody. In either case, the Pab240 antibody working concentration was doubled to increase the detection threshold.

We then repeated the experiment but translated each p53-Δ22 variant in the presence of either DMSO (as peptide blank control), or 20 μM of a specific p53-activating peptide. Within each experiment (each p53 variant), data sets pertaining to the pull-down using a particular antibody (DO-1, Pab240 or Pab1620) were represented as a normalized value to their respective 'DMSO blank' controls. Data from DO-1 pull-down in each sample acted as a benchmark and control for protein levels, as well as possible peptide-induced perturbations in p53-antibody interactions. Just by comparing all data sets, a striking trend emerged in which peptides Pap-SPT and Pap-MPH had little to no effect on the presence of both epitopes, and Pap-RLQ and Pap-VRH resulted in a drastic reduction in Pb1620 epitopes accompanied by a slight reduction in Pab240 epitopes (FIGS. 18B and C). This could suggest a mechanism whereby peptides Pap-RLQ and Pap-VRH targets the p53 core domain and actuates a con-

TABLE 12

Summary of peptide-p53 interaction via ELISA.

| Peptide reference | p53 mutant | Lowest effective concentration (μM) | Maximum fold binding | Binding preference for peptide terminal (level) | Region of p53-peptide preference |
|---|---|---|---|---|---|
| Pap-SPT | G245S | 25 | 2 | No | — |
| Pap-MPH | G245S | 25-50 | 4 | No | — |
| Pap-TAL | R273H/G245S | 10 | 14 | Yes (strong) | Ntd |
| Pap-ILN | R248Q | 25 | 9 | Yes, (strong) | Ntd |
| Pap-VSW | R248Q |  | - Not assessed - |  |  |
| Pap-RLQ | R273H | 25 | 7 | Yes (moderate) | Ntd |
| Pap-VRH | R273H | 25 | 18 | No | — |

We observed the trend of a distinct binding preference for C-terminal biotin modification, as opposed to N-terminal modification, for peptides Pap-ILN and Pap-TAL. This may suggest that the region of peptide-p53 interaction lay predominantly in the N-terminal of these peptides.

Assessing Peptide Induced Conformational Changes in Mutant p53 Using Pab240 and Pab1620 Antibodies Since we have established a physical interaction between all the peptides and the full-length mutants they were selected for, we now ask the question if this interaction led to an increase in conformational stability (as determined by the presence of Pab1620 epitope). To achieve this, we IVT-translated full-length p53 proteins, incubated the p53-WT mixture with either Pab240 or Pab1620 antibody, and captured the p53-antibody complexes onto commercial protein-G plates before detecting via CM-1 antibody. Data for all samples were normalized to p53wt-FL which was assigned an arbitrary 100%. As changes in the levels of Pab240 and Pab1620 epitopes will most likely revolve around structural changes residing within the p53 core domain, we decided to use the C-terminal truncated p53-Δ22 variants in the following assays.

formational change. Similarly, the seemingly innocuous effects from Pap-SPT and Pap-MPH may be indicative of non-core interactions, or the requirement of p53 C-terminal presence for peptide-induced activity or interactions. Notably, the panel of peptides induced a very similar Pab240/Pab1620 response in both wt-Δ22 and R273H-Δ22 p53 proteins, suggesting consistency in the interaction mechanism of the peptides in this respect. The effect of this concurrent decrease in Pab240 and Pab1620 epitopes is also induced by Pap-ILN for all p53 variants except, interestingly, the mutant (R248Q) it was selected for (FIGS. 18B and C). This may imply mechanistic differences in the function exerted by a specific peptide depending on the conformation, or predominant conformation, of the target p53. One anomaly, however, is the decreased signals for all three antibody epitopes in mutant p53 samples translated with Pap-VRH (FIGS. 18B and C). As we saw from earlier results, there were no changes in levels of mutant WT protein translation even in the presence of 100 μM of Pap-VRH (FIG. 17F—inset), leading us to conclude the possibility that the peptide, which displayed affinity towards antibodies (high background for both DO-1 and Bp53-10.1, FIG. 17F) was interfering with p53-antibody interactions.

Using Thermal Shift Assays to Determine Possible Peptide-Induced Changes in Thermal Stability.

Thermal shift assay is a fluorescence-based technique, employed to determine the apparent melting temperature ($T_m$) of a target protein. Purified target proteins are mixed with a protein binding dye (SYPRO), and exposed to thermal denaturation through gradual and small increments in temperature (typically 0.5° C.-1° C.). As protein unfolds in response to the rising temperature, the SYPRO dye binds non-covalently to the exposed hydrophobic regions, and fluoresces, allowing a real-time measurement of protein thermal stability, and $T_m$.

Figure 19:
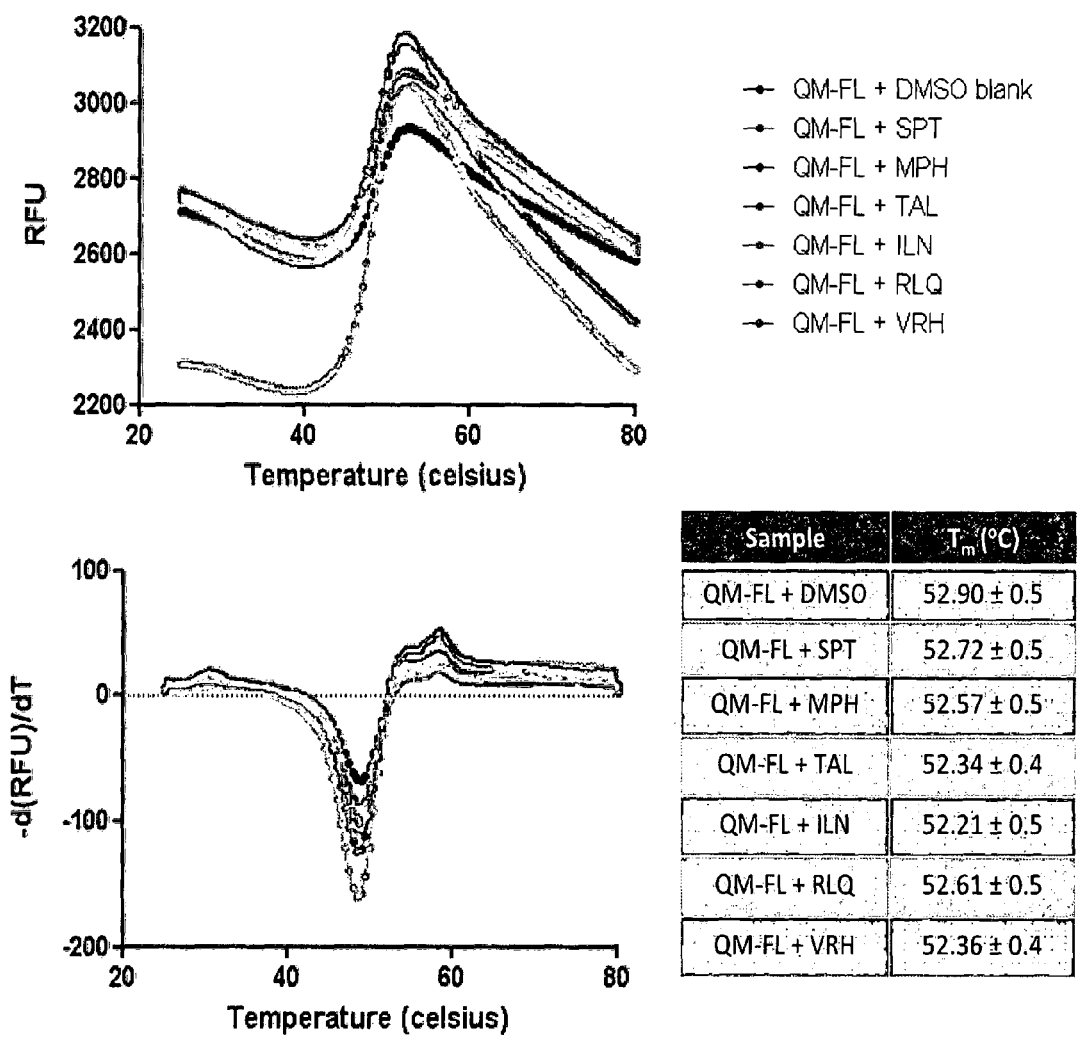
FIG. 19 (A) Thermal Shift Assay showing Tm of p53QM-FL, p53QM-FL in the presence of 5 µM control DNA, and p53QM-FL in the presence of 5 µM p21 duplex. (B) Thermal Shift Assay showing Tm of p53QM-FL in the presence of peptide. (C) (Top) Thermal Shift Assay showing Tm of p53QM-FL in the presence of peptide and 5 µM p21 duplex. (Bot) Downward shift in Tm of p53QM-FL in the presence of either Pap-ILN and Pap-VRH, and 5 µM p21 duplex. This shift is neither observed for other peptides, nor when p21 duplex is replaced with scrambled-DNA duplex (Bot Right).

As observed earlier, several peptides had rather strong effects on the presence of Pab240/Pab1620 epitopes in p53wt-Δ22 (FIGS. 18B and C). We hence, decided to test if the peptides induced any thermal stability in purified p53QM-FL (pur.p53QM-FL) proteins. Using thermal shift assay, the $T_m$ of purified p53QM-FL protein alone was determined to be 52.90±0.5° C. This figure was in good correlation with several published $T_m$ of p53 determined using differential scanning calorimetry (wt-FL=49.7±0.7, wt-core domain=42° C. and QM-core domain=46.2° C.). We then further validated the accuracy of the assay by pre-incubating pur.p53QM-FL with either 5 μM of p21 3' site RE DNA duplex, or 5 μM of scrambled DNA sequence. The results showed that, while the presence of scrambled DNA duplex can stabilize p53 slightly (55.68±0.3, FIG. 19A), the presence of a consensus DNA sequence increased the $T_m$ by 10° C. (62.95±0.7, FIG. 19A). Next, we went on to test if pre-incubating pur.p53QM-FL with 20 μM of each peptide may cause a shift in the $T_m$. Thermal shift results indicated no apparent shift in any of the $T_m$ compared to DMSO blank control (FIG. 19B). We then repeated the experiment, but included 5 μM of p21 DNA-duplex in the peptide pre-incubation step. The result showed a slight destabilization shift (reduced $T_m$) in some samples containing, interestingly, the same peptides which was previously shown to cause a reduction in Pab1620 epitopes (FIGS. 18B and C). Both Pap-VRH and Pap-ILN induced a reduction in $T_m$ (1.5° C. and 0.9° C., respectively) in the presence of 5 μM of p21 DNA-duplex (FIG. 19C), but not in the presence of scrambled DNA-duplex lacking a consensus RE (FIG. 19C).

Example 4

Development of qPCR p53-DNA Binding Assay

Materials and Methods
Synthesizing Response Element PCR Fragments

Response elements were appended onto the 5' end of a 110 bps DNA fragment (corresponding to region 5010 to 5120 on pET-b(+)) by PCR using either one of primers p21-PET-F2, PUMA2-PET-F2, RGC-PET-F2, P2XM-PET-F2 (Table 3) along with primer WPet-R1 and pET-22b as template. The resultant constructs harbor a unique RE tagged to a conserved sequence that is amplified during the real-time quantification phase of the assay. The control DNA fragment used is the exact same PCR fragment but lacking a 5' response element sequence, synthesized using primers WPET-R1 and PET-F2.

p53-DNA Binding Beads Assay (Ab-Beads)

Protein G coated magnetic beads (Dynabeads® Protein G, Invitrogen) were incubated with DO-1 antibody (1 ug per 10 μl of beads) in a 1% BSA-PBS solution at room temperature for 2 hours on the rotator, washed twice with 200 μl PBST (PBS with 0.1% Tween 20), and aliquoted out accordingly for use in the binding assay.

After protein synthesis was carried out using an IVT system, 2 μl of 6× p53 binding buffer 2 (150 mM sodium phosphate, pH 7.2, 600 mM KCl, 24 mM DTT) was added along with required amount of response element (or control) construct, and reactions were incubated at room temperature for a further 30 minutes.

For each set of experiments we used the control construct as a measurement of non-specific binding by p53 and non-specific binding of DNA to the beads. The total molar concentration of all DNA elements (RE or control DNA) was fixed at 36 nM. Data points involving REs consist of the respective concentration of RE construct added to the required amount of control DNA such that the molar concentration always add up to 36 nM (eg. 4.5 nM of RE added to 31.5 nM of control DNA to give a total DNA concentration of 36 nM). In this manner, the total molar concentration of DNA exposed to the protein is held constant across all experiments. Additionally, this significantly reduces the number of background control DNA reactions required.

5 μl anti-p53 antibody (DO-1) coated beads were then added and the bead-reaction mixture incubated for 1 hour at 4° C. with constant rotation. The beads are then washed to remove non-specifically bound response element/DNA control constructs. We have explored different ways of washing the beads and found that vortexing gave the most consistent wash across samples. For these sets of experiments, washing was done in 200 μL PBST with vortexing at 1600 rpm for 6 seconds on the MS2 Minishaker (IKA) followed by one further wash in 200 μl PBS (1600 rpm, 5 seconds). After washing, the beads are resuspended in 20 μl nuclease-free water, and the DNA eluted by heating the beads at 95° C. for 5 minutes. After heating, the tubes were removed from the heat block and quickly chilled on ice for 20 seconds before removal of the supernatant. 5 μL of this eluate is used for subsequent real-time PCR analysis p53-DNA Binding Multiplex Assay For the multiplex assay, the protocol remained unchanged apart from the binding, and elution steps. p53wt-Δ22 protein was synthesized and added into a total binding volume of 65 μl (equivalent to 5 binding reactions, with all components scaled up proportionately), containing 9 nM of each of the 4 REs (PUMA-BS2, p21 3' site, RGC, and P2XM). Due to the increased volume of the binding reaction, we eluted the DNA into 50 μl of nuclease-free water.

p53-DNA Binding Plate Assay (Ab Coated Plate)

In reconfiguring the p53-DNA binding assay from the antibody-bead format to the antibody-plate format, the protocol remains largely unchanged apart from the binding and elution steps. The procedure for coating antibodies by adsorption onto polystyrene 96-well plate is described in Section 2.3.2. After the 30 minutes incubation step where p53-DNA complexes are allowed to form, the mixture is transferred directly onto DO-1 coated 96-well plate containing 30 μL (per well) of pre-chilled plate layering buffer, and incubated for an hour at 4° C. on a shaker. The binding mixture is then removed and the wells are washed three times in WB1, three times in WB2 (200 μL wash volume) and dried. The captured DNA is eluted by adding 20 μL of 150 mM NaOH (10 minutes incubation at room temperature), followed by the sequential addition of 23 μL of 150 mM HCl, and 20 μL of 50 mM Tris-Cl (pH 7.4) to neutralize the pH. 5 μL of this eluate is used for subsequent real-time PCR analysis.

Real-Time PCR and Data Analysis

All real-time PCR quantification of the eluates, except those pertaining to the multiplex assay, were performed using 50 nM each of primers PET-F3 (5'-ATA GGC GCC AGC AAC CGC ACC TG-3'; SEQ ID NO:37) and WPET-R1 using the the iQ™ SYBR® Green Supermix (Bio-Rad Laboratories). The PCR samples were cycled on a C1000 Thermal Cycler (1 cycle of 95° C., (7 minutes) followed by 50 cycles of 95° C. (5 seconds), 55° C. (30 seconds)) and signals quantified via a CFX96 Real-Time System CCD camera (Bio-Rad Laboratories). Data were collected from 3-4 separate binding experiments, and were interpreted as fold differences (calculated based on cycle threshold differences) over non-specific DNA binding control included in each experiment (control DNA fragment only). For the multiplex assay, 100 nM of each forward primer, PumaBS2_short_F (5'-CGC GCC TGC AAG TCC TGA CTT G-3'; SEQ ID NO:43), P21_short_F (5'-TAG AGG AAG AAG ACT GGG CAT GTC TG-3'; SEQ ID NO:44), RGC_short_F (5'-CAC ATG CCT TGC CTG GAC TTG CC-3'; SEQ ID NO:45), and P2XM_short_F (5'-CTT GGG AAC AAG GGC ATG AGC TTG T-3'; SEQ ID NO:46), were used, with 100 nM of reverse primer Wpet-R1, to detect for the amount of respective RE present in the eluate. Results for the multiplex assay were normalized to the weakest binding RE by assigning an arbitrary value to the C(t)(cycle threshold) value. C(t) values for the remaining REs were calculated, and interpreted as fold-difference over binding to the weakest RE, accordingly.

Results

Constructing DNA Response Element and qPCR Tag for Real-Time PCR Quantification

Figure 21:
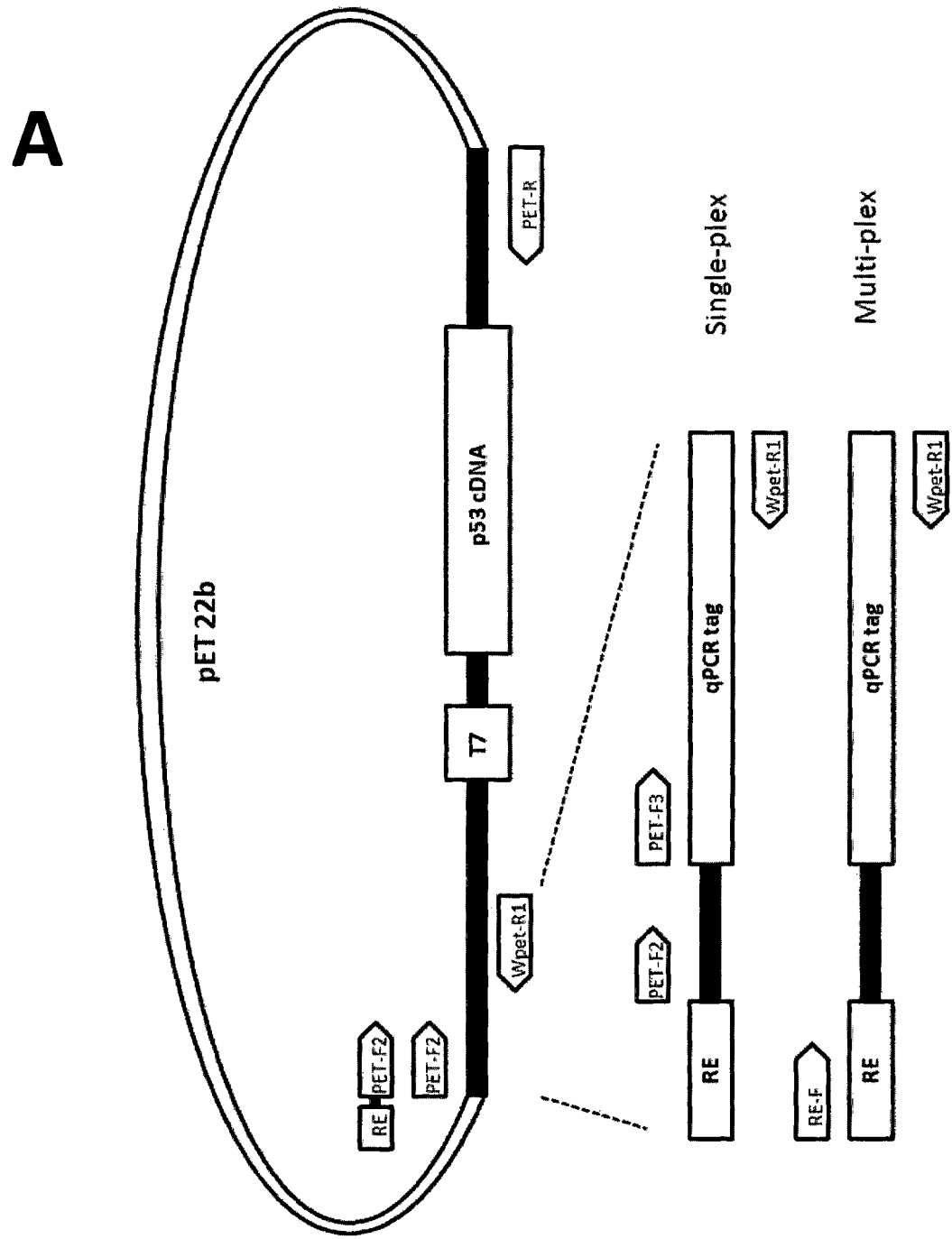
FIG. 21 shows (A) a schematic of tagged RE PCR synthesis and primer pairs for single- and multi-plex assays. (B) PCR products for primer pair optimization. (C) Optimization of PCR. (D) DNA gel showing respective purified RT-PCR tagged p53 RE.
Figure 21:

The DNA recognition element used in this assay was constructed by PCR amplifying a non coding region of the PET22b plasmid (several hundred bps upstream of the T7 promoter, (FIG. 21A) and consisted of a qPCR tag (for subsequent real-time quantification) with a 20-30 bps p53 RE appended onto the 5' end using a suitable forward primer with the respective 5' overhanging sequence (FIG. 21). Two sets of oligo-nucleotide primers are critical in this assay; one for the synthesis of the DNA construct, and a second for priming the qPCR tag (FIG. 21). After a brief optimization to identify primer pairs suitable for real-time PCR amplification, primers PET-F3 and Wpet-R1 were selected. The RE appended DNA fragment was constructed by PCR amplifying a portion of the PET vector using the PET-F2 forward primer with a 5' RE overhang (either p21 3' site, PUMA-BS2, or P2XM[21]) and WPET-R1 reverse primer. This gave a PCR fragment of approximately 150 bps (FIG. 21D). A control DNA fragment (con-DNA) was also synthesized using the Pet-F2 primer without attached RE sequence (~120 bps, FIG. 21D). The final DNA constructs were then column purified and quantified using a spectrophotometer before being used in further experiments.

Development and Optimization of Assay Protocols

In a real-time PCR measurement, the fluorescence signal (from Sybr green binding to DNA) is quantified at the end of every thermal cycle as the dsDNA doubles in quantity. As the amount of fluorescence signal increases, it crosses a detection threshold into an exponential linear phase. The C(t) (cycle threshold) value measures the amount of cycling required before a given DNA sample enters this exponential phase and is directly proportional to the amount of starting DNA template available (FIG. 22A). This DNA binding assay quantitates, essentially, the amount of DNA (with or without appended RE) bound to p53. As the qPCR tag within each of the RE construct does not discern between con- and RE-DNA, sequence-specific DNA binding is measured by comparing cycle-threshold, C(t), differences when p53 is incubated with equi-molar concentrations of either con- or RE-DNA. The data is represented as an increase in fold-difference binding over con-DNA control. FIG. 22A is an example of real-time PCR data showing duplicate measurements in which interaction between p53 and RE1 (C(t)Δ1=8-fold difference) gave a stronger sequence-specific DNA binding then with RE2 (C(t)Δ2=4-fold difference).

After a successful proof-of-concept measurement using IVT-translated p53wt-Δ22 following several refinements in the wash procedure and p53 binding buffer used, p53 sequence-specific DNA binding was characterized using different concentration of REs. The difference in concentration of RE-DNA was always balanced using control-DNA, such that the DNA molar concentration was always kept at 36 nM (i.e. 0 nM RE+36 nM con-DNA, or 18 nM RE+18 nM con-DNA). Due to the sensitivity of this assay, a real-time PCR measurement was performed to ensure that the relative concentrations of the DNA-mixture inputs are kept constant (using ~18 pg of DNA template) (FIG. 22C). Additionally, melt curve analysis was conducted and showed that the all the real-time PCR signal came from a single PCR product with a $T_m$ of 88.50° C. (FIG. 22F).

Measurement of Full Length Wild-Type p53 Binding to Physiological REs

Figure 23:
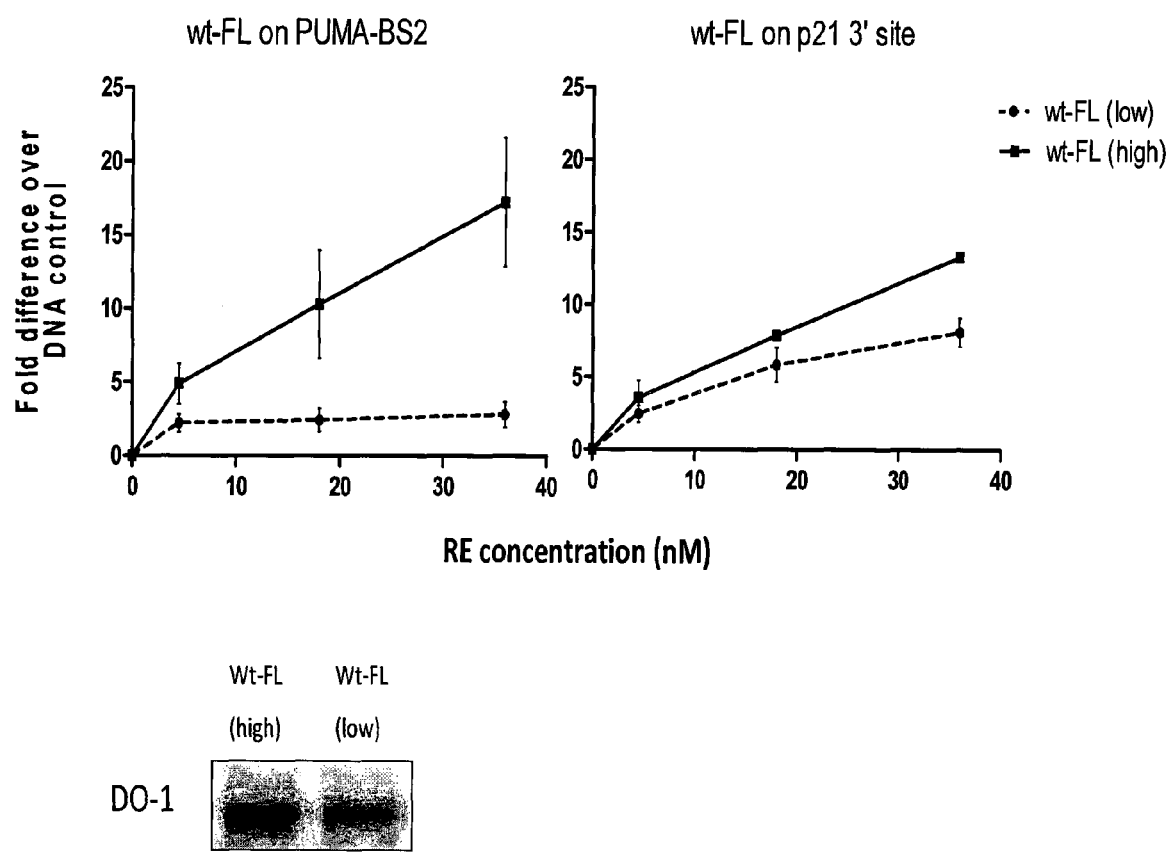
FIG. 23 shows the evaluation of p53 wild-type full length binding on PUMA-BS2 and p21 3' REs. p53wt-FL protein synthesized via WT was incubated with 4.5 nM, 18 nM, and 36 nM of either PUMA-BS2 or p21 3' site response element. Data is represented as fold-difference over non-specific DNA binding between p53wt-FL and equal molar concentrations of no-RE control DNA. 2 different concentrations of p53 were used, hashed lines represent low, and solid lines represent high. Error bars represent mean+/−SEM of 4 independent binding experiments. (Inset) Western blot of IVT extract depicting high and low concentrations of p53.

The binding of bacterially expressed full-length p53 (p53wt-FL) to a consensus RE is not observed using conventional in-vitro DNA binding assays. This form of p53 represents the inactive, latent state which intrinsically displays low affinity to REs. Therefore, the sensitivity of the assay was first ascertained using variable amounts of p53wt-FL and two physiologically relevant REs; the 3' recognition site of cyclin dependent kinase inhibitor, p21, which regulates cell-cycle arrest, and PUMA-BS2, a high affinity binding site of the pro-apoptotic effector protein PUMA (PUMA-BS2). At the lower concentration of p53wt-FL (approximately 40 nM), weak binding to PUMA-BS2 was observed at all concentrations of RE used (~2.5-fold increase over control) (FIG. 23). Contrastingly, p53wt-FL bound with similar affinity to the p21 RE at 4.5 nM (2.5-fold increase over control), which increased to ~8-fold when the concentration of the RE was highest at 36 nM. When the amount of p53 was doubled, a dose-responsive increase in binding to both RE's was observed at all concentrations tested. Binding to the PUMA-BS2 RE increased significantly, ranging from 5-fold over control at 4.5 nM to 17-fold at 36 nM. At the higher dosage of p53wt-FL, there was only a slight difference in binding to the two RE's, most likely due to an excess of p53 masking true differences in affinity. We therefore used the lower amount of p53 in all subsequent assays.

To ensure that the differences in C(t) values are a true reflection of DNA eluted in a p53-dependent manner, binding experiments were repeated as before (20 nM of p53wt-FL protein and 36 nM of DNA), but using either un-coated beads, or beads coated with a p53 non-specific monoclonal antibody (2A9, anti-Hdm2 antibody). The results show almost identical C(t) values between p21 RE-DNA and con-DNA samples (FIG. 24A), suggesting a p53-dependent sequence-specific binding in earlier results. Structural coordination of the zinc atom and proper folding of the p53 core domain requires a strong reducing environment, and is typically reflected in the high levels of DTT additive in p53 buffers (3-8 mM). We therefore investigated if the levels of DTT might destabilize the antibody structure and cause a decrease in DNA binding signal from p53wt-FL. The DNA-binding assay was repeated using p53 binding buffer 2 containing different molar concentrations of DTT (1, 2, or 4 mM). A positive correlation between sequence-specific DNA binding and DTT concentration was observed (FIG.

24B), suggesting that the importance of the DTT presence strongly outweighs any possible detriments from antibody destabilization in the context of this assay.

Increase Binding Observed with 'Activated' p53

The results above indicated the extreme sensitivity of the assay and we next tested if it could discern the putative increase in binding to target REs of an "activated" form of p53 compared to latent p53. The unstructured carboxyl terminal domain (Ctd) of p53 (residues 356-394) has been postulated to play an auto-inhibitory role by sterically interfering with the core domain's ability to interact with DNA recognition elements. A well established method to 'activate' the otherwise latent state of bacterial expressed full length p53 protein, for use in—in-vitro assays, is to either delete the C-terminal domain, or activate it with monoclonal antibodies (Pab 421, Bp53-10.1). A C-terminal deletion variant was chosen (p53wt-Δ22, lacking residues 372-393) to represent 'activated' p53. When equal amounts (~20 nM, FIG. 25A—inset) of full-length and C-terminally deleted p53 proteins were used in the binding assay, an increase in binding to p21 3' site and PUMA-BS2 REs was observed for the latter (FIG. 25A). A 19-fold increase in binding to p21 3' site RE (36 nM concentration) over control was observed for p53wt-Δ22 compared to ~8-fold for p53wt-FL. Binding to the same concentration of PUMA-BS2 increased from 2.8-fold (p53wt-FL) to ~29-fold (p53wt-Δ22). The results are consistent with previous data indicating increased binding affinity of p53 core-domain to PUMA BS2 over P21 3' site ($K_D$=7.1±1.8 and 12.0±7.0, respectively). Additionally, comparison of the binding ratios of p53wt-FL over p53wt-Δ22 for each RE indicate the pronounced effects of p53 activation on binding to PUMA-BS2 (10.4-fold relative increase) compared to p21 3' site (2.4-fold relative increase) (FIG. 25A).

As the carboxyl domain of p53 has also been described to play a part in binding DNA non-specifically, we investigated if the phenomenon was detectable in this assay and how it may affect the relative binding differences between full-length and c-terminal truncated p53. The binding reaction was repeated as before, but with 36 nM of control DNA only, and compared the amount of non-specific DNA bound between p53wt-FL and p53wt-Δ22 when subjected to either the normal washing conditions used throughout this study, or a reduced stringency wash (halved vortex duration). The results showed that p53wt-FL did bind more strongly to non-specific DNA then p53wt-Δ22 (~21-fold increase), but this interaction was weak and was completely removed under the wash conditions used in this study (FIG. 25B). This indicated that the effects of non-specific binding via p53's carboxyl terminal was unlikely to manifest in our results, and that the DNA binding measured was primarily sequence-specific.

p53wt-Δ22 Binds Different Physiological Response Elements Over a Dynamic Range

Figure 26:
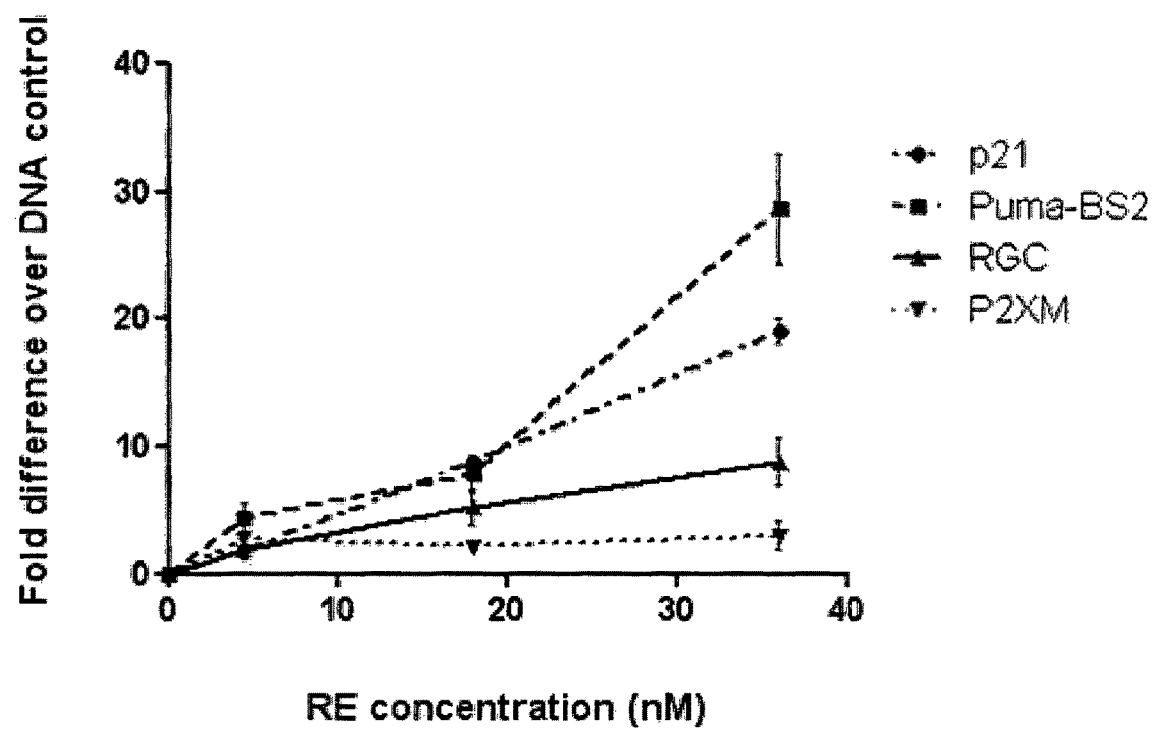
FIG. 26 shows the comparison of p53wt-Δ22 target DNA binding to different physiologically relevant response elements. p53wt-Δ22 variant was used on the p21 3' site, PUMA-BS2, RGC, and P2XM response elements across 3 different concentrations (4.5 nM, 18 nM, and 36 nM) of REs each. Data is represented as fold-difference over non-specific DNA binding between p53wt-Δ22 and equal molar concentrations of no-RE control DNA. Error bars represent mean+/−SEM of 4 independent binding experiments.

The assay was further validated by investigating the binding of p53wt-Δ22 to other physiological REs, representing different affinities in the p53 binding spectrum. Specifically, a moderate (ribosomal gene cluster recognition site, $K_D$=18.0) and a weak binding RE (P2XM recognition site, $K_D$=221±41) were chosen. P53wt-Δ22 gave a very modest response to the P2XM response element, giving an ~2.5-fold increase at the lowest concentration of RE (4.5 nM) and only reaching an ~3-fold increase at the highest dose of RE (36 nM) (FIG. 26), a stark contrast to the 29-fold increase seen with the PUMA-BS2 RE. Likewise, the RGC response element showed a dose responsive binding to p53wt-Δ22 at a moderate strength, starting off with a 2-fold binding increase at 4.5 nM, which rose to ~9-fold increase at 36 nM of RE (FIG. 26).

Measurement of RE Binding by Full Length Mutant p53 Proteins

Figure 27:
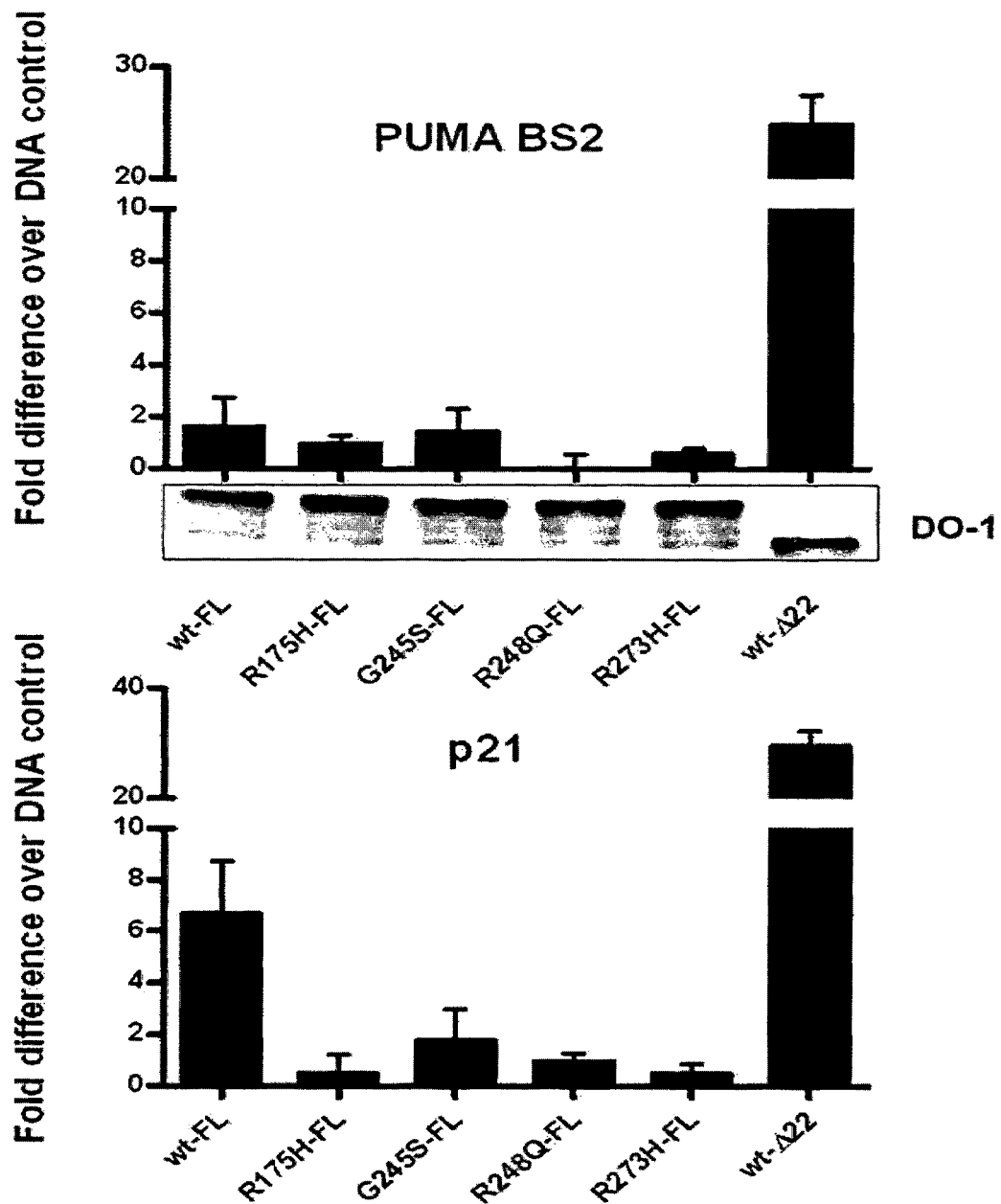
FIG. 27 shows binding of biologically significant p53 mutants to the PUMA-BS2 and p21 3' site REs. p53 full-length mutants representing different classes of mutations (R175H, G245S, R248Q, and R273H) were measured against 36 nM of either p21 3' site or PUMA-BS2 RE, and compared with latent (wt-FL) and 'activated' (wt-Δ22) p53. Data is represented as fold-difference over non-specific DNA binding between the respective p53 mutant and equal molar concentrations of no-RE control DNA. Insert between graphs shows western blot of relative protein levels using DO-1 antibody. Error bars represent mean+/−SEM of 3 independent binding experiments.

Some 95% of p53 somatic tumorigenic mutations lie in the DNA binding core domain. Of these, 75% are the result of single nucleotide missense mutations, leading to a single amino-acid substitution. When a missense mutation causes the substitution of a functionally critical amino acid it can completely abrogate p53's ability to recognize and transactivate target genes. 4 of the most commonly occurring p53 mutants were selected to represent the different functional classes of p53 core binding domain mutation: a DNA contact mutant retaining native structure (R273H), a DNA contact mutant with a distorted structure (R248Q), a weakly destabilized mutant (G245S), and a globally denatured mutant (R175H). All have been shown to be non-functional both in vivo and in vitro. At the same maximum concentration of RE used for previous experiments (36 nM), none of the full length p53 mutants bound significantly to either the p21 3' site or PUMA-BS2 response element (FIG. 27). Mutants R175H, R248Q, and R273H showed extremely low binding signals (<1-fold over non-specific control DNA binding) for both p21 3' site, and PUMA-BS2 REs. The G245S mutant showed some residual binding to the REs (1.8±1.1-fold increase for p21 3' site RE, and a 1.4±0.8-fold increase for PUMA-BS2 RE) (FIG. 27).

Multiplex Assay of p53 Binding to 4 REs with Different Affinities

After having ascertained the assay's reliability in accurately discerning binding of p53 to 4 different response elements individually, the utility and sensitivity of the system was further demonstrate by reconfiguring to a multiplex assay. P53wt-Δ22 was incubated with 9 nM each of 4 REs (PUMA-BS2, p21 3' site, RGC, and P2XM). To detect for the relative amounts of RE bound, forward primers that only complement the respective REs (FIG. 21A) were used along with a common reverse primer (Wpet-R1). To ensure that each primer pair worked properly, two control real-time PCR analyses were conducted to address issues of priming efficacy and possible cross reactivity. Similar C(t) values (threshold cycle) were obtained when real-time PCR was conducted on each primer pair with equal concentrations (50 pM) of the respective RE template (FIG. 28A—left), indicating comparable amplification efficiency of each primer pair. Additionally, melt curve analysis of the resulting PCR product indicated the presence of only one PCR product (FIG. 28A—right). To ensure that each primer pair will only amplify its respective RE from a pool of REs (possible cross reactivity of forward primer), a series of control real-time PCRs were conducted, where each reaction contained a specific RE template with a mixture of all forward primers, except the one specific for the template. The results indicated no cross-reactivity (data not shown). The multiplex binding assay results indicated significant binding for both the PUMA-BS2, and the p21 3' site REs when normalized to the weakest binder, P2XM (91.7±5.4-, and 101.6±7.8-fold binding increase over P2XM, respectively). RGC gave an intermediate response with ~14.3±0.7-fold binding increase over P2XM. The multiplex assay results yielded a trend in agreement to the individual RE binding assays (FIG. 28B).

Increased Target DNA Binding of Full Length p53 Using an Activating Peptide

Figure 29:
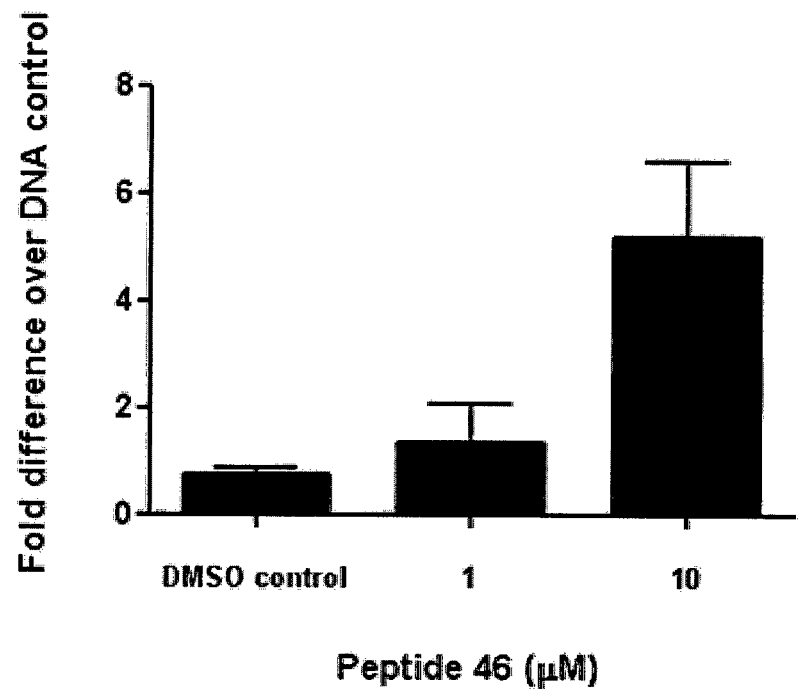
FIG. 29 shows the effects of peptide 46 on p53wt-FL binding to RGC response element. p53wt-FL protein was synthesized via IVT extract and incubated with either DMSO control, 1 uM, or 10 uM of peptide 46 for 30 mins before the addition of 36 nM of RGC response element. Data is represented as fold-difference over non-specific DNA binding between p53wt-FL and equal molar concentrations of no-RE control DNA. Error bars represent mean+/−SEM of 2 independent binding experiments.

Reactivation of mutant p53 present in around 50% of all human cancers represents an attractive means of therapy. Conversely, potentiation of the activity of the wild type protein present in the remaining cancers is also being investigated. To this end, several small molecules and peptides have been described that can either structurally stabilize or (re)activate p53 mutants both in-vitro and ex-vivo. The effect of peptide 46, which has previously been shown to 'activate' the otherwise latent binding activity of wildtype full length p53 towards a non-physiological consensus DNA recognition sequence, was therefore tested. The results showed a dose-responsive increase in sequence specific DNA binding of p53wt-FL when peptide 46 was co-incubated with 36 nM of RGC RE. At the highest dose of peptide 46 (10 uM), a 7-fold increase in binding to the RE was observed over the DMSO only control (FIG. 29).

Adaptation of p53-DNA Binding Assay into High-Throughput Plate Configuration

Figure 31:
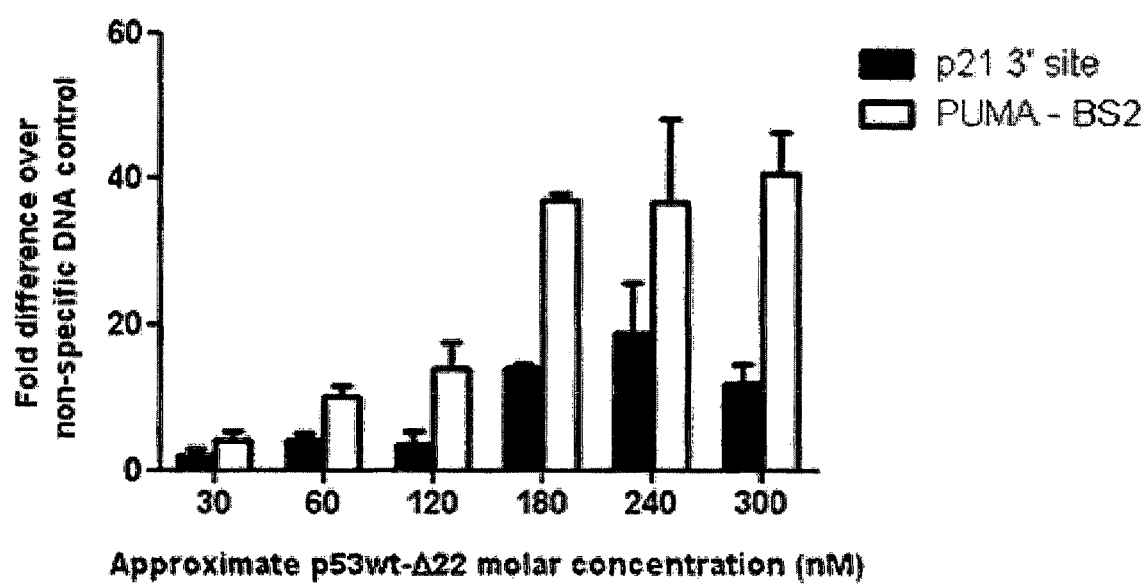
FIG. 31 shows p53wt-Δ22 protein titration on 36 nM of p21 or PUMA RE, represented by black and white bars respectively.

As the current configuration using beads in the p53-DNA binding assay (1 microtube per data point) presents a technical bottleneck that prevents the sampling of multiple binding reactions at once, the platform was extended into a higher throughput 96-well plate format. The assay is the same as before, except antibodies are now immobilized on a 96-well plate instead of beads. The system was tested initially by measuring IVT-p53wt-Δ22 binding to REs (p21 3' site and PUMA-BS2) and comparing the suitability of either (i) immobilizing DO-1 antibodies overnight by adsorption on normal polystyrene plates, or (ii) repeating the assay as before but captured on pre-coated commercial protein-G plates. As high levels of binding was detected for both REs on the adsorption plate (similar to the beads format), but not on the protein-G plate (FIG. 30A), we chose the adsorption method for future experiments. The weak signals from the protein-G plate could be due to the drastic reduction in surface area switching from beads to plate configuration (beads=~10 cm$^2$, plate=0.32 cm$^2$). To optimize the wash steps, DNA binding between IVT-p53wt-Δ22 and both con-DNA and p21 RE-DNA was compared under different wash conditions (either 1 or 3 washes of 200 μL wash buffer during each step). The results showed no difference in C(t) value between wash conditions (FIG. 30B), suggesting that background signals are significantly lower than before, and that formed DO-1-p53-DNA complexes are associating tightly, and are resilient to increased washing. Next we measured DNA binding between IVT-p53wt-Δ22 to p21 3' site and PUMA-BS2 over a range of p53 protein concentrations (15 nM-180 nM). The results showed a p53 protein concentration-dependent increase in binding to both REs that peaked between 180-240 nM of protein (FIG. 31). Like before, the results show that IVT-p53wt-Δ22 bound with higher affinity to PUMA-BS2 (37-fold increase at 180 nM of p53) compared to p21 3' site (14-fold increase). Above 180 nM of p53 (or 6 μL of IVT), signals from sequence-specific binding to both REs seem to plateau, possibly indicative of an upper detection limit due to the limited surface area in each well.

The assay we describe is sensitive enough to detect dose responsive binding between the latent wildtype full length protein (synthesized in a prokaryotic expression system) and several biologically relevant response elements. We have demonstrated that the strong binding between wildtype p53 and two of the high affinity REs (p21 3' site and PUMA-BS2) is not observed in mutants with known compromised sequence-specific DNA recognition functions, and can also be further enhanced by deleting the carboxyl terminal end of the protein, hence 'activating' the protein.

The use of freshly synthesized p53 (made in an expression system containing only the minimum essentials of the transcription/translation machinery) that has not been post-translationally modified can provide valuable insights into the unadulterated dynamics of p53's ability to recognize and bind target DNA. Our study using p53wt-Δ22 on the p21 3' site and the PUMA-BS2 recognition site indicates a possible inherent mechanism of regulating cell fate. Latent p53's ability to bind the PUMA-BS2 RE remained low at all RE concentrations, contrary to the p21 3' site binding, which showed a dose-responsive increase. However, when 'activated' p53 was used, a marked 10.4-fold increased binding over latent p53 was observed for the PUMA-BS2 RE compared to only 2.4-fold for the p21 3' site RE (FIG. 25A). This significantly increased "induction-potential" highlights the role of subtle changes in RE sequence that regulates p53 binding. Our data also show the importance of comparing the binding activities of both latent and 'activated' p53 when characterizing REs Furthermore, without being bound be any theory, the binding data seem to further reiterate an "all or nothing" scenario wherein p53 directs cell death through transactivation of pro-apoptotic genes (such as PUMA), only in the most dire of situations (irreparable cell damage) upon post-translational activation. On the other hand, the process of recognizing and binding to the p21 RE which directs the comparatively less drastic fate of cycle arrest in-vivo, is not as variant between latent and 'active' p53, and proceeds in a simple concentration dependent manner.

As a technique, the method of studying protein-DNA interactions described here presents several beneficial alternatives to other various different methods presently available. One immediate advantage is its ease to perform compared to others, specifically techniques that require work with radio isotopes like gel shift assays. As it is a quantitative PCR-based method, it can amplify and generate readouts from exceedingly small copy numbers of RE DNA template. This tremendous sensitivity allows the system to tolerate the presence of other proteins, hence allowing the use of IVT systems (and possibly nuclear extracts to study in vivo transactivation of p53 in the future), and obviates the need to purify the protein of interest. Additionally, our success in adapting the p53-DNA binding assay into a 96-well plate configuration has resulted in a technique that significantly champions others in areas of sensitivity, throughput efficiency and cost-effectiveness.

The data from the multiplex assay demonstrates its capacity to accurately discern varying extents of p53-DNA interaction in the face of rigorous competition, and highlights some promising attributes of this system. The dynamic range attainable by this assay immensely exceeds those of traditional techniques like EMSA, and ELISA-based protein-DNA binding assays (>100-fold difference between 2 physiologically functional response elements, i.e. p21 3' site and P2XM). In order to adequately represent the different degrees of interaction, a key criterion in assays involving large screens, and numerous interacting partners (especially the case for p53 and its response elements) is a large dynamic range.

Figure 20:
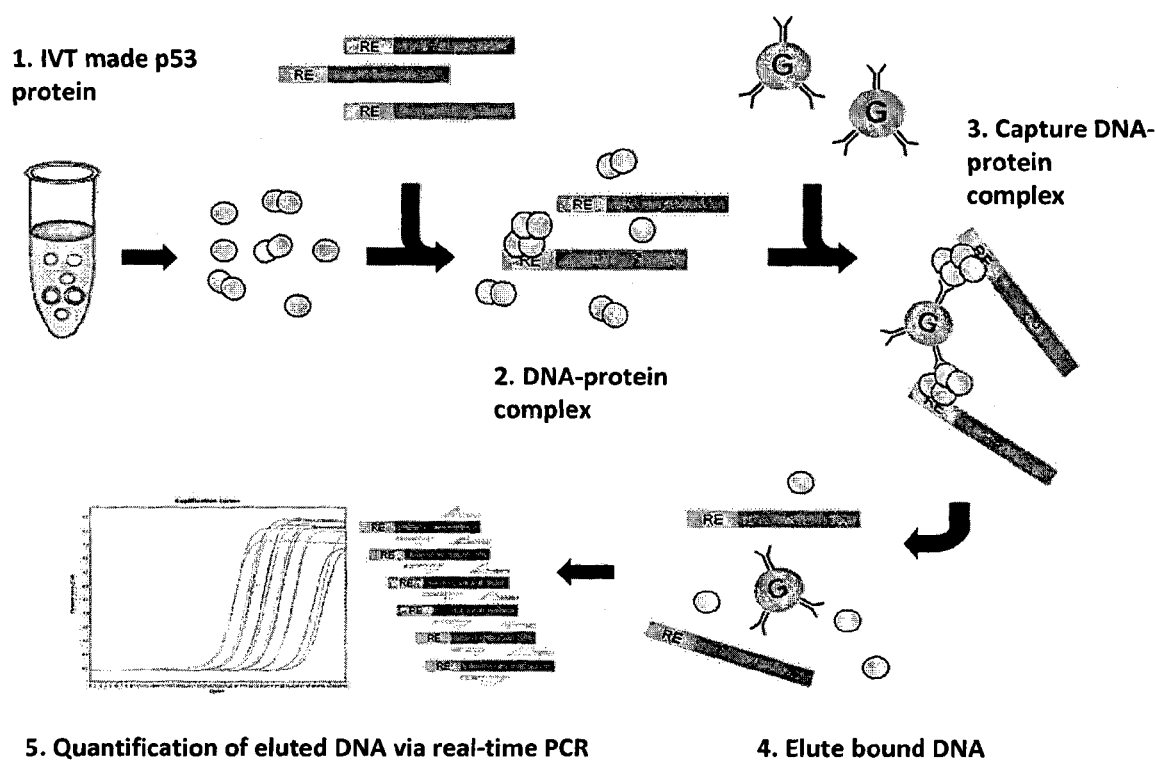
FIG. 20 shows a schematic of protein-DNA binding assay. (1) p53 protein is made in an in vitro transcription/translation extract. (2) Response element (green portion represents the RE tethered to a red universal sequence for real-time PCR quantification) is added to the newly synthesized p53, allowing DNA-protein complexes to form. (3) The DNA-protein complexes are captured on protein G beads pre-coated with an antibody that targets p53. (4) The captured complexes undergo a series of washes to remove weak and non-specific binders. Bound DNA is eluted by heating. (5) A portion of the eluted DNA is removed and quantified using real-time PCR.

The method developed here essentially inverts the configuration of the ELISA assay, to allow for accurate quantification of the bound RE via real-time PCR. The outline of the binding assay is shown in FIG. 20. Specifically, DNA carrying a RE sequence is added to IVT-expressed p53 and allowed to equilibrate. Protein-DNA complexes are then captured on beads coated with an antibody targeting p53 that does not disrupt DNA-binding, and bound DNA is eluted off the beads after a series of washes to remove weak and non-specific binding. The DNA eluates are then quantified via real-time PCR. The results show a method that allows sensitive detection of p53-DNA binding within half a day, without recourse to any protein purification Example 5

Characterizing Compound Reactivation Potential Using qPCR p53-DNA Binding Assay

Materials and Methods

Control Sequence-Specific DNA Binding of IVT Synthesized p53wt- and p53Y220C-Δ22.

Figure 32:
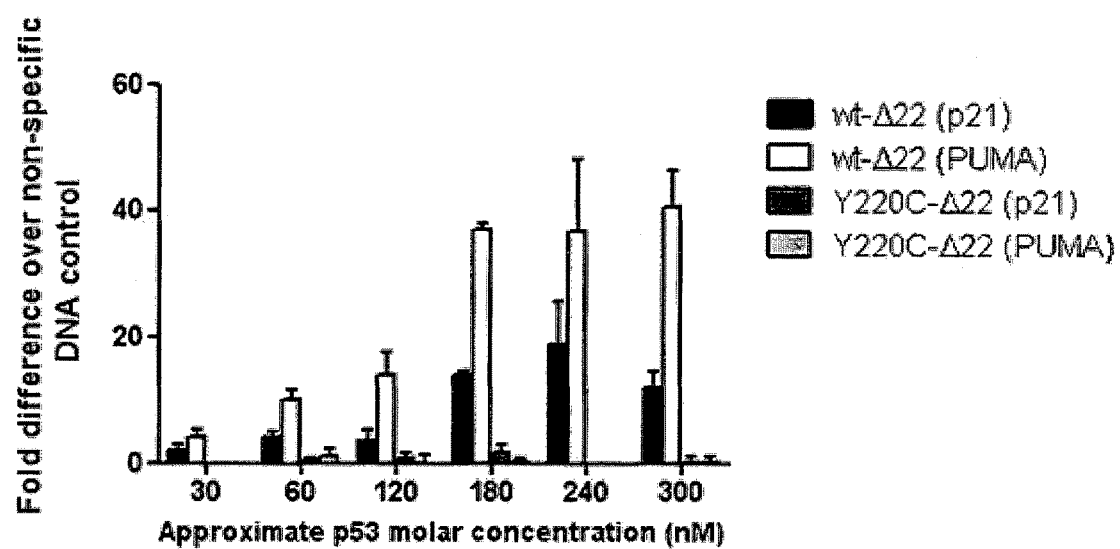
FIG. 32 shows (A) the comparison of binding to RE p21 and PUMA-BS2 between IVT synthesized p53wt-Δ22 and p53Y220C-Δ22 (using ~150 nM of p53). Right inset shows relative amounts of p53 protein used in the DNA binding assay (Lanes 1, 2 and 3 are QM-FL, wt-Δ22 and 220C-Δ22, respectively. (B) DNA RE binding titration using increasing p53 concentration. Black and white bars show binding of p53wt-Δ22 to p21 and PUMA, respectively. Third and fourth bars in each group depict residual binding of p53Y220C-Δ22 to p21 and PUMA, respectively.

We first established the levels of residual sequence-specific DNA binding from IVT-p53Y22C-Δ22. We used the c-terminal truncated p53-Δ22 instead of full-length protein for our binding measurements. In vitro expressed p53-Δ22 was used at a final concentration of ~150 nM in a control DNA binding assay, and showed an increase of ~21-fold binding over control DNA for the p21 3' site response element, and a ~37-fold increase for the PUMA-BS2 response element. In contrast, residual sequence-specific DNA binding from the structurally compromised Y220C mutant was marginal, giving only a 1.7-fold increase for the p21 site, and a 0.9-fold increase for PUMA-BS2 site (FIG. 32A). To further validate the DNA binding assay and profile the functionality of IVT expressed p53, we performed the same binding assay but titrated the amount of p53wt-Δ22 used from 30-300 nM. The results showed a clear p53 concentration-dependent increase in RE binding for both the p21 3' site and PUMA-BS2 response elements, which respectively showed between ~4 to 20-fold, and ~8 to 42-fold increases over the range sampled (FIG. 32A). A previous in-vitro study of mutant p53 DNA binding using SPR reported the Y220C mutant core domain retaining considerable levels of wild-type sequence-specific DNA binding (17% of wild-type at 37° C., and 45% of wild-type at 20° C. to Gadd45 RE). We hence investigated if we could detect an increase in sequence-specific DNA binding of the Y220C-Δ22 mutant by increasing the protein concentration. The assay was conducted using 60 nM, 120 nM, 180 nM, or 300 nM of IVT-Y220C-Δ22 protein. The results show that up to the maximum concentration of Y220C-Δ22 tested, there was no significant increase in binding (1-fold increase for both REs at 300 nM) (FIG. 32B). The apparent disparity of sequence-specific DNA binding from the Y220C mutant could be attributed to a variety of factors; including the temperature and method of synthesizing p53 protein, as well as the technique and RE used for determining sequence-specific DNA binding.

Measuring Pap Peptide Dependent Reactivation of G245S p53 Mutant Using qPCR p53-DNA Binding Assay (Cosmo IVT).

Figure 33:
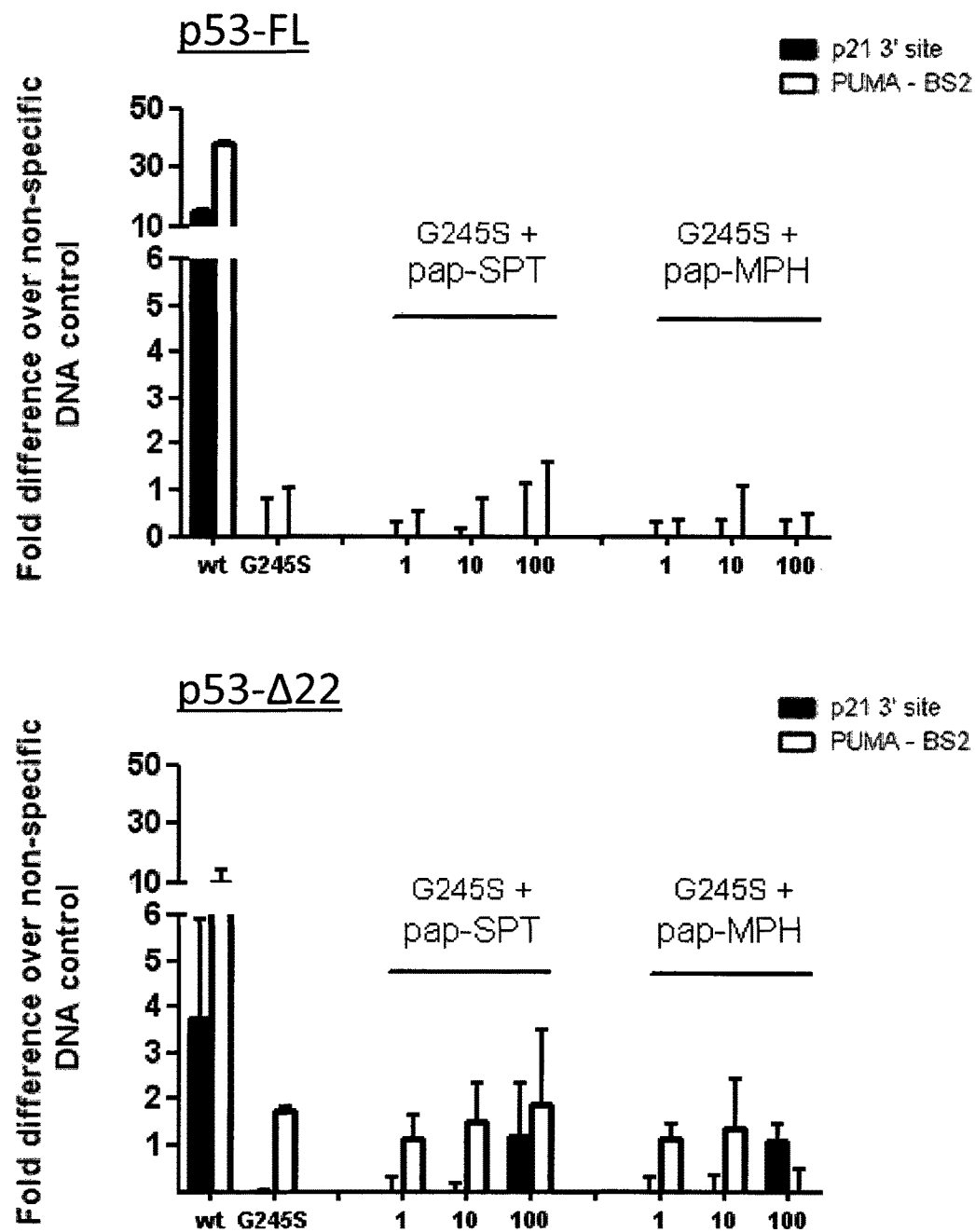
FIG. 33 shows the effects of pap-SPT and pap-MPH on mutant p53G245S-Δ22 (Top) and p53G245S-FL (Bot) binding to DNA RE using antibody-capture plate binding assay.

We next repeated the binding assay and tried to detect reactivation of the G245S mutant using two of our peptides. P53G245S-FL or -Δ22 protein were IVT-translated in the presence of either Pap-SPT or Pap-MPH (1, 10 or 100 μM), and binding to the p21 3' site and PUMA-BS2 REs were measured as before. The results showed that both peptides induced little to no sequence-specific DNA binding to either REs for both FL, or Δ22 mutant protein (FIG. 33).

Reconfiguring p53-DNA Binding Plate Assay.

It occurred to us at this point, that the format of the current DNA binding assay may have adverse effects, or a decreased detection threshold for measuring peptide activity, due to (i) the presence of antibodies, or (ii) the use of conventional polystyrene plates, both of which was shown to interact non-specifically to many of our peptides. We therefore reconfigured the DNA binding assay by introducing a streptavidin binding tag to our p53 constructs and changed the capturing matrix to the commercial streptavidin plates used earlier, thereby obviating the use of both monoclonal antibodies and conventional polystyrene plates. To minimize any non-specific effects from introducing an affinity tag to our recombinant protein, we selected the smaller nano-tag (over the conventional SBP tag that had similar binding affinity to monoclonal antibodies.

Using IP, we first examined if the introduction of the nano-tag effected protein translation, and if the nano-tagged p53wt-FL (Np53wt-FL) recombinant protein could bind to streptavidin beads. The IP results (DO-1 western blot) indicated that addition of the tag did not affect IVT translation (similar p53 protein levels in input), and that streptavidin-beads captured only nano-tagged p53 and not wild-type p53 (FIG. 34A). Next, we performed the newly configured binding assay and titrated the sequence-specific binding of IVT-Np53wt-Δ22 on p21 and PUMA-BS2 response elements, over a range of protein concentration. The results showed increased binding to both REs in a p53 concentration dependent fashion with a similar trend (p21 binding reached >20-fold, and PUMA binding reached >40-fold) to the antibody capture format (FIGS. 34B and 32B). Additionally, binding to PUMA-BS2 reached ~50-fold over non-specific DNA binding at 150 nM of p53 protein (compared to ~38-fold increase at 180 nM p53), suggesting that this configuration could be more sensitive than before.

The advantages of using Np53 and streptavidin coated plates were three-fold; (i) cost-effectiveness from precluding the use of antibodies, (ii) increased technical flexibility and efficiency as plates no longer need to be coated the night before, and (iii) increased sensitivity (seen in the results above) due possibly to the increased number of p53 captured in the wells (antibodies are sterically cumbersome, and often not oriented optimally for binding when coated using plate adsorption technique).

Using the Novagen EcoPro IVT System to Better Mimic the Cellular Milieu.

The use of the CosmoBio minimal IVT system to synthesize p53 protein was important for the development of our DNA binding assay (the lower signal-to-noise facilitated assay optimization), but was by no means symbolical of a true cellular milieu. The use of bacterial lysate IVT system would represent a more rigorous and physiologically relevant test of sequence-specific DNA binding, and could be afforded by the large dynamic detection range offered by our qPCR p53-DNA binding assay. In view of this, we sought to adapt the Np53-streptavidin DNA plate binding assay using the Novagen EcoPro bacterial lysate IVT system (used for selection).

First, we tried to recapitulate the p53 concentration dependent RE binding response seen before by repeating the exact binding experiment using Novagen IVT synthesized Np53wt-Δ22 (Nano-tagged p53 on streptavidin plates). Because the protein expression levels between both systems were relatively similar (FIG. 35A—inset), levels of p53 concentration used remain unchanged. Initial binding between Np53wt-Δ22 to response elements were barely detectable across all 4 points of p53 concentration sampled (FIG. 35A—Top). However, when we translated p53 with an increased concentration of $ZnSO_4$ (from 1.5 μM used in CosmoBio IVT system to 500 μM used in selection process), we saw a slight increase in RE binding that correlated slightly to p53's concentration (FIG. 35A—Bot). We were finally able to observe appreciable levels of RE binding when Np53 was translated using 50 μM of $ZnSO_4$ in the Novagen system. However, as expected, the levels of RE binding were significantly lower than before (especially for PUMA-BS2 RE), with binding to both REs reaching ~18-fold over non-specific DNA binding at 150 nM of protein used. We were also able to detect a similar, albeit attenuated, p53 concentration dependent sequence-specific DNA binding response for full-length p53 (Np53wt-FL), which peaked at 10-fold increase and 12-fold increase, for p21 and PUMA REs, respectively (150 nM of p53 protein).

Measuring p53 Activating Peptides Dependent Reactivation of 'Activated' C-Terminal Truncated p53 Mutant, Using qPCR Nano Tagged p53-DNA Binding Assay (Novagen IVT)

We tested the activity of our peptides on their respective mutant p53. As we did not know the site of peptide-p53 interaction, we decided to IVT-translate mutant p53 in the presence of our peptides (over a range of peptide concentration; 2 µM, 20 µM, and 200 µM), thus adhering to one of the conditions they were selecting for. Furthermore, we have also shown earlier that the peptides do not increase protein translation (potential false positive). We first tested our panel of peptides on C-terminal truncated p53 mutants (~120 nM of Np53-Δ22), thinking the 'activated' state might predispose the mutants to any restorative effects from the peptides. The results, however, indicated otherwise. Most of the peptides had little to no effects on their respective p53-Δ22 mutants, showing basal sequence-specific binding, across all concentrations of peptide, comparable to DMSO blank. These include Pap-SPT (G245S-Δ22), Pap-MPH (G245S-Δ22), Pap-ILN (R273H-Δ22), and Pap-TAL (G245S-Δ22 and R273H-Δ22) (FIG. 36A-D). These results suggest that either the mutant reactivation was undetectable by the technique used, or was not present due either to the absence of the interacting region (p53 ctd), or the required the presence of the c-terminal domain. Only peptides Pap-RLQ, and Pap-VRH elicited an increase in sequence-specific binding to response elements for R273H-Δ22 mutant. 20 µM of Pap-RLQ cause RE-binding to increase by 21-fold, and 5-fold, for p21 3' site and PUMA-BS2 REs, respectively (FIG. 36E). For Pap-VRH, an appreciable increase in RE-binding was only observed at 200 µM of peptide, and for PUMA-BS2 RE only (FIG. 20F). Notably, presence of peptide-VRH and -ILN caused a significant decrease in protein translation at the highest concentration of 200 µM (FIG. 36D- and F—inset).

Measuring p53 Activating Peptides Dependent Reactivation of 'Latent' Full-Length p53 Mutant, Using qPCR Nano Tagged p53-DNA Binding Assay (Novagen IVT)

Figure 37:
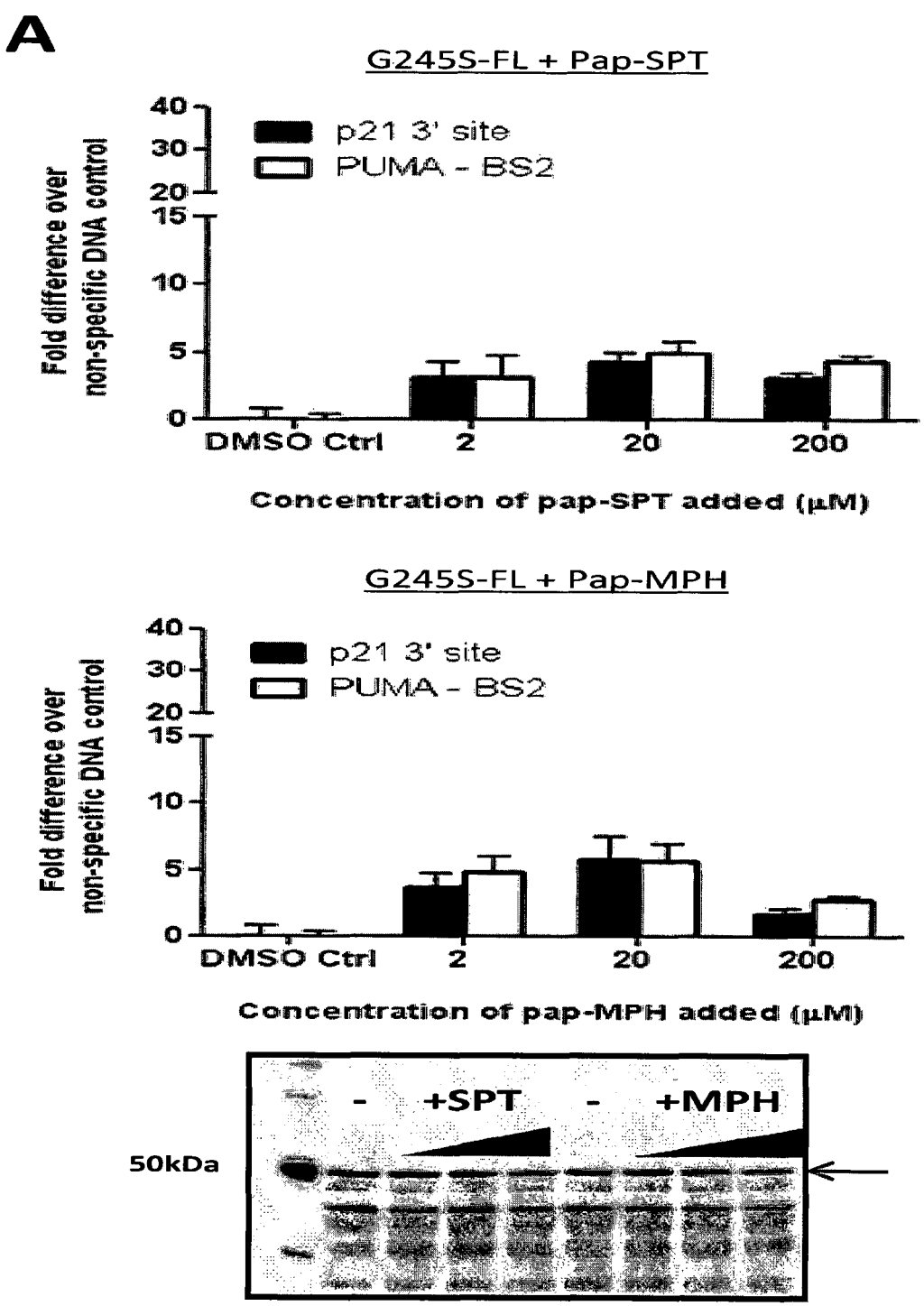
FIG. 37 shows the reactivation of 'latent' full-length p53 mutant using qPCR Nano tagged p53-DNA binding assay. (A) Np53G245S-FL+SPT and MPH, (B) Np53G245S-FL+TAL, (C) Np53R248Q-FL+TAL, (D) Np53R273H-FL+TAL, (E) Np53R248Q-FL+ILN, (F) Binding of p53wt-FL to p21 and PUMA RE in the presence of 20 μM of each p53 activating peptides.
Figure 37:
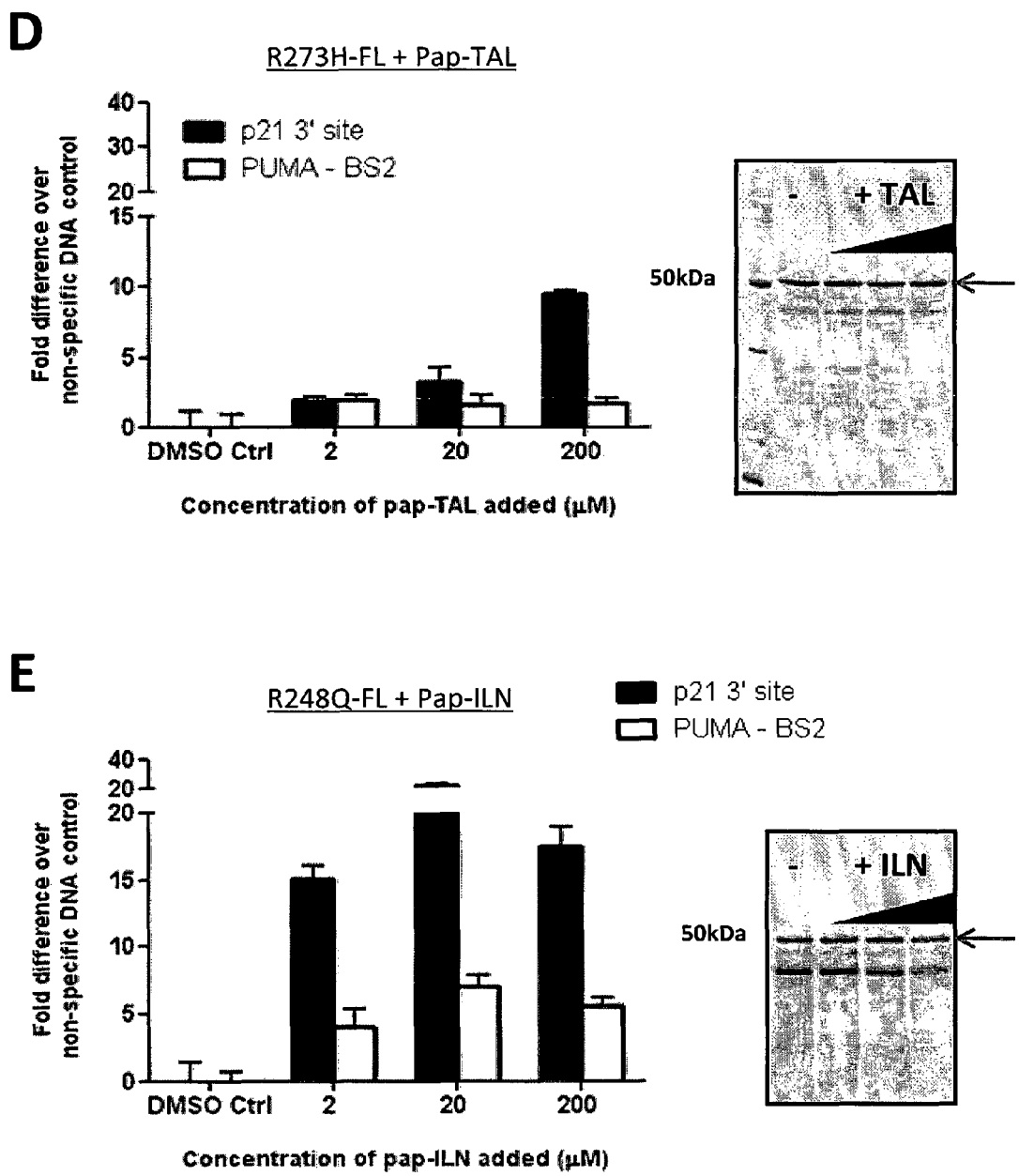
Figure 37:
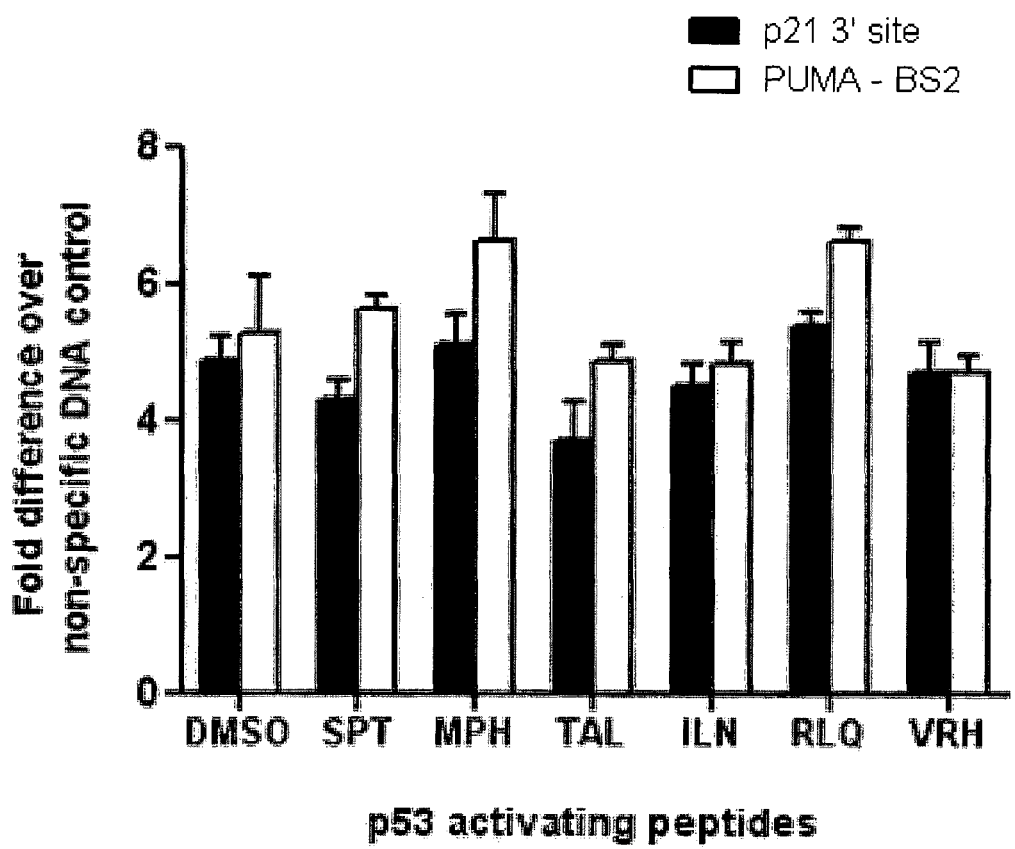

We took the peptides that appeared inactive in the previous set of experiments and sampled them on their respective full-length mutants, using the same experimental protocols. Additionally, because Pap-TAL was selected for both the G245S and R273H mutants, we also tested its effects on the R248Q mutant. The binding data showed significant levels of reactivation for all the mutant p53 (p53 protein used at ~120 nM) tested. Sequence-specific DNA binding for G245S-FL mutant increased from under 1-fold (DMSO control) to ~5-fold, and ~6-fold over control DNA, in the presence of 20 µM of Pap-SPT and Pap-MPH, respectively (FIG. 37A). Interestingly, only peptide-SPT and -MPH reactivated p53 mutant without actuating any preference in RE binding, possibly suggesting an interaction with p53 away from the core domain. The activity of Pap-TAL was very significant in restoring sequence-specific DNA binding, and notably, to all three mutants. Furthermore, a strong preference for binding to the p21 RE over the PUMA RE was seen in all the reactivated mutants. The effects of Pap-TAL was most prolific in activating G245S-FL mutant, with a significant increase in p21 RE-binding observed (~14-fold over control DNA) at a peptide concentration of only 2 µM (FIG. 37B). At 20 µM of peptide used, the RE binding reached 37-fold increase and 14-fold increase over control-DNA, for p21 and PUMA REs, respectively (FIG. 37B). Pap-TAL's induced reactivation was relatively weaker on the other two mutants; binding to p21 RE peaked at 11-fold over control-DNA for R248Q-FL mutant (at 20 µM peptide) (FIG. 37C), and 10-fold over control-DNA for R273H-FL mutant (at 200 µM peptide) (FIG. 37D). Pap-ILN also elicited a significant increase in sequence-specific DNA binding for R248Q-FL, which was not seen before when using R248Q-Δ22. At 2 µM of peptide used, RE-binding increased to 15-fold and 4-fold (for p21 and PUMA REs, respectively) over control-DNA (FIG. 37E). This peptide-dependent reactivation further intensified at 20 µM peptide concentration, eliciting a p21 RE binding of 22-fold over control-DNA (FIG. 37E). In most cases (all except Pap-ILN), 200 µM peptide caused a decrease in protein levels, which translated to an attenuation in DNA binding signal. This may be an effect specific to the Novagen IVT extract, or suggest some degree of toxicity from these peptides at higher concentrations. Also notably, all the reactivation phenotype reported here seem to be specific to mutant p53, as repeating the binding assay using p53wt-FL protein resulted in no significant increase in sequence-specific DNA binding, for any of the activating peptides (FIG. 37F).

Figure 38:
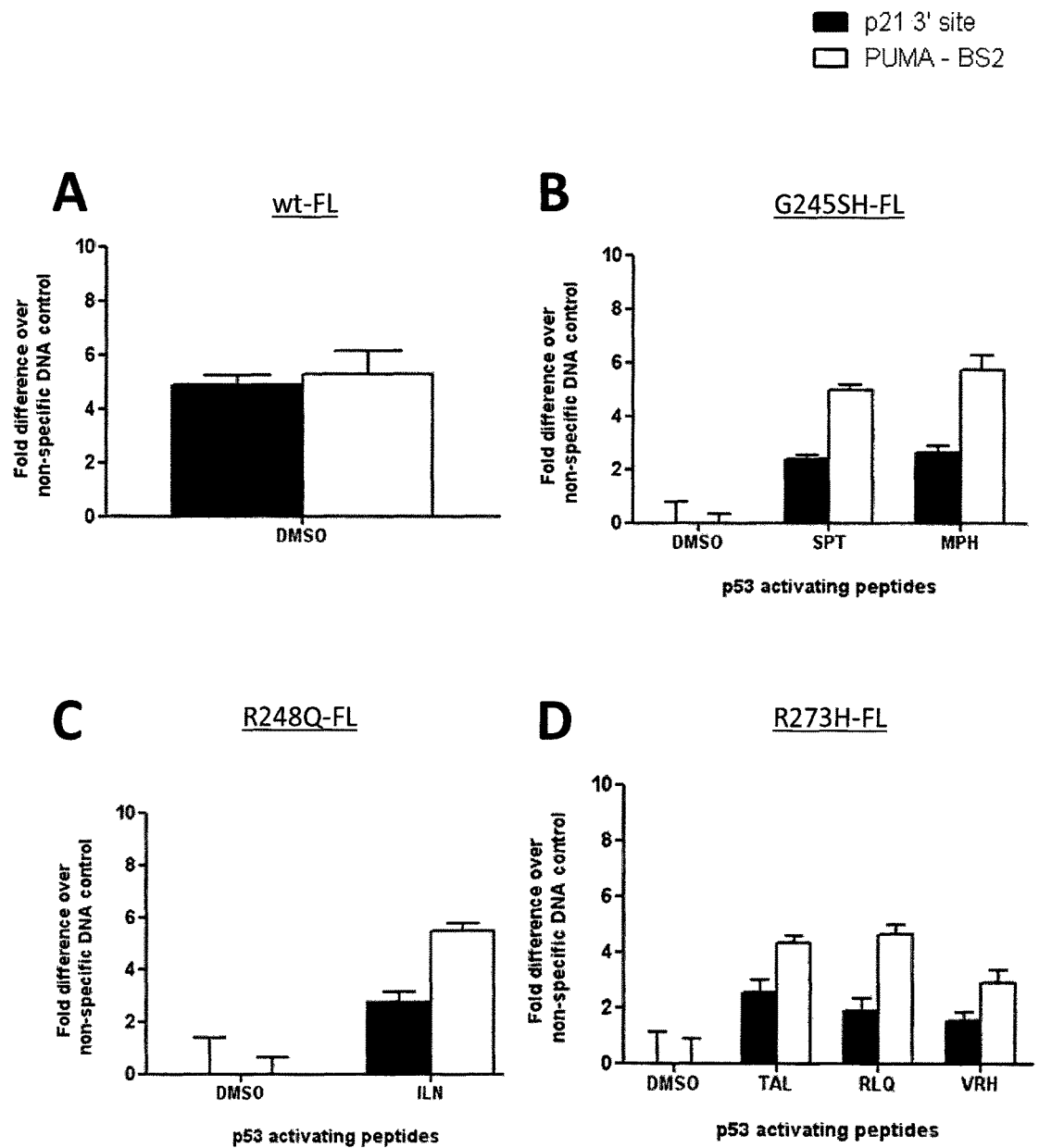
FIG. 38 shows peptide dependent sequence specific DNA binding reactivation of full-length p53 mutants in the presence of 20 μM pap added post protein synthesis. (A) p53wt-FL control (B) Effects of pap-SPT and pap-MPH on Np53G245S-FL. (C) Effects of pap-ILN on Np53R248Q-FL. (D) Effects of pap-TAL, pap-RLQ and pap-VRH on Np53R273H-FL.

Finally, we also looked at whether each of the activating peptides could assert their functions if they were added after protein translation, instead of co-translating in peptide presence as we did before. For this experiment, we compared levels of peptide-induced reactivation in full-length mutant p53 against full-length wild-type p53 (DMSO control). The results showed some degree of reactivation for all the combination sampled (FIG. 38). Peptide-induced sequence specific DNA binding reached wild-type levels for the PUMA-BS2 RE (~5-fold increase), and close to wild-type levels for the p21 RE (~2-3-fold increase), for all the mutants tested. Without being bound by any theory, collectively the data might suggest two mutant reactivation mechanisms at play. The first is peptide and mutant specific, and actuates a particular rescue phenotype (giving rise to RE preference), but requires peptide presence during p53 translation. The second elicits a more generic and weaker response, arising probably from a less specific form of interaction, and takes place when peptides interact with full-length mutant proteins.

Results

We show here, strong evidence that our p53 activating peptides are interacting with p53 mutants specifically, and restoring sequence-specific DNA binding function to the mutants they are selected for. The variation in RE binding manifested through different combinations of mutant protein and peptides further validates the accuracy of the assay, and the authenticity of the peptide induced phenotype. A striking element of the result was the apparent ability for some of the peptides to activate full-length mutant beyond its wild-type state, suggesting both restorative and inductive function from the peptides. A similar phenomenon was seen in the study of CP31398, where a secondary screen showed some compounds stabilizing mutant p53 beyond wild-type levels.

Example 6

Characterizing Reactivation of G245S Mutant in Cell Culture Model

Optimizing RGCΔFOS-LacZ Reporter Assay H1299 Cells.

We wanted to investigate if Pap-MPH could actuate a similar activity to G245S mutants, and increase sequence-specific DNA binding in a mammalian cell. Full-length p53 cDNA carrying a G245S DNA mutation was cloned into an expression vector (pcDNA 3.1) under a strong mammalian promoter (CMV). Using a p53 null human lung carcinoma cell line (H1299), we investigated mutant p53 activity by co-transfecting the mutant p53 plasmid (pcG245S-FL), across a titrated concentration range, with a reporter plasmid (pRGCΔFOS-LacZ). Transfected cells were then allowed to grow for 36 hours before being harvested and assayed for levels of β-galactosidase (β-gal) activity. Levels of luciferase (from co transfecting the luciferase expression vector, pcLuc) were also measured simultaneously, and acted as an internal control for transfection efficiency and cell number.

Western blot analysis indicated that p53 levels were undetectable in un-transfected H1299 cells, but was readily detectable when pcG245S-FL was transfected at the lowest dose of 10 ng (FIG. 39—inset). P53 levels also increased in a plasmid concentration dependent fashion indicating efficient transfection of cells. Levels of β-gal activity also indicated that overexpression of the G245S mutant proteins did not result in transactivity of the RGC reporter gene up to ~100 ng of plasmid vector used, establishing an upper transfection limit for the pcG245S-FL vector (FIG. 39).

Peptide Transfection Using Chariot Peptide Delivery Reagent.

The Chariot reagent is a commercial polypeptide mixture capable of forming non-covalent interactions with, and aiding in the internalization and delivery of, target peptides across the plasma membrane. Using the chariot reagent, we transfected different concentrations of Pap-MPH peptides into H1299 cells pre-transfected with 100 ng of either wild-type p53, or G245S mutant p53 (along with same levels of pLUC and pRGCΔFOS-LacZ), and measured the β-gal activity. Although some peptide-induced transactivity was observed (~3.5-fold over DMSO control using 10 μg/μL of peptide) from the mutant p53, p53wt-FL dependent β-gal levels were significantly higher than the maximum mutant reactivated levels (FIG. 40A). A closer look at the cell culture data revealed that the figures for wild-type p53 dependent β-gal activation was artificially inflated due to significantly decreased luciferase levels compared to mutant p53 transfected cells. This phenomenon was possibly due to the presence of extreme levels of wild-type p53 protein, which in turn, caused cells to growth arrest. The peptide-induced reactivation of G245S mp53 was not observed in either the DMSO control, or the no-p53 control (transfected with empty pcDNA plasmids in the presence of all peptide concentrations sampled) (FIG. 40B), suggesting a genuine reactivation event.

Peptide Transfection Using HIV TAT Cell Penetrating Peptide.

Figure 41:
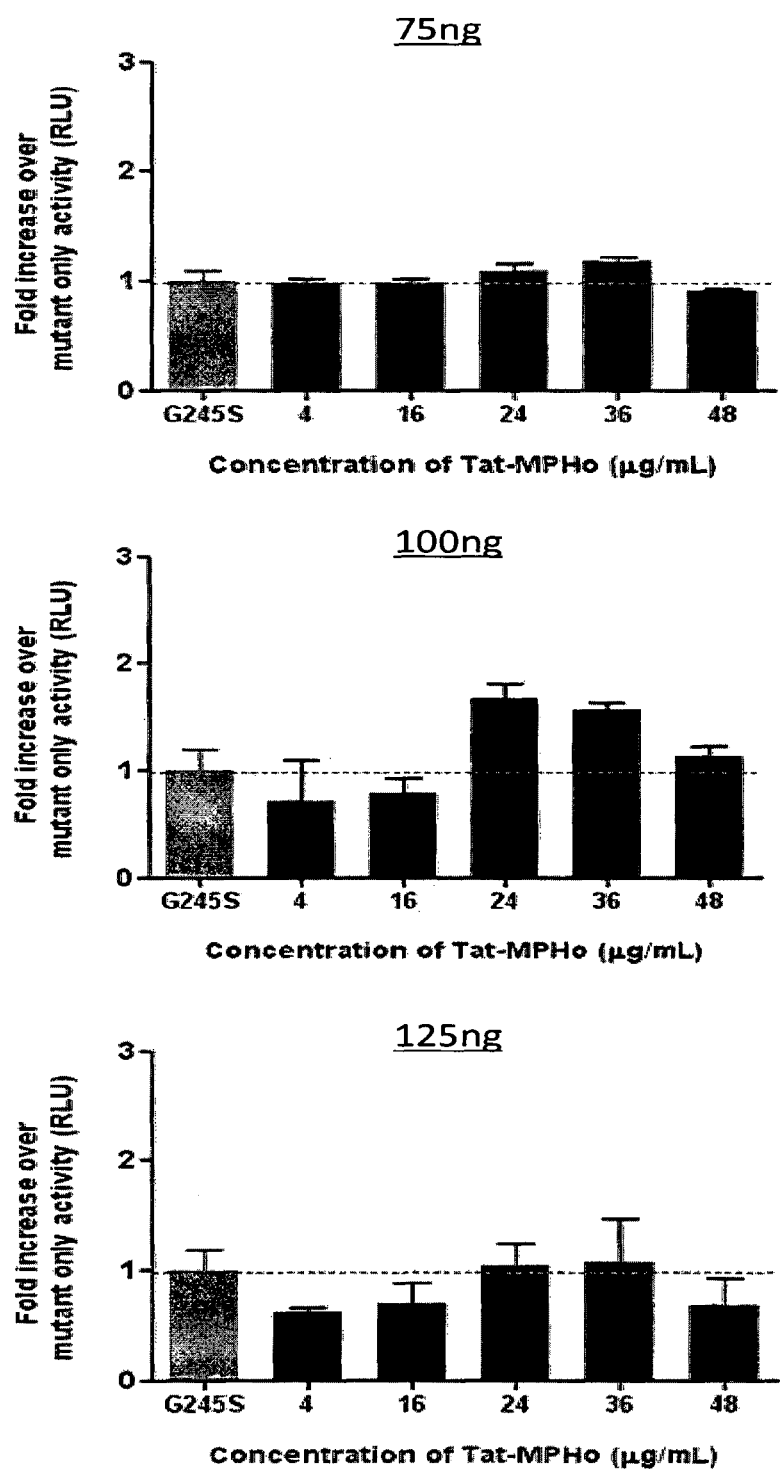
FIG. 41 shows (A) the pRGCΔfos-LacZ reporter assay showing effects of Tat-SPT and Tat-MPHo treatment in H1299 cells co-transfected with 100 ng of pG245S-FL vector. (Table) Reference table showing tat-conjugaed peptide amino acid sequences (SEQ ID NOs:56, 64 and 135-137). (B) Time course of pRGCΔfos-LacZ reporter activity in H1299 cells treated with increasing Tat-MPHo in the presence of pc53G245S-FL plasmid (50 ng), (C) Reporter gene activity in H1299 cells co-transfected with pRGCΔfos-LacZ and increasing amounts of p53G245S-FL protein, and treated with Tat-MPHo peptide for 36 hours, (D) Reporter gene activity in H1299 cells co-transfected with pRGCΔfos-LacZ and increasing amounts of p53G245S-FL protein, and treated with Tat-MPHs peptide for 36 hours, (E) pRGCΔfos-LacZ reporter assay in H1299 with 150 ng of p53G245S-FL and treated with Tat-MPHs for 24 hours (Top) or 36 hours (Bot), (F) Control β-galactosidase activity of p53G245S-FL in the presence of Tat-scram peptide. (G) Comparison of pRGCΔfos-LacZ reporter activity between p53G245S-FL mutant only (grey) and increasing Tat-peptides in the absence of p53 protein (black).
Figure 41:
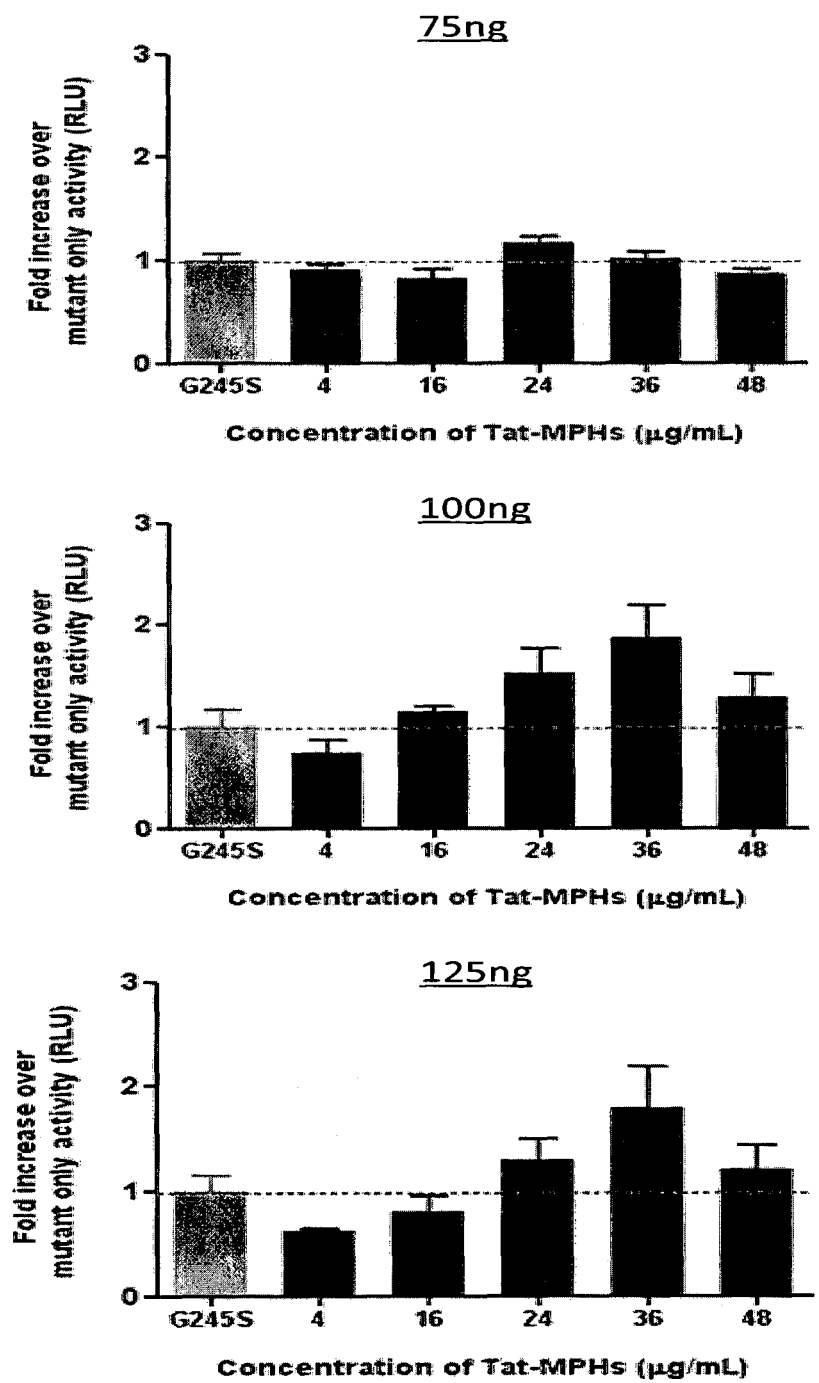

Next we examined the delivery of peptides into cells by means of attaching the HIV TAT protein transduction domain (PTD) onto our Pap peptides. The exact mechanism behind TAT-mediated cellular uptake of polypeptides is not fully understood, but is believed to heavily involve charge-dependent interaction between the very positively charged TAT sequence (RKKRRQRRR; SEQ ID NO:116), and the highly acidic polysaccharides present on the cell surface. Successful peptide delivery via the TAT PTD has been reported extensively in the past, and was also shown to work regardless of which amino acid terminal the TAT sequence is attached to. 4 peptides sequences were each synthesized with the TAT domain attached on the Ntd (FIG. 41A—table); peptide corresponding to Pap-SPT (Tat-SPT), peptide corresponding to Pap-MPH but either with (Tat-MPHo—original), or without (Tat-MPHs—short) the first methionine before the randomized region, and a scrambled Pap-MPH sequence (Tat-Scram) (FIG. 41A—table). A preliminary comparison of peptide-induced mp53 transactivity showed that activity from Tat-SPT was relatively weak (maximum induction of ~2-fold over mutant only control), and was consequently removed from subsequent experiments (FIG. 41A).

As the peptide induced transactivity may only be noticeable during a transient temporal window (due largely to the short cellular half-life of peptides), we next charted peptide induced β-gal activity at three different time points post peptide treatment (12, 24 and 36 hours), and across a peptide concentration range (1-24 μg/mL). The results indicated comparatively higher levels of signal at higher dosages of peptide treatment, and a treatment period of 36 hours (FIG. 41B). We also examined if varying the levels of plasmid pcG245S-FL transfected could increase the apparent activity from the peptides, additionally, both Tat-MPHo and Tat-MPHs were sampled and the concentration range of peptide treatment was also increased to 4-48 μg/mL. The result indicated that activity from Tat-MPHo was highest at 100 ng of plasmid (~2-fold over mutant only), but dropped to undetectable levels when transfection was increased to 125 ng plasmid (FIG. 41C). In contrast, Tat-MPHs elicited a sustained ~2-fold activity even with 125 ng of pcG245S-FL (FIG. 41D). The difference in results could be due a longer half-life, or higher activity from Tat-MPHs compared to Tat-MPHo. In light of these observations, we repeated the reporter assay using Tat-MPHs, but in cells transfected with 150 ng of mutant p53 plasmid. Tat-MPHs elicited a close to 2-fold increase in activity at 24 hours (at 36 μg/μL), which increased sharply to 4-fold over control at 36 hours drug treatment (FIG. 41E). As a control, we repeated the reporter assay using Tat-scram peptide and saw no indication of G245S mp53 reactivation across all peptide concentration sampled (FIG. 41E), suggesting a peptide-induced mutant reactivation that was reliant on an intact Pap-MPH sequence. Furthermore, β-gal activity levels resulting from the treatment of either Tat-MPHs, or Tat-SPT, in p53 null H1299 cells were well below G245S mutant only control (FIG. 41G), suggesting that the observed peptide-induced transactivity of β-gal reporter gene was p53-dependent.

Using Thioredoxin-A Aptamers as a Scaffold for Pap-MPH

Figure 42:
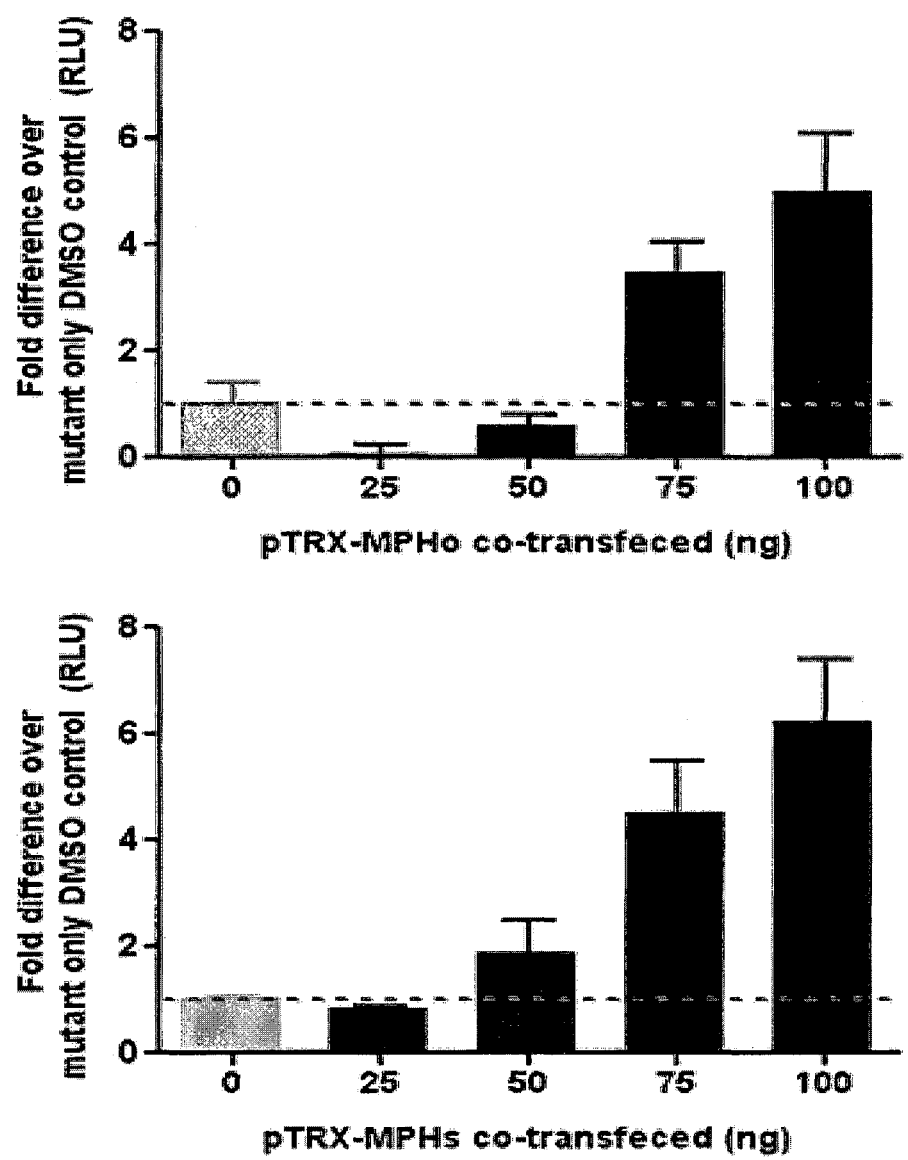
FIG. 42 shows (A) PCT insertion of MPH peptide epitopes in Thioredoxin A protein scaffold (SEQ ID NOs: 138-140). (B) pRGCΔfos-LacZ reporter activity in H1299 co-transfected with p53G245S-FL and plasmid vectors expressing Trx-MPHo or Trx-MPHs peptide aptamers, (C) pRGCΔfos-LacZ reporter activity in H1299 co-transfected with p53G245S-FL and Trx-MPHo or Trx-MPHs carrying vectors. Plasmids Trx-MPHScram were co-transfected instead of empty pcDNA vectors as transfection control plasmid.

We next studied the feasibility of constricting the Pap-MPH peptide sequence within an aptamer scaffold as a method of presenting the Pap-MPH peptide epitope for p53 interaction. Conventionally, peptide epitopes are cloned into the Trx-A cDNA through restriction endonucleation, insertion of DNA material, followed by ligation of the finished product. In order to avoid the insertion of an additional two amino acids (N and G) adjacent to the peptide epitope through the cloning method, we inserted the peptide sequences via PCR (FIG. 42A). Three of the previous sequences were inserted into the Trx-A scaffold, and designated Trx-MPHo, Trx-MPHs, and Trx-MPHScram (FIG. 42A). Both plasmids pTrx-MPHo and pTrx-MPHs were transfected at increasing amounts into H1299 cells, together with the reporter-, luciferase-vector and 100 ng of pcG245S-FL. The amount of total plasmids transfected were balanced with empty pcDNA vectors. Results from β-gal levels showed increasing transactivity with increasing levels of peptide aptamers (PAs) transfected, suggesting a PA concentration dependent mp53 reactivation response (FIG. 42B). Like before, Trx-MPHs (>6-fold over mut-only control) elicited a stronger response than Trx-MPHo (5-fold over mut-only control). To make the assay even more robust, we next repeated the experiment, but used pTrx-MPHScram (instead of empty pcDNA) as balance plasmid. This ensures an equal transcription/translation load in the cells across all the samples, and activity measured will not be an effect of differences in Trx-A protein levels. Transactivity levels are lower than before, but show the same trend where Trx-MPHs displayed stronger activity then Trx-MPHo (3-fold and >4-fold, respectively) (FIG. 42C).

Disruption of Mdm2 Interaction and Function on p53 Using Pap-MPH.

Lastly we investigated briefly if Pap-MPH could possibly confer 'nutlin' like effects in disruption p53-Mdm2 interactions, or perturb Mdm2-dependent degradation of p53.

Figure 43:
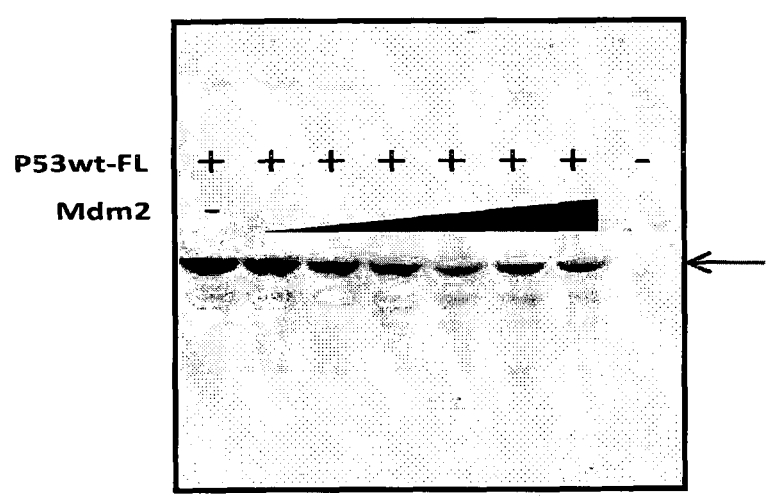
FIG. 43 (A) DO-1 western blot showing wildtype p53 levels when co-tranfected with increasing amounts of Mdm2 carrying plasmid. (B) Effects of Tat-MPHo and Tat-MPHs peptide treatment in H1299 cells co-transfected with p53wt-FL and Mdm2. (C) Effects of Tat-Scram peptide treatment in H1299 cells co-transfected with p53wt-FL and Mdm2.

We examined if the treatment of peptides might result in a change in p53 protein levels in the presence of Mdm2. First we co-transfected fixed levels of p53wt-FL (100 ng of pcP53wt-FL) with increasing titrated amounts of Mdm2 protein (ranging from 50 ng to 200 ng of Mdm2 encoding plasmid) into H1299 cells, and measured the levels of p53 protein via western blot. As expected, a steady decrease in p53 protein levels was observed which correlated with increasing Mdm2 levels. We next treated the cells for 24 hours, with 2 μM, 10 μM or 20 μM of each peptide (Tat-MPHo, Tat-MPHs, or Tat-scram) 12 hours after transfection of p53 and Mdm2 (50 ng of pcP53 wt-FL with 200 ng of pcMdm2), and analyzed the levels of p53. Interestingly, the western blot results revealed a p53 stabilizing effect exerted from the presence of both Tat-MPHo, and Tat-MPHs, which was not detected in peptide Tat-scram (FIG. 43B-C). The results also displayed a stronger response from Tat-MPHs, consistent with earlier results.

Stabilization of p53 Targets Using Peptides

Figure 44:
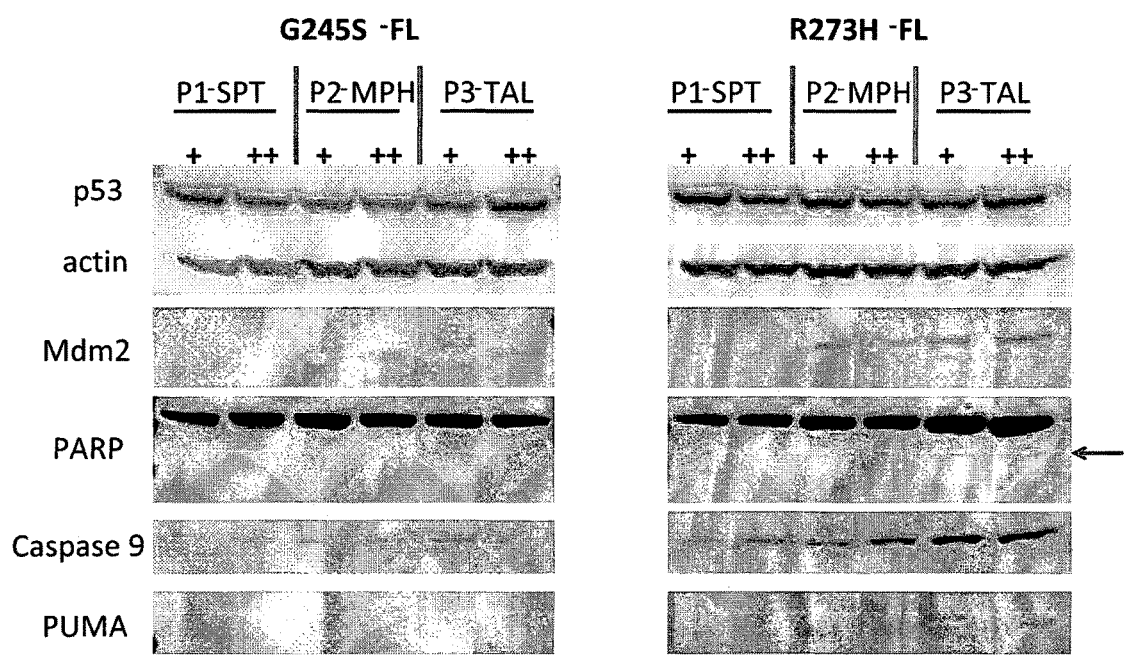
FIG. 44 shows the stabilization of many p53 targets by the peptides. p53 null H1299 cells were treated with either 5 uM (+) or 50 uM (++) of Tat-conjugated peptides (pap-SPT, pap-MPH or Pap-TAL) 4 hours after transfection (using Lipofectamine 2000 transfection reagent, Invitrogen) with pcDNA mammalian expression vector carrying either the G245S (left) or R273H (right) full-length mutant p53 protein. After a 36 hours treatment, cell lysates were collected and protein levels were visualized using western blotting. (A) shows the effect of stabilization in H1299 cells overexpressed with 2 of the mutant p53. (B) shows stabilization in H1299 cells stably transfected with the ecdysone inducible cassette that drives the expression of R248Q mutant p53. (B) Peptide activity in Ecdysone inducible R248Q mutant p53 cassette stably transfected into H1299 cells. Cells were pretreated with 20 uM of Tat-conjugated peptides (in serum free media) 2 hours before p53 induction with Ponasterone A (20 uM of respective peptide, 0.2 ug/mL Pon A in serum supplemented media) for another 24 hrs before cell lysates are collected and blotted for various p53 target proteins. Peptide-P1 (pap-SPT), a weakly active peptide was used as a negative control peptide. Negative control cells (lane U) were not treated by peptides but similarly induced by Pon A (left panel). Peptide activity in H1299 cells stably transfected with empty cassette (right panel).
Figure 44:
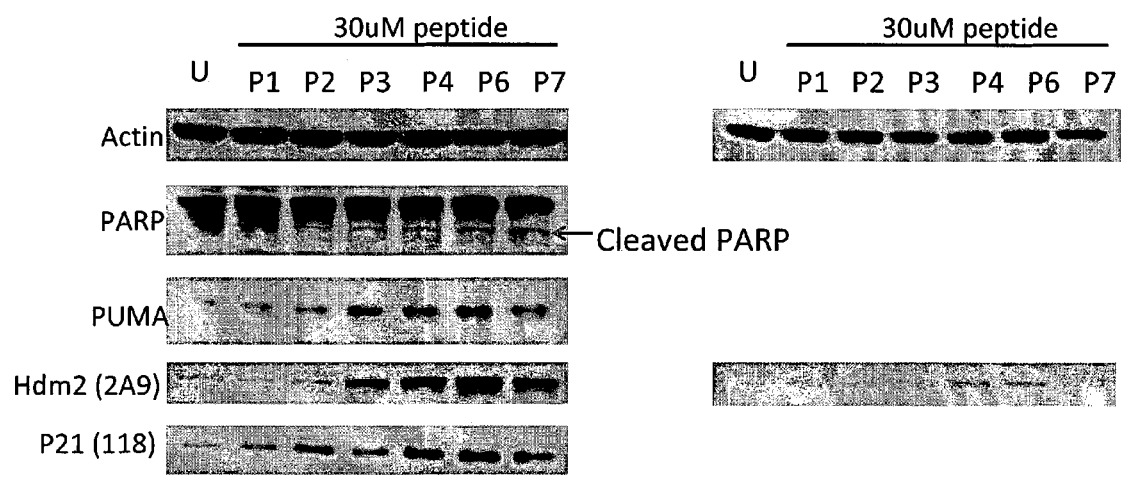

It has been shown in the earlier examples that the peptides directly bind to the mutant p53 they were selected for and restores sequence-specific binding to p53 DNA response elements. Accordingly, the stabilization of targets of p53 by the peptides was investigated. Each of the peptides was conjugated to the HIV-tat domain to help transport the peptide into cells and the results show that the peptides stabilized many of the p53 protein targets responsible for growth arrest and apoptosis in cells (FIG. 44).

p53 null H1299 cells were treated with either 5 uM (+) or 50 uM (++) of Tat-conjugated peptides (pap-SPT, pap-MPH or Pap-TAL) 4 hours after transfection (using Lipofectamine 2000 transfection reagent, Invitrogen) with pcDNA mammalian expression vector carrying either the G245S (left) or R273H (right) full-length mutant p53 protein. After a 36 hours treatment, cell lysates were collected and protein levels were visualized using western blotting (FIG. 44A).

Peptide activity in Ecdysone inducible R248Q mutant p53 cassette stably transfected into H1299 cells was also investigated. Cells were pretreated with 20 uM of Tat-conjugated peptides (in serum free media) 2 hours before p53 induction with Ponasterone A (20 uM of respective peptide, 0.2 ug/mL Pon A in serum supplemented media) for another 24 hrs before cell lysates are collected and blotted for various p53 target proteins. Peptide-P1 (pap-SPT), a weakly active peptide was used as a negative control peptide. Negative control cells (lane U) were not treated by peptides but similarly induced by Pon A (FIG. 44B, left panel). As a control, peptide activity in H1299 cells stably transfected with empty cassette was also investigated (FIG. 44B, right panel).

The results indicate that the effect for Mdm2 may be p53 dependent, as Mdm2 stabilization is not seen in cells carrying the empty ecdysone cassette.

The invention claimed is:

1. A peptide capable of restoring the sequence-specific DNA binding or transactivation function of a mutant p53, wherein the peptide:
  (a) comprises a sequence selected from the group consisting of:

S P T T N H (SEQ ID NO: 55)

M P H L M A C (SEQ ID NO: 56)

T A L I D I W E H S V L G K G Y P R M S (SEQ ID NO: 57)

I L N V L P L L A S R K P (SEQ ID NO: 58)

VSWSACVLLELCNYFPENPIEEEDWACLG (SEQ ID NO: 59)

R L Q Q V (SEQ ID NO: 60)

V R H Q H V G A T I L G W K (SEQ ID NO: 61)

V R H Q H V G A T I L G W KMGWTDH (SEQ ID NO: 62)

MS P T T N H (SEQ ID NO: 63)

MM P H L M A C (SEQ ID NO: 64)

MT A L I D I W E H S V L G K G Y P R M S (SEQ ID NO: 65)

MI L N V L P L L A S R K P (SEQ ID NO: 66)

MVSWSACVLLELCNYFPENPIEEEDWACLG (SEQ ID NO: 67)

MR L Q Q V (SEQ ID NO: 68)

MV R H Q H V G A T I L G W K (SEQ ID NO: 69)

MV R H Q H V G A T I L G W KMGWTDH (SEQ ID NO: 70)

MLM
  TTLIDIWEHSVLGKGYPRMS (SEQ ID NO: 71)

M TTLIDIWEHSVLGKGYPRMS (SEQ ID NO: 72)

RAVTDRPVPCPNPRLNLVAN (SEQ ID NO: 73)

M RAVTDRPVPCPNPRLNLVAN (SEQ ID NO: 74)

(b) is a variant of a peptide as defined in (a) above; or
  (c) is a derivative of a peptide as defined in (a) or (b) above.

2. The peptide which is a variant according to claim 1 (b), wherein the variant is a fragment of a peptide as defined in claim 1 (a).

3. The peptide which is a derivative according to claim 1 (c), wherein the derivative is a peptide which has undergone a post-translational modification.

4. The peptide according to claim 1 wherein the peptide is fused to a heterologous polypeptide sequence.

5. The peptide according to claim 1 wherein the peptide is a stably cross-linked peptide (a "stapled" peptide) wherein the cross-linked peptides contain at least two modified amino acids that together form an internal cross-link.

6. The peptide according to claim 1 wherein the mutant p53 is selected from the group consisting of: p53 G245S mutant, p53 R273H mutant p53 R248Q mutant the p53 R175H mutant.

7. An isolated nucleic acid molecule encoding a peptide according to claim 1.

8. A vector comprising an isolated nucleic acid molecule according to claim 7.

9. A pharmaceutical composition comprising a peptide according to claim 1, an isolated nucleic acid molecule according to claim 7, or a vector according to claim 8, wherein the pharmaceutical composition optionally comprises one or more pharmaceutically acceptable excipients, vehicles or carriers.

10. The pharmaceutical composition according to claim 9 wherein the pharmaceutical composition comprises a further therapeutic compound, for example an anti-cancer agent.

11. The peptide according to claim 1, an isolated nucleic acid molecule according to claim 7 or a vector according to claim 8 for use in medicine.

12. A method for obtaining a peptide which restores the sequence-specific DNA binding of a mutant p53 (mp53) the method comprising:
  a) providing a water-in-oil emulsion comprising a plurality of aqueous microcapsules dispersed in the oil phase, wherein the aqueous phase comprises a library of genes encoding a repertoire of randomized peptides, components necessary to transcribe and translate the peptide genes, and mp53 genes, so that a plurality of aqueous microcapsules each comprise a peptide gene, components necessary to transcribe and translate the gene and a mp53 gene;
  b) expressing the peptide genes and mp53 genes to produce their respective gene products within the microcapsules, wherein if the peptide gene encodes a peptide which restores the sequence-specific DNA binding of the mp53 then a mp53/peptide/peptide gene complex forms;
c) breaking the emulsion; and
d) enriching for any p53/peptide/peptide gene complexes.

13. The method according to claim 12 wherein the peptide genes comprise at least one response element (RE) to which mp53 having restored sequence-specific DNA binding can bind to.

14. The method according to claim 13 wherein the peptide genes comprise at least one response element (RE) to which mp53 having restored sequence-specific DNA binding can bind to, a randomized reading frame, and regulatory elements which are operably linked to the reading frame to thereby enable its expression.

15. The method according to claim 12 wherein the peptide genes from the p53/peptide/peptide gene complexes are amplified prior to undergoing one or more further rounds of renewed encapsulation in aqueous microcapsules of a water-in-emulsion, expression of the peptide genes within the aqueous microcapsules and the formation of mp53/peptide/peptide gene complexes, breaking of the emulsion and enrichment for any p53/peptide/peptide gene complexes or amplification.

16. A method for obtaining a peptide which increases the sequence-specific DNA binding of a wild-type p53 (p53wt) the method comprising:
  a) providing a water-in-oil emulsion comprising a plurality of aqueous microcapsules dispersed in the oil phase, wherein the aqueous phase comprises a library of genes encoding a repertoire of randomized peptides, components necessary to transcribe and translate the peptide genes, and p53wt genes, so that a plurality of aqueous microcapsules each comprise a peptide gene, components necessary to transcribe and translate the gene and a p53wt gene;
  b) expressing the peptide genes and p53wt genes to produce their respective gene products within the microcapsules, wherein if the peptide gene encodes a peptide which restores the sequence-specific DNA binding of the p53wt then a p53wt/peptide/peptide gene complex forms;
  c) breaking the emulsion; and
  d) enriching for any p53/peptide/peptide gene complexes.

17. The method according to claim 16 wherein the peptide genes comprise at least one response element (RE) to which p53wt having increased sequence-specific DNA binding can bind to.

18. The method according to claim 17 wherein the peptide genes comprise at least one response element (RE) to which p53wt having increased sequence-specific DNA binding can bind to, a randomized reading frame, and regulatory elements which are operably linked to the reading frame to thereby enable its expression.

19. The method according to claim 16 wherein the peptide genes from the p53/peptide/peptide gene complexes are amplified prior to undergoing one or more further rounds of renewed encapsulation in aqueous microcapsules of a water-in-emulsion, expression of the peptide genes within the aqueous microcapsules and the formation of p53wt/peptide/peptide gene complexes, breaking of the emulsion and enrichment for any p53/peptide/peptide gene complexes or amplification.

20. A method to treat cancer or a disorder comprising administering to a subject in need thereof a peptide according to claim 1 or an isolated nucleic acid molecule according to claim 7 wherein the subject has cancer associated with a mutant p53 or a disorder characterized by a low level or a low activity of p53.

* * * * *

SEQUENCE LISTING

```
<160> NUMBER OF SEQ ID NOS: 141

<210> SEQ ID NO 1
<211> LENGTH: 127
<212> TYPE: DNA
<213> ORGANISM: Artificial Sequence
<220> FEATURE:
<223> OTHER INFORMATION: A synthetic Ranlib Construction
<221> NAME/KEY: misc_feature
<222> LOCATION: (1)...(127)
<223> OTHER INFORMATION: n = A,T,C or G

<400> SEQUENCE: 1
aatacgactc actataggga gaggaggtat atacatgnnn nnnnnnnnnn nnnnnnnnnn      60
nnnnnnnnnn nnnnnnnnnn nnnnnnnnnn nnnnnntag aggaagaaga ctgggcatgt     120
ctgggca                                                               127

<210> SEQ ID NO 2
<211> LENGTH: 67
<212> TYPE: DNA
<213> ORGANISM: Artificial Sequence
<220> FEATURE:
<223> OTHER INFORMATION: A synthetic Ranlib Construction

<400> SEQUENCE: 2
```
cgcgcctgca agtcctgact tgtccgcggt aatacgactc actatagggga gaggaggtat    60 atacatg                                                               67

<210> SEQ ID NO 3
<211> LENGTH: 30
<212> TYPE: DNA
<213> ORGANISM: Artificial Sequence
<220> FEATURE:
<223> OTHER INFORMATION: A synthetic Ranlib Construction

<400> SEQUENCE: 3
tgcccagaca tgcccagtct tcttcctcta                                      30

<210> SEQ ID NO 4
<211> LENGTH: 19
<212> TYPE: DNA
<213> ORGANISM: Artificial Sequence
<220> FEATURE:
<223> OTHER INFORMATION: A synthetic Ranlib Construction

<400> SEQUENCE: 4
catcggtgat gtcggcgat                                                  19

<210> SEQ ID NO 5
<211> LENGTH: 24
<212> TYPE: DNA
<213> ORGANISM: Artificial Sequence
<220> FEATURE:
<223> OTHER INFORMATION: A synthetic Ranlib Construction

<400> SEQUENCE: 5
cggatatagt tcctcctttc agca                                            24

<210> SEQ ID NO 6
<211> LENGTH: 32
<212> TYPE: DNA
<213> ORGANISM: Artificial Sequence
<220> FEATURE:
<223> OTHER INFORMATION: A synthetic Ranlib Construction

<400> SEQUENCE: 6
gactcactat agggagagga ggtatataca tg                                   32

<210> SEQ ID NO 7
<211> LENGTH: 50
<212> TYPE: DNA
<213> ORGANISM: Artificial Sequence
<220> FEATURE:
<223> OTHER INFORMATION: A synthetic Ranlib Construction

<400> SEQUENCE: 7
gcgtcccatt cgccaatccg tgcccagaca tgcccagtct tcttcctcta                50

<210> SEQ ID NO 8
<211> LENGTH: 20
<212> TYPE: DNA
<213> ORGANISM: Artificial Sequence
<220> FEATURE:
<223> OTHER INFORMATION: A synthetic Ranlib Construction

<400> SEQUENCE: 8
gcgtcccatt cgccaatccg                                                 20

<210> SEQ ID NO 9
<211> LENGTH: 21

```
<212> TYPE: DNA
<213> ORGANISM: Artificial Sequence
<220> FEATURE:
<223> OTHER INFORMATION: A synthetic Peptide cDNA amplification product

<400> SEQUENCE: 9
gcggtaaacg actcactata g                                              21

<210> SEQ ID NO 10
<211> LENGTH: 25
<212> TYPE: DNA
<213> ORGANISM: Artificial Sequence
<220> FEATURE:
<223> OTHER INFORMATION: A synthetic Peptide cDNA amplification product

<400> SEQUENCE: 10
ctctactata aatgttgcta aactg                                          25

<210> SEQ ID NO 11
<211> LENGTH: 23
<212> TYPE: DNA
<213> ORGANISM: Artificial Sequence
<220> FEATURE:
<223> OTHER INFORMATION: A synthetic Peptide cDNA amplification product

<400> SEQUENCE: 11
cctctaaact atgcgtttgt aac                                            23

<210> SEQ ID NO 12
<211> LENGTH: 20
<212> TYPE: DNA
<213> ORGANISM: Artificial Sequence
<220> FEATURE:
<223> OTHER INFORMATION: A synthetic Peptide cDNA amplification product

<400> SEQUENCE: 12
tctaatggtc ggtccaaccc                                                20

<210> SEQ ID NO 13
<211> LENGTH: 19
<212> TYPE: DNA
<213> ORGANISM: Artificial Sequence
<220> FEATURE:
<223> OTHER INFORMATION: A synthetic Peptide cDNA amplification product

<400> SEQUENCE: 13
ctacgggcag tgaccgata                                                 19

<210> SEQ ID NO 14
<211> LENGTH: 22
<212> TYPE: DNA
<213> ORGANISM: Artificial Sequence
<220> FEATURE:
<223> OTHER INFORMATION: A synthetic Peptide cDNA amplification product

<400> SEQUENCE: 14
cctctaccta gtgaagaaag tg                                             22

<210> SEQ ID NO 15
<211> LENGTH: 23
<212> TYPE: DNA
<213> ORGANISM: Artificial Sequence
<220> FEATURE:
<223> OTHER INFORMATION: A synthetic Peptide cDNA amplification product

<400> SEQUENCE: 15
```

```
ctctatgaca ttcgaggata acc                                              23

<210> SEQ ID NO 16
<211> LENGTH: 30
<212> TYPE: DNA
<213> ORGANISM: Artificial Sequence
<220> FEATURE:
<223> OTHER INFORMATION: A synthetic DNA response element

<400> SEQUENCE: 16
tagaggaaga agactgggca tgtctgggca                                       30

<210> SEQ ID NO 17
<211> LENGTH: 30
<212> TYPE: DNA
<213> ORGANISM: Artificial Sequence
<220> FEATURE:
<223> OTHER INFORMATION: A synthetic DNA response element

<400> SEQUENCE: 17
tgcccagaca tgcccagtct tcttcctcta                                       30

<210> SEQ ID NO 18
<211> LENGTH: 30
<212> TYPE: DNA
<213> ORGANISM: Artificial Sequence
<220> FEATURE:
<223> OTHER INFORMATION: A synthetic DNA response element

<400> SEQUENCE: 18
cgcgcctgca agtcctgact tgtccgcggc                                       30

<210> SEQ ID NO 19
<211> LENGTH: 30
<212> TYPE: DNA
<213> ORGANISM: Artificial Sequence
<220> FEATURE:
<223> OTHER INFORMATION: A synthetic DNA response element

<400> SEQUENCE: 19
gccgcggaca agtcaggact tgcaggcgcg                                       30

<210> SEQ ID NO 20
<211> LENGTH: 30
<212> TYPE: DNA
<213> ORGANISM: Artificial Sequence
<220> FEATURE:
<223> OTHER INFORMATION: A synthetic DNA response element

<400> SEQUENCE: 20
gtcgttctga tccaggtgat gtagtcgacg                                       30

<210> SEQ ID NO 21
<211> LENGTH: 30
<212> TYPE: DNA
<213> ORGANISM: Artificial Sequence
<220> FEATURE:
<223> OTHER INFORMATION: A synthetic DNA response element

<400> SEQUENCE: 21
cgtcgactac atcacctgga tcagaacgac                                       30

<210> SEQ ID NO 22
<211> LENGTH: 49
<212> TYPE: DNA
<213> ORGANISM: Artificial Sequence
```

```
<220> FEATURE:
<223> OTHER INFORMATION: A synthetic DNA response element

<400> SEQUENCE: 22
cgcgcctgca agtcctgact tgtccgcggc catcggtgat gtcggcgat          49

<210> SEQ ID NO 23
<211> LENGTH: 43
<212> TYPE: DNA
<213> ORGANISM: Artificial Sequence
<220> FEATURE:
<223> OTHER INFORMATION: A synthetic DNA response element

<400> SEQUENCE: 23
cacatgcctt gcctggactt gcctcatcgg tgatgtcggc gat                43

<210> SEQ ID NO 24
<211> LENGTH: 49
<212> TYPE: DNA
<213> ORGANISM: Artificial Sequence
<220> FEATURE:
<223> OTHER INFORMATION: A synthetic DNA response element

<400> SEQUENCE: 24
tagaggaaga agactgggca tgtctgggca catcggtgat gtcggcgat          49

<210> SEQ ID NO 25
<211> LENGTH: 51
<212> TYPE: DNA
<213> ORGANISM: Artificial Sequence
<220> FEATURE:
<223> OTHER INFORMATION: A synthetic DNA response element

<400> SEQUENCE: 25
cttgggaaca agggcatgag cttgtctggg ctcatcggtg atgtcggcga t       51

<210> SEQ ID NO 26
<211> LENGTH: 22
<212> TYPE: DNA
<213> ORGANISM: Artificial Sequence
<220> FEATURE:
<223> OTHER INFORMATION: A synthetic DNA response element

<400> SEQUENCE: 26
taatttcgcg ggatcgagat ct                                      22

<210> SEQ ID NO 27
<211> LENGTH: 38
<212> TYPE: DNA
<213> ORGANISM: Artificial Sequence
<220> FEATURE:
<223> OTHER INFORMATION: A synthetic Site-directed mutagenesis product

<400> SEQUENCE: 27
catagtgtgg tggtgccctg tgagccgcct gagttggc                     38

<210> SEQ ID NO 28
<211> LENGTH: 39
<212> TYPE: DNA
<213> ORGANISM: Artificial Sequence
<220> FEATURE:
<223> OTHER INFORMATION: A synthetic Site-directed mutagenesis product

<400> SEQUENCE: 28
gccaacctca ggcggctcac agggcaccac cacactatg                    39
```

<210> SEQ ID NO 29
<211> LENGTH: 44
<212> TYPE: DNA
<213> ORGANISM: Artificial Sequence
<220> FEATURE:
<223> OTHER INFORMATION: A synthetic Site-directed mutagenesis product

<400> SEQUENCE: 29
cacatgacgg aggttgtgag gcactgcccc accatgagcg ctgc                    44

<210> SEQ ID NO 30
<211> LENGTH: 45
<212> TYPE: DNA
<213> ORGANISM: Artificial Sequence
<220> FEATURE:
<223> OTHER INFORMATION: A synthetic site-directed mutagenesis product

<400> SEQUENCE: 30
gcagcgctca tggtggggc agtgcctcac aacctccgtc atgtg                    45

<210> SEQ ID NO 31
<211> LENGTH: 41
<212> TYPE: DNA
<213> ORGANISM: Artificial Sequence
<220> FEATURE:
<223> OTHER INFORMATION: A synthetic site-directed mutagenesis product

<400> SEQUENCE: 31
acggaacagc tttgaggtgc atgtttgtgc ctgtcctggg a                       41

<210> SEQ ID NO 32
<211> LENGTH: 41
<212> TYPE: DNA
<213> ORGANISM: Artificial Sequence
<220> FEATURE:
<223> OTHER INFORMATION: A synthetic site-directed mutagenesis product

<400> SEQUENCE: 32
tcccaggaca ggcacaaaca tgcacctcaa agctgttccg t                       41

<210> SEQ ID NO 33
<211> LENGTH: 41
<212> TYPE: DNA
<213> ORGANISM: Artificial Sequence
<220> FEATURE:
<223> OTHER INFORMATION: A synthetic site-directed mutagenesis product

<400> SEQUENCE: 33
gtaacagttc ctgcatgggc agcatgaacc ggaggcccat c                       41

<210> SEQ ID NO 34
<211> LENGTH: 41
<212> TYPE: DNA
<213> ORGANISM: Artificial Sequence
<220> FEATURE:
<223> OTHER INFORMATION: A synthetic site-directed mutagenesis product

<400> SEQUENCE: 34
gatgggcctc cggttcatgc tgcccatgca ggaactgtta c                       41

<210> SEQ ID NO 35
<211> LENGTH: 41
<212> TYPE: DNA
<213> ORGANISM: Artificial Sequence
<220> FEATURE:
<223> OTHER INFORMATION: A synthetic site-directed mutagenesis product

<400> SEQUENCE: 35
ctgcatgggc ggcatgaacc agaggcccat cctcaccatc a                41

<210> SEQ ID NO 36
<211> LENGTH: 41
<212> TYPE: DNA
<213> ORGANISM: Artificial Sequence
<220> FEATURE:
<223> OTHER INFORMATION: A synthetic site-directed mutagenesis product

<400> SEQUENCE: 36
tgatggtgag gatgggcctc tggttcatgc cgcccatgca g                41

<210> SEQ ID NO 37
<211> LENGTH: 23
<212> TYPE: DNA
<213> ORGANISM: Artificial Sequence
<220> FEATURE:
<223> OTHER INFORMATION: A synthetic real-time PCR product

<400> SEQUENCE: 37
ataggcgcca gcaaccgcac ctg                                    23

<210> SEQ ID NO 38
<211> LENGTH: 23
<212> TYPE: DNA
<213> ORGANISM: Artificial Sequence
<220> FEATURE:
<223> OTHER INFORMATION: A synthetic real-time PCR product

<400> SEQUENCE: 38
cttccacttt ttcccgcgtt ttc                                    23

<210> SEQ ID NO 39
<211> LENGTH: 25
<212> TYPE: DNA
<213> ORGANISM: Artificial Sequence
<220> FEATURE:
<223> OTHER INFORMATION: A synthetic real-time PCR product

<400> SEQUENCE: 39
ctcctttcgc tttcttccct tcctt                                  25

<210> SEQ ID NO 40
<211> LENGTH: 25
<212> TYPE: DNA
<213> ORGANISM: Artificial Sequence
<220> FEATURE:
<223> OTHER INFORMATION: A synthetic real-time PCR product

<400> SEQUENCE: 40
ctcgatcccg cgaaattaat acgac                                  25

<210> SEQ ID NO 41
<211> LENGTH: 24
<212> TYPE: DNA
<213> ORGANISM: Artificial Sequence
<220> FEATURE:
<223> OTHER INFORMATION: A synthetic real-time PCR product

<400> SEQUENCE: 41
ccgaattaat tccgatatcc atgg                                   24

<210> SEQ ID NO 42

```
<211> LENGTH: 25
<212> TYPE: DNA
<213> ORGANISM: Artificial Sequence
<220> FEATURE:
<223> OTHER INFORMATION: A synthetic real-time PCR product

<400> SEQUENCE: 42
gtcgtattaa tttcgcggga tcgag                                            25

<210> SEQ ID NO 43
<211> LENGTH: 22
<212> TYPE: DNA
<213> ORGANISM: Artificial Sequence
<220> FEATURE:
<223> OTHER INFORMATION: A synthetic real-time PCR product

<400> SEQUENCE: 43
cgcgcctgca agtcctgact tg                                               22

<210> SEQ ID NO 44
<211> LENGTH: 26
<212> TYPE: DNA
<213> ORGANISM: Artificial Sequence
<220> FEATURE:
<223> OTHER INFORMATION: A synthetic real-time PCR product

<400> SEQUENCE: 44
tagaggaaga agactgggca tgtctg                                           26

<210> SEQ ID NO 45
<211> LENGTH: 23
<212> TYPE: DNA
<213> ORGANISM: Artificial Sequence
<220> FEATURE:
<223> OTHER INFORMATION: A synthetic real-time PCR product

<400> SEQUENCE: 45
cacatgcctt gcctggactt gcc                                              23

<210> SEQ ID NO 46
<211> LENGTH: 25
<212> TYPE: DNA
<213> ORGANISM: Artificial Sequence
<220> FEATURE:
<223> OTHER INFORMATION: A synthetic real-time PCR product

<400> SEQUENCE: 46
cttgggaaca agggcatgag cttgt                                            25

<210> SEQ ID NO 47
<211> LENGTH: 45
<212> TYPE: DNA
<213> ORGANISM: Artificial Sequence
<220> FEATURE:
<223> OTHER INFORMATION: A synthetic expression construct

<400> SEQUENCE: 47
atgatgccac acttaatggc atgtccgtgc aaaatgatcg ccccg                      45

<210> SEQ ID NO 48
<211> LENGTH: 45
<212> TYPE: DNA
<213> ORGANISM: Artificial Sequence
<220> FEATURE:
<223> OTHER INFORMATION: A synthetic expression construct

<400> SEQUENCE: 48
```

```
acatgccatt aagtgtggca tcataccgca ccactctgcc cagaa                              45

<210> SEQ ID NO 49
<211> LENGTH: 23
<212> TYPE: DNA
<213> ORGANISM: Artificial Sequence
<220> FEATURE:
<223> OTHER INFORMATION: A synthetic expression construct

<400> SEQUENCE: 49
gaaataatac gactcactat agg                                                     23

<210> SEQ ID NO 50
<211> LENGTH: 17
<212> TYPE: DNA
<213> ORGANISM: Artificial Sequence
<220> FEATURE:
<223> OTHER INFORMATION: A synthetic expression construct

<400> SEQUENCE: 50
ctaggccatc gccggct                                                            17

<210> SEQ ID NO 51
<211> LENGTH: 17
<212> TYPE: DNA
<213> ORGANISM: Artificial Sequence
<220> FEATURE:
<223> OTHER INFORMATION: A synthetic oligo

<400> SEQUENCE: 51
gtaaaacgac ggccagt                                                            17

<210> SEQ ID NO 52
<211> LENGTH: 17
<212> TYPE: DNA
<213> ORGANISM: Artificial Sequence
<220> FEATURE:
<223> OTHER INFORMATION: A synthetic oligo

<400> SEQUENCE: 52
caggaaacag ctatgac                                                            17

<210> SEQ ID NO 53
<211> LENGTH: 21
<212> TYPE: DNA
<213> ORGANISM: Artificial Sequence
<220> FEATURE:
<223> OTHER INFORMATION: A synthetic oligo

<400> SEQUENCE: 53
tgaggatccg aattcgagct c                                                       21

<210> SEQ ID NO 54
<211> LENGTH: 20
<212> TYPE: DNA
<213> ORGANISM: Artificial Sequence
<220> FEATURE:
<223> OTHER INFORMATION: A synthetic oligo

<400> SEQUENCE: 54
ggacttcagg tggctggagt                                                         20

<210> SEQ ID NO 55
<211> LENGTH: 6
<212> TYPE: PRT
```

<213> ORGANISM: Artificial Sequence
<220> FEATURE:
<223> OTHER INFORMATION: A synthetic peptide

<400> SEQUENCE: 55

Ser Pro Thr Thr Asn His
1               5

<210> SEQ ID NO 56
<211> LENGTH: 7
<212> TYPE: PRT
<213> ORGANISM: Artificial Sequence
<220> FEATURE:
<223> OTHER INFORMATION: A synthetic peptide

<400> SEQUENCE: 56

Met Pro His Leu Met Ala Cys
1               5

<210> SEQ ID NO 57
<211> LENGTH: 20
<212> TYPE: PRT
<213> ORGANISM: Artificial Sequence
<220> FEATURE:
<223> OTHER INFORMATION: A synthetic peptide

<400> SEQUENCE: 57

Thr Ala Leu Ile Asp Ile Trp Glu His Ser Val Leu Gly Lys Gly Tyr
1               5                  10                  15

Pro Arg Met Ser
            20

<210> SEQ ID NO 58
<211> LENGTH: 13
<212> TYPE: PRT
<213> ORGANISM: Artificial Sequence
<220> FEATURE:
<223> OTHER INFORMATION: A synthetic peptide

<400> SEQUENCE: 58

Ile Leu Asn Val Leu Pro Leu Leu Ala Ser Arg Lys Pro
1               5                  10

<210> SEQ ID NO 59
<211> LENGTH: 29
<212> TYPE: PRT
<213> ORGANISM: Artificial Sequence
<220> FEATURE:
<223> OTHER INFORMATION: A synthetic peptide

<400> SEQUENCE: 59

Val Ser Trp Ser Ala Cys Val Leu Leu Glu Leu Cys Asn Tyr Phe Pro
1               5                  10                  15

Glu Asn Pro Ile Glu Glu Glu Asp Trp Ala Cys Leu Gly
            20                  25

<210> SEQ ID NO 60
<211> LENGTH: 5
<212> TYPE: PRT
<213> ORGANISM: Artificial Sequence
<220> FEATURE:
<223> OTHER INFORMATION: A synthetic peptide

<400> SEQUENCE: 60

Arg Leu Gln Gln Val
1               5

<210> SEQ ID NO 61
<211> LENGTH: 14
<212> TYPE: PRT
<213> ORGANISM: Artificial Sequence
<220> FEATURE:
<223> OTHER INFORMATION: A synthetic peptide

<400> SEQUENCE: 61

Val Arg His Gln His Val Gly Ala Thr Ile Leu Gly Trp Lys
1               5                   10

<210> SEQ ID NO 62
<211> LENGTH: 20
<212> TYPE: PRT
<213> ORGANISM: Artificial Sequence
<220> FEATURE:
<223> OTHER INFORMATION: A synthetic peptide

<400> SEQUENCE: 62

Val Arg His Gln His Val Gly Ala Thr Ile Leu Gly Trp Lys Met Gly
1               5                   10                  15

Trp Thr Asp His
            20

<210> SEQ ID NO 63
<211> LENGTH: 7
<212> TYPE: PRT
<213> ORGANISM: Artificial Sequence
<220> FEATURE:
<223> OTHER INFORMATION: A synthetic peptide

<400> SEQUENCE: 63

Met Ser Pro Thr Thr Asn His
1               5

<210> SEQ ID NO 64
<211> LENGTH: 8
<212> TYPE: PRT
<213> ORGANISM: Artificial Sequence
<220> FEATURE:
<223> OTHER INFORMATION: A synthetic peptide

<400> SEQUENCE: 64

Met Met Pro His Leu Met Ala Cys
1               5

<210> SEQ ID NO 65
<211> LENGTH: 21
<212> TYPE: PRT
<213> ORGANISM: Artificial Sequence
<220> FEATURE:
<223> OTHER INFORMATION: A synthetic peptide

<400> SEQUENCE: 65

Met Thr Ala Leu Ile Asp Ile Trp Glu His Ser Val Leu Gly Lys Gly
1               5                   10                  15

Tyr Pro Arg Met Ser
            20

<210> SEQ ID NO 66
<211> LENGTH: 14
<212> TYPE: PRT
<213> ORGANISM: Artificial Sequence
<220> FEATURE:
<223> OTHER INFORMATION: A synthetic peptide

```
<400> SEQUENCE: 66

Met Ile Leu Asn Val Leu Pro Leu Leu Ala Ser Arg Lys Pro
1               5                   10

<210> SEQ ID NO 67
<211> LENGTH: 30
<212> TYPE: PRT
<213> ORGANISM: Artificial Sequence
<220> FEATURE:
<223> OTHER INFORMATION: A synthetic peptide

<400> SEQUENCE: 67

Met Val Ser Trp Ser Ala Cys Val Leu Leu Glu Leu Cys Asn Tyr Phe
1               5                   10                  15

Pro Glu Asn Pro Ile Glu Glu Glu Asp Trp Ala Cys Leu Gly
            20                  25                  30

<210> SEQ ID NO 68
<211> LENGTH: 6
<212> TYPE: PRT
<213> ORGANISM: Artificial Sequence
<220> FEATURE:
<223> OTHER INFORMATION: A synthetic peptide

<400> SEQUENCE: 68

Met Arg Leu Gln Gln Val
1               5

<210> SEQ ID NO 69
<211> LENGTH: 15
<212> TYPE: PRT
<213> ORGANISM: Artificial Sequence
<220> FEATURE:
<223> OTHER INFORMATION: A synthetic peptide

<400> SEQUENCE: 69

Met Val Arg His Gln His Val Gly Ala Thr Ile Leu Gly Trp Lys
1               5                   10                  15

<210> SEQ ID NO 70
<211> LENGTH: 21
<212> TYPE: PRT
<213> ORGANISM: Artificial Sequence
<220> FEATURE:
<223> OTHER INFORMATION: A synthetic peptide

<400> SEQUENCE: 70

Met Val Arg His Gln His Val Gly Ala Thr Ile Leu Gly Trp Lys Met
1               5                   10                  15

Gly Trp Thr Asp His
            20

<210> SEQ ID NO 71
<211> LENGTH: 20
<212> TYPE: PRT
<213> ORGANISM: Artificial Sequence
<220> FEATURE:
<223> OTHER INFORMATION: A synthetic peptide

<400> SEQUENCE: 71

Thr Thr Leu Ile Asp Ile Trp Glu His Ser Val Leu Gly Lys Gly Tyr
1               5                   10                  15

Pro Arg Met Ser
            20
```

```
<210> SEQ ID NO 72
<211> LENGTH: 21
<212> TYPE: PRT
<213> ORGANISM: Artificial Sequence
<220> FEATURE:
<223> OTHER INFORMATION: A synthetic peptide

<400> SEQUENCE: 72

Met Thr Thr Leu Ile Asp Ile Trp Glu His Ser Val Leu Gly Lys Gly
 1               5                  10                  15

Tyr Pro Arg Met Ser
            20

<210> SEQ ID NO 73
<211> LENGTH: 20
<212> TYPE: PRT
<213> ORGANISM: Artificial Sequence
<220> FEATURE:
<223> OTHER INFORMATION: A synthetic peptide

<400> SEQUENCE: 73

Arg Ala Val Thr Asp Arg Pro Val Pro Cys Pro Asn Pro Arg Leu Asn
 1               5                  10                  15

Leu Val Ala Asn
            20

<210> SEQ ID NO 74
<211> LENGTH: 21
<212> TYPE: PRT
<213> ORGANISM: Artificial Sequence
<220> FEATURE:
<223> OTHER INFORMATION: A synthetic peptide

<400> SEQUENCE: 74

Met Arg Ala Val Thr Asp Arg Pro Val Pro Cys Pro Asn Pro Arg Leu
 1               5                  10                  15

Asn Leu Val Ala Asn
            20

<210> SEQ ID NO 75
<211> LENGTH: 42
<212> TYPE: DNA
<213> ORGANISM: Artificial Sequence
<220> FEATURE:
<223> OTHER INFORMATION: A synthetic Ranlib Construction

<400> SEQUENCE: 75
cgcgcctgca agtcctgact tgtccgcggt aatacgactc ac                           42

<210> SEQ ID NO 76
<211> LENGTH: 25
<212> TYPE: DNA
<213> ORGANISM: Artificial Sequence
<220> FEATURE:
<223> OTHER INFORMATION: A synthetic Ranlib Construction

<400> SEQUENCE: 76
tatagggaga ggaggtatat acatg                                              25

<210> SEQ ID NO 77
<211> LENGTH: 59
<212> TYPE: DNA
<213> ORGANISM: Artificial Sequence
<220> FEATURE:
```

<223> OTHER INFORMATION: A synthetic oligonucleotide

<400> SEQUENCE: 77
acatattcat caccgcccctt tgggcgagca gtcgcctttg catttagcta gaaaggcgt    59

<210> SEQ ID NO 78
<211> LENGTH: 16
<212> TYPE: PRT
<213> ORGANISM: Artificial Sequence
<220> FEATURE:
<223> OTHER INFORMATION: A synthetic peptide

<400> SEQUENCE: 78

Thr Tyr Ser Ser Pro Pro Phe Gly Arg Ala Val Ala Phe Ala Phe Ser
 1               5                  10                  15

<210> SEQ ID NO 79
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 79
tttacagttt ctgttatagc ttccccattt tataatattt tccgcccttt tctcggcgga    60

<210> SEQ ID NO 80
<211> LENGTH: 20
<212> TYPE: PRT
<213> ORGANISM: Artificial Sequence
<220> FEATURE:
<223> OTHER INFORMATION: A synthetic peptide

<400> SEQUENCE: 80

Phe Thr Val Ser Val Ile Ala Ser Pro Phe Tyr Asn Ile Phe Arg Pro
 1               5                  10                  15

Phe Leu Gly Gly
            20

<210> SEQ ID NO 81
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 81
ggtggctctc gctttatagc ggcacttccg ggaacatcga cggcttcttg gattagctct    60

<210> SEQ ID NO 82
<211> LENGTH: 20
<212> TYPE: PRT
<213> ORGANISM: Artificial Sequence
<220> FEATURE:
<223> OTHER INFORMATION: A synthetic peptide

<400> SEQUENCE: 82

Gly Gly Ser Arg Phe Ile Ala Ala Leu Pro Gly Thr Ser Thr Ala Ser
 1               5                  10                  15

Trp Ile Ser Ser
            20

<210> SEQ ID NO 83
<211> LENGTH: 60
<212> TYPE: DNA

```
<213> ORGANISM: Artificial Sequence
<220> FEATURE:
<223> OTHER INFORMATION: A synthetic oligonucleotide

<400> SEQUENCE: 83
atcgtgtaga tgattctcgg attgtctctc cttggacggt aatctgagaa cctcttagat    60

<210> SEQ ID NO 84
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 84
tagccttaaa agtatgtgtt gtagactggg cctagatcca agttgttgtg gtgagatttt    60

<210> SEQ ID NO 85
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 85
gggagtgcac acgtcgtatg taagggtcct attatatctt tgtaacacta agatgcttcc    60

<210> SEQ ID NO 86
<211> LENGTH: 14
<212> TYPE: PRT
<213> ORGANISM: Artificial Sequence
<220> FEATURE:
<223> OTHER INFORMATION: A synthetic peptide

<400> SEQUENCE: 86

Gly Ser Ala His Val Val Cys Lys Gly Pro Ile Ile Ser Leu
  1               5                  10

<210> SEQ ID NO 87
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 87
acgatgtagg tcgacggcgg tccectgaat acgggccctg tacccattgc tcacagactg    60

<210> SEQ ID NO 88
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 88
tctacgaggg gcagccattg aattaacggt ttcaggaagt tctagtgata ttggagtgcg    60

<210> SEQ ID NO 89
<211> LENGTH: 6
<212> TYPE: PRT
<213> ORGANISM: Artificial Sequence
<220> FEATURE:
<223> OTHER INFORMATION: A synthetic peptide

<400> SEQUENCE: 89
```

```
Ser Thr Arg Gly Ser His
1               5
```

<210> SEQ ID NO 90
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 90
agtaggccta tcacatagag tactgtttag gtaccacggg ttcatggttg tacctcacgg    60

<210> SEQ ID NO 91
<211> LENGTH: 5
<212> TYPE: PRT
<213> ORGANISM: Artificial Sequence
<220> FEATURE:
<223> OTHER INFORMATION: A synthetic peptide

<400> SEQUENCE: 91

```
Ser Arg Pro Ile Thr
1               5
```

<210> SEQ ID NO 92
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 92
gaaactatag gcatccatct atcccgtctg cctcagcaac gtagtatcat gtggcggggt    60

<210> SEQ ID NO 93
<211> LENGTH: 20
<212> TYPE: PRT
<213> ORGANISM: Artificial Sequence
<220> FEATURE:
<223> OTHER INFORMATION: A synthetic peptide

<400> SEQUENCE: 93

```
Glu Thr Ile Gly Ile His Leu Ser Arg Leu Pro Gln Gln Arg Ser Ile
1               5                   10                  15

Met Trp Arg Gly
            20
```

<210> SEQ ID NO 94
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 94
cccacatgtt gcctaggtac acccattatg ccgccttgag agtagctttt ctgtgtgatt    60

<210> SEQ ID NO 95
<211> LENGTH: 12
<212> TYPE: PRT
<213> ORGANISM: Artificial Sequence
<220> FEATURE:
<223> OTHER INFORMATION: A synthetic peptide

<400> SEQUENCE: 95

Pro Thr Cys Cys Leu Gly Thr Pro Ile Met Pro Pro

<210> SEQ ID NO 96
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 96
gagtgaacct gagggctctt aacatgggag tatccccaat gtgatcgatg gtatcagccc      60

<210> SEQ ID NO 97
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 97
gaacgacgca tccttattta gcctttcttt ggtgagagaa cgccgggagg ccaactcgaa      60

<210> SEQ ID NO 98
<211> LENGTH: 6
<212> TYPE: PRT
<213> ORGANISM: Artificial Sequence
<220> FEATURE:
<223> OTHER INFORMATION: A synthetic peptide

<400> SEQUENCE: 98

Glu Arg Arg Ile Leu Ile
 1               5

<210> SEQ ID NO 99
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 99
actttatcgt actacataat ttgaatactc ctgatactac agtaaggcca cgaaaagata      60

<210> SEQ ID NO 100
<211> LENGTH: 7
<212> TYPE: PRT
<213> ORGANISM: Artificial Sequence
<220> FEATURE:
<223> OTHER INFORMATION: A synthetic peptide

<400> SEQUENCE: 100

Thr Leu Ser Tyr Tyr Ile Ile
 1               5

<210> SEQ ID NO 101
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 101 atgattttt cagtgacgat tgggcggagc cgcagcatac aaaaagaatg caattttaaa      60

<210> SEQ ID NO 102
<211> LENGTH: 20

```
<212> TYPE: PRT
<213> ORGANISM: Artificial Sequence
<220> FEATURE:
<223> OTHER INFORMATION: A synthetic peptide

<400> SEQUENCE: 102

Met Ile Phe Ser Val Thr Ile Gly Arg Ser Arg Ser Ile Gln Lys Glu
 1               5                  10                  15

Cys Asn Phe Lys
            20

<210> SEQ ID NO 103
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 103
tggctcaagc actcttgaag cgtaccacac actgtaagaa gcgatggcgc tttaaaggtc      60

<210> SEQ ID NO 104
<211> LENGTH: 5
<212> TYPE: PRT
<213> ORGANISM: Artificial Sequence
<220> FEATURE:
<223> OTHER INFORMATION: A synthetic peptide

<400> SEQUENCE: 104

Trp Leu Lys His Ser
 1               5

<210> SEQ ID NO 105
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 105
ggtccatatt tgcggtgtag gctcatgcca gctggtgtta ggcctccgaa tgaactattt      60

<210> SEQ ID NO 106
<211> LENGTH: 20
<212> TYPE: PRT
<213> ORGANISM: Artificial Sequence
<220> FEATURE:
<223> OTHER INFORMATION: A synthetic peptide

<400> SEQUENCE: 106

Gly Pro Tyr Leu Arg Cys Arg Leu Met Pro Ala Gly Val Arg Pro Pro
 1               5                  10                  15

Asn Glu Leu Phe
            20

<210> SEQ ID NO 107
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 107
gcacttgggg tggaagcaca cagggtcgta tctaatgtga catatcgtcg tcgcgtggcg      60
```

<210> SEQ ID NO 108
<211> LENGTH: 20
<212> TYPE: PRT
<213> ORGANISM: Artificial Sequence
<220> FEATURE:
<223> OTHER INFORMATION: A synthetic peptide

<400> SEQUENCE: 108

Ala Leu Gly Val Glu Ala His Arg Val Val Ser Asn Val Thr Tyr Arg
 1               5                  10                  15

Arg Arg Val Ala
            20

<210> SEQ ID NO 109
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 109
aataggacga cgtgaggaca tcctcggact gtctcgttgt gtgcccagtt cccgatatac    60

<210> SEQ ID NO 110
<211> LENGTH: 4
<212> TYPE: PRT
<213> ORGANISM: Artificial Sequence
<220> FEATURE:
<223> OTHER INFORMATION: A synthetic peptide

<400> SEQUENCE: 110

Asn Arg Thr Thr
 1

<210> SEQ ID NO 111
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 111
gtccctattg atcattgaat agtaggaatc accagcgttg acagaggtc ccatgtgagc    60

<210> SEQ ID NO 112
<211> LENGTH: 5
<212> TYPE: PRT
<213> ORGANISM: Artificial Sequence
<220> FEATURE:
<223> OTHER INFORMATION: A synthetic peptide

<400> SEQUENCE: 112

Val Pro Ile Asp His
 1               5

<210> SEQ ID NO 113
<211> LENGTH: 20
<212> TYPE: PRT
<213> ORGANISM: Artificial Sequence
<220> FEATURE:
<223> OTHER INFORMATION: A synthetic peptide

<400> SEQUENCE: 113

Asp Glu Leu Val Ala Ile Pro Val Arg Leu Thr Tyr Tyr Arg Gly Pro
 1               5                  10                  15

Asn Ile Ala Ile

<210> SEQ ID NO 114
<211> LENGTH: 20
<212> TYPE: PRT
<213> ORGANISM: Artificial Sequence
<220> FEATURE:
<223> OTHER INFORMATION: A synthetic peptide

<400> SEQUENCE: 114

Glu Arg Arg Phe Pro Ile Met Gly Val Asn Ser Pro Glu Gly Lys Met
 1               5                  10                  15

Trp Pro Leu Ile
            20

<210> SEQ ID NO 115
<211> LENGTH: 14
<212> TYPE: PRT
<213> ORGANISM: Artificial Sequence
<220> FEATURE:
<223> OTHER INFORMATION: A synthetic peptide

<400> SEQUENCE: 115

Ala Arg His Gln His Val Gly Ala Thr Ile Leu Gly Trp Lys
 1               5                  10

<210> SEQ ID NO 116
<211> LENGTH: 9
<212> TYPE: PRT
<213> ORGANISM: Artificial Sequence
<220> FEATURE:
<223> OTHER INFORMATION: A synthetic peptide

<400> SEQUENCE: 116

Arg Lys Lys Arg Arg Gln Arg Arg Arg
 1               5

<210> SEQ ID NO 117
<211> LENGTH: 96
<212> TYPE: DNA
<213> ORGANISM: Artificial Sequence
<220> FEATURE:
<223> OTHER INFORMATION: A synthetic oligonucleotide

<400> SEQUENCE: 117
cgcgcctgca agtcctgcct tgtccgcgga atacgactca ctatagggag aggaggtata      60
tacatgtaga ggaagaagac tgggcatgtc tgggca                                96

<210> SEQ ID NO 118
<211> LENGTH: 96
<212> TYPE: DNA
<213> ORGANISM: Artificial Sequence
<220> FEATURE:
<223> OTHER INFORMATION: A synthetic oligonucleotide

<400> SEQUENCE: 118
tgcccagaca tgcccagtct tcttcctcta catgtatata cctcctctcc ctatagtgag      60
tcgtattccg cggacaagtc aggacttgca ggcgcg                                96

<210> SEQ ID NO 119
<211> LENGTH: 138
<212> TYPE: DNA
<213> ORGANISM: Artificial Sequence
<220> FEATURE:
<223> OTHER INFORMATION: A synthetic oligonucleotide

```
<221> NAME/KEY: misc_feature
<222> LOCATION: (1)...(138)
<223> OTHER INFORMATION: n = A,T,C or G

<400> SEQUENCE: 119
gtccgcggaa tacgactcac tatagggaga ggaggtatat acatgatnca gtntctttat      60
agctgccctt ngncnaacat tcgacggctt ttgctagaaa gctgttagag gaagaagact     120
gggcatgtct gggcaaag                                                   138

<210> SEQ ID NO 120
<211> LENGTH: 136
<212> TYPE: DNA
<213> ORGANISM: Artificial Sequence
<220> FEATURE:
<223> OTHER INFORMATION: A synthetic oligonucleotide

<400> SEQUENCE: 120
gtccgcggaa tacgactcac tatagggaga ggaggtatat acatgacata ttcatcacgc      60
cctttgggcg agcagtcgcc tttgcattta gctagaaagg cgttagagga agaagactgg     120
gcatgtctgg gcaaag                                                    136

<210> SEQ ID NO 121
<211> LENGTH: 138
<212> TYPE: DNA
<213> ORGANISM: Artificial Sequence
<220> FEATURE:
<223> OTHER INFORMATION: A synthetic oligonucleotide

<400> SEQUENCE: 121
gtccgcggaa tacgactcac tatagggaga ggaggtatat acatgtttac agtttctgtt      60
atagcttccc cattttataa tattttccgc cctttttctcg gcggatagag gaagaagact    120
gggcatgtct gggcaaag                                                   138

<210> SEQ ID NO 122
<211> LENGTH: 138
<212> TYPE: DNA
<213> ORGANISM: Artificial Sequence
<220> FEATURE:
<223> OTHER INFORMATION: A synthetic oligonucleotide

<400> SEQUENCE: 122
gtccgcggaa tacgactcac tatagggaga ggaggtatat acatgggtgg ctctcccttt      60
atagcggcac ttccgggaac atcgacggct tcttggatta gctcttagag gaagaagact    120
gggcatgtct gggcaaag                                                   138

<210> SEQ ID NO 123
<211> LENGTH: 138
<212> TYPE: DNA
<213> ORGANISM: Artificial Sequence
<220> FEATURE:
<223> OTHER INFORMATION: A synthetic oligonucleotide

<400> SEQUENCE: 123
gtccgcggaa tacgactcac tatagggaga ggaggtatat acatgatcgt gtagatgatt      60
ctcggattgt ctctccttgg acggtaatct gagaacctct tagattagag gaagaagact    120
gggcatgtct gggcaaag                                                   138

<210> SEQ ID NO 124
<211> LENGTH: 12
```

```
<212> TYPE: PRT
<213> ORGANISM: Artificial Sequence
<220> FEATURE:
<223> OTHER INFORMATION: A synthetic peptide

<400> SEQUENCE: 124

Ala Leu Thr His Phe Ser Ser Pro Phe Thr Asn Asn
1               5                   10

<210> SEQ ID NO 125
<211> LENGTH: 5
<212> TYPE: PRT
<213> ORGANISM: Artificial Sequence
<220> FEATURE:
<223> OTHER INFORMATION: A synthetic peptide

<400> SEQUENCE: 125

His Leu Met Ala Cys
1               5

<210> SEQ ID NO 126
<211> LENGTH: 11
<212> TYPE: PRT
<213> ORGANISM: Artificial Sequence
<220> FEATURE:
<223> OTHER INFORMATION: A synthetic peptide

<400> SEQUENCE: 126

Lys Thr Gly His Leu Met Ala Cys Phe Thr Cys
1               5                   10

<210> SEQ ID NO 127
<211> LENGTH: 14
<212> TYPE: PRT
<213> ORGANISM: Artificial Sequence
<220> FEATURE:
<223> OTHER INFORMATION: A synthetic peptide

<400> SEQUENCE: 127

Leu Cys Asn Tyr Phe Pro Glu Asn Pro Ile Glu Glu Glu Asp
1               5                   10

<210> SEQ ID NO 128
<211> LENGTH: 11
<212> TYPE: PRT
<213> ORGANISM: Artificial Sequence
<220> FEATURE:
<223> OTHER INFORMATION: A synthetic peptide

<400> SEQUENCE: 128

Leu Cys Pro Asp Asn Ala Thr Glu Glu Glu Asp
1               5                   10

<210> SEQ ID NO 129
<211> LENGTH: 9
<212> TYPE: PRT
<213> ORGANISM: Artificial Sequence
<220> FEATURE:
<223> OTHER INFORMATION: A synthetic peptide

<400> SEQUENCE: 129

Tyr Phe Pro Glu Asn Pro Ile Glu Glu
1               5

<210> SEQ ID NO 130
<211> LENGTH: 8
<212> TYPE: PRT
```

```
<213> ORGANISM: Artificial Sequence
<220> FEATURE:
<223> OTHER INFORMATION: A synthetic peptide

<400> SEQUENCE: 130

Tyr Tyr Glu Asn Tyr Ile Glu Glu
1               5

<210> SEQ ID NO 131
<211> LENGTH: 8
<212> TYPE: PRT
<213> ORGANISM: Artificial Sequence
<220> FEATURE:
<223> OTHER INFORMATION: A synthetic peptide

<400> SEQUENCE: 131

Ile Glu Glu Glu Asp Trp Ala Cys
1               5

<210> SEQ ID NO 132
<211> LENGTH: 9
<212> TYPE: PRT
<213> ORGANISM: Artificial Sequence
<220> FEATURE:
<223> OTHER INFORMATION: A synthetic peptide

<400> SEQUENCE: 132

Arg Glu Asp Glu Asp Glu Ile Glu Trp
1               5

<210> SEQ ID NO 133
<211> LENGTH: 12
<212> TYPE: PRT
<213> ORGANISM: Artificial Sequence
<220> FEATURE:
<223> OTHER INFORMATION: A synthetic peptide

<400> SEQUENCE: 133

Thr Ala Leu Ile Asp Ile Trp Glu His Ser Val Leu
1               5                   10

<210> SEQ ID NO 134
<211> LENGTH: 21
<212> TYPE: PRT
<213> ORGANISM: Artificial Sequence
<220> FEATURE:
<223> OTHER INFORMATION: A synthetic peptide

<400> SEQUENCE: 134

Gly Pro Leu Ser Thr Thr Leu Leu Asp Phe Trp Arg Met Ile Trp Glu
1               5                   10                  15

Tyr Ser Val Leu Ile
            20

<210> SEQ ID NO 135
<211> LENGTH: 10
<212> TYPE: PRT
<213> ORGANISM: Artificial Sequence
<220> FEATURE:
<223> OTHER INFORMATION: A synthetic peptide

<400> SEQUENCE: 135

Gly Arg Lys Lys Arg Gln Arg Arg Arg
1               5                   10

<210> SEQ ID NO 136
```

```
<211> LENGTH: 7
<212> TYPE: PRT
<213> ORGANISM: Artificial Sequence
<220> FEATURE:
<223> OTHER INFORMATION: A synthetic peptide

<400> SEQUENCE: 136

Met Ser Pro Asn Thr Asn His
 1               5

<210> SEQ ID NO 137
<211> LENGTH: 8
<212> TYPE: PRT
<213> ORGANISM: Artificial Sequence
<220> FEATURE:
<223> OTHER INFORMATION: A synthetic peptide

<400> SEQUENCE: 137

Cys Met Ala Pro Met Leu His Met
 1               5

<210> SEQ ID NO 138
<211> LENGTH: 20
<212> TYPE: PRT
<213> ORGANISM: Artificial Sequence
<220> FEATURE:
<223> OTHER INFORMATION: A synthetic peptide

<400> SEQUENCE: 138

Phe Trp Ala Glu Trp Cys Gly Met Pro His Leu Met Ala Cys Pro Cys
 1               5                  10                  15

Lys Met Ile Ala
            20

<210> SEQ ID NO 139
<211> LENGTH: 21
<212> TYPE: PRT
<213> ORGANISM: Artificial Sequence
<220> FEATURE:
<223> OTHER INFORMATION: A synthetic peptide

<400> SEQUENCE: 139

Phe Trp Ala Glu Trp Cys Gly Met Met Pro His Leu Met Ala Cys Pro
 1               5                  10                  15

Cys Lys Met Ile Ala
            20

<210> SEQ ID NO 140
<211> LENGTH: 21
<212> TYPE: PRT
<213> ORGANISM: Artificial Sequence
<220> FEATURE:
<223> OTHER INFORMATION: A synthetic peptide

<400> SEQUENCE: 140

Phe Trp Ala Glu Trp Cys Gly Cys Met Ala Pro Met Leu His Met Pro
 1               5                  10                  15

Cys Lys Met Ile Ala
            20

<210> SEQ ID NO 141
<211> LENGTH: 7
```

```
<212> TYPE: PRT
<213> ORGANISM: Artificial Sequence
<220> FEATURE:
<223> OTHER INFORMATION: A synthetic peptide

<400> SEQUENCE: 141

Ile Trp Glu His Ser Val Leu
1               5
```